(12) United States Patent
Dizerega et al.

(10) Patent No.: US 12,329,858 B2
(45) Date of Patent: *Jun. 17, 2025

(54) LOCAL DELIVERY OF ANTINEOPLASTIC PARTICLES IN COMBINATION WITH SYSTEMIC DELIVERY OF IMMUNOTHERAPEUTIC AGENTS FOR THE TREATMENT OF CANCER

(71) Applicant: CRITITECH, INC., Lawrence, KS (US)

(72) Inventors: Gere S. Dizerega, Lawrence, KS (US); Michael Baltezor, Lawrence, KS (US); Sam Campbell, Lawrence, KS (US); Charles J. Decedue, Lawrence, KS (US); Matthew McClorey, Lawrence, KS (US); Holly Maulhardt, Lawrence, KS (US)

(73) Assignee: Crititech, Inc., Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,556

(22) Filed: Jan. 29, 2024

(65) Prior Publication Data

US 2024/0252441 A1 Aug. 1, 2024

Related U.S. Application Data

(63) Continuation of application No. 18/154,419, filed on Jan. 13, 2023, now Pat. No. 11,918,691, which is a continuation of application No. 17/333,629, filed on May 28, 2021, now Pat. No. 11,583,499, which is a continuation of application No. 16/834,155, filed on Mar. 30, 2020, now Pat. No. 11,058,639, which is a continuation of application No. PCT/US2018/054156, filed on Oct. 3, 2018.

(60) Provisional application No. 62/567,445, filed on Oct. 3, 2017.

(51) Int. Cl.
| | |
|---|---|
| *A61K 9/16* | (2006.01) |
| *A61K 31/337* | (2006.01) |
| *C07K 16/28* | (2006.01) |
| *A61K 9/00* | (2006.01) |
| *A61K 39/00* | (2006.01) |

(52) U.S. Cl.
CPC ......... *A61K 9/1652* (2013.01); *A61K 31/337* (2013.01); *C07K 16/2818* (2013.01); *A61K 9/0014* (2013.01); *A61K 9/0019* (2013.01); *A61K 9/0053* (2013.01); *A61K 2039/54* (2013.01)

(58) Field of Classification Search
CPC .. A61K 9/1652; A61K 31/337; A61K 9/0014; A61K 9/0019; A61K 9/0053; A61K 2039/54; A61K 9/0073; A61K 9/06; A61K 9/10; A61K 39/3955; A61K 39/395; A61K 45/06; A61K 47/26; A61K 2039/505; A61K 2300/00; C07K 16/2818; C07K 2317/24; C07K 2317/76; A61P 35/00

See application file for complete search history.

(56) References Cited

U.S. PATENT DOCUMENTS

| | | | |
|---|---|---|---|
| 5,399,363 | A | 3/1995 | Liversidge et al. |
| 5,626,862 | A | 5/1997 | Brem et al. |
| 5,833,891 | A | 11/1998 | Subramaniam et al. |
| 5,874,029 | A | 2/1999 | Subramaniam et al. |
| 5,874,481 | A | 2/1999 | Weers et al. |
| 5,886,026 | A | 3/1999 | Hunter et al. |
| 6,063,138 | A | 5/2000 | Hanna et al. |
| 6,113,795 | A | 9/2000 | Subramaniam et al. |
| 6,117,949 | A | 9/2000 | Rathi et al. |
| 6,221,153 | B1 | 4/2001 | Castor et al. |
| 6,348,209 | B2 | 2/2002 | Placke et al. |
| 6,419,901 | B2 | 7/2002 | Placke et al. |
| 6,562,952 | B1 | 5/2003 | Rajewski et al. |
| 6,616,849 | B1 | 9/2003 | Osajima et al. |
| 6,620,351 | B2 | 9/2003 | Gupta et al. |
| 6,689,803 | B2 | 2/2004 | Hunter |
| 6,749,868 | B1 | 6/2004 | Desai et al. |
| 6,811,767 | B1 | 11/2004 | Bosch et al. |
| 7,179,495 | B1 | 2/2007 | Simon et al. |
| 7,208,106 | B2 | 4/2007 | Shekunov et al. |
| 7,217,735 | B1 | 5/2007 | Au et al. |
| 7,276,190 | B2 | 10/2007 | Reverchon |
| 7,455,797 | B2 | 11/2008 | Shekunov et al. |
| 7,556,798 | B2 | 7/2009 | Edwards et al. |
| 7,566,436 | B2 | 7/2009 | Lester et al. |

(Continued)

FOREIGN PATENT DOCUMENTS

| | | |
|---|---|---|
| CN | 1463969 | 12/2003 |
| CN | 1923189 | 3/2007 |

(Continued)

OTHER PUBLICATIONS

US 10,624,886 B2, 04/2020, Baltezor et al. (withdrawn)

(Continued)

*Primary Examiner* — Jessica Worsham
(74) *Attorney, Agent, or Firm* — MCDONNELL BOEHNEN HULBERT & BERGHOFF LLP

(57) ABSTRACT

Disclosed are combination therapy methods useful for the therapeutic treatment of cancer by combining local administration of compositions containing antineoplastic particles, such as taxane particles, with systemic administration of compositions containing immunotherapeutic agents. Local administration methods include topical application, pulmonary administration, intratumoral injection, intraperitoneal injection, and intracystic injection.

19 Claims, 49 Drawing Sheets

(56) References Cited

U.S. PATENT DOCUMENTS

| | | |
|---|---|---|
| 7,744,923 B2 | 6/2010 | Rajewski et al. |
| 7,754,777 B2 | 7/2010 | Ventosa et al. |
| 7,820,788 B2 | 10/2010 | Desai et al. |
| 7,829,598 B2 | 11/2010 | Iversen et al. |
| 7,833,444 B2 | 11/2010 | Watano |
| 8,043,631 B2 | 10/2011 | Au et al. |
| 8,138,229 B2 | 3/2012 | Desai et al. |
| 8,221,779 B2 | 7/2012 | Jonas et al. |
| 8,314,156 B2 | 11/2012 | Desai et al. |
| 8,735,394 B2 | 5/2014 | Desai et al. |
| 8,778,181 B1 | 7/2014 | Johnson et al. |
| 8,906,392 B2 | 12/2014 | Berkland et al. |
| 9,233,348 B2 | 1/2016 | Johnson et al. |
| 9,278,069 B2 | 3/2016 | Berkland et al. |
| 9,301,926 B2 | 4/2016 | Indolfi et al. |
| 9,339,554 B2 | 5/2016 | Rijcken et al. |
| 9,511,046 B2 | 12/2016 | Desai et al. |
| 9,617,338 B1 | 4/2017 | Campbell et al. |
| 9,763,946 B2 | 9/2017 | Lin |
| 9,814,685 B2 | 11/2017 | Baltezor et al. |
| 9,895,197 B2 | 2/2018 | Poquet et al. |
| 9,918,957 B2 | 3/2018 | Baltezor et al. |
| 10,391,090 B2 | 8/2019 | Baltezor et al. |
| 10,398,646 B2 | 9/2019 | Baltezor et al. |
| 10,507,181 B2 | 12/2019 | Baltezor et al. |
| 10,507,195 B2 | 12/2019 | Baltezor et al. |
| 10,729,673 B2 | 8/2020 | Baltezor et al. |
| 10,874,660 B2 | 12/2020 | Baltezor et al. |
| 10,894,045 B2 | 1/2021 | Baltezor et al. |
| RE49,493 E | 4/2023 | Lee et al. |
| 2001/0029264 A1 | 10/2001 | McChesney-Harris |
| 2002/0081339 A1 | 6/2002 | Menei et al. |
| 2002/0102294 A1 | 8/2002 | Bosch et al. |
| 2003/0166509 A1 | 9/2003 | Edwards et al. |
| 2003/0190284 A1 | 10/2003 | Annapragada et al. |
| 2004/0033267 A1 | 2/2004 | Merisko-Liversidge et al. |
| 2004/0092577 A1 | 5/2004 | Lerner et al. |
| 2004/0220081 A1 | 11/2004 | Kreitz et al. |
| 2005/0059613 A1 | 3/2005 | Memarzadeh et al. |
| 2005/0131057 A1 | 6/2005 | Uneo et al. |
| 2005/0238725 A1 | 10/2005 | Cunningham et al. |
| 2006/0034925 A1 | 2/2006 | Au et al. |
| 2006/0078619 A1 | 4/2006 | Woo et al. |
| 2006/0127420 A1 | 6/2006 | Chung et al. |
| 2006/0147535 A1 | 7/2006 | Muthukumaran et al. |
| 2006/0188566 A1 | 8/2006 | Liversidge et al. |
| 2008/0063699 A1 | 3/2008 | Teifel et al. |
| 2008/0089944 A1 | 4/2008 | Rajewski et al. |
| 2008/0160095 A1 | 7/2008 | Desai et al. |
| 2009/0215882 A1 | 8/2009 | Bouzada et al. |
| 2010/0197944 A1 | 8/2010 | Palle et al. |
| 2011/0223203 A1 | 9/2011 | Berkland et al. |
| 2011/0293672 A1 | 12/2011 | Lewis et al. |
| 2012/0087984 A1 | 4/2012 | Liversidge et al. |
| 2012/0177910 A1 | 7/2012 | Weber et al. |
| 2012/0237768 A1 | 9/2012 | Hirokawa et al. |
| 2012/0321698 A1 | 12/2012 | Narain et al. |
| 2014/0038931 A1 | 2/2014 | Hirokawa et al. |
| 2014/0079782 A1 | 3/2014 | York et al. |
| 2014/0154269 A1 | 6/2014 | Tour et al. |
| 2014/0199244 A1 | 6/2014 | Rijcken et al. |
| 2014/0243364 A1 | 8/2014 | Agisim et al. |
| 2014/0294967 A1 | 10/2014 | Borbely et al. |
| 2015/0037252 A1 | 2/2015 | Hawkett et al. |
| 2015/0118222 A1 | 4/2015 | Levy et al. |
| 2015/0118311 A1 | 4/2015 | Zhou et al. |
| 2015/0273033 A1 | 10/2015 | Bosch et al. |
| 2015/0342872 A1 | 12/2015 | Williamson et al. |
| 2015/0375153 A1 | 12/2015 | Johnson et al. |
| 2016/0257752 A1 | 9/2016 | Kim et al. |
| 2016/0263232 A1 | 9/2016 | Amighi et al. |
| 2016/0339090 A1 | 11/2016 | Hacohen et al. |
| 2016/0354336 A1 | 12/2016 | Baltezor et al. |
| 2016/0362658 A1 | 12/2016 | Leen et al. |
| 2016/0374953 A1 | 12/2016 | Baltezor et al. |
| 2017/0119881 A1 | 5/2017 | Saha et al. |
| 2017/0165369 A1 | 6/2017 | Bender |
| 2018/0169058 A1 | 6/2018 | Baltezor et al. |
| 2018/0177739 A1 | 6/2018 | Johnson et al. |
| 2018/0306748 A1 | 10/2018 | Seuthe |
| 2018/0360748 A1 | 12/2018 | Baltezor et al. |
| 2019/0127803 A1 | 5/2019 | Hacohen et al. |
| 2019/0151478 A1 | 5/2019 | Valton et al. |
| 2019/0343824 A1 | 11/2019 | Baltezor et al. |
| 2020/0246326 A1 | 8/2020 | Baltezor et al. |
| 2020/0405684 A1 | 12/2020 | Baltezor et al. |
| 2021/0000786 A1 | 1/2021 | Baltezor et al. |

FOREIGN PATENT DOCUMENTS

| | | |
|---|---|---|
| CN | 101129338 | 2/2008 |
| CN | 101336899 | 1/2009 |
| CN | 101829061 | 9/2010 |
| CN | 102488682 | 6/2012 |
| CN | 107281502 | 10/2017 |
| EP | 3181123 | 6/2017 |
| JP | H11279052 | 10/1999 |
| PT | 104693 | 1/2011 |
| TW | 201408304 | 3/2014 |
| WO | WO 2000/57852 | 10/2000 |
| WO | WO 00/72827 | 12/2000 |
| WO | WO 01/36007 | 5/2001 |
| WO | WO 02/087563 | 11/2002 |
| WO | WO 03/030941 | 4/2003 |
| WO | WO 03/032906 | 4/2003 |
| WO | 2003/090722 | 11/2003 |
| WO | WO 03/090715 | 11/2003 |
| WO | WO 2004/009076 | 1/2004 |
| WO | WO 2004/089291 | 10/2004 |
| WO | WO 2005/025542 | 3/2005 |
| WO | WO 2006/068890 | 6/2006 |
| WO | WO 2006/099385 | 9/2006 |
| WO | WO 2006/103112 | 10/2006 |
| WO | WO 2007/027941 | 3/2007 |
| WO | WO 2007/104549 | 9/2007 |
| WO | WO 2008/137148 | 11/2008 |
| WO | WO 2009/111271 | 9/2009 |
| WO | WO 2011/153009 | 12/2011 |
| WO | WO 2011/156119 | 12/2011 |
| WO | WO 2012/051426 | 4/2012 |
| WO | WO 2014/105644 | 7/2014 |
| WO | WO 2014/123612 | 8/2014 |
| WO | WO 2015/103005 | 7/2015 |
| WO | 2015/187194 | 12/2015 |
| WO | WO 2016/197091 | 12/2016 |
| WO | WO 2016/205320 | 12/2016 |
| WO | WO 2017/049083 | 3/2017 |
| WO | WO 2017/053920 | 3/2017 |
| WO | WO 2017/127729 | 7/2017 |
| WO | 2017/176628 | 10/2017 |
| WO | 2018045239 | 3/2018 |
| WO | 2018/170196 | 9/2018 |
| WO | WO 2018/170207 | 9/2018 |
| WO | WO 2018/170210 | 9/2018 |
| WO | WO 2018/227037 | 12/2018 |
| WO | WO 2018/231908 | 12/2018 |

OTHER PUBLICATIONS

Chan et. al. "The immunological effects of taxanes". Cancer Immunol. Immunother. Jul. 2000;49(4-5):181-5.

Kitano, "Clinical studies of immunocheckpoint inhibition therapy" Medical History 256(7):793-798 (2016).

Pretto et al. "Preclinical evaluation of IL2-based immunocytokines supports their use in combination with dacarbazine, paclitaxel and TNF-based immunotherapy." Cancer Immunology, Immunotherapy 63.9 (2014): 901-910.

Williamson et al., "A Phase I study of intraperitoneal nanoparticulate paclitaxel (Nanotax) in patients with peritoneal malignancies" Cancer Chemother. Pharmacol. 75:1075-87 (2015).

U.S. Appl. No. 16/669,310, filed Oct. 30, 2019, Crititech, Inc.

U.S. Appl. No. 16/776,919, filed Jan. 30, 2019, Crititech, Inc.

(56) References Cited

OTHER PUBLICATIONS

U.S. Appl. No. 16/714,099, filed Dec. 13, 2019, Crititech, Inc.
U.S. Appl. No. 16/714,151, filed Dec. 13, 2019, Crititech, Inc.
U.S. Appl. No. 16/669,692, filed Oct. 31, 2019, Crititech, Inc.
U.S. Appl. No. 16/839,737, filed Apr. 3, 2020, Crititech, Inc.
Nayyar et al. "Overcoming Resistance to Natural Keller Cell Based Immunotherapies for Solid Tumors," Frontiers in Oncology, vol. 9, Article 51, Feb. 11, 2019.
O'Shaughnessy, et al. "Systemic Antitumor Immunity by PD-1/PD-L1 Inhibition Is Potentiated by Vascular-Targeted Photodynamic Therapy of Primary Tumors," Clinical Cancer Research, 24(3): 592-599, Sep. 2017.
Oh et al. "New treatment for cystic tumors of the pancreas: EUS-guided ethanol lavage with paclitaxel injection," Gastrointest Endosc. 2008;67(4):636-642.
Oh et al. "Endoscopic Ultrasonography-Guided Ethanol Lavage with Paclitaxel Injection Treats Patients with Pancreatic Cysts," Gastroenterology 2011;140:172-179.
Pankaj, et al., Nanosized Paclitaxel Particles from Supercritical Carbon Dioxide Processing and Their Biological Evaluation, Langmuir, 23(5): 2674-2679, Feb. 2007.
Pazdur, et al., (The toxoids: paclitaxel (Taxol) and docetaxel (Taxotere, Cancer treatment reviews, 19(4): 351-386 (1993).
Pettitt et al. "CAR-T Cells: A Systematic Review and Mixed Methods Analysis of the Clinical Trial Landscape," Molecular Therapy, vol. 26, No. 2, Feb. 2018.
Pitman et al. "Pancreatic Cysts Preoperative Diagnosis and Clinical Management," Cancer Cytopathology, Feb. 25, 2010, pp. 1-13, published online Dec. 30, 2009.
Podczeck, "The Influence of Particle Size Distribution and Surface Roughness of Carrier Particles on the in vitro Properties of Dry Powder Inhalations," Aerosol Science and Technology, 31(4): 301-321, 1999.
Polo, et al, "Maintenance strategies in stage IV non-small-cell lung cancer (NSCLC): in which patients, with which drugs?" Annals of Oncology 25: 1283-1293, Dec. 2013.
Williamson, et al., "Phase I clinical trial of the intraperitoneal (IP) administration of a novel nanoparticle formulation of paclitaxel (NTX)," Poster Presentation, ACS, Sep. 2013.
Provenge® Presribing Information, Rev. Jul. 2017, 2 pages.
Raju et. al. "Review of checkpoint immunotherapy for the management of non-small cell lung cancer" Immuno Targets and Therapy, 2018;7 63-75.
Rampersaud et. al. "Commentary on Hyperthermia as a treatment for bladder cancer" Oncology 2010 24(12); 1155-1160.
Ranade et al. "Clinical and economic implications of the us of nanoparticle paclitaxel (Nanoxel) in India," Annals of Oncology 24 (Supplement 5): v6-v12, 2013.
Rasenack, et al., Micronization of Anti-Inflammatory Drugs for Pulmonary Delivery by a Controlled Crystallization Process, J Pharm Sci, 92:35-44, 2003.
Ruel-Gariepy et al. "A thermosensitive chitosan-based hydrogel for the local delivery of paclitaxel," European Journal of Pharmaceutics and Biopharmaceutics 57 (2004) 53-63.
Saltus "Enhancing Immunotherapy: The Race to Make Cold Tumors Hot" published online on Apr. 27, 2018 at https://www.dana-farber.org/newsroom/publications/paths-of-progress-2018/enhancing-immunotherapy/.
Sanfilippo et al. "Phase I/II study of biweekly paclitaxel and radiation in androgen-ablated locally advanced prostate cancer," J Clin Oncol. 2008;26(18):2973-2978.
Sarr et al. "Cystic Neoplasms of the Pancreas: Benign to Malignant Epithelial Neoplasms," Surgical Clinics of North America, vol. 81, Issue 3, Jun. 1, 2001, pp. 497-509.
Sautes-Fridman et. al. "Tertiary Lymphoid Structures in Cancers: Prognostic Value, Regulation, and Manipulation for Therapeutic Intervention" Front. Immunol. 7;407, 2016.
Schumacher et. al. "Neoantigens in cancer immunotherapy" Science vol. 348, Issue 6230, Apr. 3, 2015.

Sevko Antitumor effect of paclitaxel is mediated by inhibition of myeloid-derived suppressor cells and chronic inflammation in the spontaneous melanoma model. J. Immunol. 190,2464-2471 (2013).
Sevko et al. Application of paclitaxel in low non-cytotoxic doses supports vaccination with melanoma antigens in normal mice. J Immunotoxicol. Jul.-Sep. 2012;9(3):275-81.
Sharma, et al., "Development of Stabilized Paclitaxel nanocrystals: In vitro and in vivo efficacy studies," European Jounral of Pharmaceuticals Science, 69: 51-60, Jan. 2015.
Shepard et al. "Phase II trial of neoadjuvant nab-paclitaxel in high risk patients with prostate cancer undergoing radical prostatectomy," J Urol. 2009;181:1672-1677.
Shi et. al. "PD-1 Blockade Boosts Radiofrequency Ablation-Elicited Adaptive Immune Responses against Tumor" Clin. Cancer Res; 22(5); 1179-84, 2016.
Shikanov A et al: "Paclitaxel tumor biodistribution and efficacy after intratumoral injection of a biodegradable extended release implant", International Journal of Pharmaceutics, vol. 358, No. 1-2, Jun. 2008, pp. 114-120.
Shikanov et al. "Intratumoral Delivery of Paclitaxel for Treatment of Orthotopic Prostate Cancer," Journal of Pharmaceutical Sciences, vol. 98, No. 3, Mar. 2009.
Shurin et al. "Cancer Therapy and Dendritic Cell Immunomodulation," Chapter 14, Dendritic Cells in Cancer, Shurin et al. (eds.) Springer Science + Business Media, LLC 2009.
Slovin "Chemotherapy and immunotherapy combination in advanced prostate cancer." Clin Adv Hematol Oncol 10.2 (2012): 90-100.
Snavely, et al., "Micronization of insulin from halogenated alcohol solution using supercritical carbon dioxide as an antisolvent," J Pharm Sci, 91:2026-2039, 2002.
Stark et al. "Pancreatic Cyst Disease A Review," JAMA May 3, 2016 vol. 315, No. 17.
Surapaneni et al. "Designing Paclitaxel Drug Delivery Systems Aimed at Improved Patient Outcomes: Current Status and Challenges," ISRN Pharmacology, vol. 2012, Article ID 623139, 2012.
Swartz et al. "Lymphatic and interstitial flow in the tumor microenvironment: linking mechanobiology with immunity," Nature Reviews Cancer, vol. 12, Mar. 2012.
Tanaka et al. "Clinical aspects of intraductal papillary mucinous neoplasm of the pancreas," J Gastroenterol 2005; 40:669-675.
Tanaka et al. "International consensus guidelines 2012 for the management of IPMN and MCN of the pancreas," Pacreatology 12 (2012) 183-197.
Tanaka "Current best practice and controversies in the follow up of patients with asymptomatic branch duct IPMN of the pancreas," HPB 2016, 18, 709-711.
Van Soest et al. "Irrefutable evidence for the use of docetaxel in newly diagnosed metastatic prostate cancer: results from the STAMPEDE and CHAARTED trials," BMC Medicine (2015) 13:304.
Vanneman et. al. Combining immunotherapy and targeted therapies in cancer treatment. Nat. Rev. Cancer 12, 237-251, 2012.
Vaz-Luis et. al. "Survival Benefit Needed to Undergo Chemotherapy: Patient and Physician Preferences" Cancer Aug. 1, 2017, 2821-2828, published online Mar. 21, 2017 in Wiley Online Library (wileyonlinelibrary.com).
Vemavarapu, Particle formation by rapid expansion of supercritical solutions, Dissertation 2002.
Vukelja et al. "Phase 1 study of escalating-dose OncoGel (ReGel/paclitaxel) depot injection, a controlled-release formulation of paclitaxel, for local management of superficial solid tumor lesions. Anticancer Drugs," 2007;18(3): 283-9.
Wakabayashi, et al, "CD4+ T cells in cancer stroma, not CD8+ T cells in cancer cell nests, are associated with favorable prognosis in human non-small cell lung cancers," Cancer Sci, 94(11): 1003-1009, Nov. 2003.
Wang et al. "Intratumoral Injection of Taxol In Vivo Suppresses A549 Tumor Showing Cytoplasmic Vacuolization," Journal of Cellular Biochemistry 113:1397-1406 (2012).
Weiss et al. "A phase Ib study of pembrolizumab plus chemotherapy in patients with advanced cancer (PembroPlus)." British Journal of Cancer (2017).

(56) References Cited

OTHER PUBLICATIONS

Werth, et al., "Agglomeration of Charged Nanopowders in Suspensions," Phys Rev E Stat Nonlin Soft Matter Phys. Feb. 2006;73(2 Pt 1):021402. Epub Feb. 10, 2006.
U.S. Appl. No. 16/383,023, filed Jan. 4, 2019, Crititech, Inc.
U.S. Appl. No. 16/239,531, filed Jan. 4, 2019, Crititech, Inc.
U.S. Appl. No. 16/239,530, filed Jan. 4, 2019, Crititech, Inc.
U.S. Appl. No. 16/239,533, filed Jan. 4, 2019, Crititech, Inc.
U.S. Appl. No. 16/239,527, filed Jan. 4, 2019, Crititech, Inc.
U.S. Appl. No. 16/239,529, filed Jan. 4, 2019, Crititech, Inc.
U.S. Appl. No. 15/895,197, filed Feb. 13, 2018, Crititech, Inc.
U.S. Appl. No. 15/499,397, filed Apr. 27, 2017, Crititech, Inc.
U.S. Appl. No. 15/261,108, filed Sep. 9, 2016, Crititech, Inc.
U.S. Appl. No. 15/174,505, filed Jun. 6, 2016, Crititech, Inc.
U.S. Appl. No. 16/136,502, filed Sep. 20, 2018, Crititech, Inc.
U.S. Appl. No. 16/382,446, filed Apr. 12, 2019, Crititech, Inc.
U.S. Appl. No. 16/007,095, filed Jun. 13, 2018, Crititech, Inc.
U.S. Appl. No. 16/444,299, filed Jun. 18, 2019, Crititech, Inc.
U.S. Appl. No. 17/023,098, filed Sep. 16, 2020, Crititech, Inc.
U.S. Appl. No. 17/023,635, filed Sep. 17, 2020, Crititech, Inc.
U.S. Appl. No. 16/512,044, filed Jul. 15, 2019, Crititech, Inc.
Charoenchaitrakool, et al., "Micronization by Rapid Expansion of Supercritical Solutions to Enhance the Dissolution Rates of Poorly Water-Soluble Pharmaceuticals," Ind Eng Chem Res, 2000, 39: 4794-4802.
Chen et. al. "Chemoimmunotherapy: reengineering tumor immunity". Cancer Immunol. Immunother. 62, 203-216, 2013.
Choi et al. "Long-term outcomes after endoscopic ultrasound-guided ablation of pancreatic cysts," Endoscopy, 2017; 49: 866-873.
clintrials.gov "A study of Pembrolizumab (MK-3475) in combination with chemotherapy or immunotherapy in participants with lung cancer" Jan. 16, 2014.
Colbeck et. al. "Tertiary Lymphoid Structures in Cancer: Drivers of Antitumor Immunity, Immunosuppression, or Bystander Sentinels in Disease?" Front Immunol, 8, 1830. doi:10.3389/fimmu.2017.01830.
Crown et al., "Docetaxel and Paclitaxel in the treatment of breast cancer: A review of clinical experience," The Oncologist (2004) vol. 9(2), pp. 24-32.
Della Porta and Reverchon, "Engineering Powder Properties by supercritical fluid for optimum Drug Delivery, Part One: Supercritical Antisolvent Precipitation," BioProcess Technical, Feb. 2005, 48-52.
Della Porta and Reverchon, Engineering Powder Properties by supercritical fluid for optimum Drug Delivery, Part Two: Supercritical-Assisted Atomization, BioProcess Technical, Mar. 2005, 54-60.
Deng et al. "Understanding the Structure and Stability of Paclitaxel nanocrystals," Int J Pharm May 10, 2010, 390 (2): 242-249.
Desai et al. "Improved effectiveness of nanoparticle albumin-bound (nab) paclitaxel versus polysorbate-based docetaxel in multiple xenografts as a function of HER2 and SPARC status," Anti-Cancer Drugs 2008, 19:899-909.
Desai et al. "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel," Clin Cancer Res 2006;12(4).
Desai, et al, "Pulmonary delivery of a novel, cremophor-free, protein-based nanoparticle preparation of paclitaxel," Proceedings of the American Association for Cancer Research, 44: 731-732, Abstract 2003.
De Smet et al., "Development of a Nanocrystalline Paclitaxel Formulation for Hipec Treatment" Pharm. Research 29:2398-2406 (2012).
Dewitt et al. "Alteration in cyst fluid genetics following endoscopic ultrasound-guided pancreatic cyst ablation with ethanol and paclitaxel," Endoscopy 2014; 46(06): 457-464.
Dewitt "Pancreatic cyst ablation: why are we not doing more of these procedures?" Endoscopy, 2017; 49: 839-841.
Diaz et al. "Concomitant combination of active immunotherapy and carboplatin-or paclitaxel-based chemotherapy improves anti-tumor response." Cancer Immunology, Immunotherapy 62.3 (2013): 455-469.
Eisenhauer et. al. "New response evaluation criteria in solid tumours: Revised RECIST guideline (version 1.1)" European Jounral of Cancer 45 (2009) 228-247.
Elstad et al. "OncoGel (ReGel/paclitaxel)—Clinical applications for a novel paclitaxel delivery system," Advanced Drug Delivery Reviews 61 (2009) 785-794.
Engels et al. "Alternative drug formulations of docetaxel: a review," Anti-Cancer Drugs 2007 18:95-103.
Farrell "Prevalence, Diagnosis and Management of Pancreatic Cystic Neoplasms: Current Status and Future Direction," Gut and Liver, vol. 9, No. 5, Sep. 2015, pp. 571-589.
Farrell et al. "Pancreatic Cystic Neoplasms: Management and Unanswered Questions," Gastroenterology 2013;144:1303-1315.
FDA—"Abraxane—Prescribing Information" Oct. 1, 2012, pp. 1-19.
Feng et al. "A critical review of lipid-based nanoparticles for taxane delivery," Cancer Letters 334 (2013) 157-175.
Ferenbach et. al. "Macrophages and dendritic cells: what is the difference?" Kidney International (2008) 74.
Finkelstein et. al. "Serial assessment of lymphocytes and apoptosis in the prostate during coordinated intraprostatio dendritic cell injection and radiotherapy" Immunotherapy (2012) 4 (4), 373-382.
Forde et. al. "Neoadjuvant PD-1 Blockade in Resectable Lung Cancer" N Engl J Med 2018; 378;1976-86.
Gajewski "Fast Forward—Neoadjuvant Cancer Immunotherapy" N Engl J Med 378;21 May 24, 2018, 2034-35.
Galluzzi et. al. The secret ally: immunostimulation by anticancer drugs. Nat. Rev. Drug Discov. 11, 215-233, 2012.
Garnett et. al. "Combination of docetaxel and recombinant vaccine enhances T-cell responses and antitumor activity: effects of docetaxel on immune enhancement." Clinical Cancer Research 14.11 (2008): 3536-3544.
Ghosh et al. "Nanosuspensions for improving the bioavailability of a poorly soluble drug and screening of stabilizing agents to inhibit crystal growth," International Journal of Pharmaceutics 409 (2011) 260-268.
Goel, et al., "Exploring targeted pulmonary delivery for treatment of lung cancer," IntJ Pharm Investig (2013) 3 (1):8-14.
Goldberg et al. "Intratumoral cancer chemotherapy and immunotherapy: opportunities for nonsystemic preoperative drug delivery," JPP 2002, 54: 159-180.
Gomez et al. "EUS-guided ethanol lavage does not reliably ablate pancreatic cystic neoplasms," Gastrointestinal Endoscopy vol. 83, No. 5 : 2016.
Govindan et al. "Phase III trial of ipilimumab combined with paclitaxel and carboplatin in advanced squamous non-small-cell lung cancer." Journal of Clinical Oncology (2017): JCO-2016.
Gradishar, "Taxanes for the Treatment of Metastatic Breast Cancer" Breast Cancer: Basic and Clinical Research 6 (1):159-71 (Jan. 2012).
Gruden et al., "Antitumoral effect and reduced systemic toxicity in mice after intra-tumoral injection of an in vivo solidifying calcium sulfate formulation with docetaxel", European Journal of Pharmaceutics and Biopharmaceutics, 114 (2017); 186-193.
Grünwald et al. "The role of nephrectomy in metastatic renal cell carcinoma" Nature Reviews Nephrology 14(10):601-602 (Oct. 2018).
Gu et al. "Nanoformulation of paclitaxel to enhance cancer therapy," Journal of Biomaterials Applications 28(2) 198-307 2012.
Gulley et. al. "Phase I study of intraprostatic vaccine administration in men with locally recurrent or progressive prostate cancer". Cancer Immunol Immunother, 2013;62, 1521-1531.
Hershey, et al, "Inhalation Chemotherapy for Macroscopic Primary or Metastatic Lung Tumors: Proof of Principle Using Dogs with Spontaneously Occurring Tumors as a Model," Clinical Cancer Research, 5:2653-2659, 1999.
Hiraoka, et al, "Concurrent infiltration by CD8+T cells and CD4+T cells is a favourable prognostic factor in non-small-cell lung carcinoma," British Journal of Cancer, 94: 275-280, 2006.

(56) References Cited

OTHER PUBLICATIONS

Hohenforst-Schmidt, "Intratumoral chemotherapy for lung cancer: re-challenge current targeted therapies," Drug Design, Development and Therapy, 571-583, 2013.
Hosein et al. "A phase II trial of nab-Paclitaxel as second-line therapy in patients with advanced pancreatic cancer. Am J Clin Oncol," Apr. 1, 2013; 36(2):151-6.
Hussain et al. "Long-term follow-up of a prospective trial of trimodality therapy of weekly paclitaxel, radiation, and androgen deprivation in high-risk prostate cancer with or without prior prostatectomy," Int J Radiation Oncology Biol Phys. 2012;82(1):167-174.
Indolfi et al. "A tunable delivery platform to provide local chemotherapy for pancreatic ductal adenocarcinoma. Biomaterials," 2016;93:71-82.
Jackson et al. "The Suppression of Human Prostate Tumor Growth in Mice by the Intratumoral Injection of a Slow-Release Polymeric Paste Formulation of Paclitaxel," Cancer Research 60, 4146-4151, Aug. 1, 2000.
Janeway et al. "Using the immune response to attack tumors," Immunobiology: The Immune System in Health and Disease, 5th ed, New York: Garland Science; 2001.
Javeed et. al. Paclitaxel and immune system. Eur J Pharm Sci. Nov. 5, 2009;38(4):283-90.
Al-Ghananeem et al. "Intratumoral Delivery of Paclitaxel in Solid Tumor from BiodegradableHyaluronan Nanoparticle Formulations," AAPS PharmSciTech, vol. 10, No. 2, Jun. 2009.
Amiji et al. "Intratumoral Administration of Paclitaxel in an In Situ Gelling Poloxamer 407 Formulation," Pharmaceutical Development and Technology, 7(2), 129-202 (2002).
Anastasiadis et. al. "Best practice in the treatment of nonmuscle invasive bladder cancer" Ther Adv Urol (2012) 4 (1) 13-32.
Arnone et al. "Commentary: Current status of intratumoral therapy for glioblastoma," J Neurol Neuromed (2016) 1(6): 27-31.
Asmawi et al. "Excipient selection and aerodynamic characterization of nebulized lipid-based nanoemulsion loaded with docetaxel for lung cancer treatment", Drug Delivery and Translational Research, vol. 9, No. 2, Apr. 2018, pp. 543-554.
Atar et al. "EUS Guided Injection of Albumin Bound Paclitaxel Into Mucinous Pancreatic Cysts," Gastrointestinal Endoscopy, vol. 81, No. 5S : 2015.
Axiak-Bechtel et al. "Nanoparticulate paclitaxel demonstrates antitumor activity in PC3 and Ace-1 aggressive prostate cancer cell lines," Invest New Drugs. 2013;31:1609-1615.
Barura, et al "Challenges associated with penetration of nanoparticles across cell and tissue barriers: A review of current status and future prospects," Nano Today, 9: 223-243, 2014.
Bharadwaj et al. "Topical delivery of paclitaxel for treatment of skin cancer," Drug Development and Industrial Pharmacy, vol. 42, No. 9, Mar. 2016, pp. 1482-1494.
Bilusic et. al. "Immunotherapy of Prostate Cancer: Facts and Hopes", Clin Cancer Res; 23(22); 6764-70, 2017.
Bouquet, et al., "Drug Delivery of paclitaxel for an intraperitoneal chemotherapy," Thesis, 2009.
Bracci et al. "Immune-Based mechanisms of cytotoxic chemotherapy: implications for the design of novel and rationale-Based combined treatments against cancer." Cell Death and Differentiation, vol. 21, No. 1, 2013, pp. 15-25., doi:10.1038/cdd.2013.67.
Buda et. al. "Randomised controlled trial comparing single agent paclitaxel vs epidoxorubicin plus paclitaxel in patients with advanced ovarian cancer in early progression after platinum-based chemotherapy", British Journal of Cancer (2004) 90, 2112-2117.
Butterfield "Cancer vaccines" BMJ. 2015; 350; h988.
Cao et. al. "Tumor associated macrophages and angiogenesis dual-recognizable nanoparticles for enhanced cancer chemotherapy" Nanomedicine: Nanotechnology, Biology, and Medicine 14 (2018) 651-659.
Carbone, et al "Non-Small Cell Lung Cancer: Role of the Immune System and Potential for Immunotherapy," J Thorac Oncol, 10(7): 974-984, 2015.
Castellanos, "The relationship between attractive interparticles forces and bulk behaviors in dry and uncharged fine powders," Advances in Physics, 54(4): 263-376, 2005.
Celegene "What is the optimal chemotherapy partner for immune checkpoint inhibitor drugs?" Presentation Mar. 16, 2017 by Eric Raymond at Mediterranean Institute for Life Sciences, Republic of Croatia, 73 pages.
Johnston, et al., "Nanotax Injectable Nanocystal Paclitaxel for Ovarian and Other Intraperitoneal Cancers," Datasheet, Sep. 2013.
Kakran Mitali, et al., "Modified supercritical antisolvent method with enhanced mass transfer to fabricate drug nanoparticles," Materials Science and Engineering, 33(5): 2864-2870, Mar. 2013.
Kalos et al. "T Cells with Chimeric Antigen Receptors Have Potent Antitumor Effects and Can Establish Memory in Patients with Advanced Leukemia," Sci Transl Med. Aug. 10, 2011; 3(95) 95ra73.
Khullar et al. "Nanoparticle Migration and Delivery of Paclitaxel to Regional Lymph Nodes in a Larch Animal Model," J Am Coll Surg. Mar. 2012; 214(3): 328-337.
Kirtane, et al., "EUS for pancreatuc cycstic neoplasms: The roadmap to the future us much more than just a few shades of gray," Asian Pacific Jounral of Tropical Medicine (2016) 9(12), pp. 1218-1221.
Koay et al. "Intra-tumoral heterogeneity of gemcitabine delivery and mass transport in human pancreatic cancer," Phys Biol.; 11(6): 065002 2015.
Kodumudi et. al. A novel chemoimmunomodulating property of docetaxel: suppression of myeloid-derived suppressor cells in tumor bearers. Clin. Cancer Res. 16, 4583-4594, 2010.
Koshkina, et al "Paclitaxel Liposome Aerosol Treatment Induces Inhibition of Pulmonary Metastases in Murine Renal Carcinoma Model," Clinical Cancer Research, 7: 3258-3262, Mar. 2001.
Koshkina, et al, "Cyclosporin A Aerosol Improves the Anticancer Effect of Paclitaxel Aerosol in Mice," Journal of Aerosol Medicine, 17(1): 7-14, 2004.
Koshkina, et al, "Improved respiratory delivery of the anticancer drugs, camptothecin and paclitaxel, with 5% CO2-enriched air: pharmacokinetic studies," Cancer Chemother Pharmacol, 47: 451-456, Oct. 2001.
Kulkarni, et al, "The Use of Systemic Treatment in the Maintenance of Patients with Non-Small Cell Lung Cancer: A Systematic Review," Journal of Thoracic Oncology, 11(7): 989-1002, 2016.
Lapidus et al. "Anti-tumor effect of combination therapy with intratumoral controlled-release paclitaxel (Paclimer® Microspheres) and radiation," Prostate. 2004;58:291-298.
Le Visage, et al.,"Efficacy of PaclitaxelReleased From Bio-Adhesive Polymer Microspheres on Model Superficial Bladder Cancer," Journal of Urol, vol. 171, No. 3, Mar. 2004, pp. 1324-1329.
Lee et al. "In vivo efficacy of paclitaxel-loaded injectable in situ-forming gel against subcutaneous tumor growth," International Journal of Pharmaceutics 392 (2010) 51-56.
Lee, et al., "Supercritical antisolvent production of biodegradable micro-and nanoparticles for controlled delivery of paclitaxel," Journal of Controlled Release, 125(2): 96-106, Oct. 2007.
Lee et al, "Macrophage-Based Cell Therapies: The Long and Winding Road," J Control Release. Oct. 28, 2016; 240: 527-540.
Linghu et al. "Feasibility of Endoscopic Ultrasound-Guided OncoGel (ReGel/Paclitaxel) Injection into the Pancreas in Pigs," Endoscopy 2005; 37 (11): 1140-1142.
Liu et. al. Pre-treatment with chemotherapy can enhance the antigenicity and immunogenicity of tumours by promoting adaptive immune responses. Br. J. Cancer 102, 115-123, 2010.
Liu, et al, "Enabling Anticancer Therapeutics by Nanoparticle Carriers: The Delivery of Paclitaxel," Int J. Mol. Sci., 12:4395-4413, 2011.
Liu, et al, "Paclitaxel Nanocrystals for Overcoming Multidrug Resistance in Cancer," Mol Pharm, 7(3): 863-869, 2010.
Lu et al. "Mucoadhesive polyacrylamide nanogel as a potential hydrophobic drug carrier for intravesical bladder cancer therapy", European Journal of Pharmaceutical Sciences, vol. 72, Mar. 2015, pp. 57-68.
Lu et. al. "Paclitaxel-loaded gelatin nanoparticle for intravesical bladder cancer therapy" Clinical Cancer Research vol. 10, Issue 22, Nov. 2004.

(56) References Cited

OTHER PUBLICATIONS

Lu et. al. "Paclitaxel Gelatin nanoparticles for Intravesical Bladder Cancer Therapy" The Journal of Urology vol. 185, 1478-1483, Apr. 2011.

Lu et al. "Combined PD-1 blockade and GITR triggering induce a potent antitumor immunity in murine cancer models and synergizes with chemotherapeutic drugs." Journal of translational medicine 12.1 (2014): 36.

Ma et al. "Paclitaxel Nano-Delivery Systems: A Comprehensive Review. J Nanomed Nanotechnol," 2013;4(2):1000164.

Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice" Cancer Research 61:3689-97 (May 2001).

Mallow, et al, Broncho-Adventitial Delivery of Paclitaxel to Extend Airway Patency in Malignant airway Obstruction (broadway trial), Advances in Thoracic Oncologic Diagnostics, Abstract May 2017.

Manthey et al., "Taxol increases steady-state levels of lipopolysaccharide-inducible genes and protein-tyrosine phosphorylation in murine macrophages" The Journal of Immunology 149(7):2459-2465 (Oct. 1992).

Marabelle, et al. "Starting the Fight in the Tumor: expert Recommendation for the Development of Human Intratumoral Immunotherapy (HIT-IT)" Published by Oxford University Press on behalf of the European Society for Medical Oncology. 2018.

Matthes et al. "EUS-guided injection of paclitaxel (OncoGel) provides therapeutic drug concentrations in the porcine pancreas," Gastrointest Endosc. 2007;65(3):448-453.

Maude et al. "Chimeric Antigen Receptor T Cells for Sustained Remissions in Leukemia," N Engl J Med 371;16 Oct. 16, 2014.

Mayo Clinic—Patient care and health information regarding cycstic fibrosis, accessed online Sep. 10, 2018, pp. 1-8.

McGrath "Management of incidental pancreatic cysts: which guidelines?" Endoscopy International Open 2017; 05: E209-E211.

McKiernan et al, "Phase I trail of intravesical docetaxel in the management of superficial bladder cancer refractory to standard intravesical therapy" Journal of Clinical Oncology, vol. 24, No. 19, 2006.

McKiernan et. al. "Phase II Trial of intravesical nanoparticle albumin bound paclitaxel for the treatment of nonmuscle invasive urothelial carcinoma of the bladder after bacillus Calmette-guerin treatment failure" The Jounral of Urology, vol. 192, 1633-1638, 2014.

Merisko-Liversidge et al. "Nanosizing: a formulation approach for poorly-water-soluble compounds," European Journal of Pharmaceutical Sciences 18 (2003) 113-120.

Merisko-Liversidge, et al., "Formulation and Antitumor Activity Evaluation of Nanocrystalline Suspensions of Poorly Soluble Anticancer Drugs," Pharmaceutical Research, 13(2): 272-278, 1996.

Michels et. al. "Paclitaxel promotes differentiation of myeloid-derived suppressor cells into dendritic cells in vitro in a TLR4-independent manner". J Immunotoxicol. 2012; 9:292-300.

Miele et al. "Albumin-bound formulation of paclitaxel (Abraxane® ABI-007) in the treatment of breast cancer," International Journal of Nanomedicine 2009:4 99-105.

Mills et al. "Possible Drug-Associated Pancreatitis after Paclitaxel-Cremophor Administration," Pharmacotherapy: The Journal of Human Pharmacology and Drug Therapy, vol. 20, Issue 1, Jan. 2000, pp. 95-97.

Mirvish et al. "Dendritic Cell Vaccines in Cancer: Obstacles to Overcome," Chapter 21, Dendritic Cells in Cancer, Shurin et al. (eds.) Springer Science + Business Media, LLC 2009.

Monette et al., "Chitosan thermogels for local expansion and delivery of tumor-specific T lymphocytes towards enhanced cancer immunotherapies" Biomaterials 75:237-49 (Jan. 2016).

Morales et al. "Growth-inhibiting effects on intralesional docetaxel and paclitaxel on an experimental model of malignant neuroectodermal tumor," Journal of Neuro-Oncology 59: 207-212, 2002.

Moyer et al. "Is alcohol required for the effective pancreatic cyst ablation? The prospective randomized CHARM trial pilot study," Endoscopy International Open, 2016; 04: E603-E607.

Muller et al. "Challenges and solutions for the delivery of biotech drugs—a review of drug nanocrystal technology and lipid nanoparticles," Journal of Biotechnology 113 (2004) 151-170.

Narang et al. "Pharmaceutical Development and Regulatory Considerations for Nanoparticles and Nanoparticulate Drug Delivery Systems," Journal of Pharmaceutical Sciences 2013.

Nars et. al. "Immunomodulatory effects of low dose chemotherapy and perspectives of its combination with immunotherapy." International journal of cancer 132.11 (2013): 2471-2478.

NCT00471432—clinicaltrials.gov "OGX-011 and Docetaxel in Treating Patients with Metastatic or Locally Recurrent Solid Tumors" May 10, 2007.

Nsereko et al. "Localized delivery of paclitaxel in solid tumors from biodegradable chitin microparticle formulations," Biomaterials 23 (2002) 2723-2731.

The International Search Report (ISR) with Written Opinion for PCT/US2018/054158 dated Feb. 13, 2019, pp. 1-18.

Necchi A et al. "918TIP: Pembrolizumab and nanoparticle albumin bound paclitaxel (nabpaclitaxel) for metastatic urothelial carcinoma (UC) after chemotherapy failure: the open-label, single-arm, phase 2 PEANUT study" Annals of Oncology (2017) vol. 28, No. Supplement 5, pp. v325-v326.

Inman, Silas "Atezolizumab/Nab-Paclitaxel Combo Shows High Response Rates in TNBC" Internet Citation, Dec. 10, 2015 (Dec. 10, 2015), XP002775312, Retrieved from the Internet: URL:http://www.onclive.comjconference-cove ragejsabcs-2015/atezolizumab-nab-paclitaxe 1-combo-shows-high-response-rates-in-tnbc [retrieved on Oct. 20, 2017].

Soliman, Hatem et al. "nab-Paclitaxel as a potential partner with checkpoint inhibitors in solid tumors" Oncotargets and Therapy (2016) vol. 10, pp. 101-112.

Royal et al., "Phase 2 Trial of Single Agent Ipilimumab (Anti-CTLA-4) for Locally Advanced or Metastatic Pancreatic Menocarcinoma" J Immunother_ 33(8):828-33 {Oct. 201 O).

Brigone et al. "First-line chemoimmunotherapy in metastatic breast carcinoma: combination of paclitaxel and IMP321 (LAG-3Ig) enhances immune responses and antitumor activity" Journal of Translational Medicine 2010, 8:71.

Emens et al. "Abstract OT1-01-06: A phase III randomized trial of atezolizumab in combination with nab-paclitaxel as first line therapy for patients with metastatic triple-negative breast cancer (mTNBC)" Abstracts: Thirty-Eighth Annual CTRC-AACR San Antonio Breast Cancer Symposium; Dec. 8-12, 2015; San Antonio, TX Cancer Research, vol. 76, Issue 4, Feb. 2016.

Lara et al. Abstract—398: "Combination checkpoint immunotherapy and cytotoxic chemotherapy: Pembrolizumab (Pembro) plus either docetaxel or gemcitabine in patients with advanced or metastatic urothelial cancer" 2017 Gastrointestinal Cancers Symposium—Journal of Clinical Oncology, 35, No. 6 suppl (Feb. 20, 2017) 398-398.

Sharma et al. "Immune Checkpoint Targeting in Cancer Therapy: Towards Combination Strategies with Curative Potential" Cell, Apr. 9, 2015, 161(2): 205-214.

Worley et. al. "Docetaxel accumulates in lymphatic circulation following subcutaneous delivery compared to intravenous delivery in Rats" Anticancer Research 36; 5071-5078 (2016).

Wu et al. "Physical and chemical stability of drug nanoparticles," Advanced Drug Delivery Reviews 63 (2011) 456-469.

Wysham et al. "Adding bevacizumab to single agent chemotherapy for the treatment of platinum-resistant recurrent ovarian cancer: A cost effectiveness analysis of the AURELIA trial" Gynecologic Oncology 145 (2017) 340-345.

Xing, et al, "Efficacy and safety of albumin-bound paclitaxel in treating recurrent advanced non-small-cell lung cancer," Chinese Journal of Cancer Research, 25(2):200-205, 2013.

Yoo et al. "An In Vivo Evaluation of Docetaxel Delivered Intratumorally in Head and Neck Squamous Cell Carcinoma," Arch Otolaryngol Head Neck Surg/vol. 131, May 2005.

Young, Characterisation of particle-particles interactions using the atomic force microscope, Dissertation, 2002.

(56) References Cited

OTHER PUBLICATIONS

Yu et al. "Tumor-immune profiling of murine syngeneic tumor models as a framework to guide mechanistic studies and predict therapy response in distinct tumor microenvironments," PLOS ONE https://doi.org/10.1371/journal.pone.0206223 Nov. 2, 2018.

Zarogoulidis, et al, "Inhaled chemotherapy in lung cancer: future concept of nanomedicine," International Journal of Nanomedicine, 7: 1551-1572, Mar. 2012.

Ze et al., "Paclitaxel Gelatin Nanoparticles for Intravesical Bladder Cancer Therapy," Journal of Urology, vol. 185, No. 4, Apr. 2011, pp. 1478-1483.

Zentner et al. "Biodegradable block copolymers for delivery of proteins and water-insoluble drugs," Journal of Controlled Release 91 (2001) 203-215.

Zhang et. al. MTDH/AEG-1 based DNA vaccine suppresses metastasis and enhances chemosensitivity to paclitaxel in pelvic lymph node metastasis Biomedicine & Pharmacotherapy 70 (2015) 217-226.

Zhang et al. "Endoscopic ultrasound-guided ethanol ablation therapy for tumors," World J Gastroenterol Jun. 14, 2013; 19(22): 3397-3403.

Zhao et al. "Preparation of superparamagnetic paclitaxel nanoparticles from modified chitosan and their cytotoxicity against malignant brain glioma," English Abstract, Journal of Biomedical Engineering Jun. 1, 2011, 28(3):513-516.

Zheng et. al. "Chemotherapy-induced immunomodulation in non-small-cell lung cancer: a rationale for combination chemoimmunotherapy" Immunotherapy (2017) 9(11), 913-927.

Zhong et al., "Low-dose paclitaxel prior to intrtumoral dendtritic cell vaccine modulates intratumoral cytokine network and lung cancer growth" Clinical Cancer Research 13(18):5455-62 (Sep. 2007).

Zhou et al. "Highly penetrative, drub-loaded nanocarriers improve treatment of glioblastoma," PNAS, Jul. 16, 2013, vol. 110, No. 29, 11751-11756.

Zhou, "Atomized paclitaxel liposome inhalation treatment of bleomycin-induced pulmonary fibrosis in rats," Genetics and Molecular Research, 15(2): 1-11, 2016.

Zitvogel et. al. "Mechanism of action of conventional and targeted anticancer therapies: reinstating immunosurveillance." Immunity 39.1 (2013): 74-88.

Miura et al., "Paclitaxel Enhances Antibody-dependent Cell-mediated Cytotoxicity of Trastuzumab by Rapid Recruitment of Natural Killer Cells in HER2-positive Breast Cancer," J Nippon Med Sch. 81(4):211-220 {2014).

Utreja et al., "Localized delivery of paclitaxel using elastic liposomes: Formulation development and evaluation" Drug Delivery, 18:5:367-76 (Mar. 2011).

Carson et al. "Cellular immunity in breast cancer patients completing taxane treatment" Clinical Cancer Research 10:3401-09 (May 2004).

Ma et al., "Effective antitumor activity of paclitaxel-loaded poly (epsiloncaprolactone)/pluronic F68 nanoparticles after intratumoral delivery into the murine breast cancer model," Anti-Cancer Drugs, 21(3):261-69 (2010).

Roby et al., "Syngeneic mouse model of epithelial ovarian cancer: effects of nanoparticulate paclitaxel, Nanotax®," Advances in Experimental Medicine and Biology, 622:169-81 (2008).

Saloustros et al., (Expert Opin. Pharmacother. (2008) 9(15):2603-2616) (Year: 2008).

Socinski et al. (Current Oncology, vol. 21, No. 5, Oct. 2014, pp. e691-e703 (Year: 2014).

Zheng et al., "Enhanced antitumor efficiency of docetaxel-loaded nanoparticles in a human ovarian xenograft model with lower systemic toxicities by intratumoral delivery," Oncology Reports, 23(3):717-24 (2010).

Weaver "How Taxol/paclitaxel kills cancer cells" MoL Biol_ Cell. 25(18):2677-81 (Sep. 2014).

Adams et al. "Phase Ib trial of atezolizumab in combination with nab-paclitaxel in patients with metastatic triple-negative breast cancer (mTNBC)" J. Clin Oncol. 2016, 34(15): Abstract 1009—4 pages.

NSST Technical Report, 1503-1, 1 page URL:https://www.nsst.nssmc.com/techrepo/zairyo_pdf/HRM-1503.pdf. (English summary provided).

* indicates P> 0.05 and ** indicates P> 0.01

* indicates P> 0.05 and ** indicates P> 0.01

* indicates P> 0.05 and ** indicates P> 0.01

LOCAL DELIVERY OF ANTINEOPLASTIC PARTICLES IN COMBINATION WITH SYSTEMIC DELIVERY OF IMMUNOTHERAPEUTIC AGENTS FOR THE TREATMENT OF CANCER

SUMMARY OF THE INVENTION

The present invention provides methods to treat cancer through the use of combined local and systemic therapies, i.e., local administration of antineoplastic agent particles (chemotherapeutic particles), such as taxane particles, directly to a tumor as an adjuvant to systemic administration of an immunotherapeutic agent.

In one aspect of the invention, disclosed is a method of treating cancer in a subject, the method comprising: (a) topically administering a first composition comprising antineoplastic particles to the affected area of a skin tumor of the subject and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In some embodiments, the skin tumor is a benign skin tumor, and wherein the subject has cancer in areas of the body other than in the skin. In other embodiments, the skin tumor is a skin malignancy (malignant skin tumor). In some embodiments, the subject has cancer in other areas of the body. In some embodiments, the antineoplastic particles comprise taxane particles. In some embodiments, the taxane particles comprise paclitaxel particles, docetaxel particles, cabazitaxel particles, or combinations thereof.

In another aspect of the invention, disclosed is a method of treating cancer in a subject, the method comprising: (a) administering a first composition comprising antineoplastic particles to the subject by pulmonary administration, and (b) systemically administering a second composition comprising an immunotherapeutic agent to the subject, thereby treating the cancer, wherein the antineoplastic particles have a mean particle size (number) of from 0.1 microns to 5 microns, wherein the subject has a lung disease, and wherein steps (a) and (b) can be conducted in any order or at the same time. In some embodiments, the lung disease is non-cancerous, and wherein the subject has cancer in areas of the body other than in the lung. In some embodiments, the non-cancerous lung disease is restrictive or obstructive lung disease. In other embodiments, the lung disease is cancerous. In some embodiments, the cancerous lung disease is a malignant tumor or mesothelioma. In some embodiments, the malignant tumor is a non-small cell lung cancer tumor. In some embodiments, the subject has cancer in other areas of the body. In some embodiments, the antineoplastic particles comprise taxane particles. In some embodiments, the taxane particles comprise paclitaxel particles, docetaxel particles, cabazitaxel particles, or combinations thereof. In some embodiments, the pulmonary administration comprises nebulization and wherein the nebulizing results in pulmonary delivery to the subject of aerosol droplets of the first composition. In some embodiments, the antineoplastic agent is detectable in lung tissue of the subject for at least 4 days, or at least 14 days after administration of the first composition.

In another aspect of the invention, disclosed is a method of treating cancer in a subject, the method comprising: (a) administering a first composition comprising antineoplastic particles directly into a solid tumor of the subject by intratumoral injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In some embodiments, the solid tumor is a benign tumor, and wherein the subject has cancer elsewhere in the body. In other embodiments, the solid tumor is a malignant tumor. In some embodiments, the malignant tumor comprises a sarcoma, a carcinoma, a lymphoma, a breast tumor, a prostate tumor, a head and neck tumor, a glioblastoma, a bladder tumor, a pancreatic tumor, a liver tumor, an ovarian tumor, a colorectal tumor, a skin tumor, a cutaneous metastasis, a lymphoid, and/or a gastrointestinal tumor. In some embodiments, the subject has cancer in other areas of the body. In some embodiments, the antineoplastic particles comprise taxane particles. In some embodiments, the taxane particles comprise paclitaxel particles, docetaxel particles, cabazitaxel particles, or combinations thereof.

In another aspect of the invention, disclosed is a method of treating cancer in a subject, the method comprising: (a) administering a first composition comprising antineoplastic particles to an intraperitoneal organ tumor of the subject by intraperitoneal injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In some embodiments, the tumor is benign and wherein the subject has cancer elsewhere in the body. In other embodiments, the tumor is malignant. In some embodiments, the subject has cancer in other areas of the body. In some embodiments, the tumor is an ovarian tumor. In some embodiments, the antineoplastic particles comprise taxane particles. In some embodiments, the taxane particles comprise paclitaxel particles, docetaxel particles, cabazitaxel particles, or combinations thereof.

In various embodiments of the invention, the immunotherapeutic agent of the second composition is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent. In some embodiments, the systemic administration of the second composition is intravenous (IV) injection or oral delivery. In some embodiments, the first composition is administered at least one day prior to the administration of the second composition. In other embodiments, the second composition is administered at least one day prior to the administration of the first composition. In still other embodiments, the first composition and the second composition are administered on the same day.

In various embodiments, the amount of antineoplastic particles in the first composition and the amount of immunotherapeutic agent in the second composition are at effective amounts to treat the cancer in the subject and optionally to treat the tumor of the subject. In various embodiments, the local administration of the first composition stimulates an immunological response to the immunotherapeutic agent in the subject after the systemic administration of the second composition.

In another aspect of the invention, disclosed is a kit comprising: (a) a first composition comprising taxane particles, wherein the taxane particles have a mean particle size (number) of from 0.1 microns to 5 microns, (b) a second composition comprising an immunotherapeutic agent, and (c) instructions for (i) administering the first composition locally to a subject, and (ii) administering the second composition systemically to the subject.

In another aspect of the invention, disclosed is a method of treating cancer in a subject, the method comprising: (a) administering a first composition comprising antineoplastic particles directly into a cyst of the subject by intracystic injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In various embodiments, the antineoplastic particles have a mean particle size (number) of from 0.1 microns to 1.5 microns. In some embodiments, the cyst is an epithelial cyst. In some embodiments, the cyst is a benign cyst, and the subject has cancer elsewhere in the body. In some embodiments, the cyst is a malignant cyst. In some embodiments, the malignant cyst is the only cancer in the body of the subject. In other embodiments, the subject has a malignant cyst and cancer in other areas of the body. In some embodiments, the cyst is a pancreatic cyst. In other embodiments, the antineoplastic agent is a taxane and the antineoplastic particles are taxane particles. The taxane particles can include pharmaceutically acceptable salts of the taxane particles. In some embodiments, the taxane particles are paclitaxel particles, docetaxel particles, cabazitaxel particles, or combinations thereof. In some embodiments, the local administration of the first composition stimulates an immunological response to the immunotherapeutic agent in the subject after the systemic administration of the second composition.

In another aspect of the invention, disclosed is a method of treating cancer in a subject, the method comprising: (a) administering a first composition comprising antineoplastic particles to a tumor located in a body cavity of the subject by injection into the body cavity, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In various embodiments, the antineoplastic particles have a mean particle size (number) of from 0.1 microns to 1.5 microns. In some embodiments, the tumor is a benign tumor, and the subject has cancer elsewhere in the body. In some embodiments, the tumor is a malignant tumor. In some embodiments, the malignant tumor is the only cancer in the body of the subject. In other embodiments, the subject has a malignant tumor and cancer in other areas of the body. In other embodiments, the antineoplastic agent is a taxane and the antineoplastic particles are taxane particles. The taxane particles can include pharmaceutically acceptable salts of the taxane particles. In some embodiments, the taxane particles are paclitaxel particles, docetaxel particles, cabazitaxel particles, or combinations thereof. In some embodiments, the local administration of the first composition stimulates an immunological response to the immunotherapeutic agent in the subject after the systemic administration of the second composition.

Disclosed in the context of the present invention are the following embodiments 1 to 133:

Embodiment 1 is a method of treating cancer in a subject, the method comprising: (a) topically administering a first composition comprising antineoplastic particles to the affected area of a skin tumor of the subject and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time.

Embodiment 2 is the method of embodiment 1, wherein the skin tumor is a benign skin tumor, and wherein the subject has cancer in areas of the body other than in the skin.

Embodiment 3 is the method of embodiment 2, wherein the benign skin tumor is actinic keratosis.

Embodiment 4 is the method of embodiment 1, wherein the skin tumor is a skin malignancy (malignant skin tumor).

Embodiment 5 is the method of embodiment 4, wherein the skin malignancy comprises a skin cancer.

Embodiment 6 is the method of embodiment 5, wherein the skin cancer comprises a melanoma, a basal cell carcinoma, or a squamous cell carcinoma.

Embodiment 7 is the method of embodiment 6, wherein the skin malignancy comprises a cutaneous metastasis.

Embodiment 8 is the method of embodiment 7, wherein the cutaneous metastasis is from lung cancer, breast cancer, colon cancer, oral cancer, ovarian cancer, kidney cancer, esophageal cancer, stomach cancer, liver cancer, and/or Kaposi's sarcoma.

Embodiment 9 is the method of any one of embodiments 4 to 8, wherein the subject has cancer in other areas of the body.

Embodiment 10 is the method of any one of embodiments 1 to 9, wherein the antineoplastic particles comprise taxane particles.

Embodiment 11 is the method of embodiment 10, wherein the taxane particles comprise at least 95% of the taxane, and wherein the taxane particles have a mean particle size (number) of from 0.1 microns to 1.5 microns.

Embodiment 12 is the method of any one of embodiments 10 or 11 wherein the taxane particles comprise paclitaxel particles, docetaxel particles, cabazitaxel particles, or combinations thereof.

Embodiment 13 is the method of embodiment 12, wherein the taxane particles are paclitaxel particles.

Embodiment 14 is the method of embodiment 13, wherein the paclitaxel particles have a specific surface area (SSA) of at least 18 $m^2/g$.

Embodiment 15 is the method of any one of embodiments 13 or 14, wherein the paclitaxel particles have a bulk density (not-tapped) of 0.05 $g/cm^3$ to 0.15 $g/cm^3$.

Embodiment 16 is the method of embodiment 12, wherein the taxane particles are docetaxel particles.

Embodiment 17 is the method of embodiment 16, wherein the docetaxel particles have a specific surface area (SSA) of at least 18 $m^2/g$.

Embodiment 18 is the method of any one of embodiments 16 or 17, wherein the docetaxel particles have a bulk density (not-tapped) of 0.05 $g/cm^3$ to 0.15 $g/cm^3$.

Embodiment 19 is the method of any one of embodiments 1 to 18, wherein the first composition is anhydrous.

Embodiment 20 is the method of any one of embodiments 1 to 19, wherein the first composition is hydrophobic.

Embodiment 21. is the method of embodiment 20, wherein the first composition comprises a hydrophobic carrier.

Embodiment 22 is the method of embodiment 21, wherein the hydrophobic carrier is non-volatile.

Embodiment 23 is the method of any one of embodiments 21 or 22, wherein the hydrophobic carrier is non-polar.

Embodiment 24 is the method of any one of embodiments 21 to 23, wherein the hydrophobic carrier comprises a hydrocarbon.

Embodiment 25 is the method of embodiment 24 wherein the hydrocarbon is petrolatum, mineral oil, or paraffin wax, or mixtures thereof.

Embodiment 26 is the method of embodiment 25, wherein the mineral oil is heavy mineral oil.

Embodiment 27 is the method of any one of embodiments 21 to 26, wherein the hydrophobic carrier is greater than 50% w/w of the hydrophobic composition.

Embodiment 28 is the method of any one of embodiments 1 to 27, wherein the first composition further comprises one or more volatile silicone fluids.

Embodiment 29 is the method of embodiment 28, wherein the concentration of the one or more volatile silicone fluids is from 5 to 24% w/w of the first composition.

Embodiment 30 is the method of any one of embodiments 28 or 29, wherein the volatile silicone fluid is cyclomethicone.

Embodiment 31 is the method of embodiment 30, wherein the cyclomethicone is cyclopentasiloxane.

Embodiment 32 is the method of any one of embodiments 1 to 31, wherein the first composition is a semi-solid.

Embodiment 33 is the method of embodiment 32, wherein the viscosity of the first composition is 25,000 cps to 500,000 cps as measured with a Brookfield RV viscometer on a helipath stand with the helipath on, with a T-E spindle at 10 RPM at room temperature for 45 seconds Embodiment 34 is the method of any one of embodiments 32 or 33, wherein the first composition is an ointment.

Embodiment 35 is the method of any one of embodiments 1 to 35, wherein the first composition does not contain volatile $C_1$-$C_4$ aliphatic alcohols, does not contain additional penetration enhancers, does not contain additional volatile solvents, does not contain surfactants, does not contain a protein, and/or does not contain albumin.

Embodiment 36 is the method of any one of embodiments 1 to 35, wherein the antineoplastic particles are dispersed in the first composition.

Embodiment 37 is the method of any one of embodiments 1 to 36, wherein the concertation of the antineoplastic particles in the composition is from about 0.1 to about 2% w/w.

Embodiment 38 is a method of treating cancer in a subject, the method comprising: (a) administering a first composition comprising antineoplastic particles to the subject by pulmonary administration, and (b) systemically administering a second composition comprising an immunotherapeutic agent to the subject, thereby treating the cancer, wherein the antineoplastic particles have a mean particle size (number) of from 0.1 microns to 5 microns, wherein the subject has a lung disease, and wherein steps (a) and (b) can be conducted in any order or at the same time.

Embodiment 39 is the method of embodiment 38, wherein the lung disease is non-cancerous, and wherein the subject has cancer in areas of the body other than in the lung.

Embodiment 40 is the method of embodiment 39, wherein the non-cancerous lung disease is restrictive or obstructive lung disease.

Embodiment 41 is the method of embodiment 40, wherein the restrictive lung disease is pulmonary fibrosis.

Embodiment 42 is the method of embodiment 40, wherein the obstructive lung disease is chronic obstructive lung disease (COPD).

Embodiment 43 is the method of embodiment 38, wherein the lung disease is cancerous.

Embodiment 44 is the method of embodiment 43, wherein the cancerous lung disease is a malignant tumor or mesothelioma.

Embodiment 45 is the method of embodiment 44, wherein the malignant tumor is a non-small cell lung cancer tumor.

Embodiment 46 is the method of any one of embodiments 43 to 45, wherein the subject has cancer in other areas of the body.

Embodiment 47 is the method of any one of embodiments 38 to 46, wherein the antineoplastic particles comprise taxane particles.

Embodiment 48 is the method of embodiment 47, wherein the taxane particles comprise at least 95% of the taxane, and wherein the taxane particles have a mean particle size (number) of from 0.1 microns to 1.5 microns.

Embodiment 49 is the method of any one of embodiments 48 or 49, wherein the taxane particles comprise paclitaxel particles, docetaxel particles, cabazitaxel particles, or combinations thereof.

Embodiment 50 is the method of embodiment 49, wherein the taxane particles are paclitaxel particles.

Embodiment 51 is the method of embodiment 50, wherein the paclitaxel particles have a specific surface area (SSA) of at least 18 $m^2/g$.

Embodiment 52 is the method of any one of embodiments 50 or 51, wherein the paclitaxel particles have a bulk density (not-tapped) of 0.05 $g/cm^3$ to 0.15 $g/cm^3$.

Embodiment 53 is the method of embodiment 49, wherein the taxane particles are docetaxel particles.

Embodiment 54 is the method of embodiment 53, wherein the docetaxel particles have a specific surface area (SSA) of at least 18 $m^2/g$.

Embodiment 55 is the method of any one of embodiments 53 or 54, wherein the docetaxel particles have a bulk density (not-tapped) of 0.05 $g/cm^3$ to 0.15 $g/cm^3$.

Embodiment 56 is the method of any one of embodiments 38 to 55, wherein the first composition further comprises a liquid carrier, and wherein the antineoplastic particles are dispersed in the carrier.

Embodiment 57 is the method of any one of embodiments 38 to 56, wherein the first composition is anhydrous.

Embodiment 58 is the method of embodiment 56, wherein the liquid carrier is an aqueous carrier.

Embodiment 59 is the method of embodiment 58, wherein the aqueous carrier comprises 0.9% saline solution.

Embodiment 60 is the method of any one of embodiments 58 or 59, wherein the aqueous carrier comprises a surfactant.

Embodiment 61 is the method of embodiment 60, wherein the surfactant is a polysorbate.

Embodiment 62 is the method of embodiment 61, wherein the polysorbate is polysorbate 80, and wherein the polysorbate 80 is present in the aqueous carrier at a concentration of between about 0.01% v/v and about 1% v/v.

Embodiment 63 is the method of any one of embodiments 47 to 62, wherein the concentration of the taxane particles in the first composition is between about 1 mg/ml and about 40 mg/ml, or between about 6 mg/mL and about 20 mg/mL.

Embodiment 64 is the method of any one of embodiments 38 to 63, wherein the composition does not contain a protein such as albumin.

Embodiment 65 is the method of any one of embodiments 38 to 64, wherein the pulmonary administration comprises nebulization and wherein the nebulizing results in pulmonary delivery to the subject of aerosol droplets of the first composition.

Embodiment 66 is the method of embodiment 65, wherein the aerosol droplets have a mass median aerodynamic diameter (MMAD) of between about 0.5 µm to about 6 µm diameter, or between about 1 µm to about 3 µm diameter, or about 2 µm to about 3 µm diameter.

Embodiment 67 is the method of any one of embodiments 38 to 66, wherein the antineoplastic agent is detectable in lung tissue of the subject for at least 4 days, or at least 14 days after administration of the first composition.

Embodiment 68 is a method of treating cancer in a subject, the method comprising: (a) administering a first composition comprising antineoplastic particles directly into a solid tumor of the subject by intratumoral injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time.

Embodiment 69 is the method of embodiment 68, wherein the solid tumor is a benign tumor, and wherein the subject has cancer elsewhere in the body.

Embodiment 70 is the method of embodiment 68, wherein the solid tumor is a malignant tumor.

Embodiment 71 is the method of embodiment 70, wherein the malignant tumor comprises a sarcoma, a carcinoma, a lymphoma, a breast tumor, a prostate tumor, a head and neck tumor, a glioblastoma, a bladder tumor, a pancreatic tumor, a liver tumor, an ovarian tumor, a colorectal tumor, a skin tumor, a cutaneous metastasis, a lymphoid, and/or a gastrointestinal tumor.

Embodiment 72 is the method of any one of embodiments 70 or 71, wherein the subject has cancer in other areas of the body.

Embodiment 73 is the method of any one of embodiments 68 to 72, wherein the antineoplastic particles comprise taxane particles.

Embodiment 74 is the method of embodiment 73, wherein the taxane particles comprise at least 95% of the taxane, and wherein the taxane particles have a mean particle size (number) of from 0.1 microns to 1.5 microns.

Embodiment 75 is the method of any one of embodiments 73 or 74, wherein the taxane particles comprise paclitaxel particles, docetaxel particles, cabazitaxel particles, or combinations thereof.

Embodiment 76 is the method of embodiment 75, wherein the taxane particles are paclitaxel particles.

Embodiment 77 is the method of embodiment 76, wherein the paclitaxel particles have a specific surface area (SSA) of at least 18 $m^2/g$.

Embodiment 78 is the method of any one of embodiments 76 or 77, wherein the paclitaxel particles have a bulk density (not-tapped) of 0.05 $g/cm^3$ to 0.15 $g/cm^3$.

Embodiment 79 is the method of embodiment 75, wherein the taxane particles are docetaxel particles.

Embodiment 80 is the method of embodiment 79, wherein the docetaxel particles have a specific surface area (SSA) of at least 18 $m^2/g$.

Embodiment 81 is the method of any one of embodiments 79 or 80, wherein the docetaxel particles have a bulk density (not-tapped) of 0.05 $g/cm^3$ to 0.15 $g/cm^3$.

Embodiment 82 is the method of any one of embodiments 68 to 81, wherein the first composition further comprises a liquid carrier, and wherein the antineoplastic particles are dispersed in the carrier.

Embodiment 83 is the method of embodiment 82, wherein the liquid carrier is an aqueous carrier.

Embodiment 84 is the method of embodiment 83, wherein the aqueous carrier comprises 0.9% saline solution.

Embodiment 85 is the method of any one of embodiments 83 or 84, wherein the aqueous carrier comprises a surfactant.

Embodiment 86 is the method of embodiment 85, wherein the surfactant is a polysorbate.

Embodiment 87 is the method of embodiment 86, wherein the polysorbate is polysorbate 80, and wherein the polysorbate 80 is present in the aqueous carrier at a concentration of between about 0.01% v/v and about 1% v/v.

Embodiment 88 is the method of any one of embodiments 73 to 88, wherein the concentration of the taxane particles in the first composition is between about 1 mg/ml and about 40 mg/ml, or between about 6 mg/mL and about 20 mg/mL.

Embodiment 89 is the method of any one of embodiments 68 to 88, wherein the composition does not contain a protein such as albumin.

Embodiment 90 is a method of treating cancer in a subject, the method comprising: (a) administering a first composition comprising antineoplastic particles to an intraperitoneal organ tumor of the subject by intraperitoneal injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time.

Embodiment 91 is the method of embodiment 90, wherein the tumor is benign and wherein the subject has cancer elsewhere in the body.

Embodiment 92 is the method of embodiment 90, wherein the tumor is malignant.

Embodiment 93 is the method of embodiment 92, wherein the subject has cancer in other areas of the body.

Embodiment 94 is the method of any one of embodiments 90 to 93, wherein the tumor is an ovarian tumor.

Embodiment 95 is the method of any one of embodiments 90 to 94, wherein the antineoplastic particles comprise taxane particles.

Embodiment 96 is the method of embodiment 95, wherein the taxane particles comprise at least 95% of the taxane, and wherein the taxane particles have a mean particle size (number) of from 0.1 microns to 1.5 microns.

Embodiment 97 is the method of any one of embodiments 95 or 96, wherein the taxane particles comprise paclitaxel particles, docetaxel particles, cabazitaxel particles, or combinations thereof.

Embodiment 98 is the method of embodiment 97, wherein the taxane particles are paclitaxel particles.

Embodiment 99 is the method of embodiment 98, wherein the paclitaxel particles have a specific surface area (SSA) of at least 18 $m^2/g$.

Embodiment 100 is the method of any one of embodiments 98 or 99, wherein the paclitaxel particles have a bulk density (not-tapped) of 0.05 $g/cm^3$ to 0.15 $g/cm^3$.

Embodiment 101 is the method of embodiment 97, wherein the taxane particles are docetaxel particles.

Embodiment 102 is the method of embodiment 101, wherein the docetaxel particles have a specific surface area (SSA) of at least 18 $m^2/g$.

Embodiment 103 is the method of any one of embodiments 101 or 102, wherein the docetaxel particles have a bulk density (not-tapped) of 0.05 $g/cm^3$ to 0.15 $g/cm^3$.

Embodiment 104 is the method of any one of embodiments 90 to 103, wherein the first composition further comprises a liquid carrier, and wherein the antineoplastic particles are dispersed in the carrier.

Embodiment 105 is the method of embodiment 104, wherein the liquid carrier is an aqueous carrier.

Embodiment 106 is the method of embodiment 105, wherein the aqueous carrier comprises 0.9% saline solution.

Embodiment 107 is the method of any one of embodiments 105 or 106, wherein the aqueous carrier comprises a surfactant.

Embodiment 108 is the method of embodiment 107, wherein the surfactant is a polysorbate.

Embodiment 109 is the method of embodiment 108, wherein the polysorbate is polysorbate 80, and wherein the polysorbate 80 is present in the aqueous carrier at a concentration of between about 0.01% v/v and about 1% v/v.

Embodiment 110 is the method of any one of embodiments 95 to 109, wherein the concentration of the taxane particles in the first composition is between about 1 mg/ml and about 40 mg/ml, or between about 6 mg/mL and about 20 mg/mL.

Embodiment 111 is the method of any one of embodiments 90 to 110, wherein the composition does not contain a protein such as albumin.

Embodiment 112 is the method of any one of embodiments 1 to 111, wherein the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent.

Embodiment 113 is the method of embodiment 112, wherein the immunotherapeutic agent is a monoclonal antibody.

Embodiment 114 is the method of embodiment 113, wherein the monoclonal antibody is pembrolizumab.

Embodiment 115 is the method of any one of embodiments 1 to 114, wherein the second composition comprises a pharmaceutically acceptable carrier.

Embodiment 116 is the method of any one of embodiments 1 to 115, wherein the systemic administration is intravenous (IV) injection or oral delivery.

Embodiment 117 is the method of any one of embodiment 1 to 116, wherein the first composition is administered at least one day prior to the administration of the second composition.

Embodiment 118 is the method of any one of embodiments 1 to 116, wherein the second composition is administered at least one day prior to the administration of the first composition.

Embodiment 119 is the method of any one of embodiments 1 to 116, wherein the first composition and the second composition are administered on the same day.

Embodiment 120 is the method of any one of embodiment 1 to 119, wherein the amount of antineoplastic particles in the first composition and the amount of immunotherapeutic agent in the second composition are at effective amounts to treat the cancer in the subject and optionally to treat the tumor of the subject.

Embodiment 121 is the method of any one of embodiments 1 to 120, wherein the local administration of the first composition stimulates an immunological response to the immunotherapeutic agent in the subject after the systemic administration of the second composition.

Embodiment 122 is a kit comprising: (a) a first composition comprising taxane particles, wherein the taxane particles have a mean particle size (number) of from 0.1 microns to 5 microns, (b) a second composition comprising an immunotherapeutic agent, and (c) instructions for (i) administering the first composition locally to a subject, and (ii) administering the second composition systemically to the subject.

Embodiment 123. The kit of embodiment 112, wherein the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent.

Embodiment 124 is the kit of any one of embodiments 122 or 123, wherein the taxane particles comprise at least 95% of the taxane, and wherein the taxane particles have a mean particle size (number) of from 0.1 microns to 1.5 microns.

Embodiment 125 is the kit of any one of embodiments 122 to 124 wherein the taxane particles are paclitaxel particles, docetaxel particles, cabazitaxel particles, or combination thereof.

Embodiment 126 is the kit of embodiment 125, wherein the taxane particles are paclitaxel particles.

Embodiment 127 is the kit of embodiment 126, wherein the paclitaxel particles have a specific surface area (SSA) of at least 18 $m^2/g$.

Embodiment 128 is the kit of any one of embodiments 126 or 127, wherein the paclitaxel particles have a bulk density (not-tapped) of 0.05 $g/cm^3$ to 0.15 $g/cm^3$.

Embodiment 129 is the kit of embodiment 125, wherein the taxane particles are docetaxel particles.

Embodiment 130 is the kit of embodiment 129, wherein the docetaxel particles have a specific surface area (SSA) of at least 18 $m^2/g$.

Embodiment 131 is the kit of any one of embodiments 129 or 130, wherein the docetaxel particles have a bulk density (not-tapped) of 0.05 $g/cm^3$ to 0.15 $g/cm^3$.

Embodiment 132 is the kit of embodiment 125, wherein the first composition is a hydrophobic ointment.

Embodiment 133 is the kit of embodiment 125, wherein the first composition is an aqueous suspension.

The term "antineoplastic agents" as used herein are drugs used to treat neoplasms including cancer, and include "chemotherapeutic agents", which are drugs used to treat cancer. In a preferred embodiment, the antineoplastic agent is a taxane.

The terms "antineoplastic agent particles", "antineoplastic particles" or "particles of an antineoplastic agent(s)", as used herein are particles of an antineoplastic agent and have a mean particle size (number) of from about 0.1 microns to about 5 microns (about 100 nm to about 5000 nm) in diameter. In a preferred embodiment, the antineoplastic particles are taxane particles.

The term "tumor" as used herein means one or more abnormal masses of tissue that results when cells divide more than they should or do not die when they should. Tumors may be benign (not cancer), or malignant (cancer).

The term "hydrophobic," as used herein, describes compounds, compositions, or carriers that have a solubility in water of less than or equal to 10 mg/mL at room temperature.

The term "volatile," as used herein, describes compounds, compositions, or carriers that have a vapor pressure greater than or equal to 10 Pa at room temperature.

The term "non-volatile," as used herein, describes compounds, compositions, or carriers that have a vapor pressure less than 10 Pa at room temperature.

The term "anhydrous," as used herein with regard to the compositions or carriers of the invention, means that less than 3% w/w, preferably less than 2% w/w, more preferably less than 1% w/w, or most preferably 0% w/w of water is present in the compositions or carriers. This can account for small amounts of water being present (e.g., water inherently contained in any of the ingredients of the compositions or carriers, water contracted from the atmosphere, etc.).

The terms "skin" or "cutaneous" as used herein mean the epidermis and/or the dermis.

The term "skin tumor" as used herein includes benign skin tumors and malignant skin tumors.

The terms "skin malignancy" or "malignant skin tumor" as used herein includes cancerous skin tumors which includes skin cancers and cutaneous metastases.

The "affected area" of a skin tumor or skin malignancy can include at least a portion of the skin where the skin tumor or skin malignancy is visibly present on the outermost surface of the skin or directly underneath the surface of the skin (epithelial/dermal covering), and can include areas of the skin in the proximity of the skin tumor or skin malignancy likely to contain visibly undetectable preclinical lesions.

The terms "cutaneous (skin) metastasis" or "cutaneous (skin) metastases" (plural) as used herein means the manifestation of a malignancy in the skin as a secondary growth (malignant tumor) arising from the primary growth of a cancer tumor at another location of the body. Spread from the primary tumor can be through the lymphatic or blood circulation systems, or by other means.

The terms "treat", "treating", or "treatment" as used herein with respect to treatment of cancer and/or treatment of a tumor means accomplishing one or more of the following: (a) reducing tumor size; (b) reducing tumor growth; (c) eliminating a tumor; (d) reducing or limiting development and/or spreading of metastases; (e) obtaining partial or complete remission of cancer.

The terms "subject" or "patient" as used herein mean a vertebrate animal. In some embodiments, the vertebrate animal can be a mammal. In some embodiments, the mammal can be a primate, including a human.

The term "room temperature" (RT) as used herein, means 15-30° C. or 20-25° C.

The term "penetration enhancer" or "skin penetration enhancer" as used herein, means a compound or a material or a substance that facilitates drug absorption into the skin (epidermis and dermis).

The term "surfactant" or "surface active agent" as used herein, means a compound or a material or a substance that exhibits the ability to lower the surface tension of water or to reduce the interfacial tension between two immiscible substances.

As used herein, the singular forms "a", "an" and "the" include plural referents unless the context clearly dictates otherwise. "And" as used herein is interchangeably used with "or" unless expressly stated otherwise.

The terms "about" or "approximately" as used herein mean +/−five percent (5%) of the recited unit of measure.

For this application, a number value with one or more decimal places can be rounded to the nearest whole number using standard rounding guidelines, i.e. round up if the number being rounded is 5, 6, 7, 8, or 9; and round down if the number being rounded is 0, 1, 2, 3, or 4. For example, 3.7 can be rounded to 4.

Unless the context clearly requires otherwise, throughout the description and the claims, the words "comprise", "comprising", and the like are to be construed in an inclusive or open-ended sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification. With respect to the phrase "consisting essentially of," a basic and novel property of the methods of the present invention are their ability to treat cancer by local delivery of compositions of antineoplastic particles combined with systemic delivery of compositions of immunotherapeutic agents.

It is contemplated that any embodiment discussed in this specification can be implemented with respect to any method or composition of the invention, and vice versa. Furthermore, compositions of the invention can be used to achieve methods of the invention.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

DETAILED DESCRIPTION

Figure 1:
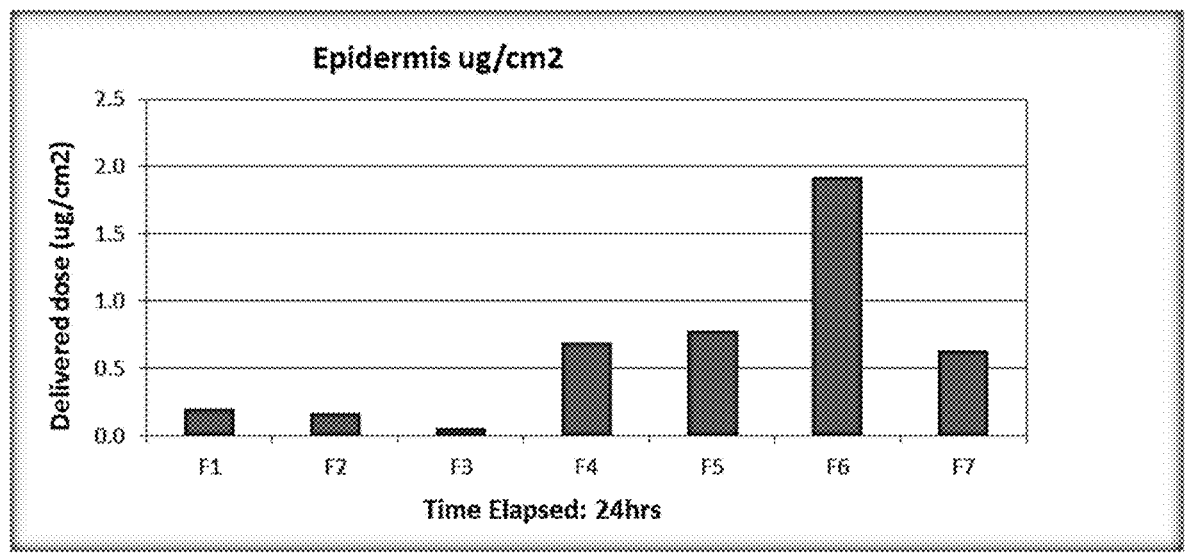
FIG. 1 graphically shows the concentration of paclitaxel (μg/cm2) delivered in vitro into the epidermis for formulas F1 through F7.

The present invention provides methods to treat cancer through the use of combined local and systemic therapies, i.e., local administration of antineoplastic agent particles (chemotherapeutic particles), such as taxane particles, directly to a tumor as an adjuvant to systemic administration of an immunotherapeutic agent.

When antineoplastic particles such as taxane particles (for example paclitaxel particles or docetaxel particles) are administered locally to either benign or malignant tumors, (i.e., injected intratumorally, injected intraperitoneally, deposited in the lung by inhalation, or administered topically onto skin tumors or skin malignancies such as cutaneous metastases), the molecules of the anti-neoplastic agent (for example paclitaxel or docetaxel) persist at the tumor site for a longer time than when antineoplastic agents are administered as solutions by IV at high concentrations. Locally administered antineoplastic particles such as taxane particles can therefore function as local adjuvants to systemic immunotherapy. Without being limited to any specific mechanism, such adjuvant effect may comprise, for example, providing sufficient time for lymphocytes to activate both their innate as well as adaptive immunological response to the tumor, all without the added associated toxicities of IV chemotherapy.

Immune system stimulation that occurs in response to the local administration of taxane particles, including activation of the local dendritic cell's response to tumor antigens, can be enhanced for example by the topical administration of taxane particles to the skin or by pulmonary inhalation of taxane particles. Without being limited to any specific mechanism, local tumor cell killing by the administration of taxane particles releases tumor cell antigens which are attached to dendritic cells. The activated dendritic cells may then present tumor-specific antigen to T-cells and other tumoricidal cells that circulate throughout the patient's vascular system as well as enter tissues that contain tumor allowing for destruction of cancer throughout the patient. Thus, the use of local particle administration allows for direct local therapy, as well as indirect immune system-mediated systemic cancer cell killing.

By local administration of taxane particles either by topical therapy of skin tumors, intratumoral injection of solid tumors, intraperitoneal injection, or inhalation therapy of lung diseases, the local taxane molecules act as an adjuvant to stimulate the immune response. Local concentration of taxane remains elevated for greater than 4 days which provides sufficient time for killing of local tumor cells as well as stimulation of the immune response appropriate for killing of cancer that may be widely disseminated through the body. This stimulation of the immune system by local administration of taxane particles occurs without producing concomitant high levels of taxane in the patient's circulating blood. Thus, local administration of particle taxane does not reduce hematopoiesis in the bone marrow involving reduction in white blood cell numbers such as lymphocytes. Bone marrow suppression is a common side effect of taxanes when given IV due to the high concentrations of circulating taxane.

Without being limited to any specific mechanism, local administration of taxane particles may produce sufficient concentrations of taxanes for a prolonged period to stimulate local immunological response to immunotherapy through activation in dendritic cells. Activation of dendritic cells can occur most notably in the skin or lung where they are found in abundance. Topical administration of taxane particles to skin tumors causes entry of paclitaxel into tumor cells which kills them during their division cycle rendering them more accessible to immune recognition by immunotherapy. The lymphocytes would then circulate throughout the patient's body producing humoral mediators that are specific to the cell surface antigens of the tumor cells. The lymphocytes destroy tumor located in the skin as well as distant metastasis. Lymphocyte tumor killing could also occur via the cellular route of immune surveillance. For example, topical administration of taxane particles to a cutaneous metastasis would result in eradication of the patient's cancer throughout their body, not just the cutaneous metastasis. The same elimination of cancer in the body would happen to metastatic lung cancer in response to inhaled taxane particles.

Thus, the cancer treatment methods of the invention include the use of combined local and systemic therapies. i.e., local administration of compositions comprising antineoplastic agent particles, such as taxane particles, directly to a tumor; combined with systemic administration of compositions comprising immunotherapeutic agents. The local administration of the antineoplastic agent particles, e.g. taxane particles, functions as local adjuvants to systemic immunotherapy providing sufficient time for lymphocytes to activate both their innate as well as adaptive immunological response to the tumor.

Treatment with the combination of the local administration of a composition comprising antineoplastic particles and the systemic administration of an immunotherapeutic agent demonstrates greater efficacy than the treatment with an immunotherapeutic agent alone and/or the treatment with a composition comprising antineoplastic particles alone (monotherapy) as evidenced by at least one of the following:

(a) greater reduction of tumor size with the animals treated with the combination of a composition comprising antineoplastic particles and an immunotherapeutic agent than with the animals treated with an immunotherapeutic agent alone, or (b) greater reduction in tumor growth with the animals treated with the combination of a composition comprising antineoplastic particles and an immunotherapeutic agent than with the animals treated with an immunotherapeutic agent alone, or (c) one or more incidences of tumor elimination with the animals treated with the combination of a composition comprising antineoplastic particles and an immunotherapeutic agent versus no incidences of tumor elimination with the animals treated with an immunotherapeutic agent alone, or (d) greater reduction of tumor size with the animals treated with the combination of a composition comprising antineoplastic particles and an immunotherapeutic agent than with the animals treated with a composition comprising antineoplastic particles alone, or (e) greater reduction in tumor growth with the animals treated with the combination of a composition comprising antineoplastic particles and an immunotherapeutic agent than with the animals treated with a composition comprising antineoplastic particles alone, or (f) one or more incidences of tumor elimination with the animals treated with the combination of a composition comprising antineoplastic particles and an immunotherapeutic agent versus no incidences of tumor elimination with the animals treated with a composition comprising antineoplastic particles alone.

Also, a synergistic effect on efficacy is realized with the combination of a composition comprising antineoplastic particles administered locally and an immunotherapeutic agent administer systemically as evidenced by at least one of the following:

(g) the reduction of tumor size of the animals treated with the combination of a composition comprising antineoplastic particles and an immunotherapeutic agent is greater than the sum of the reductions of the tumor size of the animals treated with an immunotherapeutic agent alone plus those treated with a composition comprising antineoplastic particles alone, or (h) the reduction of tumor growth of the animals treated with the combination of a composition comprising antineoplastic particles and an immunotherapeutic agent is greater than the sum of the reductions of the tumor growth of the animals treated with an immunotherapeutic agent alone plus those treated with a composition comprising antineoplastic particles alone, or (i) the number of incidences of tumor elimination of the animals treated with the combination of a composition comprising antineoplastic particles and an immunotherapeutic agent is greater than the sum of the number of incidences of tumor elimination of the animals treated with Pembrolizumab alone plus those treated with a composition comprising antineoplastic particles alone.

I. Antineoplastic Agent Particles

Antineoplastic agents are drugs used to treat neoplasms including cancer, and include "chemotherapeutic agents", which are drugs used to treat cancer. Suitable antineoplastic agents include those that stimulate an immunological response when administered to a subject. Non-limiting examples of antineoplastic agents can be found listed in the "Ashgate Handbook of Antineoplastic Agents", published by Gower Publishing Limited, 2000, herein incorporated by reference. Antineoplastic agent particles have a mean particle size (number) of from about 0.1 microns to about 5 microns (about 100 nm to about 5000 nm) in diameter. In some embodiments, the antineoplastic agent particles have a mean particle size (number) of from about 0.1 microns to about 1.5 microns (about 100 nm to about 1500 nm) in diameter. In some embodiments, the antineoplastic agent particles have a mean particle size (number) of from about 0.1 microns to less than 1 micron (about 100 nm to less than 1000 nm) in diameter. The antineoplastic agent particles are in a size range where they are unlikely to be carried out of the tumor by systemic circulation and yet benefit from the high specific surface area to provide enhanced solubilization and release of the drug.

In some embodiments, the antineoplastic particles are solid, uncoated ("neat" or "naked") individual particles. In some embodiments, the antineoplastic particles are not bound to any substance. In some embodiments, no substances are absorbed or adsorbed onto the surface of the antineoplastic particles. In some embodiments, the antineoplastic agents or antineoplastic particles are not encapsulated, contained, enclosed or embedded within any substance. In some embodiments, the antineoplastic particles are not coated with any substance. In some embodiments, the antineoplastic particles are not microemulsions, nanoemulsions, microspheres, or liposomes containing an antineoplastic agent. In some embodiments, the antineoplastic particles are not bound to, encapsulated in, or coated with a monomer, a polymer (or biocompatible polymer), a protein, a surfactant, or albumin. In some embodiments, a monomer, a polymer (or biocompatible polymer), a protein, a surfactant, or albumin is not absorbed or adsorbed onto the surface of the antineoplastic particles. In some embodiments, the antineoplastic particles are in crystalline form. In other embodiments, the antineoplastic particles are in amorphous form, or a combination of both crystalline and amorphous form. In some embodiments, the antineoplastic particles of the invention contain traces of impurities and byproducts typically found during preparation of the antineoplastic agent. In some embodiments, the antineoplastic particles comprise at least 90%, at least 95%, at least 96%, at least 97%, at least 98%, at least 99% or 100% of the antineoplastic agent, meaning the antineoplastic particles consist of or consist essentially of substantially pure antineoplastic agent.

In some embodiments, the antineoplastic particles are coated with or bound to a substance such as a protein (e.g., albumin), a monomer, a polymer, a biocompatible polymer, or a surfactant. In some embodiments, a substance such as a protein (e.g., albumin), a monomer, a polymer, a biocompatible polymer, or a surfactant is adsorbed or absorbed onto the surface of the antineoplastic particles. In some embodiments, the antineoplastic particles are encapsulated, contained, enclosed, or embedded within a substance such as a protein (e.g., albumin), a monomer, a polymer, a biocompatible polymer, or a surfactant. In some embodiments, the antineoplastic particles are microemulsions, nanoemulsions, microspheres, or liposomes containing an antineoplastic agent. In some embodiments, the antincoplastic particles are non-agglomerated individual particles and are not clusters of multiple antineoplastic particles that are bound together by interactive forces such as non-covalent interactions, van der Waal forces, hydrophilic or hydrophobic interactions, electrostatic interactions, Coulombic forces, interactions with a dispersion material, or interactions via functional groups. In some embodiments, the taxane particles are individual antineoplastic particles that are formed by the agglomeration of smaller particles which fuse together forming the larger individual antineoplastic particles, all of which occurs during the processing of the antineoplastic particles. In other embodiments, the antineoplastic particles are clusters or agglomerates of antineoplastic particles that are bound together by interactive forces such as non-covalent interactions, van der Waal forces, hydrophilic or hydrophobic interactions, electrostatic interactions, Coulombic forces, interactions with a dispersion material, or interactions via functional groups.

In a preferred embodiment, the antineoplastic particles are taxane particles. Taxanes are poorly water-soluble compounds generally having a solubility of less than or equal to 10 mg/mL in water at room temperature. Taxanes are widely used as antineoplastic agents and chemotherapy agents. The term "taxanes" as used herein include paclitaxel (I), docetaxel (II), cabazitaxel (III), and any other taxane or taxane derivatives, non-limiting examples of which are taxol B (cephalomannine), taxol C, taxol D, taxol E, taxol F, taxol G, taxadiene, baccatin III, 10-deacetylbaccatin, taxchinin A, brevifoliol, and taxuspine D, and also include pharmaceutically acceptable salts of taxanes.

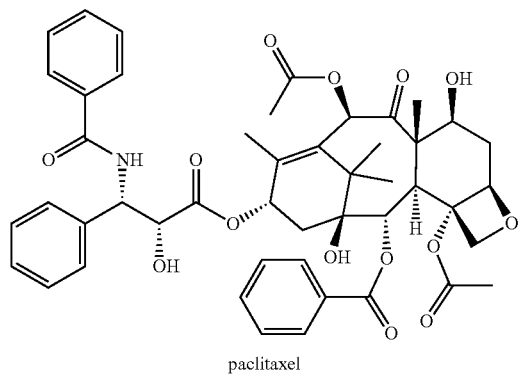

paclitaxel (I)

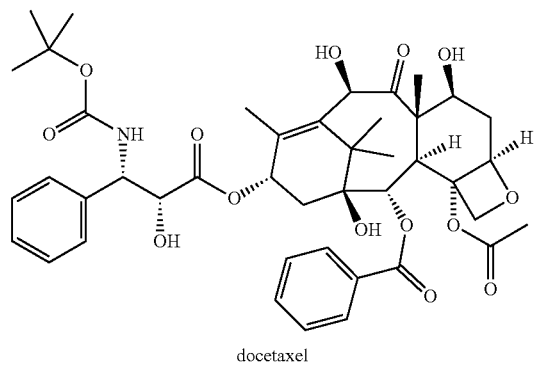

docetaxel (II)

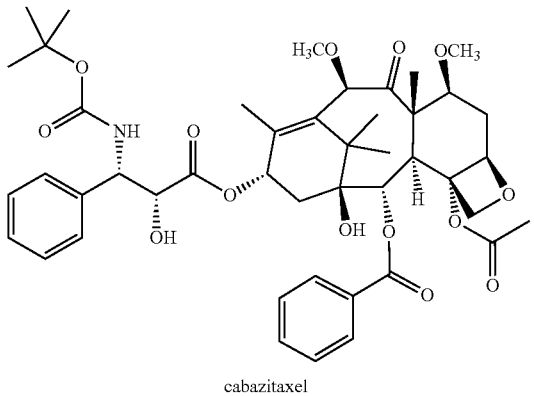

cabazitaxel (III)

Paclitaxel and docetaxel active pharmaceutical ingredients (APIs) are commercially available from Phyton Biotech LLC, Vancouver, Canada. The docetaxel API contains not less than 90%, or not less than 95%, or not less than 97.5% docetaxel calculated on the anhydrous, solvent-free basis. The paclitaxel API contains not less than 90%, or not less than 95%, or not less than 97% paclitaxel calculated on the anhydrous, solvent-free basis. In some embodiments, the paclitaxel API and docetaxel API are USP and/or EP grade. Paclitaxel API can be prepared from a semisynthetic chemical process or from a natural source such as plant cell fermentation or extraction. Paclitaxel is also sometimes referred to by the trade name TAXOL, although this is a misnomer because TAXOL is the trade name of a solution of paclitaxel in polyoxyethylated castor oil and ethanol intended for dilution with a suitable parenteral fluid prior to intravenous infusion. Taxane APIs can be used to make taxane particles. The taxane particles can be paclitaxel particles, docetaxel particles, or cabazitaxel particles, or particles of other taxane derivatives, including particles of pharmaceutically acceptable salts of taxanes.

Taxane particles have a mean particle size (number) of from about 0.1 microns to about 5 microns (about 100 nm to about 5000 nm) in diameter. In preferred embodiments, the taxane particles are solid, uncoated (neat) individual particles. The taxane particles are in a size range where they are unlikely to be carried out of the tumor by systemic circulation and yet benefit from the high specific surface area to provide enhanced solubilization and release of the drug. In some embodiments, the taxane particles are not bound to any substance. In some embodiments, no substances are absorbed or adsorbed onto the surface of the taxane particles. In some embodiments, the taxane or taxane particles are not encapsulated, contained, enclosed or embedded within any substance. In some embodiments, the taxane particles are not coated with any substance. In some embodiments, the taxane particles are not microemulsions, nanoemulsions, microspheres, or liposomes containing a taxane. In some embodiments, the taxane particles are not bound to, encapsulated in, or coated with a monomer, a polymer (or biocompatible polymer), a protein, a surfactant, or albumin. In some embodiments, a monomer, a polymer (or biocompatible polymer), a protein, a surfactant, or albumin is not absorbed or adsorbed onto the surface of the taxane particles. In some embodiments, the composition and the taxane particles exclude albumin. In some embodiments, the taxane particles are in crystalline form. In other embodiments, the taxane particles are in amorphous form, or a combination of both crystalline and amorphous form. In some embodiments, the taxane particles of the invention contain traces of impurities and byproducts typically found during preparation of the taxane. In some embodiments, the taxane particles comprise at least 90%, at least 95%, at least 96%, at least 97%, at least 98%, at least 99% or 100% of the taxane, meaning the taxane particles consist of or consist essentially of substantially pure taxane.

In some embodiments, the taxane particles are coated with or bound to a substance such as a protein (e.g., albumin), a monomer, a polymer, a biocompatible polymer, or a surfactant. In some embodiments, a substance such as a protein (e.g., albumin), a monomer, a polymer, a biocompatible polymer, or a surfactant is adsorbed or absorbed onto the surface of the taxane particles. In some embodiments, the taxane particles are encapsulated, contained, enclosed, or embedded within a substance such as a protein (e.g., albumin), a monomer, a polymer, a biocompatible polymer, or a surfactant. In some embodiments, the taxane particles are microemulsions, nanoemulsions, microspheres, or liposomes containing a taxane. In some embodiments, the taxane particles are non-agglomerated individual particles and are not clusters of multiple taxane particles that are bound together by interactive forces such as non-covalent interactions, van der Waal forces, hydrophilic or hydrophobic interactions, electrostatic interactions, Coulombic forces, interactions with a dispersion material, or interactions via functional groups. In some embodiments, the taxane particles are individual taxane particles that are formed by the agglomeration of smaller particles which fuse together forming the larger individual taxane particles, all of which occurs during the processing of the taxane particles. In some embodiments, the taxane particles are clusters or agglomerates of taxane particles that are bound together by interactive forces such as non-covalent interactions, van der Waal forces, hydrophilic or hydrophobic interactions, electrostatic interactions, Coulombic forces, interactions with a dispersion material, or interactions via functional groups.

The antineoplastic particles or taxane particles (including paclitaxel particles, docetaxel particles, or cabazitaxel particles) can have a mean particle size (number) of from 0.1 microns to 5 microns, or from 0.1 microns to 2 microns, or from 0.1 microns to 1.5 microns, or from 0.1 microns to 1.2 microns, or from 0.1 microns to 1 micron, or from 0.1 microns to less than 1 micron, or from 0.1 microns to 0.9 microns, or from 0.1 microns to 0.8 microns, or from 0.1 microns to 0.7 microns, or from 0.2 microns to 5 microns, or from 0.2 microns to 2 microns, or from 0.2 microns to 1.5 microns, or from 0.2 microns to 1.2 microns, or from 0.2 microns to 1 micron, or from 0.2 microns to less than 1 micron, or from 0.2 microns to 0.9 microns, or from 0.2 microns to 0.8 microns, or from 0.2 microns to 0.7 microns, or from 0.3 microns to 5 microns, or from 0.3 microns to 2 microns, or from 0.3 microns to 1.5 microns, or from 0.3 microns to 1.2 microns, or from 0.3 microns to 1 micron, or from 0.3 microns to less than 1 micron, or from 0.3 microns to 0.9 microns, or from 0.3 microns to 0.8 microns, or from 0.3 microns to 0.7 microns, or from 0.4 microns to 5 microns, or from 0.4 microns to 2 microns, or from 0.4 microns to 1.5 microns, or from 0.4 microns to 1.2 microns, or from 0.4 microns to 1 micron, or from 0.4 microns to less than 1 micron, or from 0.4 microns to 0.9 microns, or from 0.4 microns to 0.8 microns, or from 0.4 microns to 0.7 microns, or from 0.5 microns to 5 microns, or from 0.5 microns to 2 microns, or from 0.5 microns to 1.5 microns, or from 0.5 microns to 1.2 microns, or from 0.5 microns to 1 micron, or from 0.5 microns to less than 1 micron, or from 0.5 microns to 0.9 microns, or from 0.5 microns to 0.8 microns, or from 0.5 microns to 0.7 microns, or from 0.6 microns to 5 microns, or from 0.6 microns to 2 microns, or from 0.6 microns to 1.5 microns, or from 0.6 microns to 1.2 microns, or from 0.6 microns to 1 micron, or from 0.6 microns to less than 1 micron, or from 0.6 microns to 0.9 microns, or from 0.6 microns to 0.8 microns, or from 0.6 microns to 0.7 microns. The antineoplastic particles or taxane particles are in a size range where they are unlikely to be carried out of the tumor by systemic circulation and yet benefit from the high specific surface area to provide enhanced solubilization and release of the drug.

The particle size of the antineoplastic particles including taxane particles can be determined by a particle size analyzer instrument and the measurement is expressed as the mean diameter based on a number distribution (number). A suitable particle size analyzer instrument is one which employs the analytical technique of light obscuration, also referred to as photozone or single particle optical sensing (SPOS). A suitable light obscuration particle size analyzer instrument is the ACCUSIZER, such as the ACCUSIZER 780 SIS, available from Particle Sizing Systems, Port Richey, Florida. Another suitable particle size analyzer instrument is one which employs laser diffraction, such as the Shimadzu SALD-7101.

Antineoplastic agent particles including taxane particles can be manufactured using various particle size-reduction methods and equipment known in the art. Such methods include, but are not limited to conventional particle size-reduction methods such as wet or dry milling, micronizing, disintegrating, and pulverizing. Other methods include "precipitation with compressed anti-solvents" (PCA) such as with supercritical carbon dioxide. In various embodiments, the antineoplastic and/or taxane particles are made by PCA methods as disclosed in U.S. Pat. Nos. 5,874,029, 5,833,891, 6,113,795, 7,744,923, 8,778,181, 9,233,348; US publications US 2015/0375153, US 2016/0354336, US 2016/0374953; and international patent application publications WO 2016/197091, WO 2016/197100, and WO 2016/197101; all of which are herein incorporated by reference.

In PCA particle size reduction methods using supercritical carbon dioxide, supercritical carbon dioxide (anti-solvent) and solvent, e.g. acetone or ethanol, are employed to generate uncoated antineoplastic or taxane particles as small as 0.1 to 5 microns within a well-characterized particle-size distribution. The carbon dioxide and solvent are removed during processing (up to 0.5% residual solvent may remain), leaving antineoplastic or taxane particles as a powder. Stability studies show that the paclitaxel particle powder is stable in a vial dose form when stored at room temperature for up to 59 months and under accelerated conditions (40° C./75% relative humidity) for up to six months.

Taxane particles produced by various supercritical carbon dioxide particle size reduction methods can have unique physical characteristics as compared to taxane particles produced by conventional particle size reduction methods using physical impacting or grinding, e.g., wet or dry milling, micronizing, disintegrating, comminuting, microfluidizing, or pulverizing. As disclosed in US publication 2016/0374953, herein incorporated by reference, such unique characteristics include a bulk density (not tapped) between 0.05 g/cm$^3$ and 0.15 g/cm$^3$ and a specific surface area (SSA) of at least 18 m$^2$/g of taxane (e.g., paclitaxel and docetaxel) particles, which are produced by the supercritical carbon dioxide particle size reduction methods described in US publication 2016/0374953 and as described below. This bulk density range is generally lower than the bulk density of taxane particles produced by conventional means, and the SSA is generally higher than the SSA of taxane particles produced by conventional means. These unique characteristics result in significant increases in dissolution rates in water/methanol media as compared to taxanes produced by conventional means. As used herein, the "specific surface area" (SSA) is the total surface area of the taxane particle per unit of taxane mass as measured by the Brunauer-Emmett-Teller ("BET") isotherm by the following method: a known mass between 200 and 300 mg of the analyte is added to a 30 mL sample tube. The loaded tube is then mounted to a Porous Materials Inc. SORPTOMETER®, model BET-202A. The automated test is then carried out using the BETWIN® software package and the surface area of each sample is subsequently calculated. As will be understood by those of skill in the art, the "taxane particles" can include both agglomerated taxane particles and non-agglomerated taxane particles; since the SSA is determined on a per gram basis it takes into account both agglomerated and non-agglomerated taxane particles in the composition. The agglomerated taxane particles are defined herein as individual taxane particles that are formed by the agglomeration of smaller particles which fuse together forming the larger individual taxane particles, all of which occurs during the processing of the taxane particles. The BET specific surface area test procedure is a compendial method included in both the United States Pharmaceopeia and the European Pharmaceopeia. The bulk density measurement can be conducted by pouring the taxane particles into a graduated cylinder without tapping at room temperature, measuring the mass and volume, and calculating the bulk density.

As disclosed in US publication 2016/0374953, studies showed a SSA of 15.0 $m^2/g$ and a bulk density of 0.31 $g/cm^3$ for paclitaxel particles produced by milling paclitaxel in a Deco-PBM-V-0.41 ball mill suing a 5 mm ball size, at 600 RPM for 60 minutes at room temperature. Also disclosed in US publication 2016/0374953, one lot of paclitaxel particles had a SSA of 37.7 $m^2/g$ and a bulk density of 0.085 $g/cm^3$ when produced by a supercritical carbon dioxide method using the following method: a solution of 65 mg/ml of paclitaxel was prepared in acetone. A BETE MicroWhirl® fog nozzle (BETE Fog Nozzle, Inc.) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel particles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Additional lots of paclitaxel particles produced by the supercritical carbon dioxide method described above had SSA values of: 22.27 $m^2/g$, 23.90 $m^2/g$, 26.19 $m^2/g$, 30.02 $m^2/g$, 31.16 $m^2/g$, 31.70 $m^2/g$, 32.59 $m^2/g$, 33.82 $m^2/g$, 35.90 $m^2/g$, 38.22 $m^2/g$, and 38.52 $m^2/g$.

As disclosed in US publication 2016/0374953, studies showed a SSA of 15.2 $m^2/g$ and a bulk density of 0.44 $g/cm^3$ for docetaxel particles produced by milling docetaxel in a Deco-PBM-V-0.41 ball mill suing a 5 mm ball size, at 600 RPM for 60 minutes at room temperature. Also disclosed in US publication 2016/0374953, docetaxel particles had a SSA of 44.2 $m^2/g$ and a bulk density of 0.079 $g/cm^3$ when produced by a supercritical carbon dioxide method using the following method: A solution of 79.32 mg/ml of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel particles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerated particles and smaller docetaxel particles were then collected from the supercritical carbon dioxide as the mixture is pumped through the stainless steel mesh filter. The filter containing the particles of docetaxel was opened and the resulting product was collected from the filter.

As disclosed in US publication 2016/0374953, dissolution studies showed an increased dissolution rate in methanol/water media of paclitaxel and docetaxel particles made by the supercritical carbon dioxide methods described in US publication 2016/0374953 as compared to paclitaxel and docetaxel particles made by milling paclitaxel and docetaxel using a Deco-PBM-V-0.41 ball mill suing a 5 mm ball size, at 600 RPM for 60 minutes at room temperature. The procedures used to determine the dissolution rates are as follows. For paclitaxel, approximately 50 mg of material were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 µm filter and analyzed on a UV/VIS spectrophotometer at 227 nm. Absorbance values of the samples were compared to those of standard solutions prepared in dissolution media to determine the amount of material dissolved. For docetaxel, approximately 50 mg of material was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 µm filter, and analyzed on a UV/VIS spectrophotometer at 232 nm. Absorbance values of the samples were compared to those of standard solutions prepared in dissolution media to determine the amount of material dissolved. For paclitaxel, the dissolution rate was 47% dissolved in 30 minutes for the particles made by the supercritical carbon dioxide method versus 32% dissolved in 30 minutes for the particles made by milling. For docetaxel, the dissolution rate was 27% dissolved in 30 minutes for the particles made by the supercritical carbon dioxide method versus 9% dissolved in 30 minutes for the particles made by milling.

In some embodiments, the antineoplastic particles have a SSA of at least 10, at least 12, at least 14, at least 16, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In one embodiment, the antineoplastic particles have an SSA of between about 10 $m^2/g$ and about 50 $m^2/g$. In some embodiments, the antineoplastic particles have a bulk density between about 0.050 $g/cm^3$ and about 0.20 $g/cm^3$.

In further embodiments, the antineoplastic particles have a SSA of:
(a) between 16 m²/g and 31 m²/g or between 32 m²/g and 40 m²/g;
(b) between 16 m²/g and 30 m²/g or between 32 m²/g and 40 m²/g;
(c) between 16 m²/g and 29 m²/g or between 32 m²/g and 40 m²/g;
(d) between 17 m²/g and 31 m²/g or between 32 m²/g and 40 m²/g;
(e) between 17 m²/g and 30 m²/g or between 32 m²/g and 40 m²/g;
(f) between 17 m²/g and 29 m²/g, or between 32 m²/g and 40 m²/g;
(g) between 16 m²/g and 31 m²/g or between 33 m²/g and 40 m²/g;
(h) between 16 m²/g and 30 m²/g or between 33 m²/g and 40 m²/g;
(i) between 16 m²/g and 29 m²/g or between 33 m²/g and 40 m²/g;
(j) between 17 m²/g and 31 m²/g or between 33 m²/g and 40 m²/g;
(k) between 17 m²/g and 30 m²/g or between 33 m²/g and 40 m²/g;
(l) between 17 m²/g and 29 m²/g, or between 33 m²/g and 40 m²/g;
(m) between 16 m²/g and 31 m²/g, or ≥32 m²/g;
(h) between 17 m²/g and 31 m²/g, or ≥32 m²/g;
(i) between 16 m²/g and 30 m²/g, or ≥32 m²/g;
(j) between 17 m²/g and 30 m²/g, or ≥32 m²/g;
(k) between 16 m²/g and 29 m²/g, or ≥32 m²/g;
(l) between 17 m²/g and 29 m²/g, or ≥32 m²/g;
(m) between 16 m²/g and 31 m²/g, or ≥33 m²/g;
(n) between 17 m²/g and 31 m²/g, or ≥33 m²/g;
(o) between 16 m²/g and 30 m²/g, or ≥33 m²/g;
(p) between 17 m²/g and 30 m²/g, or ≥33 m²/g;
(q) between 16 m²/g and 29 m²/g, or ≥33 m²/g; or
(r) between 17 m²/g and 29 m²/g, or ≥33 m²/g.

In some embodiments, the antineoplastic particles are taxane particles. In some embodiments, the antineoplastic particles or taxane particles are individual taxane particles that are formed by the agglomeration of smaller particles which fuse together forming the larger individual taxane particles, all of which occurs during the processing of the taxane particles. In some embodiments, the antineoplastic particles or taxane particles are non-agglomerated individual particles and are not clusters of multiple antineoplastic or taxane particles that are bound together by interactive forces such as non-covalent interactions, van der Waal forces, hydrophilic or hydrophobic interactions, electrostatic interactions, Coulombic forces, interactions with a dispersion material, or interactions via functional groups.

In some embodiments, the taxane particles are paclitaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 m²/g. In other embodiments, the paclitaxel particles have an SSA of 18 m²/g to 50 m²/g, or 20 m²/g to 50 m²/g, or 22 m²/g to 50 m²/g, or 25 m²/g to 50 m²/g, or 26 m²/g to 50 m²/g, or 30 m²/g to 50 m²/g, or 35 m²/g to 50 m²/g, or 18 m²/g to 45 m²/g, or 20 m²/g to 45 m²/g, or 22 m²/g to 45 m²/g, or 25 m²/g to 45 m²/g, or 26 m²/g to 45 m²/g or 30 m²/g to 45 m²/g, or 35 m²/g to 45 m²/g, or 18 m²/g to 40 m²/g, or 20 m²/g to 40 m²/g, or 22 m²/g to 40 m²/g, or 25 m²/g to 40 m²/g, or 26 m²/g to 40 m²/g, or 30 m²/g to 40 m²/g, or 35 m²/g to 40 m²/g.

In some embodiments, the paclitaxel particles have a bulk density (not-tapped) of 0.05 g/cm³ to 0.15 g/cm³, or 0.05 g/cm³ to 0.20 g/cm³.

In some embodiments, the paclitaxel particles have a dissolution rate of at least 40% w/w dissolved in 30 minutes or less in a solution of 50% methanol/50% water (v/v) in a USP II paddle apparatus operating at 75 RPM, at 37° C., and at a pH of 7.

In some embodiments, the taxane particles are docetaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 m²/g. In other embodiments, the docetaxel particles have an SSA of 18 m²/g to 60 m²/g, or 22 m²/g to 60 m²/g, or 25 m²/g to 60 m²/g, or 30 m²/g to 60 m²/g, or 40 m²/g to 60 m²/g, or 18 m²/g to 50 m²/g, or 22 m²/g to 50 m²/g, or 25 m²/g to 50 m²/g, or 26 m²/g to 50 m²/g, or 30 m²/g to 50 m²/g, or 35 m²/g to 50 m²/g, or 40 m²/g to 50 m²/g.

In some embodiments, the docetaxel particles have a bulk density (not-tapped) of 0.05 g/cm³ to 0.15 g/cm³.

In some embodiments, the docetaxel particles have a dissolution rate of at least 20% w/w dissolved in 30 minutes or less in a solution of 15% methanol/85% water (v/v) in a USP II paddle apparatus operating at 75 RPM, at 37° C., and at a pH of 7.

II. Compositions for Local Administration

The compositions useful for local administration are compositions that comprise the antineoplastic particles, including taxane particles, described herein and throughout this disclosure, and are compositions suitable for the various types of local administration, i.e. topical application, pulmonary administration, intratumoral (IT) injection, and intraperitoneal (IP) injection. The composition can be a suspension. For example, the composition can comprise a carrier wherein the antineoplastic particles are dispersed within the carrier such that the carrier is a continuous phase and the antineoplastic particles are a dispersed (suspended) phase. The antineoplastic particles can be completely dispersed, or partially dispersed and partially dissolved in the composition and/or carrier, but the antineoplastic particles cannot be completely dissolved in the composition and/or carrier.

A. Compositions for Topical Application

The compositions for topical application (topical compositions) comprise antineoplastic particles, such as taxane particles. The antineoplastic particles can be dispersed (suspended) in the topical composition. The topical composition can be any composition suitable for topical delivery. The topical composition can be a hydrophobic composition. The topical composition can be an anhydrous composition, which can include an anhydrous, hydrophilic composition or an anhydrous, hydrophobic composition. Non-limiting examples of anhydrous, hydrophilic compositions include compositions based on polyols, glycols (e.g. propylene glycol, PEG), and/or poloxamers. The topical composition can be non-anhydrous, such as an aqueous-based composition. The topical compositions can be sterile, can be self-preserved, or can include preservatives.

The topical compositions can be formulated in various forms suitable for topical delivery. Non-limiting examples include semi-solid compositions, lotions, liquid suspensions, emulsions, creams, gels, ointments, pastes, aerosol sprays, aerosol foams, non-aerosol sprays, non-aerosol foams, films, and sheets. Semi-solid compositions include ointments, pastes, and creams. The topical compositions can be impregnated in gauzes, bandages, or other skin dressing materials. In some embodiments, the topical compositions are semi-solid compositions. In some embodiments, the topical compositions are ointments. In other embodiments, the topical compositions are gels. In still other embodiments, the topical compositions are liquid suspensions. In some embodiments, the topical compositions are not sprays and are not sprayable.

In some embodiments, the topical compositions are free of/do not include or contain a polymer/copolymer or biocompatible polymer/copolymer. In some embodiments, the compositions are free of/do not include or contain a protein. In some aspects of the invention, the compositions are free of/do not include or contain albumin. In some aspects of the invention, the compositions are free of/do not include or contain hyaluronic acid. In some aspects of the invention, the compositions are free of/do not include or contain a conjugate of hyaluronic acid and a taxane. In some aspects of the invention, the compositions are free of/do not include or contain a conjugate of hyaluronic acid and paclitaxel. In some aspects of the invention, the compositions are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), Vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), Poly (bis(P-carboxyphenoxy)propane-sebacic acid, poly(d,l-lactic acid) (PLA), poly(d,l-lactic acid-co-glycolic acid) (PLAGA), and/or poly(D, L lactic-co-glycolic acid) (PLGA).

The topical compositions can be packaged in any package configuration suitable for topical products. Non-limiting examples include bottles, bottles with pumps, tottles, tubes (aluminum, plastic or laminated), jars, non-aerosol pump sprayers, aerosol containers, pouches, and packets. The packages can be configured for single-dose or multiple-dose administration.

Non-limiting examples of suitable topical compositions are disclosed in international patent publication WO 2017/049083, herein incorporated by reference.

1. Hydrophobic Topical Compositions

In some embodiments, the topical composition is a hydrophobic composition. For purposes of this disclosure, a hydrophobic composition is a composition in which the total amount of the hydrophobic constituents in the composition is greater than the total amount of the non-hydrophobic constituents in the composition. In some embodiments, the hydrophobic composition is anhydrous. In some embodiments, the hydrophobic composition comprises a hydrophobic carrier.

The hydrophobic carrier can comprise substances from plant, animal, paraffinic, and/or synthetically derived sources. Hydrophobic substances are generally known as substances that lack an affinity for and repel water. The hydrophobic carrier can be the continuous phase of the topical composition and the antineoplastic particles can be the dispersed phase. In various embodiments, the hydrophobic carriers are non-polar and/or non-volatile. Non-limiting examples of hydrophobic carriers include fats, butters, greases, waxes, solvents, and oils; mineral oils; vegetable oils; petrolatums; water insoluble organic esters and triglycerides; and fluorinated compounds. The hydrophobic carriers can also comprise silicone materials. Silicone materials are defined as compounds based on polydialkylsiloxanes and include polymers, elastomers (crosslinked silicones), and adhesives (branched silicones). Non-limiting examples of silicone materials include dimethicone (polydimethylsiloxane), dimethicone copolyol, cyclomethicone, simethicone, silicone elastomers such as ST-elastomer 10 (DOW CORNING), silicone oils, silicone polymers, volatile silicone fluids, and silicone waxes. In some embodiments, the hydrophobic carrier does not comprise silicone materials. Plant derived materials include, but are not limited to, arachis (peanut) oil, balsam Peru oil, carnauba wax, candellila wax, castor oil, hydrogenated castor oil, cocoa butter, coconut oil, corn oil, cotton seed oil, jojoba oil, macadamia seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil. Non-limiting examples of animal derived materials include beeswax (yellow wax and white wax), cod liver oil, emu oil, lard, mink oil, shark liver oil, squalane, squalene, and tallow. Non-limiting examples of paraffinic materials include isoparaffin, microcrystalline wax, heavy mineral oil, light mineral oil, ozokerite, petrolatum, white petrolatum, and paraffin wax. Non-limiting examples of organic esters and triglycerides include C12-15 alkyl benzoate, isopropyl myristate, isopropyl palmitate, medium chain triglycerides, mono- and di-glycerides, trilaurin, and trihydroxystearin. A non-limiting example of a fluorinated compound is perfluoropolyether (PFPE), such as FOMBLIN®HC04 commercially available from Solvay Specialty Polymers. The hydrophobic carrier can comprise pharmaceutical grade hydrophobic substances.

In various embodiments, the hydrophobic carrier comprises petrolatum, mineral oil, or paraffin, or mixtures thereof. Petrolatum is a purified mixture of semi-solid saturated hydrocarbons obtained from petroleum, and varies from dark amber to light yellow in color. White petrolatum is wholly or nearly decolorized and varies from cream to snow white in color. Petrolatums are available with different melting point, viscosity, and consistency characteristics. Petrolatums may also contain a stabilizer such as an antioxidant. Pharmaceutical grades of petrolatum include Petrolatum USP and White Petrolatum USP. Mineral oil is a mixture of liquid hydrocarbons obtained from petroleum. Mineral oil is available in various viscosity grades, such as light mineral oil, heavy mineral oil, and extra heavy mineral oil. Light mineral oil has a kinematic viscosity of not more than 33.5 centistokes at 40° C. Heavy mineral oil has a kinematic viscosity of not less than 34.5 centistokes at 40° C. Pharmaceutical grades of mineral oil include Mineral Oil USP, which is heavy mineral oil, and Light Mineral Oil NF, which is light mineral oil. In some embodiments, the mineral oil is heavy mineral oil. Paraffin wax is a purified mixture of solid hydrocarbons obtained from petroleum. It may also be synthetically derived by the Fischer-Tropsch process from carbon monoxide and hydrogen which are catalytically converted to a mixture of paraffin hydrocarbons. Paraffin wax may contain an antioxidant. Pharmaceutical grades of paraffin wax include Paraffin NF and Synthetic Paraffin NF.

In some embodiments, the concentration of the hydrophobic carrier in the hydrophobic composition is greater than 10% w/w of the total composition weight. In other embodiments, the concentration of the hydrophobic carrier in the hydrophobic composition is greater than 15%, or greater than 20%, or greater than 25%, or greater than 30%, or greater than 35%, or greater than 40%, or greater than 45%, or greater than 50%, or greater than 55%, or greater than 60%, or greater than 65%, or greater than 70%, or greater than 75%, or greater than 80%, or greater than 82%, or greater than 85%, or greater than 87%, or greater than 90% w/w of the total composition weight. In other embodiments, the concentration of the hydrophobic carrier in the hydrophobic composition is from greater than 10% w/w to 95% w/w of the total composition weight. In other embodiments, the concentration of the hydrophobic carrier in the hydrophobic composition is from 11% w/w to 95% w/w, or from 12% w/w to 95% w/w, or from 13% w/w to 95% w/w, or from 14% w/w to 95% w/w, or from 15% w/w to 95% w/w, or from 16% w/w to 95% w/w, or from 17% w/w to 95% w/w, or from 18% w/w to 95% w/w, or from 19% w/w to 95% w/w, or from 20% w/w to 95% w/w of the total composition weight. In a preferred embodiment, the hydrophobic carrier in the hydrophobic composition is greater than 50% of the hydrophobic composition.

The hydrophobic composition can comprise a hydrophobic carrier and further comprise one or more volatile silicone fluids. Volatile silicone fluids, also known as volatile silicone oils, are volatile liquid polysiloxanes which can by cyclic or linear. They are liquid at room temperature. Volatile silicone fluids are hydrophobic materials. Linear volatile silicone fluids include polydimethylsiloxane, hexamethyldisiloxane and octamethyltrisiloxane and are commercially available from Dow Corning under the trade names DOW CORNING Q7-9180 Silicone Fluid 0.65 cSt and DOW CORNING Q7-9180 Silicone Fluid 1.0 cSt, respectively. Cyclic volatile silicone fluids are generally known as cyclomethicones. Cyclomethicone is a fully methylated cyclic siloxane containing repeating units of formula (IV):

$$[\text{---}(CH_3)_2SiO\text{---}]_n \quad (IV)$$

in which n is 3, 4, 5, 6, or 7; or mixtures thereof. Cyclomethicone is a clear, colorless volatile liquid silicone fluid. Cyclomethicone has emollient properties and helps to improve the tactile feel of an oil based product by making it feel less greasy on the skin. Pharmaceutical grade cyclomethicone includes Cyclomethicone NF. Cyclomethicone NF is represented by formula (IV) in which n is 4 (cyclotetrasiloxane), 5 (cyclopentasiloxane), or 6 (cyclohexasiloxane); or mixtures thereof. Cyclopentasiloxane, also known as decamethylcylcopentasiloxane, cyclomethicone D5, or cyclomethicone 5, is the cyclomethicone represented by formula (IV) in which n is 5 (pentamer), but it can contain small amounts (generally less than 1%) of one or more of the other cyclic chain length cyclomethicones. Cyclopentasiloxane is available in a pharmaceutical grade as Cyclomethicone NF. Cyclomethicones are commercially available from Dow Corning under the trade names DOW CORNING ST-Cyclomethicone 5-NF, DOW CORNING ST-Cyclomethicone 56-NF, and XIAMETER PMX-0245. It is also commercially available from the Spectrum Chemical Mfg. Corp. Cyclopentasiloxane has a vapor pressure of about 20 to about 27 Pa at 25° C.

In one embodiment, the concentration of cyclomethicone in the hydrophobic composition is less than 25% w/w. In another embodiment, the cyclomethicone in the hydrophobic composition is at a concentration from 5 to 24% w/w. In another embodiment, the concentration of cyclomethicone is from 5 to 20% w/w. In another embodiment, the cyclomethicone is at a concentration of from 5 to 18% w/w. In another embodiment, the concentration of cyclomethicone is 13% w/w. In various embodiments, the concentration of cyclomethicone can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight. In some embodiments, the volatile silicone fluid is a cyclomethicone. In some embodiments, the cyclomethicone is cyclopentasiloxane.

The hydrophobic composition can be a suspension of the antineoplastic particles, such as taxane particles, within a mixture of the hydrophobic carrier and the volatile silicone fluid. The antineoplastic particles can be completely dispersed, or partially dispersed and partially dissolved in the hydrophobic composition, but the antineoplastic particles cannot be completely dissolved in the hydrophobic composition. The hydrophobic carrier can be the continuous phase of the hydrophobic composition and the antineoplastic particles can be the dispersed phase. Therefore, the hydrophobic compositions can include at least two phases, a continuous hydrophobic carrier phase and a dispersed (suspended) antineoplastic particle phase. The volatile silicone fluid can be solubilized and/or dispersed within the continuous phase.

In some embodiments, the hydrophobic compositions are free of/do not include or contain additional penetration enhancers. In some embodiments, the hydrophobic compositions are free of/do not include or contain laurocapram. In some embodiments, the hydrophobic compositions are free of/do not include diethylene glycol monoethyl ether (DGME). In some embodiments, the hydrophobic compositions are free of/do not include isopropyl myristate. In other embodiments, the hydrophobic compositions are free of/do not include alpha tocopherol. In other embodiments, the hydrophobic compositions are free of/do not include or contain additional volatile solvents or compounds. In some embodiments, the hydrophobic compositions are free of/do not include or contain any alcohols or $C_1$-$C_4$ aliphatic alcohols. In some embodiments, the hydrophobic compositions are free of/do not include or contain alcohol or $C_1$-$C_5$ aliphatic alcohols. In other embodiments, the hydrophobic compositions are free of/do not include or contain surfactants. In other embodiments, the hydrophobic compositions are free of/do not include polymers/copolymers (or biodegradable polymers/copolymers). In other embodiments, the hydrophobic compositions are free of/do not include poloxamers, styrene-isobutylene-styrene (SIBS), a polyanhydride copolymer, polycaprolactone, polyethylene glycol, Poly (bis (P-carboxyphenoxy)propane-sebacic acid, and/or poly(D, L lactic-co-glycolic acid (PLGA).

In some embodiments, the hydrophobic compositions are semi-solid compositions. In some embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a SC4-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,000 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

2. Aqueous-Based Topical Compositions

Topical aqueous-based compositions comprise antineoplastic particles, such as taxane particles, and an aqueous carrier. The aqueous compositions are dispersions (suspensions) of the antineoplastic particles in an aqueous carrier. The antineoplastic particles can be completely dispersed, partially dispersed and partially dissolved, but not completely dissolved in the aqueous carrier. An aqueous-based composition is a composition in which water is the major constituent (greater than 50%). Aqueous carriers can include single phase aqueous solutions, and multi-phase aqueous-based emulsions such as oil-in-water and water-in-oil emulsions. Non-limiting examples of aqueous carriers include water and buffer solutions.

A non-limiting example of a topical aqueous-based composition comprises an aqueous carrier (e.g. water) comprising poloxamer 407, a quaternary ammonium compound, and/or or a cross-linked acrylic acid polymer, as disclosed in international patent publication WO 2017/049083. Non-limiting examples of a quaternary ammonium compound include benzalkonium chloride and benzethonium chloride. Non-limiting examples of cross-linked acrylic acid polymers include Carbomer (INCI name), Acrylates Copolymer (INCI name), Acrylates/C 10-30 Alkyl Acrylate Crosspolymer (INCI name), Acrylates Crosspolymer-4 (INCI name), and Polyacrylate-1 Crosspolymer (INCI name).

3. Additional Ingredients and Excipients for Topical Compositions

The topical compositions can further comprise functional ingredients suitable for use in topical compositions. Non-limiting examples include absorbents, acidifying agents, antimicrobial agents, antioxidants, binders, biocides, buffering agents, bulking agents, crystal growth inhibitors, chelating agents, colorants, deodorant agents, emulsion stabilizers, film formers, fragrances, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of the examples of the functional ingredients described herein are disclosed in The International Cosmetic Ingredient Dictionary and Handbook (INCI), 12th Edition, 2008, herein incorporated by reference.

In some embodiments, the topical compositions comprise penetration enhancers. In other embodiments, the topical compositions are free of/do not include additional penetration enhancers. The term "penetration enhancer" has been used to describe compounds or materials or substances that facilitate drug absorption through the skin. These compounds or materials or substances can have a direct effect on the permeability of the skin, or they can augment percutaneous absorption by increasing the thermodynamic activity of the penetrant, thereby increasing the effective escaping tendency and concentration gradient of the diffusing species. The predominant effect of these enhancers is to either increase the stratum corneum's degree of hydration or disrupt its lipoprotein matrix, the net result in either case being a decrease in resistance to drug (penetrant) diffusion (Remington, The Science and Practice of Pharmacy, $22^{nd}$ ed.). Non-limiting examples of skin penetration enhancers include oleyl alcohol, isopropyl myristate, dimethyl isosorbide (DMI) available under the tradename ARLASOLVE DMI, and Diethylene Glycol Monoethyl Ether (DGME) which is available under the trade name TRANSCUTOL P. Other examples of skin penetration enhancers can be found in "Skin Penetration Enhancers Cited in the Technical Literature", Osborne, David W., and Henke, Jill J., Pharmaceutical Technology, November 1997, herein incorporated by reference. Such examples include: Fatty alcohols such as aliphatic alcohols, Decanol, Lauryl alcohol (dodecanol), Linolenyl alcohol, Nerolidol, 1-Nonanol, n-Octanol, Oleyl alcohol, Fatty acid esters, Butylacetate, Cetyl lactate, Decyl N,N-dimethylamino acetate, Decyl N,N-dimethylamino isopropionate, Diethyleneglycol oleate, Diethyl sebacate, Diethyl succinate, Diisopropyl sebacate, Dodecyl N,N-dimethylamino acetate, Dodecyl (N,N-dimethylamino)-butyrate, Dodecyl N,N-dimethylamino isopropionate, Dodecyl 2-(dimethylamino) propionate, EO-5-oleyl ester, Ethyl acetate, Ethylaceto acetate, Ethyl propionate, Glycerol monoethers, Glycerol monolaurate, Glycerol monooleate, Glycerol monolinoleate, Isopropyl isostearate, Isopropyl linoleate, Isopropyl myristate, Isopropyl myristate/fatty acid monoglyceride combination, Isopropyl myristate/ethanol/L-lactic acid (87:10:3) combination, Isopropyl palmitate, Methyl acetate, Methyl caprate, Methyl laurate, Methyl propionate, Methyl valerate, 1-Monocaproyl glycerol, Monoglycerides (medium chain length), Nicotinic esters (benzyl), Octyl acetate, Octyl N,N-dimethylamino acetate, Oleyl oleate, n-Pentyl N-acetylpropionate, Propylene glycol monolaurate, Sorbitan dilaurate, Sorbitan dioleate, Sorbitan monolaurate, Sorbitan monooleates, Sorbitan trilaurate, Sorbitan trioleate, Sucrose coconut fatty ester mixtures, Sucrose monolaurate, Sucrose monooleate, and Tetradecyl N,N-dimethylamino acetate; Fatty acids such as Alkanoic acids, Capric acid, Diacid, Ethyloctadecanoic acid, Hexanoic acid, Lactic acid, Lauric acid, Linoclaidic acid, Linoleic acid, Linolenic acid, Neodecanoic acid, Oleic acid, Palmitic acid, Pelargonic acid, Propionic acid, and Vaccenic acid; Fatty alcohol ethers such as α-Monoglyceryl ether, EO-2-oleyl ether, EO-5-oleyl ether, EO-10-oleyl ether, and Ether derivatives of polyglycerols and alcohols (1-O-dodecyl-3-O-methyl-2-O-(2', 3'-dihydroxypropyl) glycerol); Biologics such as L-α-amino-acids, Lecithin, Phospholipids, Saponin/phospholipids, Sodium deoxycholate, Sodium taurocholate, and Sodium tauroglycocholate; Enzymes such as Acid phosphatase, Calonase, Orgelase, Papain, Phospholipase A-2, Phospholipase C, and Triacylglycerol hydrolase; Amines and Amides such as Acetamide derivatives, Acyclic amides, N-Adamantyl n-alkanamides, Clofibric acid amides, N,N-Didodecyl acetamide, Di-2-ethylhexylamine, Diethyl methyl benzamide, N,N-Diethyl-m-toluamide, N,N-Dimethyl-m-toluarnide, Ethomeen S12 [bis-(2-hydroxyethyl) oleylamine], Hexamethylene lauramide, Lauryl-amine (dodecylamine), Octyl amide, Oleylamine, Unsaturated cyclic ureas, and Urea; Complexing Agents such as, β- and γ-cyclodextrin complexes, Hydroxypropyl methylcellulose, Liposomes, Naphthalene diamide diimide, and Naphthalene diester diimide; Macrocyclics such as Macrocyclic lactones, ketones, and anhydrides (optimum ring-16), and Unsaturated cyclic ureas; Classical surfactants such as Brij 30, Brij 35, Brij 36T, Brij 52, Brij 56, Brij 58, Brij 72, Brij 76, Brij 78, Brij 92, Brij 96, Brij 98, Cetyl trimethyl ammonium bromide, Empicol ML26/F, HCO-60 surfactant, Hydroxypolyethoxydodecane, Ionic surfactants (ROONa, $ROSO_3Na$, $RNH_3Cl$, R=8-16), Lauroyl sarcosine, Nonionic surface active agents, Nonoxynol, Octoxynol, Phenylsulfonate CA, Pluronic F68, Pluronic F 127, Pluronic L62, Polyoleates (nonionic surfactants), Rewopal HV 10, Sodium laurate, Sodium lauryl sulfate (sodium dodecyl sulfate), Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Triton X-100, Tween 20, Tween 40, Tween 60, Tween 80, and Tween 85; N-methyl pyrrolidone and related compounds such as N-Cyclohexyl-2-pyrrolidone, 1-Butyl-3-dodecyl-2-pyrrolidone, 1,3-Dimethyl-2-imidazolikinone, 1,5 Dimethyl-2-pyrrolidone, 4,4-Dimethyl-2-undecyl-2-oxazoline, 1-Ethyl-2-pyrrolidone, 1-Hexyl-4-methyloxycarbonyl-2-pyrrolidone, 1-Hexyl-2-pyrrolidone, 1-(2-Hydroxyethyl) pyrrolidinone, 3-Hydroxy-N-methyl-2-pyrrolidinone, 1-Isopropyl-2-undecyl-2-imidazoline, 1-Laury 1-4-methyloxycarbonyl-2-pyrrolidone, N-Methyl-2-pyrrolidone, Poly(N-vinylpyrrolidone), Pyroglutamic acid esters, and 2-Pyrrolidone (2-pyrrolidinone); Ionic compounds such as Ascorbate, Amphoteric cations and anions, Calcium thioglycolate, Cetyl trimethyl ammonium bromide, 3,5-Diiodosalicylate sodium, Lauroylcholine iodide, 5-Methoxysalicylate sodium, Monoalkyl phosphates, 2-PAM chloride, 4-PAM chloride (derivatives of N-methyl picolinium chloride), Sodium carboxylate, and Sodium hyaluronate; Dimethyl sulfoxide and related compounds such as Cyclic sulfoxides, Decylmethyl sulfoxide, Dimethyl sulfoxide (DMSO), and 2-Hydroxyundecyl methyl sulfoxide; Solvents and related compounds such as Acetone, n-Alkanes (chain length between 7 and 16), Cyclohexyl-1,1-dimethylethanol, Dimethylacetamide, Dimethyl formamide, Ethanol, Ethanol/d-limonene combination, 2-Ethyl-1,3-hexanediol, Ethoxydiglycol (TRANSCUTOL), Glycerol, Glycols, Lauryl chloride, Limonene, N-Methylformamide, 2-Phenylethanol, 3-Phenyl-1-propanol, 3-Phenyl-2-propen-1-ol, Polyethylene glycol, Polyoxyethylene sorbitan monoesters, Polypropylene glycol, Primary alcohols (tridecanol), Propylene glycol, Squalene, Triacetin, Trichloroethanol, Trifluoroethanol, Trimethylene glycol, and Xylene; Azone and related compounds such as N-Acyl-hexahydro-2-oxo-1H-azepines, N-Alkyl-dihydro-1,4-oxazepine-5,7-diones, N-Alkylmorpholine-2,3-diones, N-Alkylmorpholine-3,5-diones, Azacycloalkane derivatives (-ketone, -thione), Azacycloalkenone derivatives, 1-[2-(Decylthio)ethyl]azacyclopentan-2-one (HPE-101), N-(2,2-Dihydroxyethyl)dodecylamine, 1-Dodecanoylhexahydro-1-H-azepine, 1-Dodecyl azacycloheptan-2-one (AZONE or laurocapram), N-Dodecyl diethanolamine, N-Dodecylhexahydro-2-thio-1H-azepine, N-Dodecyl-N-(2-methoxyethyl)acetamide, N-Dodecyl-N-(2-methoxyethyl) isobutyramide, N-Dodecyl-piperidine-2-thione, N-Dodecyl-2-piperidinone, N-Dodecyl pyrrolidine-3,5-dione, N-Dodecyl pyrrolidine-2-thione, N-Dodecyl-2-pyrrolidone, 1-Famesylazacycloheptan-2-one, 1-Famesylazacyclopentan-2-one, 1-Geranylazacycloheptan-2-one, 1-Geranylazacyclopentan-2-one, Hexahydro-2-oxo-azepine-1-acetic acid esters, N-(2-Hydroxyethyl)-2-pyrrolidone, 1-Laurylazacycloheptane, 2-(1-Nonyl)-1,3-dioxolane, 1-N-Octylazacyclopentan-2-one, N-(1-Oxododecyl)-hexahydro-1H-azepine, N-(1-Oxododecyl)-morpholines, 1-Oxohydrocarbyl-substituted azacyclohexanes, N-(1-Oxotetradecyl)-hexahydro-2-oxo-1H-azepine, and N-(1-Thiododecyl)-morpholines; and others such as Aliphatic thiols, Alkyl N,N-dialkyl-substituted amino acetates, Anise oil, Anticholinergic agent pretreatment, Ascaridole, Biphasic group derivatives, Bisabolol, Cardamom oil, 1-Carvone, Chenopodium (70% ascaridole), Chenopodium oil, 1,8 Cineole (eucalyptol), Cod liver oil (fatty acid extract), 4-Decyloxazolidin-2-one, Dicyclohexylmethylamine oxide, Diethyl hexadecylphosphonate, Diethyl hexadecylphosphoramidate, N,N-Dimethyl dodecylamine-N-oxide, 4,4-Dimethyl-2-undecyl-2-oxazoline, N-Dodecanoyl-L-amino acid methyl esters, 1,3-Dioxacycloalkanes (SEPAs), Dithiothreitol, Eucalyptol (cincole), Eucalyptus oil, Eugenol, Herbal extracts, Lactam N-acetic acid esters, N-Hydroxyethalaceamide, N-Hydroxyethylacetamide, 2-Hydroxy-3-oleoyloxy-1-pyroglutamyloxypropane, Menthol, Menthone, Morpholine derivatives, N-Oxide, Nerolidol, Octyl-β-D-(thio)glucopyranosides, Oxazolidinones, Piperazine derivatives, Polar lipids, Polydimethylsiloxanes, Poly [2-(methylsulfinyl)cthyl acrylate], Polyrotaxanes, Polyvinylbenzyldimethylalkylammonium chloride, Poly(N-vinyl-N-methyl acetamide), Sodium pyroglutaminate, Terpenes and azacyclo ring compounds, Vitamin E (α-tocopherol), Vitamin E TPGS and Ylang-ylang oil. Additional examples of penetration enhancers not listed above can be found in "Handbook of Pharmaceutical Excipients", Fifth edition, and include glycofurol, lanolin, light mineral oil, myristic acid, polyoxyethylene alky ethers, and thymol. Other examples of penetration enhancers include ethanolamine, diethanolamine, triethanolamine, diethylene glycol, monoethyl ether, citric acid, succinic acid, borage oil, tetrahydropiperine (THP), methanol, ethanol, propanol, octanol, benzyl alcohol, myristyl alcohol, cetyl alcohol, stearyl alcohol, and polyethylene glycol monolaurate.

In some embodiments, the topical compositions comprise alcohols, $C_1$-$C_4$ aliphatic alcohols, and/or $C_1$-$C_5$ aliphatic alcohols. In other embodiments, the topical compositions are free of/do not include or contain $C_1$-$C_4$ aliphatic alcohols, and/or $C_1$-$C_5$ aliphatic alcohols. In some embodiments, the topical compositions comprise volatile solvents. In other embodiments, the topical compositions are free of/do not include volatile solvents. Volatile solvents are also known as "fugitive" solvents. Non-limiting examples of volatile solvents include volatile alcohols, such as $C_1$ to $C_4$ aliphatic alcohols; $C_1$ to $C_5$ alcohols; and volatile $C_1$ to $C_4$ aliphatic ketones, such as acetone.

In some embodiments, the topical compositions comprise surfactants. In other embodiments, the topical compositions are free of/do not include surfactants. The term "surfactant" or "surface active agent" means a compound or material or substance that exhibits the ability to lower the surface tension of water or to reduce the interfacial tension between two immiscible substances and includes anionic, cationic, nonionic, amphoteric, and/or phospholipid surfactants. Non-limiting examples of surfactants can be found in McCutcheon's Emulsifiers & Detergents, 2001 North American Edition herein incorporated by reference and also in the International Cosmetic Ingredient Dictionary and Handbook (INCI), 12th Edition, 2008, herein incorporated by reference. Such examples include, but are not limited to, the following: block polymers, e.g., Poloxamer 124; ethoxylated alcohols e.g., Ceteth-2, Ceteareth-20, Laureth-3; ethoxylated fatty esters and oils, e.g., PEG-40 Hydrogenated Castor Oil, PEG-36 Castor Oil, PEG-150 Distearate; glycerol esters, e.g., Polyglyceryl-3 Diisostearate, Glyceryl Stearate; glycol esters, PEG-12 Dioleate, LEXEMUL P; phosphate esters, e.g., Cetyl Phosphate; polymeric surfactants, e.g., PVM/MA Copolymer, Acrylates/C10-30 Alkyl Acrylate Crosspolymer; quaternary surfactants, e.g., Cetrimonium Chloride; Silicone Based Surfactants, e.g., PEG/ PPG-20/6 Dimethicone; Sorbitan Derivatives, e.g., Sorbitan Stearate, Polysorbate 80; sucrose and glucose esters and derivatives, e.g., PEG-20 Methyl Glucose Sesquistearate; and sulfates of alcohols, e.g., Sodium Lauryl Sulfate. More generally, surfactants can be classified by their ionic type such as anionic, cationic, nonionic, or amphoteric. They can also be classified by their chemical structures, such as block polymers, ethoxylated alcohols, ethoxylated fatty esters and oils, glycerol esters, glycol esters, phosphate esters, polymeric surfactants, quaternary surfactants, silicone-based surfactants, sorbitan derivatives, sucrose and glucose esters and derivatives, and sulfates of alcohols.

In some embodiments, the topical compositions comprise proteins, such as albumin. In other embodiments, the topical compositions are free of/do not include proteins, such as albumin.

In a preferred embodiment, the topical composition is a hydrophobic composition comprising a hydrophobic carrier, one or more volatile silicone fluids, and taxane particles, wherein the mean particle size (number) of the taxane particles is from 0.1 microns to 1.5 microns. In further preferred embodiments, the hydrophobic carrier comprises petrolatum, mineral oil, or paraffin wax, or mixtures thereof. In further preferred embodiments, the one or more volatile silicone fluid is cyclomethicone at a concentration of from 5 to 25% w/w of the composition. In further preferred embodiments, the taxane particles are paclitaxel particles.

4. Concentration of Antineoplastic Particles in Topical Compositions

The concentration or amount of the antineoplastic particles in the topical composition is at an "effective amount" to (1) stimulate an immunological response to the immunotherapeutic agent in the subject, and (2) treat the tumor(s) of the subject, i.e., to provide a therapeutic effect on the tumor by accomplishing one or more of the following: (a) reducing tumor size; (b) reducing tumor growth rate; (c) eliminating the tumor. The concentration of the antineoplastic particles, which can be taxane particles, can be from 0.05 to 10% w/w, or the concentration of the antineoplastic particles can be from 0.05 to 5% w/w, or the concentration of the antineoplastic particles can be from 0.1 to 5% w/w, or the concentration of the antineoplastic particles can be 0.05, 0.1, 0.15, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, 3.0, 3.1, 3.2, 3.25, 3.3, 3.4, 3.5, 3.6, 3.7, 3.75, 3.8, 3.9, 4.0, 4.1, 4.2, 4.25, 4.3, 4.4, 4.5, 4.6, 4.7, 4.75, 4.8, 4.9, 5, 6, 7, 8, 9, or 10% w/w or any percentage derivable therein of the total composition weight. In some embodiments, the antineoplastic particles are taxane particles, such as paclitaxel nanoparticles, docetaxel nanoparticles, or cabazitaxel nanoparticles. In some embodiments, the taxane particles are paclitaxel particles. In some embodiments, the taxane particles are at a concentration of about 0.05 to less than 3% w/w, or about 0.05 to about 2% w/w, or about 0.05 to about 1% w/w, or about 0.05 to about 0.3% w/w, or about 0.05 to about 0.2% w/w, or about 0.05 to about 0.15% w/w, or about 0.1 to about 2% w/w, or about 0.1 to about 1% w/w, or about 0.1 to about 0.3% w/w, or about 0.1 to about 0.2% w/w, or about 0.15 to about 2% w/w, or about 0.15 to about 1% w/w, or about 0.15 to about 0.3% w/w, or about 0.3 to about 2% w/w, or about 0.3 to about 1% w/w, or about 1 to about 2% w/w, or about 0.2 to about 0.4% w/w, or about 0.5 to about 1.5% w/w, or about 1.5 to about 2.5% w/w in the compositions. In other embodiments, the concentration of the taxane particles is 80 to 120% of 1% w/w (i.e., 0.8 to 1.2% w/w), or 80 to 120% of 0.05% w/w, or 80 to 120% of 0.1% w/w, or 80 to 120% of 0.15% w/w, or 80 to 120% of 0.2% w/w, or 80 to 120% of 0.25% w/w, or 80 to 120% of 0.3% w/w, or 80 to 120% of 0.35% w/w, or 80 to 120% of 0.4% w/w, or 80 to 120% of 0.45% w/w, or 80 to 120% of 0.5% w/w, or 80 to 120% of 0.55% w/w, or 80 to 120% of 0.6% w/w, or 80 to 120% of 0.65% w/w, or 80 to 120% of 0.7% w/w, or 80 to 120% of 0.75% w/w, or 80 to 120% of 0.8% w/w, or 80 to 120% of 0.85% w/w, or 80 to 120% of 0.9% w/w, or 80 to 120% of 0.95% w/w, or 80 to 120% of 1.5% w/w, or 80 to 120% of 2% w/w, or 80 to 120% of 2.5% w/w.

B. Compositions for Pulmonary Administration, Intratumoral (IT) Injection and/or Intraperitoneal (IP) Injection The compositions suitable for pulmonary administration, intratumoral (IT) injection and/or intraperitoneal (IP) injection comprise antineoplastic particles, such as taxane particles and are described below. The compositions can further comprise a carrier. The compositions can be anhydrous and include an anhydrous carrier. The carrier can be a liquid (fluid) carrier, such as an aqueous carrier. Non-limiting examples of suitable aqueous carriers include water, such as Sterile Water for Injection USP; 0.9% saline solution (normal saline), such as 0.9% Sodium Chloride for Injection USP; dextrose solution, such as 5% Dextrose for Injection USP; and Lactated Ringer's Solution for Injection USP. Non-aqueous based liquid carriers and other aqueous-based liquid carriers can be used. The carrier can be a pharmaceutically acceptable carrier, i.e., suitable for administration to a subject by injection, pulmonary route, or other routes of administration. The carrier can be any other type of liquid such as emulsions or flowable semi-solids. Non-limiting examples of flowable semisolids include gels and thermosetting gels. The composition can be a suspension, i.e., a suspension dosage form composition where the antineoplastic particles, such as taxane particles, are dispersed (suspended) within a continuous carrier/and or diluent. The antineoplastic particles can be completely dispersed, partially dispersed and partially dissolved, but not completely dissolved in the carrier. In some embodiments, the composition is a suspension of taxane particles dispersed within a continuous carrier. In a preferred embodiment, the carrier is a pharmaceutically acceptable carrier. In preferred embodiments, the composition is sterile. In various embodiments, the composition comprises, consists essentially of, or consists of antineoplastic particles and a liquid carrier, wherein the composition is a suspension of the antineoplastic particles dispersed within the liquid carrier. In some embodiments, the composition consists essentially of or consists of antineoplastic particles and a carrier, wherein the carrier is an aqueous carrier and wherein the composition is a suspension.

The composition of antineoplastic particles and a carrier can be administered as-is. Optionally, the composition of antineoplastic particles and a carrier can further comprise a suitable diluent to dilute the composition in order to achieve a desired concentration (dose) of antineoplastic particles. In some embodiments, the carrier can serve as the diluent; stated another way, the amount of carrier in the composition provides the desired concentration of antineoplastic particles in the composition and no further dilution is needed. A suitable diluent can be a fluid, such as an aqueous fluid. Non-limiting examples of suitable aqueous diluents include water, such as Sterile Water for Injection USP; 0.9% saline solution (normal saline), such as 0.9% Sodium Chloride for Injection USP; dextrose solution, such as 5% Dextrose for Injection USP; and Lactated Ringer's Solution for Injection USP. Other liquid and aqueous-based diluents suitable for administration by injection can be used and can optionally include salts, buffering agents, and/or other excipients. In preferred embodiments, the diluent is sterile. The composition can be diluted with the diluent at a ratio to provide a desired concentration dosage of the antineoplastic particles. For example, the volume ratio of composition to diluent might be in the range of 1:1-1:100 v/v or other suitable ratios. In some embodiments, the composition comprises antineoplastic particles, a carrier, and a diluent, wherein the carrier and diluent form a mixture, and wherein the composition is a suspension of antineoplastic particles dispersed in the carrier/diluent mixture. In some embodiments, the carrier/diluent mixture is a continuous phase and the antineoplastic particles are a dispersed phase.

The composition, carrier, and/or diluent can further comprise functional ingredients such as buffers, salts, osmotic agents, surfactants, viscosity modifiers, rheology modifiers, suspending agents, pH adjusting agents such as alkalinizing agents or acidifying agents, tonicity adjusting agents, preservatives, antimicrobial agents including quaternary ammonium compounds such as benzalkonium chloride and benzethonium chloride, demulcents, antioxidants, antifoaming agents, chelating agents, and/or colorants. For example, the composition can comprise taxane particles and a carrier comprising water, a salt, a surfactant, and optionally a buffer. In one embodiment, the carrier is an aqueous carrier and comprises a surfactant, wherein the concentration of the surfactant is 1% or less on a w/w or w/v basis; in other embodiments, the surfactant is less than 0.5%, less than 0.25%, less than 0.1%, or about 0.1%. In other embodiments, the aqueous carrier excludes the surfactants GELUCIRE® (polyethylene glycol glycerides composed of mono-, di- and triglycerides and mono- and diesters of polyethylene glycol) and/or CREMOPHOR® (polyethoxylated castor oil). In some embodiments, the composition or carrier excludes polymers, proteins (such as albumin), polyethoxylated castor oil, and/or polyethylene glycol glycerides composed of mono-, di- and triglycerides and mono- and diesters of polyethylene glycol.

The composition, carrier, and/or diluent can comprise one or more surfactants. Suitable surfactants include by way of example and without limitation polysorbates, lauryl sulfates, acetylated monoglycerides, diacetylated monoglycerides, and poloxamers, such as poloxamer 407. Polysorbates are polyoxyethylene sorbitan fatty acid esters which are a series of partial fatty acid esters of sorbitol and its anhydrides copolymerized with approximately 20, 5, or 4 moles of ethylene oxide for each mole of sorbitol and its anhydrides. Non-limiting examples of polysorbates are polysorbate 20, polysorbate 21, polysorbate 40, polysorbate 60, polysorbate 61, polysorbate 65, polysorbate 80, polysorbate 81, polysorbate 85, and polysorbate 120. Polysorbates containing approximately 20 moles of ethylene oxide are hydrophilic nonionic surfactants. Examples of polysorbates containing approximately 20 moles of ethylene oxide include polysorbate 20, polysorbate 40, polysorbate 60, polysorbate 65, polysorbate 80, polysorbate 85, and polysorbate 120. Polysorbates are available commercially from Croda under the tradename TWEEN™. The number designation of the polysorbate corresponds to the number designation of the TWEEN, e.g., polysorbate 20 is TWEEN 20, polysorbate 40 is TWEEN 40, polysorbate 60 is TWEEN 60, polysorbate 80 is TWEEN 80, etc. USP/NF grades of polysorbate include polysorbate 20 NF, polysorbate 40 NF, polysorbate 60 NF, and polysorbate 80 NF. Polysorbates are also available in PhEur grades (European Pharmacopoeia), BP grades, and JP grades. The term "polysorbate" is a non-proprietary name.

The chemical name of polysorbate 20 is polyoxyethylene 20 sorbitan monolaurate. The chemical name of polysorbate 40 is polyoxyethylene 20 sorbitan monopalmitate. The chemical name of polysorbate 60 is polyoxyethylene 20 sorbitan monostearate. The chemical name of polysorbate 80 is polyoxyethylene 20 sorbitan monooleate. In some embodiments, the composition, carrier, and/or diluent can comprise mixtures of polysorbates. In some embodiments, the composition, carrier, and/or diluent comprises polysorbate 20, polysorbate 40, polysorbate 60, polysorbate 65, polysorbate 80, polysorbate 85, and/or polysorbate 120. In some embodiments, the composition, carrier, and/or diluent comprises polysorbate 20, polysorbate 40, polysorbate 60, and/or polysorbate 80. In one embodiment, the composition, carrier, and/or diluent comprises polysorbate 80.

In some embodiments, the composition comprises antineoplastic particles, a carrier, and optionally a diluent, wherein the carrier and/or diluent comprises water and a polysorbate. In one embodiment, the composition is a suspension, the antineoplastic particles are taxane particles, and the polysorbate is polysorbate 80. In other embodiments, the polysorbate or polysorbate 80 is present in the composition, carrier, and/or diluent at a concentration of between about 0.01% v/v and about 1.5% v/v. The inventors have surprisingly discovered that the recited very small amounts of polysorbate 80 reduce the surface tension at the interface of the antineoplastic particles and the aqueous carrier (such as saline solution). These embodiments are typically formulated near the time of use of the composition. In some embodiments, the particles may be coated with the polysorbate or polysorbate 80. In other embodiments, the particles are not coated with the polysorbate or polysorbate 80. In various other embodiments, the polysorbate or polysorbate 80 is present in the composition, carrier, and/or diluent at a concentration of between: about 0.01% v/v and about 1% v/v, about 0.01% v/v and about 0.5% v/v, about 0.01% v/v and about 0.4% v/v, about 0.01% v/v and about 0.35% v/v, about 0.01% v/v and about 0.3% v/v, about 0.01% v/v and about 0.25% v/v, about 0.01% v/v and about 0.2% v/v, about 0.01% v/v and about 0.15% v/v, about 0.01% v/v and about 0.1% v/v, about 0.05% v/v and about 1% v/v, about 0.05% v/v and about 0.5% v/v, about 0.05% v/v and about 0.4% v/v, about 0.05% v/v and about 0.35% v/v, about 0.05% v/v and about 0.3% v/v, about 0.05% v/v and about 0.25% v/v, about 0.05% v/v and about 0.2% v/v, about 0.05% v/v and about 0.15% v/v, about 0.05% v/v and about 0.1% v/v, about 0.1% v/v and about 1% v/v, about 0.1% v/v and about 0.5% v/v, about 0.1% v/v and about 0.4% v/v, about 0.1% v/v and about 0.35% v/v, about 0.1% v/v and about 0.3% v/v, about 0.1% v/v and about 0.25% v/v, about 0.1% v/v and about 0.2% v/v, about 0.1% v/v and about 0.15% v/v, about 0.2% v/v and about 1% v/v, about 0.2% v/v and about 0.5% v/v, about 0.2% v/v and about 0.4% v/v, about 0.2% v/v and about 0.35% v/v, about 0.2% v/v and about 0.3% v/v, about 0.2% v/v and about 0.25% v/v, about 0.3% v/v and about 1% v/v, about 0.3% v/v and about 0.5% v/v, about 0.3% v/v and about 0.4% v/v, or about 0.3% v/v and about 0.35% v/v; or about 0.01%, about 0.05%, about 0.1% v/v, about 0.15% v/v, about 0.16% v/v, about 0.2% v/v, about 0.25% v/v, about 0.3% v/v, about 0.35% v/v, about 0.4% v/v, about 0.45% v/v, about 0.5% v/v, or about 1% v/v.

The composition, carrier, and/or diluent can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

The composition, carrier, and/or diluent can comprise one or more buffering agents. Suitable buffering agents include by way of example and without limitation, dibasic sodium phosphate, monobasic sodium phosphate, citric acid, sodium citrate, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The composition, carrier, and/or diluent can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, and propylene glycol; polyvinyl alcohol from about 0.1 to about 4%; povidone from about 0.1 to about 2%; and dextran 70 from about 0.1% when used with another polymeric demulcent described herein.

The composition, carrier, and/or diluent can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The composition, carrier, and/or diluent can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The composition, carrier, and/or diluent can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

The composition, carrier, and/or diluent can comprise one or more viscosity modifiers that increase or decrease the viscosity of the suspension. Suitable viscosity modifiers include methylcellulose, hydroxypropyl methycellulose, mannitol, polyvinylpyrrolidone, cross-linked acrylic acid polymers such as carbomer, and others known to those of ordinary skill in the art. The composition, carrier, and/or diluent can further comprise rheology modifiers to modify the flow characteristics of the composition to allow it to adequately flow through devices such as injection needles or tubes. Non-limiting examples of viscosity and rheology modifiers can be found in "Rheology Modifiers Handbook-Practical Use and Application" Braun, William Andrew Publishing, 2000.

The concentration or amount of antineoplastic particles in a composition for pulmonary administration, intratumoral injection, or intraperitoneal injection is at an "effective amount" to (1) stimulate an immunological response to the immunotherapeutic agent in the subject, and (2) treat the tumor(s) of the subject, i.e., to provide a therapeutic effect on the tumor by accomplishing one or more of the following: (a) reducing tumor size; (b) reducing tumor growth rate; (c) eliminating the tumor. In one embodiment, the concentration of the antineoplastic particles, which can be taxane particles, in the composition is between about 0.1 mg/mL and about 100 mg/mL. In various further embodiments, the concentration of antineoplastic particles, which can be taxane particles, in the composition is between: about 0.5 mg/mL and about 100 mg/mL, about 1 mg/mL and about 100 mg/mL, about 2 mg/mL and about 100 mg/mL, about 5 mg/mL and about 100 mg/mL, about 10 mg/mL and about 100 mg/mL, about 25 mg/mL and about 100 mg/mL, about 30 mg/mL and about 100 mg/mL, about 0.1 mg/mL and about 75 mg/mL, about 0.5 mg/mL and about 75 mg/mL, about 1 mg/mL and about 75 mg/mL, about 2 mg/mL and about 75 mg/mL, about 5 mg/mL and about 75 mg/mL, about 10 mg/mL and about 75 mg/mL, about 25 mg/mL and about 75 mg/mL, about 30 mg/mL and about 75 mg/mL, about 0.1 mg/mL and about 50 mg/mL, about 0.5 mg/mL and about 50 mg/mL, about 1 mg/mL and about 50 mg/mL, about 2 mg/mL and about 50 mg/mL, about 5 mg/mL and about 50 mg/mL, about 10 mg/mL and about 50 mg/mL, about 25 mg/mL and about 50 mg/mL, about 30 mg/mL and about 50 mg/mL, about 0.1 mg/mL and about 40 mg/mL, about 0.5 mg/mL and about 40 mg/mL, about 1 mg/mL and about 40 mg/mL, about 2 mg/mL and about 40 mg/mL, about 5 mg/mL and about 40 mg/mL, about 10 mg/mL and about 40 mg/mL, about 25 mg/mL and about 40 mg/mL, about 30 mg/mL and about 40 mg/mL, about 0.1 mg/mL and about 30 mg/mL, about 0.5 mg/mL and about 30 mg/mL, about 1 mg/mL and about 30 mg/mL, about 2 mg/mL and about 30 mg/mL, about 5 mg/mL and about 30 mg/mL, about 10 mg/mL and about 30 mg/mL, about 25 mg/mL and about 30 mg/mL, about 0.1 mg/mL and about 25 mg/mL, about 0.5 mg/mL and about 25 mg/mL, about 1 mg/mL and about 25 mg/mL, about 2 mg/mL and about 25 mg/mL, about 5 mg/mL and about 25 mg/mL, about 10 mg/mL and about 25 mg/mL, about 0.1 mg/mL and about 20 mg/mL, about 0.5 mg/mL and about 20 mg/mL, about 1 mg/mL and about 20 mg/mL, about 2 mg/mL and about 20 mg/mL, about 5 mg/mL and about 20 mg/mL, about 10 mg/mL and about 20 mg/mL, about 0.1 mg/mL and about 15 mg/mL, about 0.5 mg/mL and about 15 mg/mL, about 1 mg/mL and about 15 mg/mL, about 2 mg/mL and about 15 mg/mL, about 5 mg/mL and about 15 mg/mL, about 10 mg/mL and about 15 mg/mL, about 0.1 mg/mL and about 10 mg/mL, about 0.5 mg/mL and about 10 mg/mL, about 1 mg/mL and about 10 mg/mL, about 2 mg/mL and about 10 mg/mL, about 5 mg/mL and about 10 mg/mL, about 0.1 mg/mL and about 5 mg/mL, about 0.5 mg/mL and about 5 mg/mL, about 1 mg/mL and about 5 mg/mL, about 2 mg/mL and about 5 mg/mL, about 0.1 mg/mL and about 2 mg/mL, about 0.5 mg/mL and about 2 mg/mL, about 1 mg/mL and about 2 mg/mL, about 0.1 mg/mL and about 1 mg/mL, about 0.5 mg/mL and about 1 mg/mL, about 0.1 mg/mL and about 0.5 mg/mL, about 3 mg/mL and about 8 mg/mL, or about 4 mg/mL and about 6 mg/mL; or at least about 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 61, 65, 70, 75, or 100 mg/mL; or about 0.1, 0.5, 1, 2, 3, 4, 5, 6, 7, 8, 9, 10, 11, 12, 13, 14, 15, 16, 17, 18, 19, 20, 25, 30, 35, 40, 41, 42, 43, 44, 45, 46, 47, 48, 49, 50, 55, 60, 61, 65, 70, 75, or 100 mg/mL. The antineoplastic particles may be the sole therapeutic agent administered, or may be administered with other therapeutic agents.

In various embodiments, the composition comprises taxane particles (paclitaxel particles or docetaxel particles), a carrier, and a diluent, wherein the concentration of taxane particles in the composition (including the carrier and diluent) is between: about 1 mg/ml and about 40 mg/mL, about 5 mg/mL and about 20 mg/mL, about 5 mg/mL and about 15 mg/mL, about 5 mg/mL and about 10 mg/mL, about 6 mg/mL and about 20 mg/mL, about 6 mg/mL and about 15 mg/mL, about 6 mg/mL and about 10 mg/mL, about 10 mg/mL and about 20 mg/mL, or about 10 mg/mL and about 15 mg/mL; or about 6 mg/mL, about 10 mg/mL, or about 15 mg/mL. In further embodiments, the carrier is an aqueous carrier which can be saline solution, such as about 0.9% sodium chloride solution and the diluent is an aqueous diluent which can be saline solution, such as about 0.9% sodium chloride solution. In further embodiments, the aqueous carrier comprises a polysorbate, such as polysorbate 80.

In some embodiments, the compositions are free of/do not include or contain a polymer/copolymer or biocompatible polymer/copolymer. In some embodiments, the compositions are free of/do not include or contain a protein. In some aspects of the invention, the compositions are free of/do not include or contain albumin. In some aspects of the invention, the compositions are free of/do not include or contain hyaluronic acid. In some aspects of the invention, the compositions are free of/do not include or contain a conjugate of hyaluronic acid and a taxane. In some aspects of the invention, the compositions are free of/do not include or contain a conjugate of hyaluronic acid and paclitaxel. In some aspects of the invention, the compositions are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), Vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), Poly (bis(P-carboxyphenoxy)propane-sebacic acid, poly(d,l-lactic acid) (PLA), poly(d,l-lactic acid-co-glycolic acid) (PLAGA), and/or poly(D, L lactic-co-glycolic acid (PLGA).

In a preferred embodiment, the composition suitable for pulmonary administration, intratumoral injection, and/or intraperitoneal injection comprises taxane particles and a liquid carrier, wherein the taxane particles have a mean particle size (number) of from 0.1 microns to 1.5 microns. In further preferred embodiments, the taxane particles are paclitaxel particles. In further preferred embodiments, the liquid carrier is an aqueous carrier.

III. Immunotherapeutic Agents and Compositions for Systemic Delivery of Immunotherapeutic Agents There are several classes of immunotherapeutic agents used in the treatment of cancer and include, but are not limited to, the following classes:

Monoclonal Antibodies: drugs that are designed to bind to specific targets in the body. Non-limiting examples of monoclonal antibodies include pertuzumab, trastuzumab, ado-tastruzumab emtansine, bevacizumab, ramucirumab, margetuximab, vantictumab, glembatumumab vedotin, cetuximab, bavituximab, rilotumumab, nivolumab, pembrolizumab, and atezolizumab.

Cancer Vaccines: These agents work against cancer by boosting the immune system's response to cancer cells. Non-limiting examples of cancer vaccines include nelipepimut-S, tergenpumatucel-L, and racotumomab.

Non-specific Immunotherapies/Cytokines: proteins that are made by the body's cells; play important roles in the body's normal immune responses and also in the immune system's ability to respond to cancer. Non-limiting examples include colony stimulating factors, interferon, and interleukin such as interleukin-2 and interleukin-7.

Immune Checkpoint Inhibitors/Immune Modulators: take the 'brakes' off the immune system, which helps it recognize and attack cancer cells. Non-limiting examples include ipilimumab, pembrolizumab, and nivolumab.

Adoptive Cell Transfer/T Cell Therapy/Cellular Therapy: attempts to boost the natural ability of your T cells to fight cancer. Non-limiting examples include tumor infiltrating lymphocytes, T-cells targeting HER2, cMET proteins, CEA, VEGFR-2, MAGE-A3, and lung cancers expressing NY-ESO-1 cancer antigen.

Oncolytic Virus Therapy: uses genetically modified viruses to kill cancer cells. Non-limiting examples include reovirus.

BCG (Bacillus Calmette-Guérin): weakened form of the bacteria that causes tuberculosis; causes an immune response against cancer cells.

In some embodiments, the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent. In some embodiments, the immunotherapeutic agent is pembrolizumab.

The compositions useful for systemic administration, i.e., the second composition of the invention, are compositions that comprise the immunotherapeutic agents described herein and throughout this disclosure, and are suitable for systemic administration, such as enteral administration or parenteral administration. Non-limiting examples of routes of systemic administration include intravenous (IV), intramuscular, intraarticular, infusion, oral, rectal, buccal, and sublingual. The compositions can comprise a suitable carrier such as a pharmaceutical carrier. In preferred embodiments, the compositions are sterile.

IV. Methods of Administration and Treatment

In one aspect of the invention, disclosed is a method of treating cancer in a subject, the method comprising: (a) administering locally to a malignant tumor of the subject, a first composition comprising antineoplastic particles, and (b) administering systemically to the subject, a second composition comprising an immunotherapeutic agent, thereby treating the cancer, wherein the antineoplastic particles have a mean particle size (number) of from 0.1 microns to 5 microns.

A. Local Administration Methods

Local administration of compositions comprising antineoplastic agent particles directly to a tumor include topical application, pulmonary administration, intratumoral injection, and intraperitoneal injection. The compositions for local administration as described herein and throughout this disclosure are compositions suitable for use in the various types of local administration, i.e., topical application, pulmonary administration, intratumoral injection, and intraperitoneal injection.

1. Topical Application Methods

In one aspect of the invention, disclosed is a method of treating cancer in a subject, the method comprising: (a) topically administering a first composition comprising antineoplastic particles to the affected area of a skin tumor of the subject and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. The skin tumor can be benign, e.g., actinic keratosis; or malignant (skin malignancy), e.g. skin cancer or cutaneous metastasis. In some embodiments, the tumor in step (a) is a benign tumor, and the subject has cancer elsewhere in the body. In some embodiments, the tumor in step (a) is a malignant tumor and is the only cancer in the body of the subject. In other embodiments, the tumor in step (a) is a malignant tumor and the subject also has cancer elsewhere in the body. The "affected area" of a benign skin tumor or skin malignancy can include at least a portion of the skin where the benign skin tumor or skin malignancy is visibly present on the outermost surface of the skin or directly underneath the surface of the skin (epithelial/dermal covering), and can include areas of the skin in the proximity of the benign skin tumor or skin malignancy likely to contain visibly undetectable preclinical lesions. The skin malignancy can be a skin cancer or a cutaneous metastasis. In some embodiments, the skin malignancy is a cutaneous metastasis. In other embodiments, the skin malignancy is a skin cancer. The cutaneous metastasis can be from a variety of primary cancers, such as the following non-limiting examples of primary cancers: breast, lung, nasal, sinus, larynx, oral cavity, colon (large intestine), rectum, stomach, ovary, testis, bladder, prostate, cervical, vaginal, thyroid, endometrial, kidney, esophagus, pancreas, liver, melanoma, and Kaposi's sarcoma (including AIDS-related Kaposi's sarcoma). In some embodiments, the cutaneous metastasis is from lung cancer, breast cancer, colon cancer, oral cancer, ovarian cancer, kidney cancer, esophageal cancer, stomach cancer, or liver cancer. In some embodiments, the cutaneous metastasis is from breast cancer. Non-limiting examples of skin cancers include melanoma, basal cell carcinoma, and squamous cell carcinoma. In some embodiments, the method does not include additional skin-directed therapies, such as electrochemotherapy (ECT), photodynamic therapy (PDT), radiotherapy (RT), or intralesional therapy (ILT).

The amount of the composition topically applied to the affected area of the skin malignancy can vary depending on the size of the affected area and the concentration of the antineoplastic particles in the composition, but generally can be applied at approximately the thickness of a dime to fully cover the affected area. Another suitable method for determining the amount of composition to apply is the "Finger-Tip Unit" (FTU) approach. One FTU is the amount of topical composition that is squeezed out from a standard tube along an adult's fingertip (This assumes the tube has a standard 5 mm nozzle). A fingertip is from the very end of the finger to the first crease in the finger. The composition can be applied with a gloved hand or spatula or other means of topical administration. In some embodiments, the composition is applied to skin malignancies which have an intact skin covering (epithelial/dermal covering). In some embodiments, the composition is applied to ulcerated areas where the skin malignancy lesion is on the surface of the skin or where the skin covering is degraded and the skin malignancy lesion is exposed. The affected area can be gently cleansed with water (and mild soap if required) and dried prior to application. Once the composition is applied, the application site can be covered with an occlusive dressing such as TEGADERM® or SOLOSITE®. The dosing of the composition can vary, but generally can include an application once, twice, or three times daily at approximately the same time each day until the condition is improved or eliminated.

2. Pulmonary Administration Methods

Disclosed herein is a method of treating cancer in a subject, the method comprising: (a) administering a first composition comprising antineoplastic particles to the subject by pulmonary administration, and (b) systemically administering a second composition comprising an immunotherapeutic agent to the subject, thereby treating the cancer, wherein the antineoplastic particles have a mean particle size (number) of from 0.1 microns to 5 microns, wherein the subject has a lung disease, and wherein steps (a) and (b) can be conducted in any order or at the same time. The lung disease can be non-cancerous or cancerous. In some embodiments, the lung disease is non-cancerous, and the subject has cancer in areas of the body other than in the lung. The non-cancerous lung disease can be restrictive lung disease such as pulmonary fibrosis or obstructive lung disease such as chronic obstructive lung disease (COPD). In other embodiments, the lung disease is cancerous. In some embodiments, the cancerous lung disease is a malignant tumor or mesothelioma. A malignant lung tumor is any tumor present within the lungs, and may be a primary or a metastatic lung tumor. Non-limiting examples of a malignant lung tumor include small-cell lung carcinoma (SCLC) and non-small-cell lung carcinoma (NSCLC). In one embodiment, the malignant lung tumor is a SCLC. In another embodiment, the malignant lung tumor is a NSCLC. It has been shown that pulmonary administration of taxane particles according to the methods of the invention result in much longer residency times of the taxane in the lungs than was previously possible using any other taxane formulation. As shown in the examples that follow, the taxane remains detectable in lung tissue of the subject for at least 96 hours (4 days) or at least 336 hours (14 days) after the administration. In various further embodiments, the taxane remains detectable in lung tissue of the subject for at least: 108, 120, 132, 144, 156, 168, 180, 192, 204, 216, 228, 240, 252, 264, 276, 288, 300, 312, 324, or 336 hours after the administration. In some embodiments, the cancerous lung disease is the only cancer in the body. In some embodiments, the subject has cancerous lung disease and cancer in other areas of the body.

In one specific embodiment of the invention, pulmonary administration comprises inhalation of the first composition comprising the antineoplastic particles, such as by nasal, oral inhalation, or both. In this embodiment, the first composition comprising the antineoplastic particles may be formulated as an aerosol (i.e.: liquid droplets of a stable dispersion or suspension of the antineoplastic particles in a gaseous medium). Antineoplastic particles delivered as an aerosol composition may be deposited in the airways by gravitational sedimentation, inertial impaction, and/or diffusion. Any suitable device for generating the aerosol may be used, including but not limited to pressurized metered-dose inhalers (pMDI), nebulizers, and soft-mist inhalers. In some embodiments, the antineoplastic particles may be in dry powder form and used in dry powder inhalers (DPI). The drug particles are typically placed in a capsule in a DPI device. Upon actuation, the capsule is ruptured and the cloud of dry powder is expelled. The drug powder can be adjusted to the desired mass median aerodynamic diameter (MMAD) but the most common practice is to blend the small drug powders with a carrier like lactose for pulmonary delivery. The drug particles adhere to the lactose particles by static adhesion. The lactose for pulmonary delivery can be sized to the desired MMAD, such as about 2.5 microns. Other sugars such as mannitol can also be used.

In one specific embodiment, the methods comprise inhalation of the first composition comprising antineoplastic particles aerosolized via nebulization. Nebulizers generally use compressed air or ultrasonic power to create inhalable aerosol droplets of the composition comprising the aerosol particles. In this embodiment, the nebulizing results in pulmonary delivery to the subject of aerosol droplets of the composition comprising the antineoplastic particles. In a preferred embodiment, the antineoplastic particles are taxane particles. In a further preferred embodiment, the taxane particles are paclitaxel particles. A suitable nebulizer is a Hospitak compressed air jet nebulizer.

In another embodiment, the methods comprise inhalation of the first composition comprising antineoplastic particles aerosolized via a pMDI, wherein the composition comprising the antineoplastic particles are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the composition comprising antineoplastic particles. In a preferred embodiment, the antineoplastic particles are taxane particles. In a further preferred embodiment, the taxane particles are paclitaxel particles.

In embodiments where the compositions comprising the antineoplastic particles are aerosolized for administration, the mass median aerodynamic diameter (MMAD) of the aerosol droplets of the compositions comprising the antineoplastic particles may be any suitable diameter for use in the invention. In one embodiment, the aerosol droplets have a MMAD of between about 0.5 µm to about 6 µm diameter. In various further embodiments, the aerosol droplets have a MMAD of between about 0.5 µm to about 5.5 µm diameter, about 0.5 µm to about 5 µm diameter, about 0.5 µm to about 4.5 µm diameter, about 0.5 µm to about 4 µm diameter, about 0.5 µm to about 3.5 µm diameter, about 0.5 µm to about 3 µm diameter, about 0.5 µm to about 2.5 µm diameter, about 0.5 µm to about 2 µm diameter, about 1 µm to about 5.5 µm diameter, about 1 µm to about 5 µm diameter, about 1 µm to about 4.5 µm diameter, about 1 µm to about 4 µm diameter, about 1 µm to about 3.5 µm diameter, about 1 µm to about 3 µm diameter, about 1 µm to about 2.5 µm diameter, about 1 µm to about 2 µm diameter, about 1.5 µm to about 5.5 µm diameter, about 1.5 µm to about 5 µm diameter, about 1.5 µm to about 4.5 µm diameter, about 1.5 µm to about 4 µm diameter, about 1.5 µm to about 3.5 µm diameter, about 1.5 µm to about 3 µm diameter, about 1.5 µm to about 2.5 µm diameter, about 1.5 µm to about 2 µm diameter, about 2 µm to about 5.5 µm diameter, about 2 µm to about 5 µm diameter, about 2 µm to about 4.5 µm diameter, about 2 µm to about 4 µm diameter, about 2 µm to about 3.5 µm diameter, about 2 µm to about 3 µm diameter, and about 2 µm to about 2.5 µm diameter. In preferred embodiments, the antineoplastic particles are taxane particles and the aerosol droplets have a mass median aerodynamic diameter (MMAD) of between about 0.5 µm to about 6 µm diameter, or between about 1 µm to about 3 µm diameter, or about 2 µm to about 3 µm diameter. A suitable instrument for measuring the mass median aerodynamic diameter (MMAD) and geometric standard deviation (GSD) of the aerosol droplets is a seven-stage aerosol sampler such as the Mercer-Style Cascade Impactor.

3. Intratumoral (IT) Injection Methods

Disclosed herein is a method of treating cancer in a subject, the method comprising: (a) administering a first composition comprising antineoplastic particles directly into a solid tumor of the subject by intratumoral injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time.

As used herein, a "solid tumor" is an abnormal mass of tissue that usually does not contain cysts or liquid areas. Solid tumors may be benign (not cancer) or malignant (cancer). Different types of solid tumors are named for the type of cells that form them. Examples of solid malignant tumors are sarcomas, carcinomas, and lymphomas. In some embodiments, the solid tumor is a benign tumor, and the subject has cancer elsewhere in the body. In one particular embodiment, the solid tumor is a malignant solid tumor. In some embodiments, the malignant solid tumor is the only cancer in the body of the subject. In other embodiments, the subject has a malignant solid tumor and cancer in other areas of the body.

As used herein, "directly injected into the tumor" or "intratumoral injection (IT)" means that some or all of the composition, such as a suspension, is injected into the tumor mass. As will be understood by those of skill in the art, such direct injection may include injection of some portion of the composition, such as a suspension, for example, drug on the periphery of the solid tumor ("peritumorally"), such as if the amount of composition or suspension thereof is too large to all be directly injected into the solid tumor mass. In one embodiment, the composition or suspension thereof is injected in its entirety into the solid tumor mass. As used herein the tumor includes both the tumor mass and tumor metastases, including but not limited to bone and soft tissue metastases.

Intratumoral injection of compositions of the antineoplastic particles into the tumor may be accomplished by any suitable means known by one of skill in the art. In non-limiting embodiments, the injection may be carried out via magnetic resonance imaging-transrectal ultrasound fusion (MR-TRUS) guidance (such as for injecting prostate tumors), or via endoscopic ultrasound-guided fine needle injection (EUS-FNI). Suitable intratumoral injection methods and compositions are disclosed in international patent application PCT/US17/25718, herein incorporated by reference.

In various embodiments, the solid tumor is selected from sarcomas, carcinomas, and lymphomas, breast tumors, prostate tumors, head and neck tumors, glioblastomas, bladder tumors, pancreatic tumors, liver tumors, ovarian tumors, colorectal tumors, pulmonary, cutaneous, lymphoid, and/or gastrointestinal tumors. In a specific embodiment, the solid tumor is a prostate tumor and the chemotherapeutic particles are paclitaxel or docetaxel particles. In another specific embodiment, the solid tumor is an ovarian tumor and the chemotherapeutic particles are paclitaxel or docetaxel particles. In another specific embodiment, the solid tumor is a breast tumor and the chemotherapeutic particles are docetaxel particles. In another specific embodiment, the solid tumor is a pancreatic tumor and the chemotherapeutic particles are paclitaxel or docetaxel particles. In any of these embodiments, the tumor may be, for example, an adenocarcinoma.

4. Intraperitoneal (IP) Injection Methods

Disclosed herein is a method of treating cancer in a subject, the method comprising: (a) administering a first composition comprising antineoplastic particles to an intraperitoneal organ tumor of the subject by intraperitoneal injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In some embodiments, the tumor is benign and the subject has cancer elsewhere in the body. In some embodiments, the tumor is malignant. In some embodiments, the malignant tumor is the only cancer in the subject. In other embodiments, the subject has a malignant tumor and cancer elsewhere in the body.

Intraperitoneal organs include the stomach, ileum, jejunum, transverse colon, appendix, sigmoid colon, spleen, the liver, the tail of the pancreas, the first five centimeters of the duodenum, and the upper third part of the rectum. In females, because their peritoneal cavity is open and communicates with their reproductive organs (the oviducts facilitate this communication), the uterus, ovaries, fallopian tubes, and gonadal blood vessels are all within the intraperitoneum and are included as intraperitoneal organs for purposes of this disclosure.

Intraperitoneal injection of the compositions of antineoplastic particles into the tumor may be accomplished by any suitable means known by one of skill in the art. Suitable intraperitoneal injection methods and compositions are disclosed in U.S. Pat. No. 8,221,779, herein incorporated by reference.

In some embodiments, the malignant tumor is ovarian cancer, uterine cancer, stomach cancer, colon cancer, spleen cancer, liver cancer, rectal cancer, and/or pancreatic cancer. In some embodiments, the tumor is an ovarian cancer tumor. In some embodiments, the benign tumor is an ovarian, uterine, stomach, colon, spleen, liver, rectal, and/or pancreatic benign tumor. In some embodiments, the benign tumor is an ovarian tumor.

5. Intracystic Injection Methods

Disclosed herein is a method of treating cancer in a subject, the method comprising: (a) administering a first composition comprising antineoplastic particles directly into a cyst of the subject by intracystic injection, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In various embodiments, the antineoplastic particles have a mean particle size (number) of from 0.1 microns to 1.5 microns. In some embodiments, the cyst is an epithelial cyst. In some embodiments, the cyst is a benign cyst, and the subject has cancer elsewhere in the body. In some embodiments, the cyst is a malignant cyst. In some embodiments, the malignant cyst is the only cancer in the body of the subject. In other embodiments, the subject has a malignant cyst and cancer in other areas of the body. In some embodiments, the cyst is a pancreatic cyst. In other embodiments, the antineoplastic agent is a taxane and the antineoplastic particles are taxane particles. The taxane particles can include pharmaceutically acceptable salts of the taxane particles. In some embodiments, the taxane particles are paclitaxel particles, docetaxel particles, cabazitaxel particles, or combinations thereof. In some embodiments, the local administration of the first composition stimulates an immunological response to the immunotherapeutic agent in the subject after the systemic administration of the second composition.

As used herein, the term "cyst" means an abnormal sac in the body that may be filled with a liquid or semisolid substance. An "epithelial" cyst, has an epithelial inner lining. In some embodiments, the cyst is benign and/or precancerous. In some embodiments, the cyst is cancerous (malignant). Non-limiting examples of epithelial cysts include gastrointestinal cysts such as hepatic cysts, pancreatic cysts, splenic cysts, colon cysts; urologic cysts such as renal cysts, epididymal cysts, prostatic cysts; gynecological cysts such as ovarian cysts and vaginal cysts; head and neck cysts such as thyroid cysts, parathyroid cysts, and other head and neck cysts; as well as other cysts such as Baker's cysts, lung cysts, lymphatic cysts, and pericardial cysts. In some embodiments, the epithelial cyst is a pancreatic cyst. A pancreatic cyst can be an intraductal papillary mucinous neoplasm (IPMN), a mucinous cystic neoplasms (MCN), or a serous cystadenoma. In some embodiments, the pancreatic cyst is an intraductal papillary mucinous neoplasm (IPMN). In other embodiments, the pancreatic cyst is a mucinous cystic neoplasms (MCN). In still other embodiments, the pancreatic cyst is a serous cystadenoma.

The injection of the composition into an epithelial cyst (intracystic injection) can be conducted by use of a procedure known as "endoscopic ultrasound-guided fine needle injection" (EUS-FNI), which is a procedure in which endoscopy is combined with ultrasound to aid in the location of the cyst and to facilitate the injection of the composition into the cyst. A non-limiting exemplary procedure for injection of the composition into a pancreatic cyst is as follows: a linear array echoendoscope is inserted via the mouth and advanced to the stomach or duodenum, whichever provides the best access to the cyst. A 22-gauge fine needle aspiration (FNA) needle is luer locked into the accessory channel of the echoendoscope. The needle tip is maintained in the cyst for the duration of the procedure. Using a syringe, the cyst fluid is aspirated from the cyst (usually up to 80% of the original volume of the cyst, but more than 80% of the cyst fluid can be aspirated). The volume of cyst fluid withdrawn is determined. The needle is then filled with the composition, and is injected directly into the cyst. The volume of the composition injected into the cyst can be at a volume equal to the volume of cyst fluid aspirated.

6. Methods of Injection into a Body Cavity

Disclosed herein is a In another aspect of the invention, disclosed is a method of treating cancer in a subject, the method comprising: (a) administering a first composition comprising antineoplastic particles to a tumor located in a body cavity of the subject by injection into the body cavity, and (b) systemically administering a second composition comprising an immunotherapeutic agent to the subject, thereby treating the cancer, wherein the antineoplastic particles have a mean particle size (number) of from 0.1 microns to 5 microns, and wherein steps (a) and (b) can be conducted in any order or at the same time. In various embodiments, the antineoplastic particles have a mean particle size (number) of from 0.1 microns to 1.5 microns. In some embodiments, the tumor is a benign tumor, and the subject has cancer elsewhere in the body. In some embodiments, the tumor is a malignant tumor. In some embodiments, the malignant tumor is the only cancer in the body of the subject. In other embodiments, the subject has a malignant tumor and cancer in other areas of the body. In other embodiments, the antineoplastic agent is a taxane and the antineoplastic particles are taxane particles. The taxane particles can include pharmaceutically acceptable salts of the taxane particles. In some embodiments, the taxane particles are paclitaxel particles, docetaxel particles, cabazitaxel particles, or combinations thereof. In some embodiments, the local administration of the first composition stimulates an immunological response to the immunotherapeutic agent in the subject after the systemic administration of the second composition. A body cavity is any fluid-filled space other than vessels (such as blood vessels). Human body cavities include the ventral cavity and the dorsal cavity. The ventral cavity includes the thoracic and abdominopelvic cavities and their subdivisions. The dorsal cavity includes the cranial and spinal cavities.

B. Systemic Administration Methods

Systemic administration methods of systemic compositions, i.e., the second composition of the invention, include suitable methods as known by one of skill in the art, such as enteral administration methods and/or parenteral administration methods. Non-limiting examples of routes of systemic administration include intravenous (IV), intramuscular, intraarticular, infusion, oral, rectal, buccal, and sublingual.

C. Combination Therapy Methods

Disclosed herein is a method of treating cancer in a subject, the method comprising: (a) administering locally to a tumor or cyst of the subject, a first composition comprising antineoplastic particles, and (b) administering systemically to the subject, a second composition comprising an immunotherapeutic agent, thereby treating the cancer, wherein the antineoplastic particles have a mean particle size (number) of from 0.1 microns to 5 microns. In preferred embodiments, the local administration of the first composition stimulates an immunological response to the immunotherapeutic agent in the subject after the systemic administration of the second composition. Steps (a) and (b) can be conducted in any order or at the same time. In some embodiments, the first composition is administered at least one day prior to the administration of the second composition. In some embodiments, the first composition is administered 1, 2, 3, 4, 5, 6, 7, 8, 9, 10, 11, 12, 13, 14, 15, 16, 17, 18, 19, 20, or 21 days prior to the administration of the second composition. In other embodiments, the second composition is administered at least one day prior to the administration of the first composition. In some embodiments, the second composition is administered 1, 2, 3, 4, 5, 6, 7, 8, 9, 10, 11, 12, 13, 14, 15, 16, 17, 18, 19, 20, or 21 days prior to the administration of the first composition. In still other embodiments, the first composition and the second compositions are administered on the same day. In some embodiments, the cancer in the subject and the malignant tumor of the subject are the same cancer. In some embodiments, the amount of antineoplastic particles in the first composition and the amount of immunotherapeutic agent in the second composition are at effective amounts to treat the cancer in the subject, and optionally to treat the tumor or cyst of the subject. In some embodiments, the tumor or cyst in step (a) is a benign tumor or cyst, and the subject has cancer elsewhere in the body. In some embodiments, the tumor in step (a) is a malignant tumor or cyst and is the only cancer in the body of the subject. In other embodiments, the tumor or cyst in step (a) is a malignant tumor or cyst and the subject also has cancer elsewhere in the body. In preferred embodiments, the antineoplastic particles are taxane particles.

The combination therapy methods are especially useful for treating subjects where prior chemotherapeutic treatments did not show a positive effect against the cancer. In some embodiments, prior to receiving the combination therapy treatment of the invention, the subject received at least one other form of chemotherapy treatment where the cancer progressed during and/or after the other form of chemotherapy treatment. In some embodiments, the prior chemotherapy treatment is a platinum based chemotherapy regimen.

V. Kits

In one aspect of the invention, disclosed is a kit comprising: (a) a first composition comprising antineoplastic particles, wherein the antineoplastic particles have a mean particle size (number) of from 0.1 microns to 5 microns (b) a second composition comprising an immunotherapeutic agent, and (c) instructions for (i) administering the first composition locally to a malignant tumor of a subject, and (ii) administering the second composition systemically to a subject. In preferred embodiments, the antineoplastic particles are taxane particles. In some embodiments, the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent. In some embodiments, the taxane particles comprise at least 95% of the taxane, and wherein the taxane particles have a mean particle size (number) of from 0.1 microns to 1.5 microns. In some embodiments, the taxane particles are paclitaxel particles, docetaxel particles, or cabazitaxel particles. In some embodiments, the paclitaxel particles or docetaxel particles have a specific surface area (SSA) of at least 18 $m^2/g$. In some embodiments, the paclitaxel particles or docetaxel particles have a bulk density (not-tapped) of 0.05 $g/cm^3$ to 0.15 $g/cm^3$. In some embodiments, the first composition is a hydrophobic ointment. In some embodiments, the first composition is an aqueous suspension.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1—Particle Size, SSA, and Bulk Density Analysis of Paclitaxel Particles

The particle size of the paclitaxel particles lots used in the formulas listed in Table 1 and Table 9 were analyzed by the following particle size method using an ACCUSIZER 780:

Instrument parameters: Max. Concentration: 9000 particles/mL, No. containers: 1, Sensor Range: Summation, Lower Detection Limit: 0.5 μm, Flow Rate: 30 mL/min, No. Analysis pulls: 4, Time between pulls: 1 see, Pull volume: 10 mL, Tare Volume: 1 mL, Prime volume: 1 mL, Include First Pull: Not Selected.

Sample preparation: Placed a scoop of paclitaxel particle API into a clean 20 mL vial and added approximately 3 mL of a filtered (0.22 μm) 0.1% w/w solution of SDS to wet the API, then filled the remainder of the vial with the SDS solution. Vortexed for 5-10 minutes and sonicated in a water batch for 1 minute.

Method: Filled a plastic bottle with filtered (0.22 μm) 0.1% w/w SDS solution and analyzed the Background. Pipetted a small amount of the paclitaxel particles sample suspension, <100 μL, into the bottle of 0.1% w/w SDS solution while stirring; placed the ACCUSIZER inlet tube into the bottle and ran sample through instrument. As necessary, added more SDS solution or paclitaxel sample suspension to reach a desired run concentration of 6000-8000 particle count.

Particles size results (based on number-weighted differential distribution): Paclitaxel particles lot used in formulas listed in Table 1: Mean: 0.861 μm. Paclitaxel particles lot used in formulas listed in Table 9: Mean: 0.83 μm.

The specific surface area (SSA) of the paclitaxel particles lots used in the formulas listed in Table 1 and Table 9 were analyzed by the Brunauer-Emmett-Teller ("BET") isotherm method described above. The paclitaxel particles lot used in the formulas listed in Table 1 had an SSA of 41.24 $m^2/g$. The paclitaxel particles lot used in the formulas listed in Table 9 had an SSA of 26.72 $m^2/g$.

The bulk density (not-tapped) of the paclitaxel particles lot used in the formulas listed in Table 1 was 0.05 $g/cm^3$. The bulk density (not-tapped) of the paclitaxel particles lot used in the formulas listed in Table 9 was 0.09 $g/cm^3$.

Example 2—Anhydrous Hydrophobic Topical Compositions of Paclitaxel Particles with Hydrophobic Carriers Anhydrous hydrophobic topical compositions of paclitaxel particles with hydrophobic carriers are listed in Table 1.

TABLE 1

| Component (% w/w) | F4 | F5 | F6 | F7 | F8 | F9 | F10 | F11 | F12 | F13 | A | B | C |
|---|---|---|---|---|---|---|---|---|---|---|---|---|---|
| Paclitaxel Particles | 1.0 | 1.0 | 1.0 | 1.0 | 0.5 | 2.0 | 1.0 | 1.0 | 1.0 | 1.0 | 0.5 | 0.5 | 0.5 |
| FOMBLIN HC04 | — | — | — | 15.0 | — | — | — | — | — | — | — | — | — |
| Mineral Oil USP | 10.0 | — | 5.0 | — | 5.0 | 5.0 | — | — | — | — | — | — | — |
| ST-Cyclomethicone 5 NF(Dow Corning) | — | 5.0 | 13.0 | — | 13.0 | 13.0 | 13.0 | 13.0 | 18.0 | 15.0 | qs ad 100 | qs ad 100 | qs ad 100 |
| Oleyl Alcohol | — | 5.0 | — | — | — | — | 1.0 | — | — | — | — | — | 5.0 |
| Isopropyl Myristate NF | — | 5.0 | — | — | — | — | 5.0 | 1.0 | — | 3.0 | — | 35 | 5.0 |
| Dimethicone | — | — | — | — | — | — | — | — | — | — | 5.0 | 5.0 | 5.0 |
| Fumed Silica | — | — | — | — | — | — | — | — | — | — | 5.5 | 5.5 | 2.8 |
| Cetostearyl Alcohol NF | — | — | — | — | — | — | — | — | 0.5 | — | — | — | — |
| Paraffin Wax NF | 5.0 | 5.0 | 5.0 | 5.0 | 5.0 | 5.0 | 5.0 | 5.0 | 5.0 | 5.0 | — | — | — |
| White Petrolatum USP (Spectrum) | qs ad 100 | qs ad 100 | qs ad 100 | qs ad 100 | qs ad 100 | qs ad 100 | qs ad 100 | qs ad 100 | qs ad 100 | qs ad 100 | — | — | — |

Procedure for F4-F13: Prepared a slurry of the paclitaxel particles with a portion of the cyclomethicone (or mineral oil (F4) or FOMBLIN (F7)). Heated the petrolatum to 52±3° C. and added the remaining ingredients and mixed until melted and homogeneous. Added the paclitaxel slurry and mixed until homogenous. Mixed and allowed the batch to cool to 35° C. or below. An ointment was formed.

Example 3—Physical and Chemical Stability of Anhydrous Topical Compositions of Paclitaxel Particles with Hydrophobic Carriers The anhydrous hydrophobic topical composition samples were stored at 25° C. and 30° C. in 20 mL glass scintillation vials. The assay of paclitaxel was conducted using HPLC. The results of the assay and appearance stability studies are shown in Table 2 and Table 3 below. The viscosity was measured at room temperature with a Brookfield RV viscometer using a small sample adapter with a SC4-14 spindle and a 6R chamber at 5 rpm with an equilibration time of 2 minutes. The viscosity results are shown in Table 4 below.

TABLE 2

Stability at 25° C.

| Formula | Assay (% of target) | | | | Appearance | | | |
|---|---|---|---|---|---|---|---|---|
| | T = 0 | 1 month | 2 month | 3 month | T = 0 | 1 month | 2 month | 3 month |
| F4 | 95.3 | 99.6 | 100.3 | 99.5 | Off-white ointment | Off-white to yellow ointment | Off-white to yellow ointment | Off-white to yellow ointment |
| F5 | 98.2 | 101.7 | 101.0 | 100.9 | Off-white ointment | Off-white to yellow ointment | Off-white to yellow ointment | Off-white to yellow ointment |
| F6 | 97.2 | 100.5 | 97.9 | 98.4 | Off-white ointment | Off-white to yellow ointment | Off-white to yellow ointment | Off-white to yellow ointment |
| F6** | 98.0 | 98.5 | 100.2 | NP | Off-white to yellow ointment | Off-white to yellow ointment | Off-white to yellow ointment | NP |
| F8 | 107.6 | 100.5 | 101.1 | NP | Off-white to yellow ointment | Off-white to yellow ointment | Off-white to yellow ointment | NP |
| F9 | 95.6 | 98.3 | 101.2 | NP | Off-white to yellow ointment | Off-white to yellow ointment | Off-white to yellow ointment | NP |
| F10 | 98.6 | 103.8 | 101.2 | NP | Off-white to yellow ointment | Off-white to yellow ointment | Off-white to yellow ointment | NP |
| F11 | 99.8 | 99.8 | 100.9 | NP | Off-white to yellow ointment | Off-white to yellow ointment | Off-white to yellow ointment | NP |
| F12 | 98.7 | 98.3 | 99.1 | NP | Off-white to yellow ointment | Off-white to yellow ointment | Off-white to yellow ointment | NP |
| F13 | 96.5 | 93.9 | 96.0 | NP | Off-white to yellow ointment | Off-white to yellow ointment | Off-white to yellow ointment | NP |

**repeat batch

TABLE 3

Stability at 30° C.

| Formula | Assay (% of target) | | | | Appearance | | | |
|---|---|---|---|---|---|---|---|---|
| | T = 0 | 1 month | 2 month | 3 month | T = 0 | 1 month | 2 month | 3 month |
| F4 | 95.3 | 99.5 | 100.1 | 99.7 | Off-white ointment | Off-white to yellow ointment | Off-white to yellow ointment | Off-white to yellow ointment |
| F5 | 98.2 | 103.2 | 101.3 | 99.2 | Off-white ointment | Off-white to yellow ointment | Off-white to yellow ointment | Off-white to yellow ointment |
| F6 | 97.2 | 102.1 | 98.0 | 95.0 | Off-white ointment | Off-white to yellow ointment | Off-white to yellow ointment | Off-white to yellow ointment |
| F6** | 98.0 | 98.7 | 102.0 | NP | Off-white to yellow ointment | Off-white to yellow ointment | Off-white to yellow ointment | NP |
| F8 | 107.6 | 99.9 | 103.0 | NP | Off-white to yellow ointment | Off-white to yellow ointment | Off-white to yellow ointment | NP |
| F9 | 95.6 | 101.4 | 101.9 | NP | Off-white to yellow ointment | Off-white to yellow ointment | Off-white to yellow ointment | NP |
| F10 | 98.6 | 100.9 | 102.9 | NP | Off-white to yellow ointment | Off-white to yellow ointment | Off-white to yellow ointment | NP |
| F11 | 99.8 | 99.8 | 99.1 | NP | Off-white to yellow ointment | Off-white to yellow ointment | Off-white to yellow ointment | NP |
| F12 | 98.7 | 99.8 | 99.5 | NP | Off-white to yellow ointment | Off-white to yellow ointment | Off-white to yellow ointment | NP |
| F13 | 96.5 | 95.6 | 96.5 | NP | Off-white to yellow ointment | Off-white to yellow ointment | Off-white to yellow ointment | NP |

**repeat batch

TABLE 4

Viscosity Stability

| | Viscosity (cps) | | | |
|---|---|---|---|---|
| | F4 | F5 | F6 | F7 |
| T = 0 | 87,500 | 44,300 | 49,500 | 81,800 |
| 1 month @ 25° C. | 90,300 | 68,800 | 57,000 | NP |
| 3 month @ 25° C. | 101,000 | 47,800 | 38,000 | NP |
| 1 month @ 30° C. | 123,300 | 49,300 | 50,800 | NP |
| 2 month @ 30° C. | 112,300 | 53,500 | 38,000 | NP |
| 3 month @ 30° C. | 121,300 | 60,500 | 54,000 | NP |

Example 4—Particle Size Analysis of Paclitaxel Particles in Anhydrous Topical Compositions with Hydrophobic Carriers Particle Size Method Using an ACCUSIZER Model 770/770A.

Instrument parameters: Sensor: LE 0.5 µm-400 µm, Sensor Range: Summation, Lower Detection Limit: 0.5 µm, Collection time: 60 sec, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 2% Lecithin in ISOPAR-GTM (C10-11 isoparaffin) solution to the vial. Sonicated the vial for 1 minute. Insured that the sample had adequately dispersed in the solution.

Method: Filled the sample vessel with a filtered (0.22 µm) 2% Lecithin in ISOPAR-G solution and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 5 and Table 6 below.

TABLE 5

Particle size stability at 25° C.

| | Mean particle size, µm (number) | | | | |
|---|---|---|---|---|---|
| Formula | Initial | 1 month | 3 month | 6 month | 12 month |
| F4 | 0.77 | 0.71 | NP | NP | NP |
| F5 | 0.72 | 0.71 | NP | NP | NP |

TABLE 5-continued

Particle size stability at 25° C.

Mean particle size, μm (number)

| Formula | Initial | 1 month | 3 month | 6 month | 12 month |
|---|---|---|---|---|---|
| F6 | 0.72 | 0.71 | NP | 0.71 | 0.72 |
| F6** | 0.70 | NP | 0.70 | NP | NP |
| F8 | 0.71 | NP | 0.71 | NP | NP |
| F9 | 0.70 | NP | 0.70 | NP | NP |
| F10 | 0.69 | NP | 0.69 | NP | NP |
| F11 | 0.69 | NP | 0.69 | NP | NP |
| F12 | 0.70 | NP | 0.70 | NP | NP |
| F13 | 0.69 | NP | 0.70 | NP | NP |
| A | 0.72 | NP | NP | NP | NP |
| B | 0.77 | NP | NP | NP | NP |
| C | 0.84 | NP | NP | NP | NP |

**repeat batch

TABLE 6

Particle size stability at 30° C.

Mean particle size, μm (number)

| Formula | Initial | 1 month | 3 month | 6 month | 12 month |
|---|---|---|---|---|---|
| F4 | 0.77 | 0.73 | NP | NP | NP |
| F5 | 0.72 | 0.70 | NP | NP | NP |
| F6 | 0.72 | 0.70 | NP | 0.70 | 0.73 |
| F6** | 0.70 | NP | 0.72 | NP | NP |
| F8 | 0.71 | NP | 0.71 | NP | NP |
| F9 | 0.70 | NP | 0.71 | NP | NP |
| F10 | 0.69 | NP | 0.69 | NP | NP |
| F11 | 0.69 | NP | 0.70 | NP | NP |
| F12 | 0.70 | NP | 0.71 | NP | NP |
| F13 | 0.69 | NP | 0.71 | NP | NP |

**repeat batch

Example 5—Aqueous Based Topical Compositions of Paclitaxel Particles

Aqueous based topical compositions of paclitaxel particles are shown in Table 7.

TABLE 7

| Component (% w/w) | Formula Number | | | | | | | |
|---|---|---|---|---|---|---|---|---|
| | F1 | F2 | F3 | D | E | F | G | H |
| Paclitaxel Particles | 1.0 | 1.0 | 1.0 | 0.5 | 0.5 | 0.5 | 0.5 | 0.5 |
| DGME (TRANSCUTOL P) | 5.0 | 5.0 | — | 5.0 | 5.0 | 5.0 | 5.0 | 5.0 |
| PEG 400 | 5.0 | 5.0 | 5.0 | 5.0 | 5.0 | 5.0 | 5.0 | 5.0 |
| Glycerin | 10.0 | 10.0 | 10.0 | 5.0 | 5.0 | 5.0 | 5.0 | 5.0 |
| Polysorbate 80 | 1.0 | 1.0 | 1.0 | 0.1 | 0.1 | 0.1 | 0.1 | 0.1 |
| Poloxamer 407 | 2.0 | 2.0 | 2.0 | — | — | — | — | — |
| Povidone K90 | 0.15 | 0.15 | 0.15 | 0.1 | 0.1 | 0.1 | 0.1 | 0.1 |
| Benzyl Alcohol | 0.5 | 0.5 | 0.5 | — | — | — | — | — |
| Methylparaben | 0.15 | 0.15 | 0.15 | 0.15 | 0.15 | 0.15 | 0.15 | 0.15 |
| Propylparaben | 0.02 | 0.02 | 0.02 | 0.02 | 0.02 | 0.02 | 0.02 | 0.02 |
| Benzalkonium Chloride (50%) | — | 1.0 | 1.0 | — | — | 0.1 | 0.1 | — |
| CARBOPOL 974 P | — | — | — | 0.75 | — | — | — | — |
| CARBOPOL ULTREZ 10 | 0.5 | — | — | — | 0.5 | — | — | — |
| Trolamine Solution (10%) | qs pH 5.5 | — | — | qs pH 5.5 | qs pH 5.5 | — | — | — |
| Hydroxypropyl Methylcellulose (K200M Pharm) | — | 1.0 | 1.0 | — | — | 2.0 | — | — |
| Purified Water | qs ad 100 | qs ad 100 | qs ad 100 | qs ad 100 | qs ad 100 | qs ad 100 | qs ad 100 | qs ad 100 |

Example 6—Particle Size Analysis of Paclitaxel Particles in Aqueous Based Topical Compositions Particle Size Method Using an ACCUSIZER Model 770/770A.

Instrument parameters: Sensor: LE 0.5 µm-400 µm, Sensor Range: Summation, Lower Detection Limit: 0.5 µm, Collection time: 60 see, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 0.2 µm filtered distilled water to the vial. Sonicated the vial for 1 minute. Insured that the sample had adequately dispersed in the solution.

Method: Filled the sample vessel with 0.2 µm filtered distilled water and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 8 below.

TABLE 8

Particle size of aqueous based topical compositions

| Formula | Mean particle size, µm (number) | |
|---|---|---|
| | Initial | 6 month at RT |
| F1 | 1.06 | 0.82 |
| F2 | 0.74 | 0.77 |
| F3 | 0.70 | 0.77 |
| D | 0.80 | NP |
| E | 0.79 | NP |
| F | 0.85 | NP |

Example 7—Topical Compositions of Paclitaxel Particles for Use in Topical Application to Skin Malignancies The following ointment formulations shown in Table 9 were prepared for use in topical application to skin malignancies.

TABLE 9

| | Formula No. | | | |
|---|---|---|---|---|
| Component (% w/w) | F14 (0.15%) | F15 (0.3%) | F16 (1%) | F17 (2%) |
| Paclitaxel Particles | 0.15 | 0.3 | 1.0 | 2.0 |
| Mineral Oil USP | 5.0 | 5.0 | 5.0 | 5.0 |
| ST-Cyclomethicone 5 NF (Dow Corning) | 13.0 | 13.0 | 13.0 | 13.0 |
| Paraffin Wax NF | 5.0 | 5.0 | 5.0 | 5.0 |
| White Petrolatum USP (Spectrum) | qs ad 100 | qs ad 100 | qs ad 100 | qs ad 100 |

TABLE 9-continued

The formulas listed in Table 9 containing paclitaxel particles were manufactured each in a 6 kg batch size. The formulas were then packaged in 15 gm laminate tubes.

The manufacturing processes for lots F14, F15, and F16 were as follows: The petrolatum, mineral oil, paraffin wax, and a portion of the cyclomethicone were added to a vessel and heated to 52±3° C. while mixing with a propeller mixer until melted and homogeneous. The paclitaxel particles were added to a vessel containing another portion of cyclomethicone and first mixed with a spatula to wet the particles, then mixed with an IKA Ultra Turrax Homogenizer with a S25-25G dispersing tool until a homogeneous slurry is obtained while keeping the container in an ice/water bath. The slurry was then added to the petrolatum/paraffin wax container while mixing with the propeller mixer followed by rinsing with the remaining portion of cyclomethicone and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The manufacturing process for lot F17 was as follows: The petrolatum and paraffin wax were added to a vessel and heated to 52±3° C. while mixing with a propeller mixer until melted and homogeneous. The paclitaxel particles were added to a vessel containing the cyclomethicone and a portion of mineral oil, and first mixed with a spatula to wet the particles, then mixed with an IKA Ultra Turrax Homogenizer with a S25-25G dispersing tool until a homogeneous slurry is obtained while keeping the container in an ice/water bath. The slurry was then added to the petrolatum/paraffin wax container while mixing with the propeller mixer followed by rinsing with the remaining portion of mineral oil and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The chemical and physical analytical results for each formula in Table 9 are shown in Tables 10-13 for T=0, 1 month, and 3 months at 25° C.

TABLE 10

| | Formula No. F14 (0.15%) | | |
|---|---|---|---|
| Test | T = 0 | 1 month | 3 month |
| Appearance (note1) | conforms | conforms | conforms |
| Assay, % target | 103.4 | 103.2 | 101.1 |
| Viscosity (note 2) | 131000 cps | 147000 cps | 159500 cps |
| Mean Particle Size (number) | 0.71 µm | 0.70 µm | 0.70 µm |

(note1):
Off-white to yellow ointment (note 2):
Brookfield RV viscometer on a helipath stand with the helipath on, with a T-E spindle at 10 RPM at room temperature for 45 seconds.

TABLE 11

| | Formula No. F15 (0.3%) | | |
|---|---|---|---|
| Test | T = 0 | 1 month | 3 month |
| Appearance (note1) | conforms | conforms | conforms |
| Assay, % target | 101.2 | 101.9 | 102.5 |
| Viscosity (note 2) | 195500 cps | 154000 cps | 153500 cps |
| Mean Particle Size (number) | 0.72 μm | 0.71 μm | 0.70 μm |

(note1):
Off-white to yellow ointment
(note 2):
Brookfield RV viscometer on a helipath stand with the helipath on, with a T-E spindle at 10 RPM at room temperature for 45 seconds.

TABLE 12

| | Formula No. F16 (1%) | | |
|---|---|---|---|
| Test | T = 0 | 1 month | 3 month |
| Appearance (note1) | conforms | conforms | conforms |
| Assay, % target | 102.1 | 102.2 | 102.7 |
| Viscosity (note 2) | 205000 cps | 218000 cps | 180000 cps |
| Mean Particle Size (number) | 0.70 μm | 0.70 μm | 0.70 μm |

(Note1):
Off-white to yellow ointment
(Note 2):
Brookfield RV viscometer on a helipath stand with the helipath on, with a T-E spindle at 10 RPM at room temperahire for 45 seconds.

TABLE 13

| | Formula No. F17 (2%) | | |
|---|---|---|---|
| Test | T = 0 | 1 month | 3 month |
| Appearance (note1) | conforms | conforms | conforms |
| Assay, % target | 101.7 | 101.1 | 105.0 |
| Viscosity (note 2) | 158000 cps | 177000 cps | 162000 cps |
| Mean Particle Size (number) | 0.70 μm | 0.69 μm | 0.69 μm |

(Note1):
Off-white to yellow ointment
(Note 2):
Brookfield RV viscometer on a helipath stand with the helipath on, with a T-E spindle at 10 RPM at room temperature for 45 seconds.

Example 8—In Vitro Skin Penetration Diffusion Study

A study to determine the rate and extent of in vitro skin permeation of the formulas F1 through F13 into and through intact human cadaver skin using a Franz diffusion cell system was conducted. Concentrations of paclitaxel were measured in the receptor chamber of the diffusion cell at varying time points. Upon conclusion of the diffusion study, the skin was tape stripped and split into epidermal and dermal layers. The paclitaxel in the epidermal and dermal tissue was extracted using an extraction solvent and also analyzed.

Analytical Method: A Mass spectrometry (MS) method was developed for analyzing the paclitaxel. The MS conditions were as follows in Table 14 below.

TABLE 14

| Instrument: | Agilent 1956B MS (TM-EQ-011) |
|---|---|
| Column: | XBridge C18 4.6 × 100 mm, 5 μm |
| Mobile Phase: | A: Acetonitrile |
| | B: 0.1% Formic acid in water |

| Gradient: | Time (minutes) | % B |
|---|---|---|
| | 0 | 50% |
| | 2 | 5% |
| | 5 | 5% |

| Flow Rate: | 1 mL/min |
|---|---|
| Column Temperature: | 30° C. |
| MS Detection: | SIM 854.4 + Frag 180, Gain 20 |
| Injection Volume: | 20 μL |
| Retention time: | ~2.86 min |

Franz Diffusion Cell (FDC) Study—Methodology

Skin Preparation: Intact human cadaver skin was purchased from New York Firefighters Tissue Bank (NFFTB). The skin was collected from the upper back and dermatomed by the tissue bank to a thickness of ~ 500 μm. Upon receipt of the skin from the tissue bank, the skin was stored frozen at −20° C. until the morning of the experiment. Prior to use, the skin was removed from the freezer and allowed to fully thaw at room temperature. The skin was then briefly soaked in a PBS bath to remove any residual cryoprotectants and preservatives. Only areas of the skin that were visually intact were used during the experiment. For each study, two separate donors were used, each donor having a corresponding three replicates.

Receptor Fluid Preparation: Based on the results of preliminary solubility data, a receptor fluid of 96 wt % phosphate buffered saline ("PBS") at pH 7.4 and 4 wt % hydroxyl propyl beta cyclodextrin (HPBCD) was chosen. The solubility of the active in the receptor fluid (~0.4 μg/mL) was shown to be adequate to maintain sink conditions during the studies. The receptor fluid was degassed by filtering the receptor fluid through a ZapCap™ CR 0.2 μm membrane while pulling vacuum. The filtered receptor fluid was stirred for an additional 20 minutes while maintaining vacuum to ensure complete degassing.

Diffusion Cell Assembly: The cadaver skin was removed from the freezer and allowed to defrost in a bio-safety hood for 30 minutes. The skin was thoroughly defrosted prior to opening the package. The cadaver skin was removed from the package and placed on the bio-safety hood countertop with the stratum corneum side up. The skin was patted dry with a Kim Wipe, then sprayed with fresh PBS and patted dry again. This process was repeated 3 more times to remove any residues present on the skin. The receptor wells were then filled with the degassed receptor fluid. A Teflon coated stir bar was added to each receptor well. The defrosted cadaver skin was examined and only areas with even thickness and no visible damage to the surface were used. The skin was cut into ~ 2 cm×2 cm squares. The skin piece was centered on the donor wells, stratum corneum (SC) side up. The skin was centered and the edges flattened out. The donor and receptor wells were then aligned and clamped together with a clamp. Additional receptor fluid was added where necessary. Any air bubbles present were removed by tilting the cell, allowing air to escape along the sample port. Diffusion cells were then placed in to the stirring dry block heaters and allowed to rehydrate for 20 minutes from the receptor fluid. The block heaters were maintained at 32° C. throughout the experiment with continuous stirring. The skin was allowed to hydrate for 20 minutes and the barrier integrity of each skin section was tested. Once the membrane integrity check study was complete, the entire receptor chamber volume was replaced with the receptor fluid.

Formulation Application Procedure: The formulations were applied to the stratum corneum of the skin. A one-time dosing regimen was used for this study. The test articles were applied as 10 µl doses to the skin using a positive displacement Nichiryo™ pipetter. The formulations were then spread across the surface of the skin using a glass rod. Cells were left uncapped during the experiment. The theoretical dose of paclitaxel per cell is shown in Table 15 below.

TABLE 15

| Formula Number | % w/w Paclitaxel in formula | Nominal formulation dose per cell | Theoretical Paclitaxel dose per cell |
|---|---|---|---|
| F1 | 1.0 wt % | 10 µl | 182 µg/cm² |
| F2 | 1.0 wt % | 10 µl | 182 µg/cm² |
| F3 | 1.0 wt % | 10 µl | 182 µg/cm² |
| F4 | 1.0 wt % | 10 µl | 182 µg/cm² |
| F5 | 1.0 wt % | 10 µl | 182 µg/cm² |
| F6 | 1.0 wt % | 10 µl | 182 µg/cm² |
| F7 | 1.0 wt % | 10 µl | 182 µg/cm² |
| F6* | 1.0 wt % | 10 µl | 182 µg/cm² |
| F8 | 0.5 wt % | 10 µl | 91 µg/cm² |
| F9 | 2.0 wt % | 10 µl | 364 µg/cm² |
| F10 | 1.0 wt % | 10 µl | 182 µg/cm² |
| F11 | 1.0 wt % | 10 µl | 182 µg/cm² |
| F12 | 1.0 wt % | 10 µl | 182 µg/cm² |
| F13 | 1.0 wt % | 10 µl | 182 µg/cm² |

*repeat analysis

Sampling of Receptor Fluid: At 3, 6, 12 and 24 hours, 300 µL sample aliquots were drawn from the receptor wells using a graduated Hamilton type injector syringe. Fresh receptor medium was added to replace the 300 µL sample aliquot.

Tape Stripping and Heat Splitting: At 24 hours, the skin was wiped clean using PBS/ethanol soaked KimWipes™. After the residual formulation was wiped off and the skin dried with KimWipes™, the stratum corneum was tape stripped three times—each tape stripping consisting of applying cellophane tape to the skin with uniform pressure and peeling the tape off. The tape strips were collected and frozen for future analysis. The first three tape strips remove the uppermost layer of the stratum corneum and act as an extra skin cleaning step. The active is typically not considered fully absorbed in this area. These tape strips are usually only analyzed for a mass balance assay. After the skin was tape stripped, the epidermis of each piece was then separated from the underlying dermal tissue using tweezers or a spatula. The epidermis and dermal tissue were collected and placed in 4 mL borosilicate glass vials. After all the skin pieces were separated, an aliquot of the extraction solvent was added to the glass vial. This process consisted of adding 2 mL of DMSO to the vial and incubating for 24 hours at 32° C. After the extraction time was over, 300 L sample aliquots of the extraction fluid were collected and filtered.

Analysis of Samples: Sample aliquots were analyzed for paclitaxel using the analytical method as described above.

Figure 2:
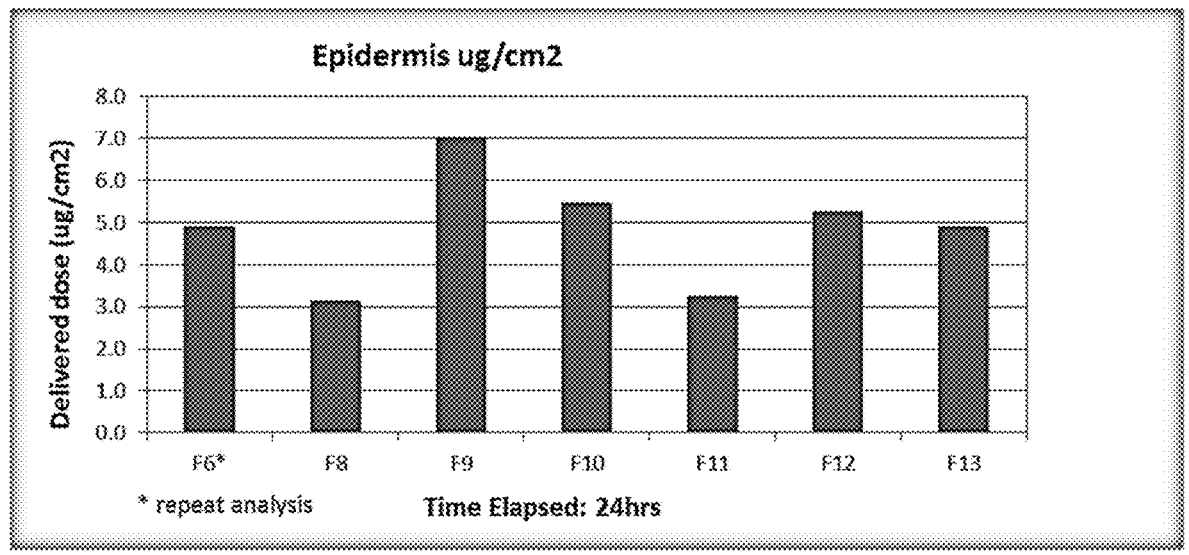
FIG. 2 graphically shows the concentration of paclitaxel (μg/cm2) delivered in vitro into the epidermis for formulas F6*(repeat analysis) and F8 through F13.
Figure 3:
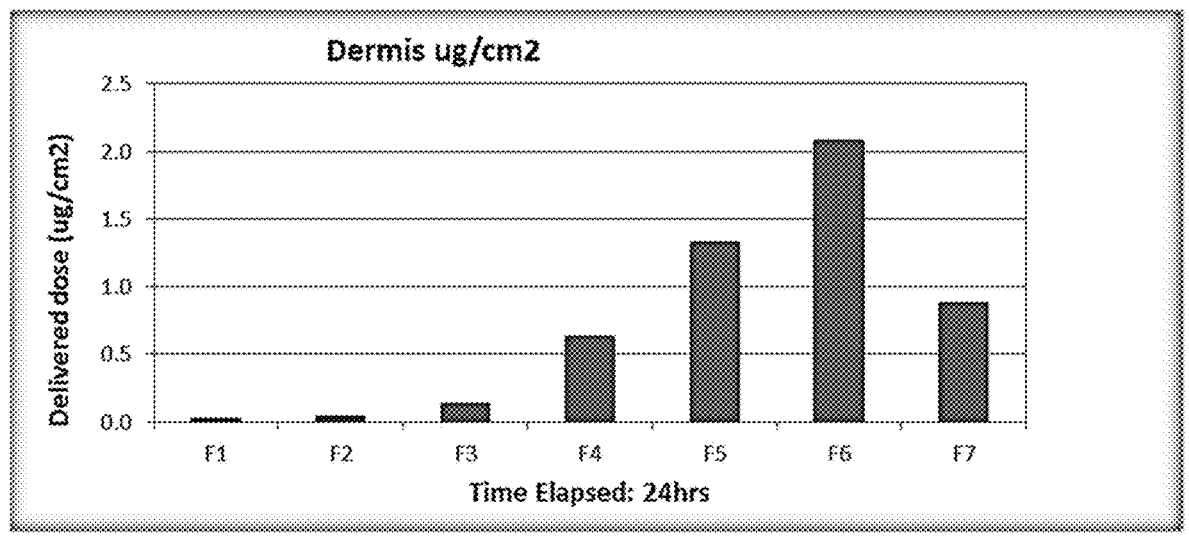
FIG. 3 graphically shows the concentration of paclitaxel (μg/cm2) delivered in vitro into the dermis for formulas F1 through F7.
Figure 4:
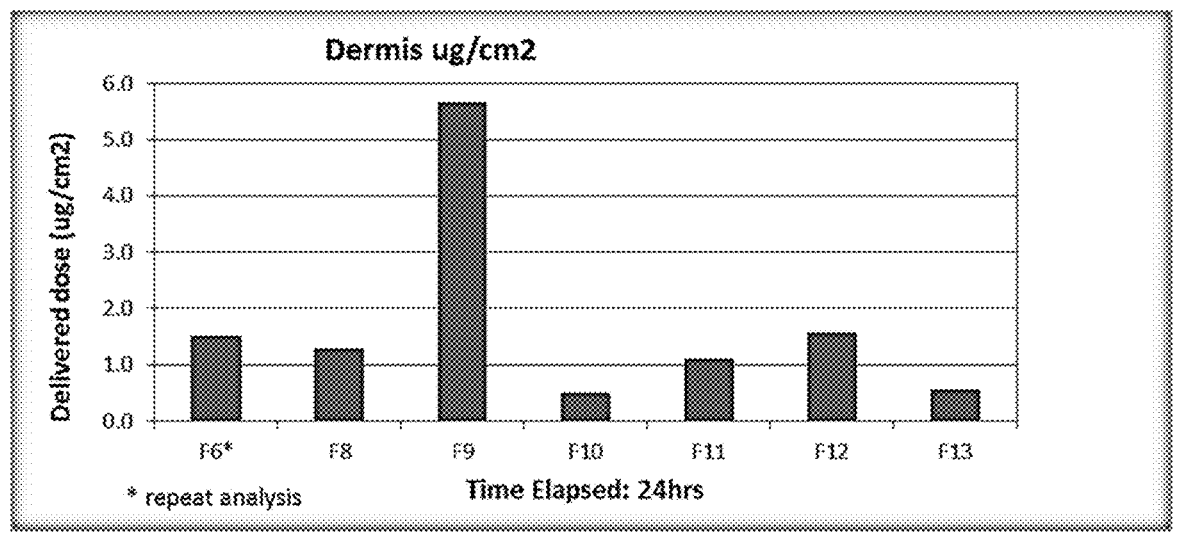
FIG. 4 graphically shows the concentration of paclitaxel (μg/cm2) delivered in vitro into the dermis for formulas F6*(repeat analysis) and F8 through F13.

Results:

The results in Table 16 below show the delivered dose of paclitaxel (µg/cm²) in the receptor fluid at various time points (transdermal flux) and the concentration of paclitaxel (µg/cm²) delivered into the epidermis and dermis (penetration) after 24 hours elapsed time for formulations F1 through F13. FIG. 1 graphically shows the concentration of paclitaxel (µg/cm²) delivered into the epidermis for formulas F1 through F7. FIG. 2 graphically shows the concentration of paclitaxel (µg/cm²) delivered into the epidermis for formulas F6*(repeat analysis) and F8 through F13. FIG. 3 graphically shows the concentration of paclitaxel (µg/cm²) delivered into the dermis for formulas F1 through F7. FIG. 4 graphically shows the concentration of paclitaxel (µg/cm²) delivered into the dermis for formulas F6*(repeat analysis) and F8 through F13.

Note: Formulas F1 through F6 were tested in one in vitro study, and formulas F6* and F8 through F13 were tested in a second separate in vitro study, with different cadaver skin lots. Analysis of formula F6 was repeated in the second study (and notated as F6*) so that it could be evaluated and compared with the other formulas in the second study.

TABLE 16

| | Paclitaxel Delivered Dose (µg/cm²) | | | | | |
|---|---|---|---|---|---|---|
| Formula | Receptor Fluid 3 hrs | Receptor Fluid 6 hrs | Receptor Fluid 12 hrs | Receptor Fluid 24 hrs | Epidermis | Dermis |
| F1 | 0.000 | 0.000 | 0.000 | 0.000 | 0.202 | 0.030 |
| F2 | 0.000 | 0.000 | 0.000 | 0.000 | 0.161 | 0.042 |
| F3 | 0.000 | 0.000 | 0.000 | 0.000 | 0.056 | 0.138 |
| F4 | 0.000 | 0.000 | 0.000 | 0.000 | 0.690 | 0.639 |
| F5 | 0.000 | 0.000 | 0.000 | 0.004 | 0.780 | 1.337 |
| F6 | 0.000 | 0.000 | 0.000 | 0.000 | 1.927 | 2.088 |
| F7 | 0.000 | 0.000 | 0.000 | 0.000 | 0.633 | 0.882 |
| F6* | 0.000 | 0.000 | 0.000 | 0.000 | 4.910 | 1.508 |
| F8 | 0.000 | 0.000 | 0.000 | 0.000 | 3.155 | 1.296 |
| F9 | 0.000 | 0.000 | 0.000 | 0.000 | 7.010 | 5.679 |
| F10 | 0.000 | 0.000 | 0.000 | 0.000 | 5.470 | 0.494 |
| F11 | 0.000 | 0.000 | 0.000 | 0.000 | 3.262 | 1.098 |
| F12 | 0.000 | 0.000 | 0.000 | 0.000 | 5.269 | 1.571 |
| F13 | 0.000 | 0.000 | 0.000 | 0.000 | 4.903 | 0.548 |

*repeat analysis

As can be seen by the results in Table 16, the transdermal flux of the paclitaxel through the skin (epidermis and dermis) was none or only a negligible amount, i.e., less than 0.01 µg/cm². As can be seen by the results in Table 16 and FIGS. 1, 2, 3 & 4, the penetration of paclitaxel into the skin (epidermis and dermis) was far greater with the anhydrous hydrophobic formulations (F4 through F13) than with the aqueous formulations (F1 through F3), even though the aqueous formulations contained the skin penetration enhancer DGME (TRANSCUTOL P). The results also show that the anhydrous hydrophobic formulations with cyclomethicone exhibited greater skin penetration (epidermis and dermis) over the anhydrous hydrophobic formulations without cyclomethicone. Additionally, the results show that the addition of other skin penetration enhancers to the anhydrous hydrophobic formulations containing cyclomethicone had little or no effect on the skin penetration (epidermis and dermis) of these compositions.

Example 9—Phase 1/2 Dose-Rising, Safety, Tolerability and Efficacy Study for Cutaneous Metastases Three of the formulations in Table 9, F14 (0.15%), F16 (1.0%), and F17 (2.0%), above were used in an FDA-approved Phase 1/2 dose-rising, safety, tolerability and efficacy study for cutaneous metastases in humans. The study is currently on-going. This was a Phase 1/2, open-label, dose-rising study evaluating the safety tolerability, and preliminary efficacy of three of the formulations from Table 7: F14 (0.15%), F16 (1.0%), and F17 (2.0%) applied topically twice daily for 28 days to non-melanoma cutaneous metastases.

A treatment area of 50 cm² on the trunk or extremities containing at least one eligible lesion was determined at baseline by the RECIST (version 1.1) definition of measurable tumors (greater than or equal to 10 mm in its longest diameter). All lesions within the treatment area were measured by caliper to confirm eligibility. Using a gloved hand, subjects applied one fingertip unit (FTU) of the formulation to the 50 cm² treatment area twice daily at approximately the same time each day for 28 days. A FTU is defined as the amount of ointment formulation expressed from a tube with a 5-mm diameter nozzle, applied from the distal skin-crease to the tip of the index finger of an adult. Subjects attended the clinic on Day 1 for dose application training and observation of the first treatment application. Additional visits were on Days 8, 15, 29, and 43. The final visit was completed 30 days after the last study drug dose to review adverse events. Study participation is separated into a dose-escalation phase and a dose expansion phase.

Dose Escalation Phase: During the dose-escalation phase the study followed a standard 3+3 dose-ascending design, with the first cohort of three subjects commencing treatment with formulation F14 (0.15%). A safety monitoring committee reviewed all available data after the last subject in each cohort of three subjects completed 15 days of treatment to determine whether dose escalation may continue.

Dose Expansion Phase: In the dose-expansion phase, additional subjects were enrolled to reach a maximum of 12 total subjects at the dose level determined in the dose escalation phase. Subjects in the dose expansion phase attended the clinic on the same visit days and received the same evaluations as the dose escalation phase above.

Objectives: The primary objective of the study was to determine the preliminary safety and tolerability of the formulations. The secondary objectives were to determine the preliminary efficacy of the formulations, to study potential reduction in pain in the treatment area, and to describe the pharmacokinetics of the formulations applied to metastatic lesions.

Population: A minimum of two up to a maximum of 24 male and female human subjects, greater than or equal to 18 years of age, with non-melanoma cutaneous metastases.

Primary Endpoint: Safety and tolerability, as demonstrated by adverse events, changes in laboratory assessments, physical examination findings, and vital signs.

Secondary Endpoints: For the purposes of the following secondary endpoint for efficacy, eligible lesions were determined at baseline by the RECIST (Version 1.1) definition of measurable tumors (greater than or equal to 10 mm in its longest diameter (EISENHAUER et al. New response evaluation criteria in solid tumors: revised RECIST guideline (version 1.1). European Journal of Cancer. 2009; 45; 228-247).

Objective Tumor Response, defined as the difference in the sum of eligible tumor diameter(s) within the treatment area between baseline and Day 43 (i.e., 14 days after the last dose in the dose escalation and expansion phases depending on dose regimen). Tumor surface area and response were assessed at all visits. Change in surface area was assessed using a calibrated grid measurement system (ImageJ freeware) provided by the National Institutes of Health (NIH). Lesions were measured and analyzed using ImageJ.

Objective Clinical Response is defined as subjects with Complete Clinical Response (CR)+Partial Response (PR), further defined as the percentage of patients who achieve complete clinical response or partial response 14 days after the last treatment with the formulation, measured as change in the sum of the longest diameter(s) of eligible target lesion(s) within the treatment area 14 days after last treatment. The response to treatment was evaluated as a function of post-treatment total diameter divided by pre-treatment total diameter.

Best Overall Response is defined as the best response recorded from the start of the study treatment until the end of treatment, i.e., Day 43.

Complete Clinical Response (CR) is defined as absence of any detectable residual disease in eligible lesion(s) within the treatment area; Partial Response (PR) is at least a 30% decrease in the sum of the diameters of the eligible lesions(s) within the treatment area compared to bassline; and Progressive Disease (PD) is at least a 20% increase in the sum of diameters of eligible lesion(s) within the treatment area, taking as a reference the smallest sum on study. In addition, the sum must also demonstrate an absolute increase of at least 5 mm. Stable Disease (SD) is defined as the sum of eligible lesion diameter(s) between that defined as PR or PD. The appearance of new non-target lesions during participation in this study does not constitute progressive disease.

Pain at the treatment area will be measures by the Numeric Rating Scale (NRS-11). Change in pain will be analyzed from baseline to Day 43.

Systemic exposure as determined by: $T_{max}$, $C_{max}$, AUC.

Figure 5:
FIG. 5 is a photo of a skin metastatic lesion on the chest of a woman with Stage 4 breast cancer at baseline (Day 1) in cutaneous metastasis study.
Figure 6:
FIG. 6 is a photo of a skin metastatic lesion on the chest of a woman with Stage 4 breast cancer at Day 8 during topical treatment in cutaneous metastasis study.
Figure 7:
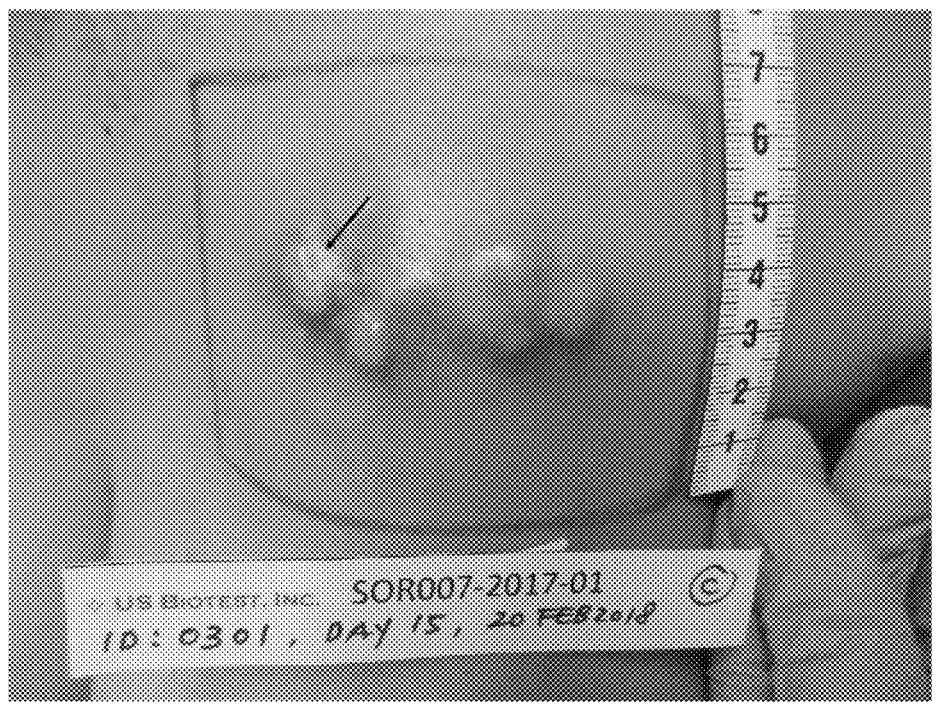
FIG. 7 is a photo of a skin metastatic lesion on the chest of a woman with Stage 4 breast cancer at Day 15 during topical treatment in cutaneous metastasis study.
Figure 8A:
FIG. 8*a* is a photo of a skin metastatic lesion on the chest of a woman with Stage 4 breast cancer at Day 29 during topical treatment at study end in cutaneous metastasis study.
Figure 8B:
FIG. 8*b* is a photo of a skin metastatic lesion on the chest of a woman with Stage 4 breast cancer at Day 43 two weeks after topical treatment ended in cutaneous metastasis study.

Preliminary Results: Preliminary results for the on-going study include photos of skin metastatic lesions on the chest of a woman with Stage 4 breast cancer. The subject was enrolled in the study after completing IV therapy with nab-Paclitaxel for breast cancer. One month later, the treatment began by topical application of formulation F14 (0.15%). FIG. 5 is a photo taken at baseline (Day 1) and shows the index lesion (arrow) covered with congealed exudate from an ulcerated lesion. FIG. 6 is a photo taken at Day 8 after topical treatment of the formulation F14 (0.15%) applied over the same treatment site twice per day. The surface of the lesion contains an area of epidermal loss and presumptive ulceration limited to the dermis. FIG. 7 is a photo at Day 15 after topical treatment of the formulation F14 (0.15%) applied over the same treatment site twice per day. A small amount of old exudate can be seen on the medial portion of the lesion as well as no apparent epidermal ulceration. FIG. 8a is a photo at Day 29 after topical treatment of the formulation F14 (0.15%) applied over the same treatment site twice per day. During the 28 days of treatment, the subject's cutaneous lesions were surrounded by erythema and expanded without ulceration, indicative of a local immune response (FIG. 8a). Eleven days after treatment ended, the subject was again treated with systemic paclitaxel. Three days after treatment with systemic paclitaxel, two weeks after the study treatment ended, the subject's lesions significantly decreased in size and volume as shown in FIG. 8b. The local treatment with topical formulation F14 (0.15%) sensitized the cutaneous lesion to subsequent response to IV paclitaxel. The lesion appears to be epithelialized with no evidence of ulceration. In contrast, the natural history of an ulcerative cutaneous breast cancer metastasis is rapid expansion and further penetration through the dermis once the epidermal surface is breached by the tumor typically resulting in ulceration.

Example 10—Dermal Toxicity Study

A dermal toxicity study was conducted using the topical compositions shown in Table 17.

TABLE 17

| | Formula No. | | | |
|---|---|---|---|---|
| Component (% w/w) | F18 (0.0%) Placebo | F19 (0.3%) | F20 (1%) | F21 (3%) |
| Paclitaxel Particles | 0.0 | 0.3 | 1.0 | 3.0 |
| Mineral Oil USP | 5.0 | 5.0 | 5.0 | 5.0 |
| ST-Cyclomethicone 5 NF (Dow Corning) | 13.0 | 13.0 | 13.0 | 13.0 |
| Paraffin Wax NF | 5.0 | 5.0 | 5.0 | 5.0 |
| White Petrolatum USP (Spectrum) | qs ad 100 | qs ad 100 | qs ad 100 | qs ad 100 |

The GLP-compliant study was conducted in Göttingen minipigs to characterize the toxicity of the formulations applied topically to 10% body surface area daily for 28 days. The 4 formulations shown in Table 17 were applied at the maximal feasible volume of 2 mL/kg, correlating to dose concentrations of 0.0, 0.3, 1.0, and 3%, which translate to dose levels of 0, 4.9, 16.5, and 49.9 mg/kg/day respectively. Reversibility of findings was also evaluated following a 2-week recovery period. Parameters evaluated included clinical observations, mortality and moribundity checks, dermal scoring, body weight, food consumption, eye examinations, test site photographs, electrocardiology, clinical pathology, bioanalysis and toxicokinetic evaluation, organ weights, macroscopic pathology and histopathology. There were no formulation-related effects on survival, clinical signs, dermal irritation, body weights, body weight gains, food consumption, ophthalmic findings, or cardiology parameters. Minimal dermal irritation was observed in all groups during the dosing phase and was considered vehicle or procedurally related as the frequency and severity of the findings were comparable between the placebo controls and active formulation-treated groups. Thus, the presence of the paclitaxel particles in the formulations had a negligible effect on dermal irritation.

Example 11—NanoPac® (i.e.: Paclitaxel Particles as Disclosed Herein, Approximately 99% Paclitaxel with a Mean Particle Size (Number) of 0.878 Microns in these Examples) Inhalation Safety and Efficacy Development Program—Pilot Pharmacokinetic Study in Sprague Dawley Rats Summary The objective of this pilot study was to define sampling time points for a complete pharmacokinetic (PK) study with NanoPac®. Due to the potential for the NanoPac® formulation to result in increased retention in the lungs, nine time points from 0.5 to 168 hours were evaluated to determine the appropriate sampling strategy for a complete pharmacokinetic study.

Sixteen (16) Sprague Dawley rats were exposed to NanoPac® (paclitaxel; target dose of 0.37 mg/kg) by nose only inhalation on a single occasion. Two animals (n=2) were euthanatized at their designated time point of 0.5, 6, 12, 24, 48, 72, 120 and 168 hours post exposure. Samples of blood (plasma) and lung tissue were collected.

On the day of exposure, the NanoPac® suspension formulation (6 mg/mL) was prepared as per instructions provided by the sponsor Total aerosol exposure time was 63 minutes for all animals. Aerosol concentration was monitored throughout the 63 minute NanoPac® formulation aerosol exposure by measuring the amount of formulation accumulated on 47-mm GF/A filters positioned at the breathing zone in a nose-only exposure chamber. The aerosol particle size (droplet size) was measured using Mercer style cascade impactor from animal breathing zone on the exposure chamber.

NanoPac® suspension formulation was aerosolized using two Hospitak compressed air jet nebulizers (average Paclitaxel aerosol concentration: target 82.65 µg/L). The overall average aerosol concentration as measured from the GF/A filters was 0.24 mg/L, and the average Paclitaxel aerosol concentration was 73.5 µg/mL. The particle size distribution was measured to be 2.0 µm MMAD with a GSD of 2.2. The measured average Paclitaxel aerosol concentration of 73.5 µg/L was ~ 11% lower from target average Paclitaxel aerosol concentration of 82.65 µg/L (within the accuracy/recovery performance criteria of the analytical assay of ±15% as reported in example 3). Oxygen and temperature were monitored throughout the NanoPac® formulation aerosols exposure. The recorded oxygen and temperature ranges were 19.7%-20.9% and 20.4° C.-20.8° C., respectively.

Paclitaxel deposited dose to the lung was calculated based on the Paclitaxel average aerosol concentration of 73.5 µg/L, average rodent body weight of 326 g, assumed deposition fraction of 10% and exposure duration of 63 minutes. The average achieved rodent deposited dose was determined to be 0.33 mg/kg. The average achieved deposited dose was ~11% lower when compared to target deposited dose of 0.37 mg/kg, but was within the expected variability (+15% from target) for nebulized exposures.

All animals survived to their designated necropsy timepoint. At necropsy, several animals had minimal, red discolorations on the lungs. No other abnormal gross observations were noted at necropsy. From body and lung weights obtained at necropsy, average terminal bodyweight among animals at all timepoints (standard deviation) was 346.26 g (24.01); and average lung weight (standard deviation) was 1.60 g (0.13).

Systemic blood (in the form of plasma from $K_2$EDTA) was assayed via the liquid chromatography-mass spectrometry (LCMS) assay and lung tissue was assayed as briefly described in section (Bioanalytical Analysis) to quantify the amount of paclitaxel as a function of time. The lung tissue analysis showed lung exposure with detectable amounts of Paclitaxel out to 168 hours. The systemic blood showed no detectable Paclitaxel (under 1 ng/mL) after 24 hours. Based on these data the following sampling timepoints are suggested for the PK study: 0.5 (±10 minutes), 6 (±10 minutes), 12 (±10 minutes), 24 (±30 minutes), 48 (±30 minutes), 72 (±30 minutes), 120 (±30 minutes) 168 (±30 minutes), 240 (±30 minutes) and 336 (±30 minutes) hours post inhalation exposure.

Objectives

The objective of this pilot study was to define sampling timepoints for a complete pharmacokinetic (PK) study with NanoPac®. The preliminary data with NanoPac® dosed by intraperitoneal (IP) injection indicate a significant retention time in the intraperitoneal cavity. Due to the potential for the NanoPac® formulation to result in increased retention in the lungs, time points out to 168 hours were evaluated to determine the appropriate sampling strategy for a complete pharmacokinetic study.

Materials and Methods

Test System:
　Species/Strain: Sprague Dawley Rats
　Age of Animals at Study Start: 8-10 weeks of age
　Body Weight Range at Study Start: 308-353 g
　Number on Study/Sex: 18 Males (16 study animals and 2 spares)
　Source: Charles River Laboratories (Kingston, NY)
　Identification: Permanent maker tail marking Test and Control Article Formulation and Administration NanoPac® suspension formulation (6 mg/mL) was prepared as per instructions provided by the sponsor. Briefly, 5.0 mL of 1% Polysorbate 80 was added to the vial containing NanoPac® (306 mg) particles. NanoPac® vial was shaken vigorously and inverted to ensure wetting of all particles present in the NanoPac® vial. Immediately after shaking, 46 mL of 0.9% Sodium Chloride was added to the NanoPac® vial and the vial was shaken for at least 1 minute to make sure sufficient mixing and proper dispersion of suspension. Resultant formulation was left undisturbed for at least 5 minutes to reduce any air/foam in the vial before placing it in the nebulizer for aerosolization work. The final formulation was kept at room temperature and used within 3 hours after reconstitution.

Experimental Design

Sixteen (16) Sprague Dawley rats were exposed to NanoPac® (paclitaxel; target dose of 0.37 mg/kg) by nose only inhalation on a single occasion. Two animals (n=2) were euthanatized at 0.5 (±10 minutes), 6 (±10 minutes), 12 (±10 minutes), 24 (±30 minutes), 48 (±30 minutes), 72 (±30 minutes), 120 (±30 minutes) and 168 (±30 minutes) hours post exposure for blood (plasma) and lung tissue collections. No specific PK modeling was done; rather, data will define the duration for detectable amounts of paclitaxel post exposure for the PK Study.

Husbandry, Quarantine and Assignment to Study

Male Sprague Dawley rats (6-8 weeks old) were obtained from Charles River Laboratories (Kingston, NY) and quarantined for 14 days. At the end of quarantine, animals were weighed and then randomized by weight for assignment to study. Animals were identified by tail marking and cage card. Water, lighting, humidity, and temperature control were maintained and monitored using standard techniques. Rats were fed a standard rodent diet ad libitum during non-exposure hours.

Body Weights and Daily Observations

Body weights were collected at randomization, daily throughout the study and at euthanasia. Each animal on study was observed twice daily by Comparative Medicine Animal Resources (CMAR) personnel for any clinical signs of abnormality, moribundity or death.

Nose-Only Aerosol Exposures

Conditioning

Animals were conditioned to nose-only exposure tubes for up to 70 minutes using standard techniques. Three conditioning sessions occurred over three days prior to exposure, with the first session lasting 30 minutes, the second 60 minutes and the third 70 minutes. They were monitored closely throughout the conditioning periods and during exposures to assure that they did not experience more than momentary distress.

Exposure System

The inhalation exposure system consisted of two compressed air jet nebulizer (Hospitak) and a rodent nose-only inhalation exposure chamber. Exposure oxygen levels (%) were monitored throughout the exposure. NanoPac® suspension aerosol was generated with a set of two compressed air jet nebulizers (used for up to 40 (±1) minutes, then replaced with a second set of two compressed air jet nebulizers for remaining exposure duration) with an inlet pressure of 20 psi. The aerosol was directed through a 24-inch stainless steel aerosol delivery line (with a 1.53 cm diameter) into a nose-only exposure chamber.

Concentration Monitoring

Aerosol concentration monitoring was conducted by collecting aerosols onto pre-weighed GF/A 47-mm filters. The filters were sampled from rodent breathing zones of the nose-only exposure chamber throughout the rodent exposure. The aerosol sampling flow rate through GF/A filters were maintained at 1.0±0.5 L/minute. A total of six GF/A filters were collected, one every 10 minutes throughout the exposure duration with an exception of the last filter which was collected after 13 minutes. After sample collection, filters were weighed to determine the total aerosol concentration in the exposure system. The filters were extracted and analyzed by high performance liquid chromatography (HPLC) to quantify the amount of Paclitaxel collected on each filter. The total aerosol concentration and Paclitaxel aerosol concentrations were calculated for each filter by dividing the total amount of aerosols and Paclitaxel aerosols collected with total air flow through the filter. The average Paclitaxel aerosol concentration was used to calculate the achieved average deposited dose of Paclitaxel to the rodent lungs using equation 1 as shown below.

Aerosol Particle (Droplet) Size Determination

Particle size distribution of aerosols was measured from rodent breathing zone of the nose-only exposure chamber by a Mercer-style, seven-stage cascade impactor (Intox Products, Inc., Albuquerque, NM). The particle size distribution was determined in terms of mass median aerodynamic diameter (MMAD) and geometric standard deviation (GSD). Cascade impactor sample was collected at a flow rate of 2.0±0.1 L/min.

Determination of Dose

Deposited dose was calculated using Equation 1. In this calculation, the average aerosol concentration measured from the exposures along with average group body weights for rats were used. In this manner the estimated amount of Paclitaxel that was deposited in the rat lungs was calculated using the measured Paclitaxel aerosol concentration.

$$DD(\mu g/kg) = \frac{AC(\mu g/L) \times RMV(L/min.) \times DF \times T(min.)}{BW(kg)} \quad \text{Equation 1}$$

where:

Deposited Dose=(DD) µg/kg $^2$Respiratory minute volume (RMV)=0.608×BW$^{0.852}$ Aerosol exposure concentration (AC)=Paclitaxel aerosol concentration (µg/L)

Deposition Fraction (DF)=assumed deposition fraction of 10%

BW=average body weight (at randomization; Day −1) of animals on study (kg)

Euthanasia and Necropsy

Animals were euthanized at their respective time points by an IP injection of euthanasia solution. During necropsy, blood (for plasma) was collected by cardiac puncture into K$_2$EDTA tube, lungs were weighed, lung tissue samples were collected and snap frozen in liquid nitrogen for bioanalytical analyses. Additionally, a full gross examination was performed by qualified necropsy personnel. External surfaces of the body, orifices, and the contents of the cranial, thoracic, and abdominal cavities were examined. Lesions were described and recorded using a set of glossary terms for morphology, quantity, shape, color, consistency, and severity.

Bioanalytical Analyses

Systemic blood (in the form of plasma from K$_2$fEDTA) and lung tissue were assayed via the liquid chromatography-mass spectrometry (LCMS) assay to quantify the amount of paclitaxel as a function of time. In brief, the assay utilizes an ultra-performance liquid chromatography tandem mass spectrometry (UPLC-MS/MS) assay to quantify paclitaxel. Plasma samples are extracted via a protein precipitation method and separation is achieved via reversed phase chromatography. Lung samples were homogenized with water at a ratio of 4:1 (water:lung tissue). The homogenate then underwent a similar protein precipitation method prior to analysis on the LCMS. Quantification was conducted with a matrix based calibration curve.

No pharmacokinetic modeling was conducted on these data; however, the concentration at which paclitaxel drops below the sensitivity limits of the assay (1 ng/ml) was used to define the sampling timepoints for the main PK study.

Results

Clinical Observations and Survival

All animals survived to their designated necropsy timepoint and gained weight. No abnormal clinical observations were noted through the duration of the study.

NanoPac® Exposures

Aerosol Concentration

Table 18 shows total aerosol and Paclitaxel aerosol concentrations measured by sampling each GF/A filter during exposures. The inhalation exposure average Paclitaxel aerosol concentration of 73.5 µg/L was ~11% lower from target average Paclitaxel aerosol concentration of 82.65 µg/L. The average exposure aerosol concentration was within ±15% of target aerosol concentration which was expected for nebulized inhalation exposures.

TABLE 18

Aerosol concentrations during inhalation exposure.

| Filter ID | Total Aerosol Conc. (mg/L) | Paclitaxel Aerosol Conc. (µg/L) |
| --- | --- | --- |
| FS-1 | 0.230 | 68.97 |
| FS-2 | 0.236 | 71.82 |
| FS-3 | 0.240 | 77.58 |
| FS-4 | 0.268 | 87.11 |
| FS-5 | 0.205 | 62.11 |
| FS-6 | 0.237 | 73.12 |
| Average | 0.24 | 73.5 |
| SD | 0.02 | 8.4 |
| % RSD | 8.55 | 11.5 |

Oxygen and Temperature

The recorded oxygen and temperature ranges were 19.7%-20.9% and 20.4° C.-20.8° C., respectively.

Particle Size

The particle size distribution was determined in terms of MMAD (GSD) for 6.0 mg/mL NanoPac® formulation aerosols using cascade impactor was 2.0 (2.2) µm.

Deposited Dose

Based on Paclitaxel average aerosol concentration of 73.5 µg/L, average rodent Day −1 (randomization) body weight of 326 g, assumed deposition fraction of 10% and exposure duration of 63 minutes; the average achieved rodent deposited dose was determined to be 0.33 mg/kg. The average achieved deposited dose was ~11% lower when compared to target deposited dose of 0.37 mg/kg due to expected variability (±15% from target) in exposure average aerosol concentration.

Necropsy

All animals survived to their designated necropsy timepoint. At necropsy several animals had minimal, red discolorations on the lungs. No other abnormal gross observations were noted at necropsy. Individual and average lung weights, body weights and ratios were determined. Average terminal bodyweight (standard deviation) was 346.26 g (24.01). Average lung weight (standard deviation) was 1.60 g (0.13). Organ lung weights and lung weight to body weight ratios are common parameters used to assess potential toxicological responses to inhaled materials. Overall, the data are in line with historical data and indicate that there was not a response with either of these endpoints.

Bioanalytical

Results are summarized below in Table 19. Average paclitaxel concentration in plasma was 16.705 ng/mL at 0.5 hours post exposure, then decreased gradually through the 24 hour timepoint and was below the lower limit of quantification (1 ng/mL) for all subsequent timepoints. Average paclitaxel concentration in lung tissue was 21940 ng/g at 0.5 hours post exposure and decreased gradually to 419.6 ng/g by the 168 hour timepoint. This indicates significant NanoPac® retention in the lung with minimal systemic exposure.

TABLE 19

Lung tissue and plasma results

| Animal Number | Time-point (hr) | Plasma Concentration (ng/mL) | Lung Tissue Concentration (ng/g) | Plasma Average Conc. (ng/mL) Per timepoint | Lung Tissue Average Conc. (ng/g) Per timepoint |
| --- | --- | --- | --- | --- | --- |
| 1001 | 0.5 | 8.81 | 16680 | 16.705 | 21940 |
| 1002 | | 24.6 | 27200 | | |
| 1003 | 6 | 4.46 | 7800 | 4.695 | 7160 |
| 1004 | | 4.93 | 6520 | | |

TABLE 19-continued

Lung tissue and plasma results

| Animal Number | Time-point (hr) | Plasma Concentration (ng/mL) | Lung Tissue Concentration (ng/g) | Plasma Average Conc. (ng/mL) Per timepoint | Lung Tissue Average Conc. (ng/g) Per timepoint |
|---|---|---|---|---|---|
| 1005 | 12 | 3.72 | 8240 | 3.720 | 6320 |
| 1006 |  | <LLOQ | 4400 |  |  |
| 1007 | 24 | <LLOQ | 3144 | 3.140 | 4452 |
| 1008 |  | 3.14 | 5760 |  |  |
| 1009 | 48 | <LLOQ | 2300 | <LLOQ | 2652 |
| 1010 |  | <LLOQ | 3004 |  |  |
| 1011 | 72 | <LLOQ | 1760 | <LLOQ | 2028 |
| 1012 |  | <LLOQ | 2296 |  |  |
| 1013 | 120 | <LLOQ | 608 | <LLOQ | 486.8 |
| 1014 |  | <LLOQ | 366 |  |  |
| 1015 | 168 | <LLOQ | 572 | <LLOQ | 419.6 |
| 1016 |  | <LLOQ | 267 |  |  |

Conclusions

Sixteen (16) male Sprague Dawley rats were exposed to NanoPac® (paclitaxel; target dose of 0.37 mg/kg) by nose only inhalation on a single occasion. Two animals (n=2) were euthanatized at 0.5, 6, 12, 24, 48, 72, 120 and 168 hours post exposure for blood (plasma) and lung tissue collections.

The average Paclitaxel aerosol concentration of 73.5 µg/L during the 63 minute inhalation exposure was ~11% lower from target average Paclitaxel aerosol concentration of 82.65 µg/L. The average exposure aerosol concentration was within ±15% of target aerosol concentration which was expected for nebulized inhalation exposures. The particle size distribution was determined in terms of MMAD (GSD) for 6.0 mg/mL NanoPac® formulation aerosols using cascade impactor as 2.0 (2.2) µm. The recorded oxygen and temperature ranges were 19.7%-20.9% and 20.4° C.-20.8° C., respectively.

Paclitaxel deposited dose was calculated based on Paclitaxel average aerosol concentration of 73.5 µg/L, average rodent body weight of 326 g, assumed deposition fraction of 10% and exposure duration of 63 minutes. The average achieved rodent deposited dose was determined to be 0.33 mg/kg. The average achieved deposited dose was ~11% lower when compared to target deposited dose of 0.37 mg/kg due to expected variability (±15% from target).

All animals survived to their planned necropsy timepoint. At necropsy, several animals had minimal, red discolorations on the lungs. No other abnormal gross observations were noted at necropsy. From body and lung weights obtained at necropsy, average terminal bodyweight (standard deviation) was 346.26 g (24.01); and average lung weight (standard deviation) was 1.60 g (0.13). Organ lung weights and lung weight to body weight ratios are common parameters used to assess potential toxicological responses to inhaled materials. Overall, the data indicate that there was not a response with either of these endpoints.

Average paclitaxel concentration in plasma was 16.705 ng/mL at 0.5 hours post exposure, then decreased gradually through the 24 hour timepoint and was below the lower limit of quantification at all timepoints after 24 hours. Average paclitaxel concentration in lung tissue was 21940 ng/g at 0.5 hours post exposure and decreased gradually to 419.6 ng/g by the 168 hour timepoint. This indicates significant NanoPac® retention in the lung with minimal systemic exposure. The following sampling timepoints are suggested for the PK study: 0.5 (±10 minutes), 6 (±10 minutes), 12 (±10 minutes), 24 (±30 minutes), 48 (±30 minutes), 72 (±30 minutes), 120 (±30 minutes) 168 (±30 minutes), 240 (±30 minutes) and 336 (±30 minutes) hours post exposure.

Example 12—NanoPac® (i.e.: (i.e.: Paclitaxel Particles as Disclosed Herein, Approximately 98% Paclitaxel with a Mean Particle Size (Number) of 0.83 Microns, a SSA of 27.9 m²/g, and a Bulk Density (not Tapped) of 0.0805 g/Cm³) Inhalation Study in Rats—Low Dose and High Dose Summary The overall objective of this work was to conduct nose-only inhalation exposure to male rats with NanoPac® suspension formulations of 6.0 mg/mL and 20.0 mg/mL. Rat inhalation exposures were conducted for 65 minutes each.

NanoPac® suspension formulation of 6.0 mg/mL and 20.0 mg/mL were prepared as per instructions provided by the sponsor. Two Hospitak compressed air jet nebulizers were used simultaneously at 20 psi for aerosolization of NanoPac® formulation into the rodent inhalation exposure chamber. During each exposure, aerosol concentration was measured from animal breathing zone by sampling onto 47-mm GF/A filters at a flow rate of 1.0±0.5 L/minute. Particle size was determined by sampling aerosols from animal breathing zone using Mercer style cascade impactor at a flow rate of 2.0±0.1 L/minute. Filters were analyzed gravimetrically to determine total NanoPac® aerosol concentration and via high performance liquid chromatography (HPLC) to determine Paclitaxel aerosol concentration for each exposure. Oxygen and temperature were monitored and recorded throughout the inhalation exposures.

The average total NanoPac® aerosol concentration and Paclitaxel aerosol concentration were determined to be 0.25 mg/L with a RSD of 7.43% and 85.64 µg/L with a RSD of 10.23%, respectively for inhalation exposures conducted with 6.0 mg/mL NanoPac® formulation. The measured average mass median aerodynamic diameter (geometric standard deviation) using cascade impactor was 1.8 (2.0) µm for 6.0 mg/mL NanoPac® formulation aerosols. The average total NanoPac® aerosol concentration and Paclitaxel aerosol concentration were determined to be 0.46 mg/L with a RSD of 10.95% and 262.27 µg/L with a RSD of 11.99%, respectively for inhalation exposures conducted with 20.0 mg/mL NanoPac® formulation. The measured average mass median aerodynamic diameter (geometric standard deviation) using cascade impactor was 2.3 (1.9) µm for 20.0 mg/mL NanoPac® formulation aerosols.

The average Paclitaxel deposited dose of 0.38 mg/kg and 1.18 mg/kg were calculated using equation 1 for a 65 minute exposure for 6.0 mg/mL and 20.0 mg/mL NanoPac® formulation, respectively.

Formulation and Inhalation Exposure

Formulation Preparation

Materials

Test Article: The test article used for inhalation exposure is shown below:

NanoPac®:

Identity: NanoPac® (sterile nanoparticulate Paclitaxel)

Description: Novel dry powder formulation of Paclitaxel delivered as 306 mg/vial Vehicle The vehicles used for preparation of NanoPac® formulations are shown below:

1% Polysorbate 80 Solution
  Identity: Sterile 1% Polysorbate 80 in 0.9% sodium chloride for injection
  Description: Clear liquid
Normal Saline Diluent
  Identity: Sterile 0.9% sodium chloride for injection, USP
  Description: Clear liquid Formulation and Inhalation Exposure
Formulation Preparation NanoPac® formulation of 6.0 mg/mL was prepared as follows: Briefly, 5.0 mL of 1% Polysorbate 80 was added to the vial containing NanoPac® (306 mg, particles. NanoPac® vial was shaken vigorously and inverted to ensure wetting of all particles present in the NanoPac® vial. Immediately after shaking, 46 mL of 0.9% Sodium Chloride solution was added to the NanoPac® vial and vial was shaken for at least 1 minute to make sure sufficient mixing and proper dispersion of suspension.

The NanoPac® formulation procedure described above for 6.0 mg/mL formulation was used to prepare 20.0 mg/mL NanoPac® formulation with an exception of 10.3 mL of 0.9% sodium chloride solution was added to the NanoPac® vial instead of 46 mL used for 6.0 mg/mL formulation.

Resultant formulations were left undisturbed for at least 5 minutes to reduce any air/foam in the vial before placing it in nebulizer for aerosolization work. The final formulation of 6.0 mg/mL was kept at room temperature and nebulized within 2 hours after reconstitution. The final formulation of 20.0 mg/mL was kept at room temperature and nebulized within 30 minutes after reconstitution.

Exposure System Set-up/Aerosol Generation: As in example 11
Aerosol Concentration Monitoring: As in Example 11
Particle Size Distribution: As in Example 11
Deposited Dose Calculation: As in Example 11
Results
Aerosol Concentration and Particle Size Aerosol concentration was monitored throughout each NanoPac® formulation aerosol exposure using 47-mm GF/A filters from breathing zone of the animals on nose-only exposure chamber. Seven 47-mm GF/A filters were sampled during each exposure. Filters FS-1 through FS-6 were sampled for 10 minutes each and filter FS-7 was sampled for 5 minutes during each low and high dose groups. Particle size was measured using Mercer style cascade impactor from animal breathing zone on the exposure chamber. Tables 20 and 21 show total and Paclitaxel aerosol concentrations measured by sampling GF/A filters during low dose and high dose exposures, respectively.

TABLE 20

Aerosol concentrations during FY17-008B low dose inhalation exposure.

| Filter ID | Total Aerosol Conc. (mg/L) | Paclitaxel Aerosol Conc. (µg/L) |
| --- | --- | --- |
| FS-1-L | 0.247 | 80.05 |
| FS-2-L | 0.242 | 81.79 |
| FS-3-L | 0.252 | 87.09 |
| FS-4-L | 0.296 | 104.38 |
| FS-5-L | 0.247 | 78.47 |
| FS-6-L | 0.249 | 82.50 |
| FS-7-L | 0.244 | 85.19 |
| Average | 0.25 | 85.64 |
| SD | 0.02 | 8.76 |
| % RSD | 7.43 | 10.23 |

TABLE 21

Aerosol concentrations during FY17-008B high dose inhalation exposure.

| Filter ID | Total Aerosol Conc. (mg/L) | Paclitaxel Aerosol Conc. (µg/L) |
| --- | --- | --- |
| FS-1-H | 0.383 | 212.53 |
| FS-2-H | 0.412 | 239.28 |
| FS-3-H | 0.494 | 291.44 |
| FS-4-H | 0.516 | 296.56 |
| FS-5-H | 0.456 | 254.67 |
| FS-6-H | 0.501 | 289.50 |
| FS-7-H | 0.431 | 251.88 |
| Average | 0.46 | 262.27 |
| SD | 0.05 | 31.45 |
| % RSD | 10.95 | 11.99 |

Figure 9:
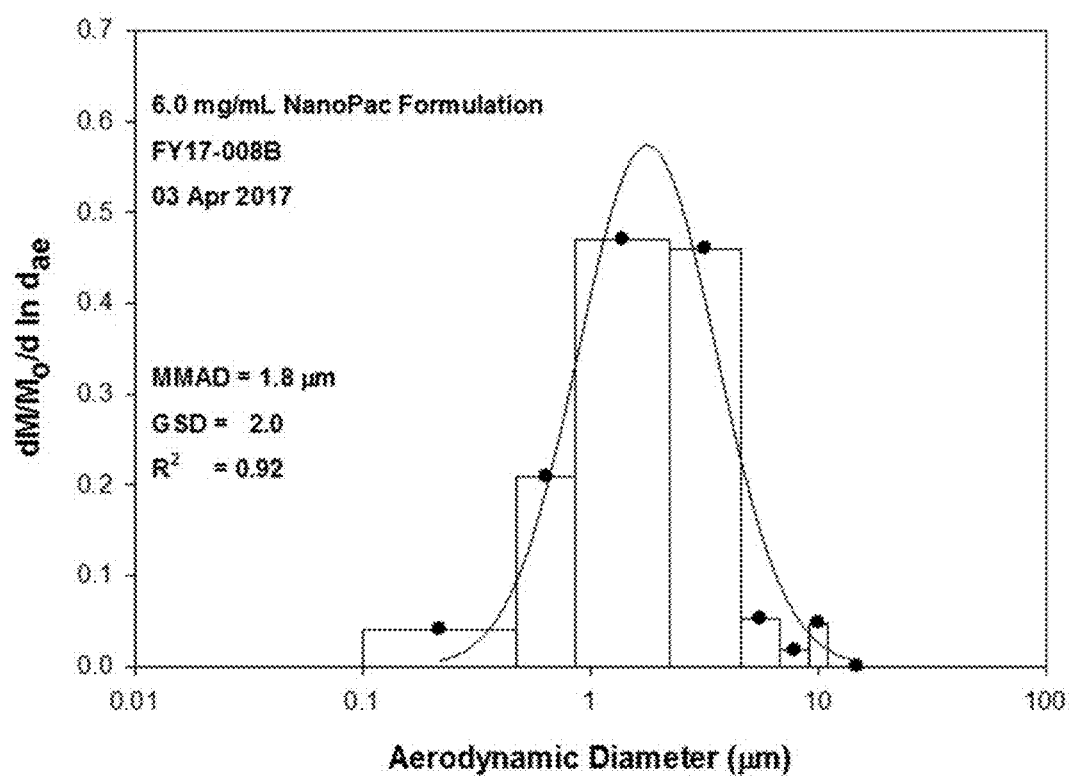
FIG. 9 is a plot of the particle size distribution for 6.0 mg/mL NanoPac® formulation aerosols as FIG. 12 is a graph of paclitaxel levels in lung tissue over time after pulmonary administration in rats.
Figure 10:
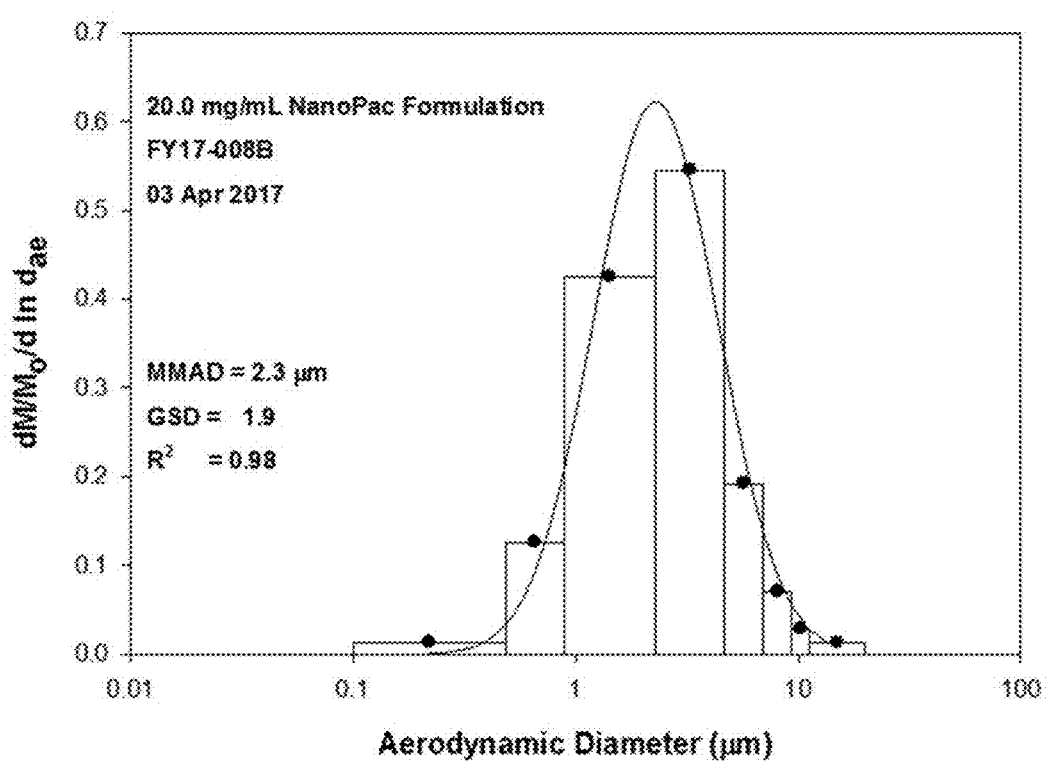

The particle size (aerosol droplet size) distribution was determined in terms of MMAD (Median of the distribution of airborne particle mass with respect to the aerodynamic diameter) (GSD; accompanies the MMAD measurement to characterize the variability of the particle size distribution) for each NanoPac® formulation aerosols using cascade impactor. For 6.0 mg/mL and 20.0 mg/mL NanoPac® aerosols the MMAD (GSD) were determined to be 1.8 (2.0) µm and 2.3 (1.9) µm, respectively. FIGS. 9 and 10 show particle size distribution for 6.0 mg/mL and 20.0 mg/mL NanoPac® formulations aerosols, respectively.

Deposited Dose

Paclitaxel deposited dose was calculated based on Paclitaxel average aerosol concentration, average rat body weight, assumed deposition fraction of 10% and exposure duration of 65 minutes for each low dose and high dose NanoPac® formulation exposures by using equation 1. Table 22 shows average Paclitaxel aerosol concentration, average rat body weight, exposure time and deposited dose for each exposure. The average achieved rodent deposited dose was determined to be 0.38 mg/kg and 1.18 mg/kg for 6.0 mg/kg and 20.0 mg/kg NanoPac® formulation exposures, respectively.

TABLE 22

Paclitaxel deposited dose for low and high dose NanoPac® inhalation exposures.

| Dose Level | NanoPac® Formulation Conc. (mg/mL) | Paclitaxel Avg. Aerosol Conc. (µg/L) | Avg. Rat Weight (g) | Exposure Time (min.) | Deposited Dose (mg/kg) |
| --- | --- | --- | --- | --- | --- |
| Low | 6.0 | 85.64 | 420.4 | 65 | 0.38 |
| High | 20.0 | 262.27 | 420.5 | 65 | 1.18 |

Oxygen and Temperature

Oxygen and temperature were monitored throughout the NanoPac® formulation aerosols exposures. The recorded oxygen and temperature ranges were 19.8%-20.9% and 20.7° C.-20.8° C., respectively for 6.0 mg/mL NanoPac® exposure. For 20.0 mg/mL NanoPac® formulation exposure, the recorded oxygen value was 19.8% throughout the exposure and temperature range was 20.7° C.-20.8° C.

Figure 11:
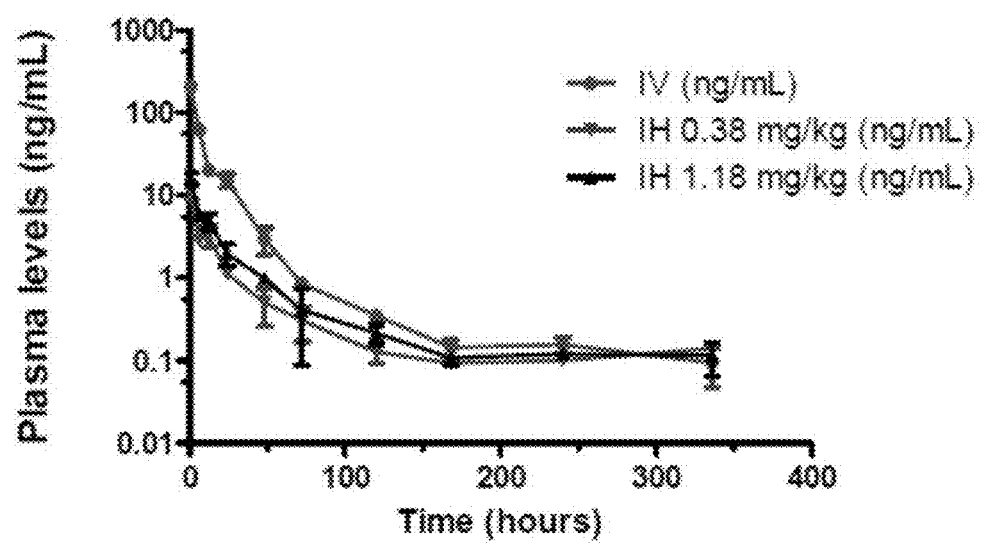
Figure 12:
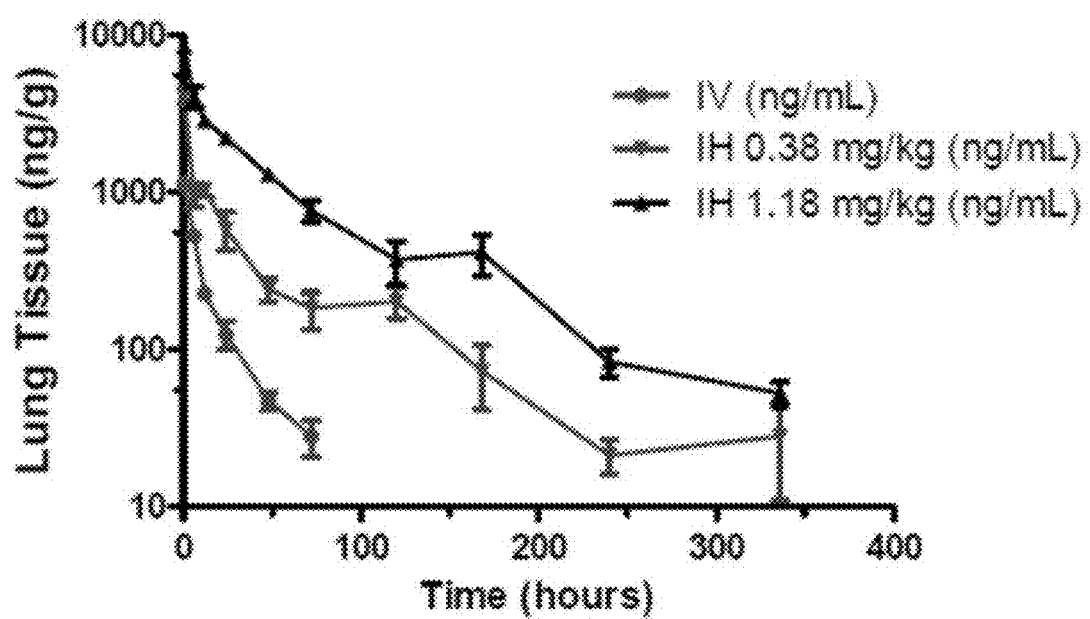

Preliminary Data: See FIGS. 11 and 12.

Example 13—Evaluating Efficacy of Inhaled NanoPac® (i.e.: Paclitaxel Particles as Disclosed Herein, Approximately 98% Paclitaxel with a Mean Particle Size (Number) of 0.83 Microns, a SSA of 27.9 m²/g, and a Bulk Density (not Tapped) of 0.0805 g/Cm³) in the Nude Rat Orthotopic Lung Cancer Model—Study FY17-095

Executive Summary

One hundred twenty-seven (127) NIH-rnu Nude Rats were x-irradiated to induce immunosuppression on Day −1. On Day 0 animals were dosed with Calu3 tumor cells by intratracheal (IT) instillation. Animals underwent a growth period of three weeks. During the third week, animals were randomized by body weight stratification into 5 study groups. Starting Week 4, animals in Group 2 received a once weekly dose of Abraxane® by intravenous (IV) dosing (5 mg/kg) on Days 22, 29 and 36. Animals in Groups 3 and 4 received once weekly (Monday) inhalation (INH) dose of NanoPac® at low (0.5 mg/kg) and high (1.0 mg/kg) target doses, respectively. Animals in Groups 5 and 6 received a twice weekly (Monday and Thursday) target inhalation dose of NanoPac® at low (0.50 mg/kg) and high (up to 1.0 mg/kg) doses respectively. Animals in Group 1 were left untreated as a control of normal tumor cell growth. All animals were necropsied during Week 8.

All animals survived to their designated necropsy timepoint. Clinical observations related to the model included skin rash and labored breathing. All groups gained weight at about the same rate throughout the course of the study.

The inhalation exposure average Paclitaxel aerosol concentration for once weekly Low Dose and twice weekly Low Dose NanoPac® groups was 270.51 μg/L and 263.56 μg/L, respectively. The inhalation exposure average Paclitaxel aerosol concentration for once weekly High Dose and twice weekly High Dose NanoPac® groups was 244.82 μg/L and 245.76 μg/L, respectively.

Doses were based on average aerosol paclitaxel concentration, most recent average group bodyweight, the assumed deposition fraction of 10%, and an exposure duration of 33 (Low-Dose) or 65 (High-Dose) minutes. During four weeks of treatment, the average achieved rodent deposited dose for the once weekly Low Dose NanoPac® group and twice weekly Low Dose NanoPac® group were 0.655 mg/kg and 0.640 mg/kg (1.28 mg/kg/week), respectively. The average achieved rodent deposited dose for the once weekly High Dose NanoPac® group and twice weekly High Dose NanoPac® group were 1.166 mg/kg and 1.176 mg/kg (2.352 mg/kg/week), respectively. For the group receiving IV injections of Abraxane®, the average dose on Day 22, 29 and 36 was 4.94, 4.64 and 4.46 mg/kg respectively.

At scheduled necropsy, the majority of animals from each group had tan nodules on the lungs and/or red or tan patchy discolorations of the lung. Other sporadic observations included an abdominal hernia in one animal and a nodule on the pericardium in another animal. No other abnormal gross observations were noted at necropsy.

In the Abraxane treated animal's lung weights, the lung to BW ratios and lung to brain weight ratios were significantly lower compared to Untreated Controls. The once weekly NanoPac® High Dose group had similar weights to the Abraxane group and significantly lower lung weights and lung to brain ratios compared to Untreated Controls.

Histologically, lungs of the majority of animals in all groups contained some evidence of tumor formation. Tumor formation was characterized by the presence of expansile variably sized small masses randomly scattered within the lung parenchyma and larger expanded and coalescing masses that effaced up to 75% of the lung parenchyma, smaller airways and blood vessels. The larger masses were distributed primarily in the hilar regions or juxtaposed at the axial airway and the smaller masses were generally located peripherally.

The primary morphologic cellular characteristics of the lung tumor masses varied from the presence of undifferentiated to a fairly well differentiated pattern of adenocarcinoma of the lung. The predominant tumor cell type showed an undifferentiated adenocarcinoma morphology; the cells were pleomorphic, large, anaplastic, pale amphophilic-staining with fine intracytoplasmic vacuoles resembling mucoid vesicles, exhibited moderate to marked anisokaryosis, and were observed to be individualized or growing in sheets and lacking clear-cut features towards differentiation to adenocarcinoma. However, the cellular morphologic characteristics that were observed within other masses or growing within the previously described undifferentiated masses were more organized and consistent with well differentiated lung adenocarcinoma demonstrating clear acinar gland differentiation. These amphophilic staining tumor cells were primarily arranged in nests or glandular patterns which were observed to be bound by alveolar septae. Mitotic figures were rarely observed in this tumor cell population. Less frequently observed within these masses were focal areas of primitive-appearing relatively small Primitive Tumor Cells with small to moderate amounts of pale basophilic staining cytoplasm, ovoid and variably vesicular nuclei, and moderate anisokaryosis. These Primitive Tumor Cells were observed to be growing randomly and in sheets. Increased numbers of mitotic figures and apoptotic bodies were noted most often in this basophilic Primitive Tumor Cell population. Inflammation, characterized by mixed inflammatory cell (predominately eosinophils, lymphocytes, foamy macrophages and the occasional giant cell) infiltration accompanied by interstitial fibrosis was commonly observed. Significant parenchymal necrosis was uncommon to absent.

The pathologist considered the presence of scalloping of the edges of the individual tumor masses characterized by gradual loss of tumor cells, to complete loss of tumor cells with residual fibrosis connective tissue scaffolding of the lung parenchyma and accompanied by invasion of foamy macrophages to be evidence of Tumor Regression.

Compared to the positive control Grp. 1 and the Abraxane treated comparative Grp. 2, there was a decreased overall lung tumor burden in the NanoPac® treated groups (Grp. 3-6) characterized by a decrease in the severity of adenocarcinoma tumor masses and Primitive Tumor Cell population as well as evidence of Tumor Regression. No other treatment-related lesions or findings were observed. Extensive mononuclear cell infiltration was observed in the lungs of animals receiving NanoPac® through inhalation. As the model used is T cell deficient, it is likely that the cells are B cells or NK cells. It is hypothesized that the localized, likely higher concentration exposure of the tumor to NanoPac® affected the tumors leading to an alteration in the environment to draw the mononuclear cellular infiltrate into the lung.

Objectives

The objective of this study was to evaluate the efficacy of inhaled NanoPac® formulation compared to a clinical reference dose of intravenous administered Abraxane in reducing tumor burden in an orthotopic model of lung cancer.

Materials and Methods

Test System
Species/Strain: NIH-rnu Nude Rats
Age of Animals at Study Start: 3-5 weeks old
Body Weight Range at Study Start: Approximately 150-200 g
Number on Study/Sex: 127 Males (120 study animals and 7 spares)
Source: Envigo
Identification: Permanent maker tail marking
Abraxane Formulation The clinical reference material used for IV formulation was the drug product Abraxane®. The drug product was reconstituted to 5.0 mg/mL with saline on the day of dosing and was stored per manufacturer's instructions.
NanoPac® Formulation The 20.0 mg/ml NanoPac® formulations for exposures were prepared per the sponsor recommendations. Specifically, the NanoPac® was reconstituted with 1% polysorbate 80. The vial was shaken by hand until all particles were wetted. Additional 0.9% sodium chloride for injection was added (to the desired concentration target) and the vial was shaken by hand for another minute. Shaking continued until no large clumps were visible and the suspension was properly dispersed.

Resultant formulations were left undisturbed for at least 5 minutes to reduce any air/foam in the vial before placing it in a nebulizer for aerosolization work. The final formulation was kept at room temperature and nebulized within 2 hours after reconstitution. The final 20.0 mg/mL was kept at room temperature and nebulized within 30 (+5) minutes after reconstitution.
Experimental Design One hundred twenty-seven (127) animals were used for study. Prior to x-irradiation and dosing of tumor cells, 7 animals were designated as spares (spare animals did not have irradiations or cell line instillations). On Day −1 all study animals were x-irradiated to induce immunosuppression. On Day 0 animals were dosed with Calu3 tumor cells by intratracheal (IT) instillation. Animals underwent a growth period of three weeks. During the third week, animals were randomized by body weight stratification into the groups outlined in Table 23 below. Starting Week 4, animals in Group 2 received a once weekly target dose of Abraxane® by intravenous (IV) dosing (5 mg/kg). Animals in Groups 3 and 4 received once weekly (Monday) inhalation (INH) target dose of NanoPac® at low (0.5 mg/kg) and high (1.0 mg/kg) doses, respectively. Animals in Groups 5 and 6 received a twice weekly (Monday and Thursday) inhalation target dose of NanoPac® at low (0.50 mg/kg) and high (1.0 mg/kg) respectively. Animals in Group 1 were left untreated as a control of normal tumor cell growth. All animals were necropsied during Week 8.

TABLE 23

Experimental Design

| Group Description | N= | Irradiation | Cell Line | Route | Target Dose and Frequency* | Treatment Formulation | Exposure Duration | Necropsy* |
|---|---|---|---|---|---|---|---|---|
| 1 Control | 20 | Day-1 | Calu 3, IT instillation | N/A | N/A | N/A | N/A | Week 8 |
| 2 IV Abraxane | 20 | | | IV | up to 5 mg/kg** | Abraxane (5 mg/ml) | N/A | |
| 3 NanoPac® Low Once Weekly (1×) | 20 | | Day 0 | INH | 0.5 mg/kg, once weekly | 20.0 mg/mL NanoPac® | 33 min | |
| 4 NanoPac High Once Weekly (1×) | 20 | | | INH | 1.0 mg/kg, once weekly | 20.0 mg/mL NanoPac® | 65 min | |
| 5 NanoPac® Low- Twice Weekly (2×) | 20 | | | INH | 0.5 mg/kg, twice weekly | 20.0 mg/mL NanoPac® | 33 min | |
| 6 NanoPac® High Twice Weekly (2×) | 20 | | | INH | 1.0 mg/kg, twice weekly | 20.0 mg/mL NanoPac® | 65 min | |

*Treatment occurred during Week 4-8. Necropsy occurred during Week 8.

**Abraxane® target dose: 5.0 mg/kg based on bodyweight; target dose volume: not to exceed 250 µL, frequency: Day 1, 8, and 15 of each 21 day cycle beginning during Week 4.

Husbandry, Quarantine and Assignment to Study

After quarantine all animals were weighed and randomized to remove the 7 spares based on body weights. From Week 1 to Week 3 animals were identified by cage cards (LC numbers) and tail markings.

During Week 3, prior to beginning treatment, animals were weighed and randomized into the groups listed above by body weight stratification and assigned a Study ID. From this point forward, animals were identified by cage cards and sharpie tail marking.

Immunosuppression and Irradiation

On Day −1, animals underwent whole body x-ray exposure with ~500 rads (Phillips RT 250 X-ray Therapy Unit, Phillips Medical Systems, Shelton, CT) set at 250 kVp, 15 mA, and a source-to-object distance of 100 cm. The animals were placed in a pie chamber unit, 2-3 animals per slice of pic. The irradiation process took ~ 10-15 minutes.

Tumor Cell Implantation

On Day 0, animals received tumor cells (Calu3) administered by IT. Briefly, after being anesthetized by 3-5% isoflurane in an induction chamber, the animal was placed with upper incisors hooked on an inclined hanging instillation platform. The animals tongue was gently secured while the stylet is inserted just past the larynx and into the trachea. A volume of cells in EDTA suspension (target dose volume: 500 µL; concentration: approximately 20×106 per 0.5 mL) was delivered to the lungs via intratracheal instillation. After the instillation, the animals' breathing and movement was monitored carefully. Following tumor cell implantation, animals underwent a tumor growth period of approximately 3 weeks prior to treatment to allow for tumor cell engraftment and the development of lung cancer.

Calu3 Growth and Preparation

Calu3 cells were grown at 37° C. with 5% $CO_2$ in cell culture flasks. They were grown in Roswell Park Memorial Institute (RPMI) 1640 media with 10% fetal bovine serum (FBS) until 80% confluence. Cells were maintained until the day of instillation. Prior to instillation they were harvested by washing with PBS, then trypsin was added to remove cells from the flask. The cells were neutralized with RPMI 1640 media containing 10% FBS. They were then centrifuged at 100×g for 5 minutes; the media was removed and the cells were resuspended to a concentration of 20 million cells in 450 µL of serum free RPMI. Prior to instillation, 50 µL of 70 µM EDTA was added to the cell suspension for a total IT dose volume of 500 µL per rat.

Body Weights and Daily Observations

Body weights were collected for randomization, weekly through Week 3, twice weekly beginning at Week 4 through the end of the study, and at necropsy.

Each animal on study was observed twice daily for any clinical signs of abnormality, morbidity or death. Technicians observed animals during dosing and bodyweight sessions.

Abraxane Administration IV-Tail Vein Injections

Abraxane (5 mg/mL, maximum dose volume of 250 µL) was administered to animals in Group 2 by IV tail vein injection on Days 22, 29 and 36.

NanoPac® Administration—Nose-only Aerosol Exposures

Conditioning

Animals were conditioned to nose-only exposure tubes for up to 70 minutes. Three conditioning sessions occurred over three days prior to exposure, with the first session lasting 30 minutes, the second 60 minutes and the third 70 minutes. They were monitored closely throughout the conditioning periods and during exposures to assure that they did not experience more than momentary distress.

Exposure System

Aerosols were generated with two compressed air jet Hospitak at a nebulizer pressure of 20 psi. NanoPac® suspension formulation of 20.0 mg/mL was used for low dose and high dose exposures. Aerosols were directed through a delivery line into a 32-port nose-only exposure chamber. The rodent inhalation exposures were conducted for 33 or 65 minutes. NanoPac® suspension aerosol was generated with a set of two Hospitak compressed air jet nebulizers (used for up to 40 (±1) minutes), then replaced with a second set of two Hospitak nebulizers for remaining exposure duration. Oxygen and temperature were monitored and recorded throughout each inhalation exposure Concentration Monitoring Aerosol concentration monitoring was conducted by collecting aerosols onto pre-weighed GF/A 47-mm filters. The filters were sampled from animals breathing zones of the nose-only exposure chamber throughout each inhalation exposure. The aerosol sampling flow rate through GF/A filters was maintained at 1.0±0.5 L/minute. Filters were collected throughout each exposure duration every 10-minutes except for the last filter. With the low-dose exposures (groups 3 and 5) lasting 33 minutes, the final filter was collected after 13 minutes and with the high-dose exposures (groups 4 and 6) lasting 65 minutes, the final filter was collected after 15 minutes. After sample collection filters were weighed to determine the total aerosol concentration in the exposure system.

Post weighing, each filter was placed in a 7 mL glass vial. The filters in glass vials were extracted and analyzed by High Performance Liquid Chromatography (HPLC) to quantify the amount of Paclitaxel collected onto the filters. The total aerosol concentration and Paclitaxel aerosol concentrations were calculated for each filter by dividing the total amount of aerosols and Paclitaxel aerosols collected with total air flow through the filter. The average Paclitaxel aerosol concentration was used to calculate the achieved average deposited dose of Paclitaxel to the rodent lungs using Equation 1 as shown in the Determination of Dose section below.

Determination of Dose

Deposited dose was calculated using Equation 1 same as in Example 4 Euthanasia and Necropsy At scheduled necropsy, animals were euthanized by intraperitoneal injection of an overdose of a barbiturate-based sedative.

Blood and Tissue Collection

For all necropsies a terminal body weight and brain weight was collected. For scheduled euthanasia blood (for plasma) was collected by cardiac puncture into a K2EDTA tube. The lungs were removed and weighed. A section of lung tissue containing a tumor, a tracheobronchial lymph node, was frozen in liquid nitrogen for potential future analysis. The remaining lung was fixed for potential histopathology.

Histopathology

Fixed left lung lobes were trimmed in a "bread loaf" manner and alternate sections were placed in 2 cassettes to yield 2 slides each with 3 representative sections of the left lung. Tissues were processed routinely, paraffin embedded, sectioned at ~4 µm, mounted, and stained with hematoxylin and eosin (H&E) for microscopic examination. Findings were graded subjectively, semi-quantitatively.

Sections of lung (1-4/animal) obtained from 60 out of the 120 treated nude rats on study, trimmed longitudinally, were processed to H&E stained glass slides for light microscopic evaluation.

During this review, the microscopic findings were recorded and then transferred to an electronic pathology reporting system (PDS-Ascentos-1.2.0, V.1.2), which summarized the incidence and severities of the lung burden characteristics data and tabulated the results and generated the individual animal data. The lungs from the 60 nude rats were examined histologically: Group 1 [1001-1010], Group 2 [2001-2010], Group 3 [3001-3010], Group 4 [4001-4010], Group 5 [5001-5010] and Group 6 [6001-6010]). In order to assess the level of tumor burden in these lungs, the lungs were evaluated and scored during histopathologic examination. For each cumulative lung burden characteristic diagnosis: 1) Adenocarcinoma (undifferentiated and differentiated), 2) Primitive Tumor Cells (poorly differentiated pleomorphic cells) and 3) Tumor Regression, the lungs were graded semi-quantitatively using a 4-point grading scale indicating the percent involvement of the overall lung tissue provided as follows: 0=no evidence, 1=minimal (~1-25% total area of lung sections involved), 2=mild (~25-50% total area of lung sections involved), 3=moderate (~50-75% total area of lung sections involved), and 4=marked (~75-100% total area of lung sections involved).

Histomorphometry

Histomorphometric analyses was performed using fixed left lung lobes of the first 10 animals from each group. Tissue was trimmed using a morphometry ("bread slice") style trim. Briefly, trimming started at a random point between 2 and 4 mm from the cranial end of the lung. Each lung section was cut approximately 4 mm thick. Odd numbered sections were placed caudal side down in cassette 1 while even numbered sections were placed in cassette 2. Tissue sections were then processed, paraffin embedded, and sectioned at 4 µm and stained with hematoxylin and eosin (H&E) for examination. Both slides (odd and even slices) were used to determine an average tumor fraction per animal.

Morphometric analysis was performed on the hematoxylin and eosin (H&E) stained lung tissue from the designated animals by Lovelace Biomedical. Whole slides (2 per animal containing transverse sections of the entire left lung) were scanned using a Hamamatsu Nanozoomer™. Scans were analyzed with Visiopharm Integrator System software (VIS, version 2017.2.5.3857). Statistical analysis of tumor area fraction was performed in GraphPad Prism 5 (version 5.04).

Computerized image quantification designed to quantify the amount of tumor area present on each slide was performed on all left lung tissue using the whole slide scans. The Visiopharm Application for quantifying the area of lung metastases was used to differentiate tumor cells from normal lung tissue based on cell density, staining intensity, and size and staining intensity. It is noted that this quantitation based upon simple H&E staining will not be perfect (i.e. it is not capable of fully discriminating between types of tumor tissue, necrotic and viable tumor tissue, and some normal structures may be included as tumor). The value in application of this process to H&E sections is that it is an unbiased approach to tumor quantification. The area of the whole piece of lung is determined, and the area occupied by structures identified as metastases is then expressed as a percentage of the total area. Minor adjustment of the area to be analyzed to ensure extrapulmonary structures are excluded and the entire lung is included may be performed manually. Other manual manipulations are avoided in order to ensure consistency across all groups and remove potential for introduction of bias. If possible, development of specific immunohistochemical stains to identify only tumor tissue would increase specificity of this analysis.

Blood Collection and Processing

Blood collected at necropsy was processed to plasma by centrifugation at a minimum of 1300 g at 4° C. for 10 minutes. Plasma samples were stored at −70 to −90° C. until analysis or shipment to sponsor.

Additional Morphologic and Immunohistochemical (IHC) Studies

A subset of 17 animals was chosen to review morphologic and immunohistochemical (IHC) features using slides prepared with Hematoxylin & Eosin, Masson's Trichrome, AE1/AE3 (pan-keratin), and CD11b (dendritic cells, natural killer cells and macrophages). This subset included Control animals (n=2) and Treated animals from each treatment group (n=3 per group). Rat lung blocks were sectioned at 4 µm thickness and collected on positively charged slides.

Methods

H&E and Masson's trichrome staining were performed according to standard protocols. For Anti-Pan Cytokeratin antibody [AE1/AE3], rat uterus was sectioned from a tissue bank as controls. Optimization was performed on formalin-fixed paraffin-embedded (FFPE) rat uterus tissue from the tissue bank using a Leica Bond automated immunostainer and a mouse Anti-Pan Cytokeratin [AE1/AE3] (Abcam, #ab27988, Lot #GR3209978-1) antibody at four different dilutions plus a negative control: no primary antibody, 1:50, 1:100, 1:200, and 1:400. Heat induced antigen retrieval was performed using Leica Bond Epitope Retrieval Buffer 1 (Citrate Buffer solution, pH6.0) for 20 minutes (ER 1(20)) and Leica Bond Epitope Retrieval Buffer 2 (EDTA solution, pH9.0) for 20 minutes (ER2(20)). Non-specific background was blocked with Rodent Block M (Biocare, #RBM961H, Lot #062117).

Anti-pan Cytokeratin antibody [AE1/AE3] antibody was detected using Mouse-on-Mouse HRPPolymer (Biocare, #MM620H, Lot #062016) and visualized with 3'3-diaminobenzidine (DAB; brown). A Hematoxylin nuclear counterstain (blue) was applied. Optimization slides were examined, and optimal staining conditions for sample slides were determined with Anti-Pan Cytokeratin antibody [AE1/AE3] at 1:50 dilution with ER2(20).

For Anti-CD-11b antibody, optimization was performed on formalin-fixed paraffin-embedded (FFPE) rat lymph nodes tissue from a tissue bank using a Leica Bond automated immunostainer and a rabbit anti-CD11b antibody at four different dilutions plus a negative control: no primary antibody, 1:250, 1:500, 1:1000 and 1:2000.

Heat induced antigen retrieval was performed using Leica Bond Epitope Retrieval Buffer 1 (Citrate Buffer, pH6.0) for 20 minutes (ER1(20)) or Leica Bond Epitope Retrieval Buffer 2 (EDTA solution, pH9.0) for 20 minutes (ER2(20)).

Anti-CD11b antibody was detected using Novocastra Bond Refine Polymer Detection and visualized with 3'3-diaminobenzidine (DAB; brown). A Hematoxylin nuclear counterstain (blue) was applied. Optimization slides were examined, and optimal staining conditions for FFPE tissue were determined with anti-CD11b at 1:2000 dilution with ER2(20). Rat lymph nodes controls were used alongside rat lung samples.

Study Results

Clinical Observation, Survival, and Bodyweights

All animals survived to their designated necropsy timepoint. Clinical observations related to the model included skin rash and labored breathing. One animal was observed to have an upper abdominal hernia. Per vet recommendation the animal was switched with a Group 1 (Untreated Control) that would not undergo inhalation exposures therefore no exposure tube restraint would be necessary.

Figure 13:
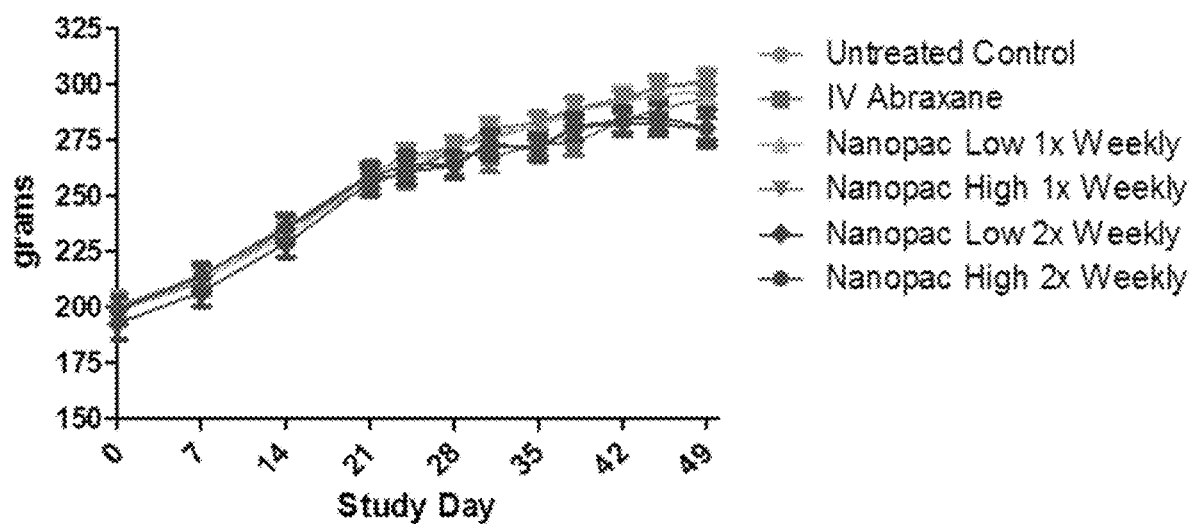
FIG. 13 is a graph of animal body weight over time from Orthotopic Lung Cancer study.
Figure 14:
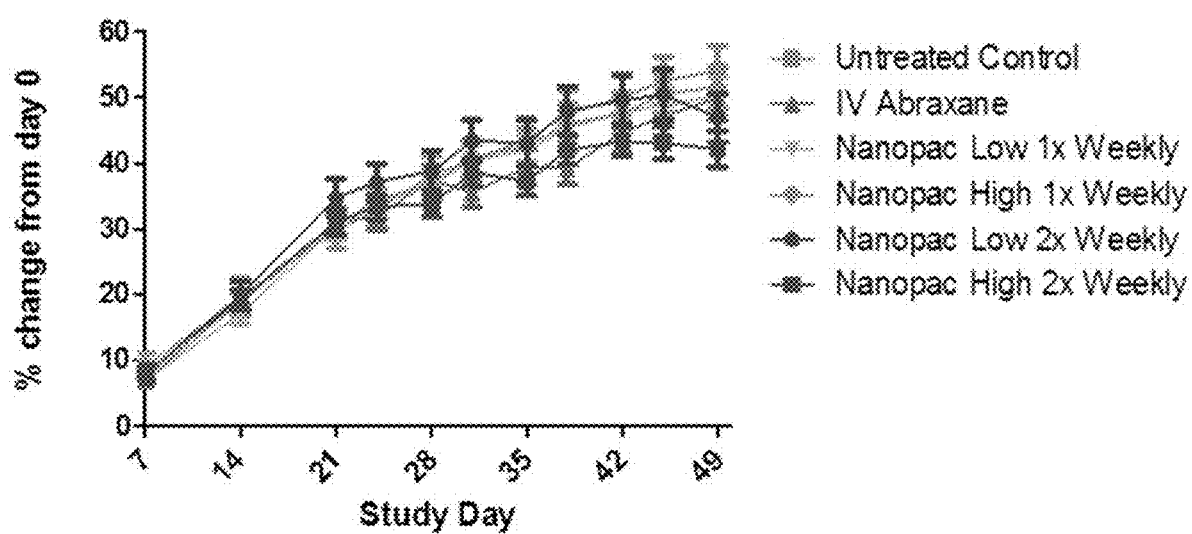
FIG. 14 is a graph of animal body weight change over time from Orthotopic Lung Cancer study.

FIG. 13 shows the average body weights through the duration of the study. FIG. 14 shows the percent change in average body weights from Day 0. All groups gained weight at about the same rate through the course of the study.

Abraxane IV Tail Vein Injections

For the group receiving IV injections of Abraxane, the average dose on Day 22, 29 and 36 was 4.94, 4.64 and 4.46 mg/kg respectively.

NanoPac® Exposures

Aerosol Concentrations and Deposited Dose

Total aerosol and Paclitaxel aerosol concentrations were measured by sampling of GF/A filters during each exposure. The inhalation exposure average Paclitaxel aerosol concentration for once weekly Low Dose and twice weekly Low Dose NanoPac® groups was of 270.51 µg/L and 263.56 µg/L, respectively. The inhalation exposure average Paclitaxel aerosol concentration for once weekly High Dose and twice weekly High Dose NanoPac® groups was of 244.82 µg/L and 245.76 µg/L, respectively. The oxygen and temperature levels were monitored throughout each exposure.

Doses were based on average aerosol paclitaxel concentration, most recent average group bodyweight, the assumed deposition fraction of 10% and an exposure duration of 33 or 65 minutes. During four weeks of treatment, the average achieved rodent deposited dose for the once weekly Low Dose NanoPac® group and twice weekly Low Dose NanoPac® group were 0.655 mg/kg and 0.640 mg/kg (1.28 mg/kg/week), respectively.

The average achieved rodent deposited dose for the once weekly High Dose NanoPac® group and twice weekly High Dose NanoPac® group were 1.166 mg/kg and 1.176 mg/kg (2.352 mg/kg/week), respectively.

Particle Size (MMAD & GSD)

The particle size distribution was determined in terms of Mass Median Aerodynamic Diameter (MMAD) and Geometric Standard Deviation (GSD) for each NanoPac® formulation aerosols using cascade impactor. For the 20.0 mg/mL NanoPac® aerosols the average MMAD was determined to be 2.01 µm and a GSD of 1.87.

Necropsy Observations and Organ Weights

All animals survived to their designated necropsy timepoint. At necropsy animals from each group had tan nodules on the lungs and/or red or tan patchy discolorations of the lung. Other sporadic observations included an abdominal hernia in one animal and a nodule on the pericardium in another animal. No other abnormal gross observations were noted at necropsy. One animal did not have any visible tumors (nodules) at the time of necropsy.

Figure 15:
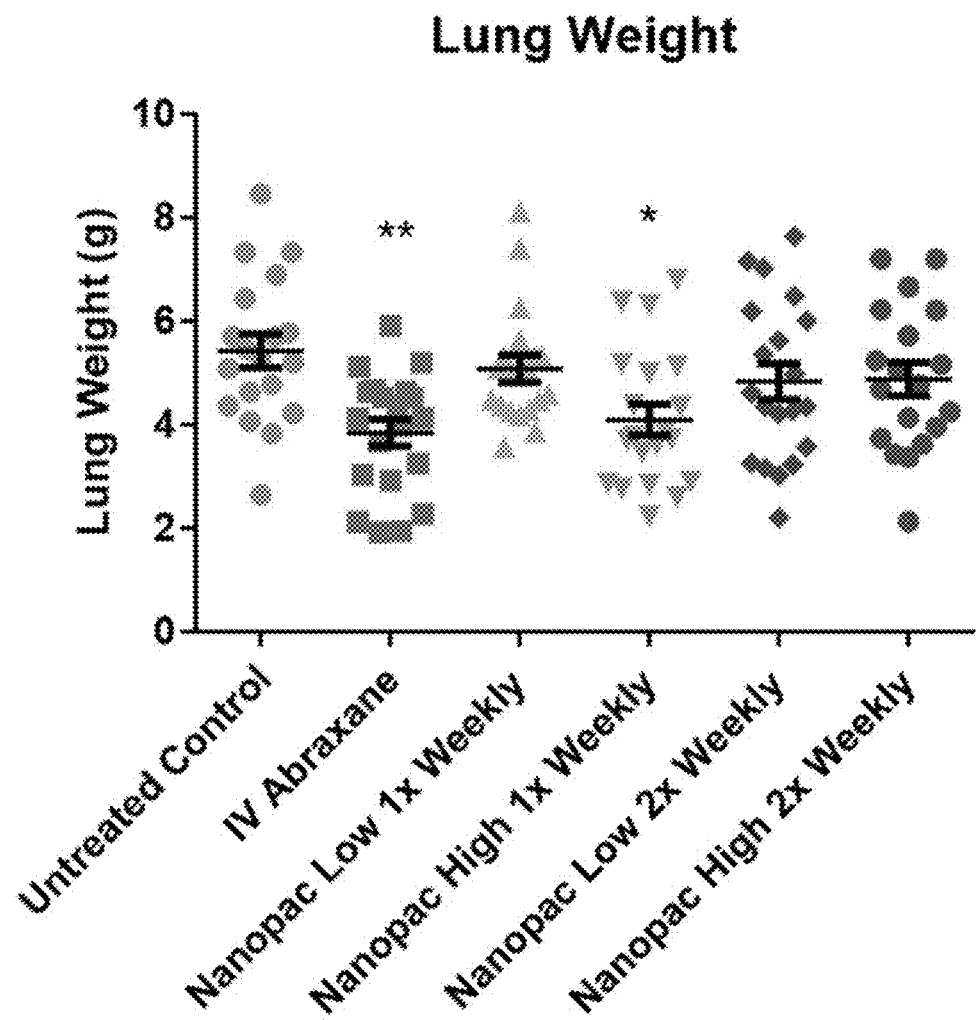
FIG. 15 is a plot of animal lung weights from Orthotopic Lung Cancer study.
Figure 16:
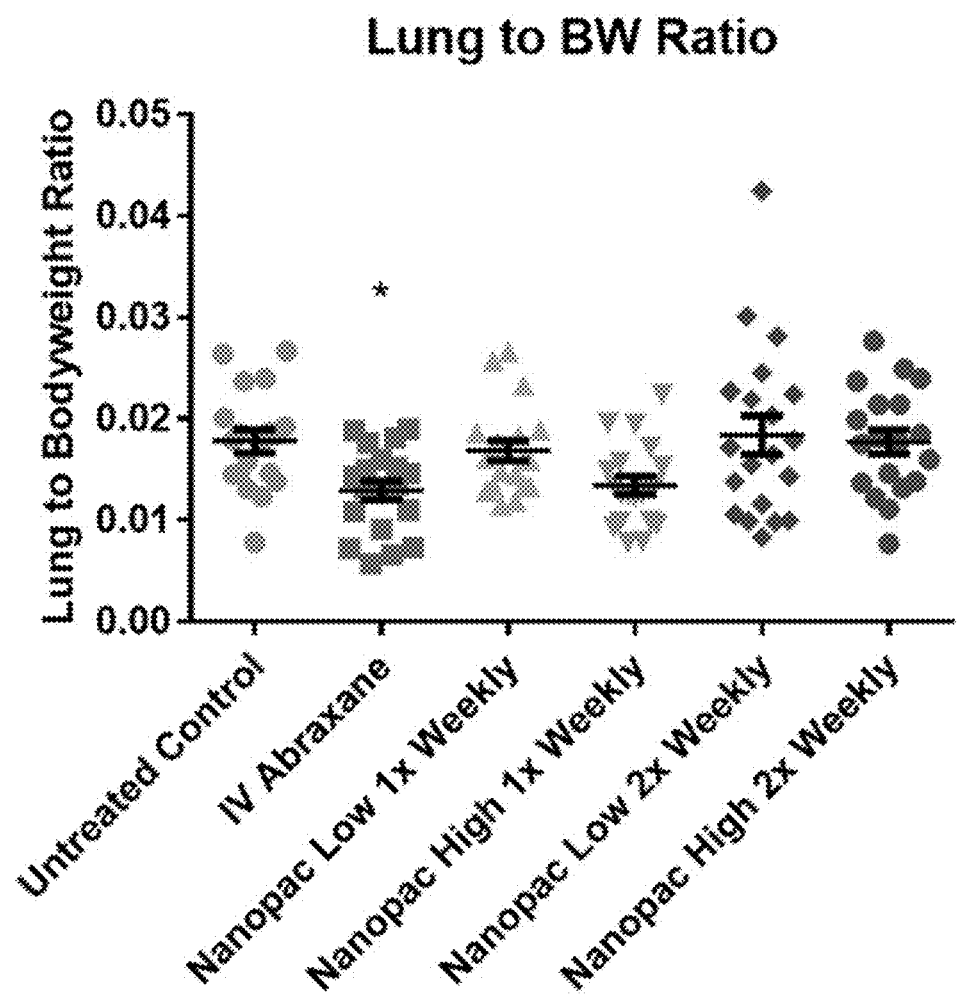
FIG. 16 is a plot of animal lung to body weight ratios from Orthotopic Lung Cancer study.
Figure 17:
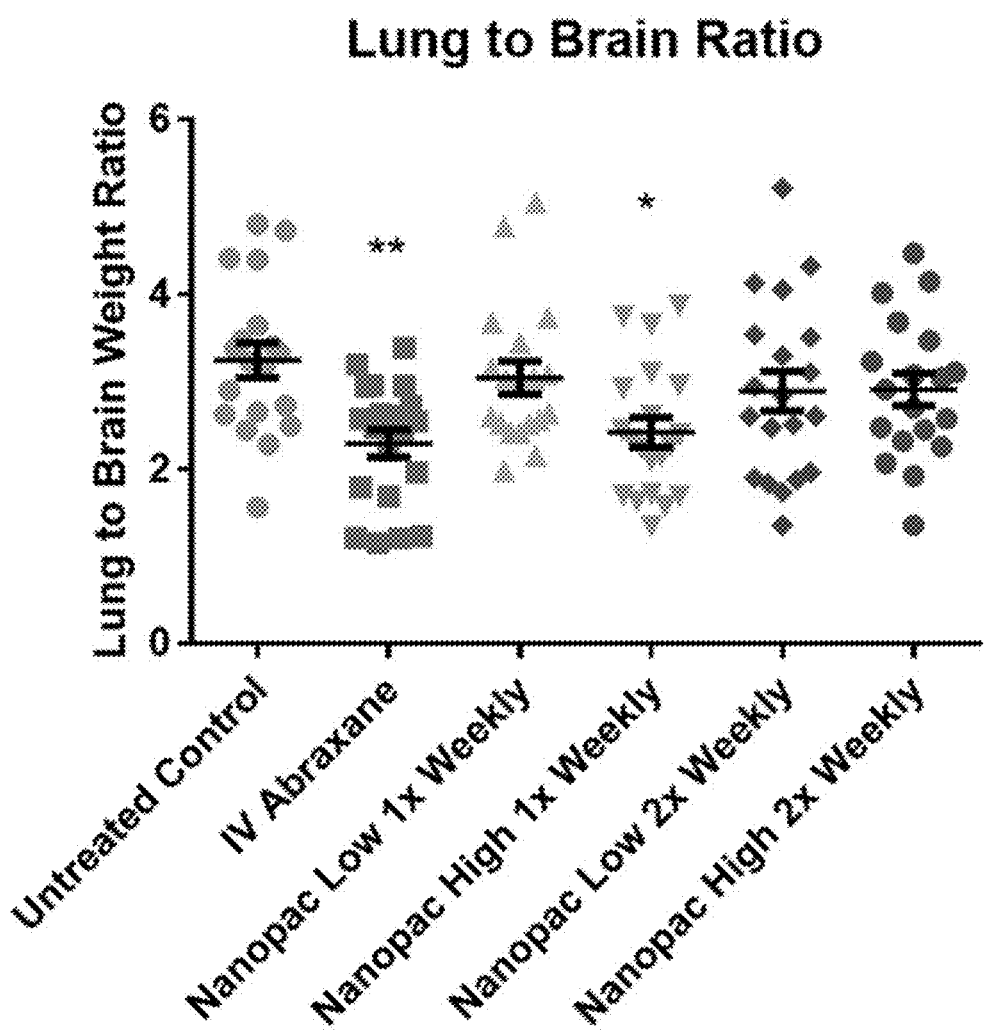
FIG. 17 is a plot of animal lung to brain weight ratios from Orthotopic Lung Cancer study.

Individual animal organ weight data is shown graphically in FIG. 15, FIG. 16 and FIG. 17. In Abraxane treated animal's lung weights, lung to BW ratios and lung to brain weight ratios were significantly lower compared to Untreated Controls. The once weekly NanoPac® High Dose group had similar weights to the Abraxane group and significantly lower lung weights and lung to brain ratios compared to Untreated Controls. The once weekly Low Dose, NanoPac® twice weekly Low Dose and twice weekly High Dose NanoPac® groups generally had similar average lung weights and ratios.

Morphometry

Figure 18:
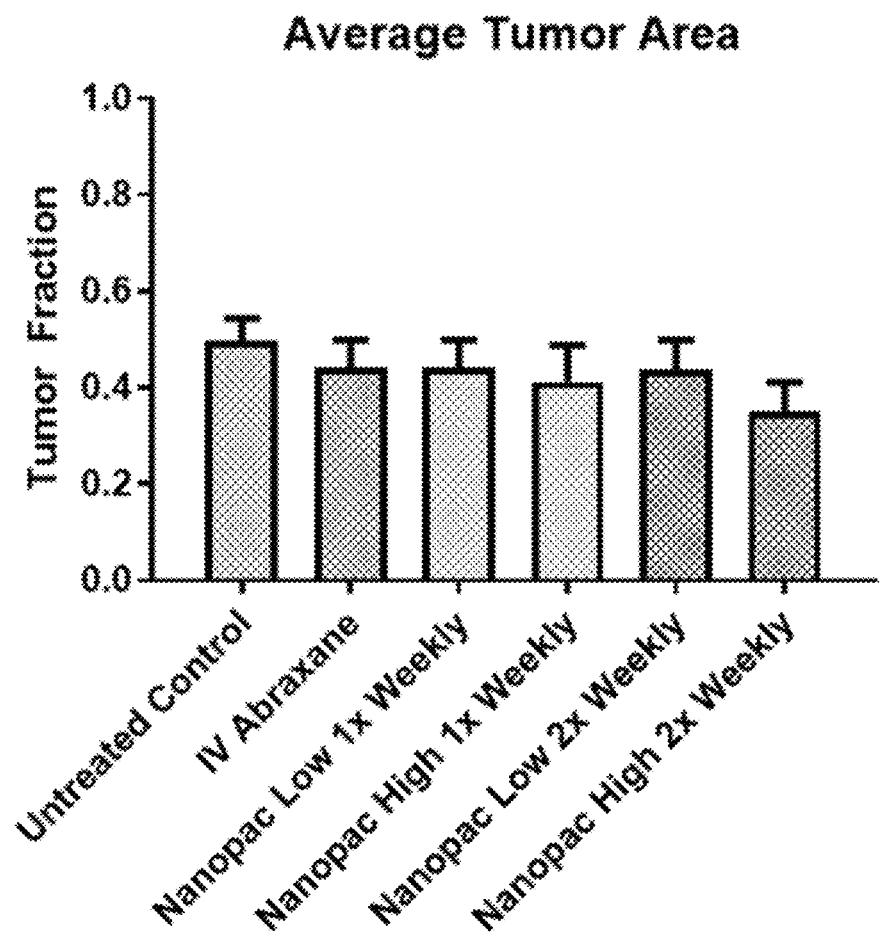
FIG. 18 is a graph of average tumor areas from Orthotopic Lung Cancer study.
Figure 19:
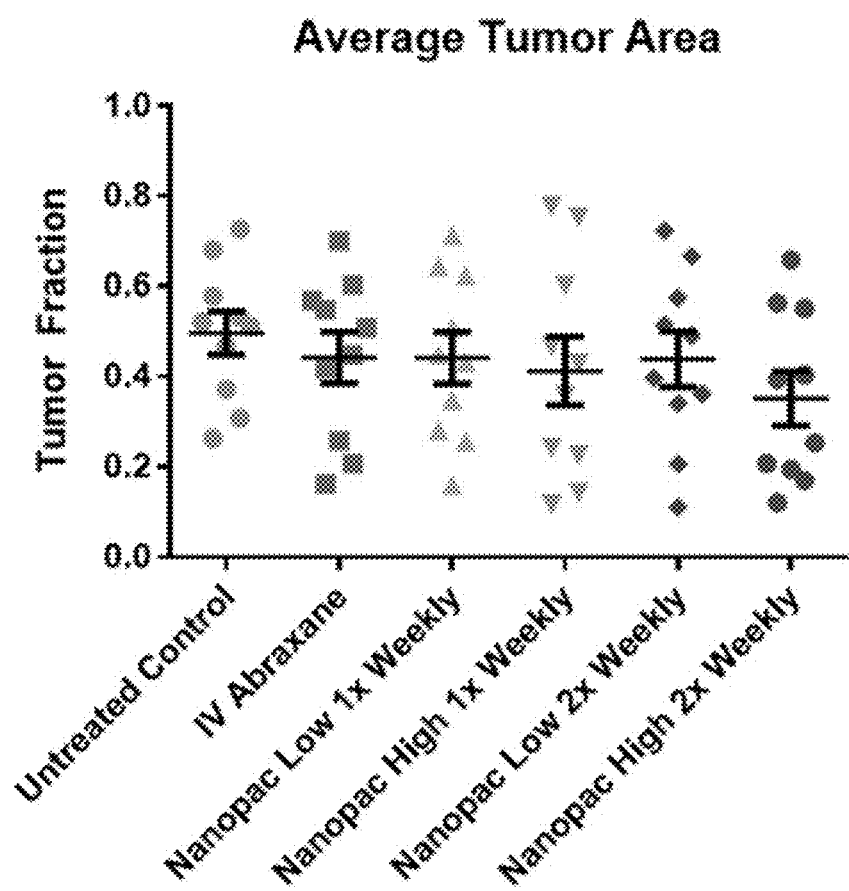
FIG. 19 is a plot of average tumor areas from Orthotopic Lung Cancer study.

All treatment groups showed a decrease in average lung tumor fraction when compared to the control group; however, there was no statistically significant difference between groups. There was also no statistically significant difference between IV Abraxane treatment and any of the NanoPac® treatment regimens in regards to the tumor area fraction examined on cross sectional lung slides. As is typical of this model, there is wide variability between animals within all groups in the tumor fraction. These data should be considered in combination with other indicators of lung tumor burden in this model including lung to brain weight ratios and standard histopathology for final interpretation. It is important to note that morphometric analysis and histopathologic examination was performed on fixed lung tissue from the left lobe while other analyses on lung tissue may be performed on frozen tissue from the right lung lobes. Average tumor area is shown in FIG. 18 and FIG. 19.

Pathology Results

H&E Stained lung slides are shown in FIGS. 20, 21, 22, 23, 24, and 25. As a result of the slide examination of the identified populations of neoplastic cells, the pathologist determined: (1) There was a slight decrease in severity of an overall lung tumor burden of Adenocarcinoma (undifferentiated and differentiated cells) in all treated groups (Grp. 2 (1.7), Grp, 3 (1.8), Grp. 4 (1.7), Grp 5 (1.6) and Grp. 6 (1.6) compared to the untreated Control Grp. 1 (2.1). (2) There was reduction in the Primitive Tumor Cell population evident by a decrease in the severity in Grp. 3 (0.3), Grp. 4 (0.3), Grp 5 (0.2) and Grp 6 (0.2) compared to the corresponding control Grp 1 (0.9) and Grp 2 (1.0), and 3). There was Tumor Regression present in Grp 3 (0.6), Grp 4 (1.0), Grp 5 (0.8) and Grp 6 (1.0) compared to the corresponding control Grp 1 (0.0) and Grp 2 (0.1). The incidence and severities of the lung burden characteristics data are summarized in Table 24, and in FIG. 26.

TABLE 24

Incidences and Severities of Cumulative Lung Burden

| | GROUPS | | | | | |
|---|---|---|---|---|---|---|
| | 1 | 2 | 3 | 4 | 5 | 6 |
| | Control | IV Abraxane | Low 1× | High 1× | Low 2× | High 2× |
| Animal Nos. | 1001-1010 | 2001-2010 | 3001-3010 | 4001-4010 | 5001-5010 | 6001-6010 |
| LUNG (NO. EX) | (10) | (10) | (10) | (10) | (10) | (10) |
| Adenocarcinoma | 10 | 10 | 10 | 9 | 10 | 10 |
| Minimal | 2[a] | 4 | 5 | 3 | 5 | 5 |
| Mild | 5 | 5 | 2 | 4 | 4 | 3 |
| Moderate | 3 | 1 | 3 | 2 | 1 | 2 |
| Marked | 0[b] | 0 | 0 | 0 | 0 | 0 |
| Average Severity Grade | 2.1 | 1.7 | 1.8 | 1.7 | 1.6 | 1.7 |
| Primitive Tumor Cells | 9 | 10 | 2 | 3 | 2 | 2 |

TABLE 24-continued

Incidences and Severities of Cumulative Lung Burden

| | GROUPS | | | | | |
|---|---|---|---|---|---|---|
| Animal Nos. | 1<br>Control<br>1001-<br>1010 | 2<br>IV Abraxane<br>2001-<br>2010 | 3<br>Low 1×<br>3001-<br>3010 | 4<br>High 1×<br>4001-<br>4010 | 5<br>Low 2×<br>5001-<br>5010 | 6<br>High 2×<br>6001-<br>6010 |
| Minimal | 9 | 10 | 1 | 3 | 2 | 2 |
| Mild | 0 | 0 | 1 | 0 | 0 | 0 |
| Moderate | 0 | 0 | 0 | 0 | 0 | 0 |
| Marked | 0 | 0 | 0 | 0 | 0 | 0 |
| Average Severity Grade | 0.9 | 1.0 | 0.3 | 0.3 | 0.2 | 0.2 |
| Tumor Regression | 0 | 1 | 6 | 5 | 6 | 5 |
| Minimal | 0 | 1 | 6 | 3 | 5 | 2 |
| Mild | 0 | 0 | 0 | 0 | 0 | 2 |
| Moderate | 0 | 0 | 0 | 1 | 1 | 0 |
| Marked | 0 | 0 | 0 | 1 | 0 | 1 |
| Average Severity Grade | 0 | 0.1 | 0.6 | 1.0 | 0.8 | 1.0 |

[a]Severity Grade is based on a 4-point grading scale of 1 to 4: 1 = minimal, 2 = mild, 3 = moderate, 4 = marked
[b]The presence of a (0) indicates that there in no evidence histopathologically of the lesion in question Observations of H&E Stained Lung slides are shown in FIGS. 20, 21, 22, 23, 24, and 25:

General Observations:

Control: Extensive levels of viable tumor with proliferating cells and little to no immune cell infiltration.

Abraxane IV: Many viable appearing tumor masses with some lymphocytic response along with some tumor regression.

NanoPac® 1× per week, High: Clearance of tumor from the lung with few viable tumor cells remaining. Masses remaining appear to be immune cell infiltrate and fibrosis.

NanoPac® 2× per week, Low: Some remaining tumor nodules surrounded by immune cell infiltrate including macrophages and mononuclear cells.

NanoPac® 2× per week, High: Few tumor nodules with immune infiltrate and stromal fibrosis replacing tumor.

Extensive mononuclear tumoricidal cell infiltration was observed in the lungs of animals receiving NanoPac® through inhalation. As the model used is T cell deficient, it is likely that the cells are B cells or NK cells, or both. B cells are responsible for the production of antibodies and can be involved in tumor cell killing through antibody-dependent cell mediated cytotoxicity (the antibodies bind to cells expressing Fc Receptors and enhance the killing ability of these cells). NK cells are innate lymphoid cells that are crucial in the killing of tumor cells. In patients with tumors, NK cell activity is reduced allowing for the growth of the tumor. Along with T cells, NK cells are the target of some check point inhibitors to increase their activity.

By the use of a wide array of surface receptors capable of delivering either triggering or inhibitory signals, NK cells can monitor cells within their environment to ascertain if the cell is abnormal (tumor or virally infected) and should be eliminated through cytotoxicity.

The cytotoxicity and chemotaxis of NK cells can be modified by many pathological processes including tumor cells and their byproducts. In response to certain signals their functions are enhanced or potentiated. In response to several Pathogen Associated Molecular Patterns (PAMPs) by using different Toll Like Receptors (TLR); NK cells can increase cytokine production and/or cytolytic activity. Cytokines, including IL-2, IL-15, IL-12, IL-18, and IFNs α/β can also modify the activity of NK cells. NK cells are not simple cells that are only cytolytic effectors capable of killing different tumor cell targets; rather, they represent a heterogeneous population which can finely tune their activity in variable environmental contexts.

The tumor burden seems to be significantly reduced in the lungs of the animals treated with NanoPac® and is lower than that for Abraxane IV. Therefore, the localized administration of paclitaxel in the form of NanoPac® provides additional potency. This is likely due to both the longer exposure to the chemotherapy over time and the vigorous cellular infiltration to the site of the tumor. This latter response appeared to be dependent on the dose density (actual dose and dose frequency).

Figure 20:
FIG. 20 is a photomicrograph of H&E Stained Orthotopic Lung Cancer tissue slide—1006 (Control) Adenocarcinoma-3, Primitive-1, Regression-0. Primary characteristics of the lung tumor masses. (2×).

Observations of Specific Photomicrographs:

FIG. 20: Subject 1006 (Control) Adenocarcinoma-3, Primitive-1, Regression-0. Low-power magnification (2×) showing the general distribution of undifferentiated, pleomorphic, large, anaplastic tumor cells within alveolar spaces or lining the alveolar septae. The majority of cells do not have features of adenocarcinoma and appear in sheets of contiguous tumor. Many cells have basophilic staining cytoplasm, while others are large, anaplastic and contain pale amphophilic-staining. Note the presence of a pre-existing resident population of alveolar macrophages and the absence of tumor regression.

Figure 21:
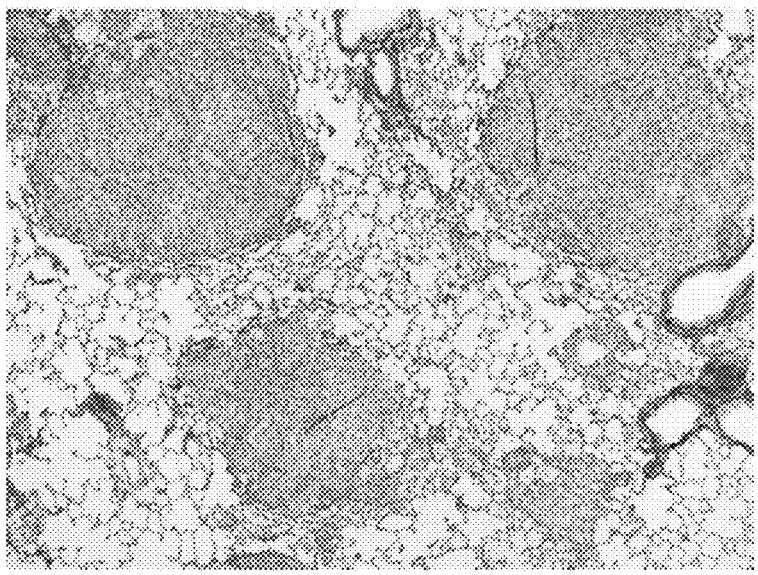
FIG. 21 is a photomicrograph of H&E Stained Orthotopic Lung Cancer tissue slide—2003 (IV Abraxane) Adenocarcinoma-1, Primitive-1, Regression-1. Characteristics of the lung tumor masses undergoing regression. (4×).

FIG. 21: Subject 2003 (IV Abraxane) Adenocarcinoma-1, Primitive-1, Regression-1. Low-power magnification (4×) showing the general distribution of tumor masses predominantly at the periphery as well as multiple smaller expansive tumor masses filling alveolar spaces. The tumor cells are pleomorphic, large, anaplastic and have pale amphophilic-staining, varying from undifferentiated to differentiated patterns of adenocarcinoma. Evidence of tumor regression is present around the periphery of the mass and primarily characterized by the infiltration of macrophages.

Figure 22:
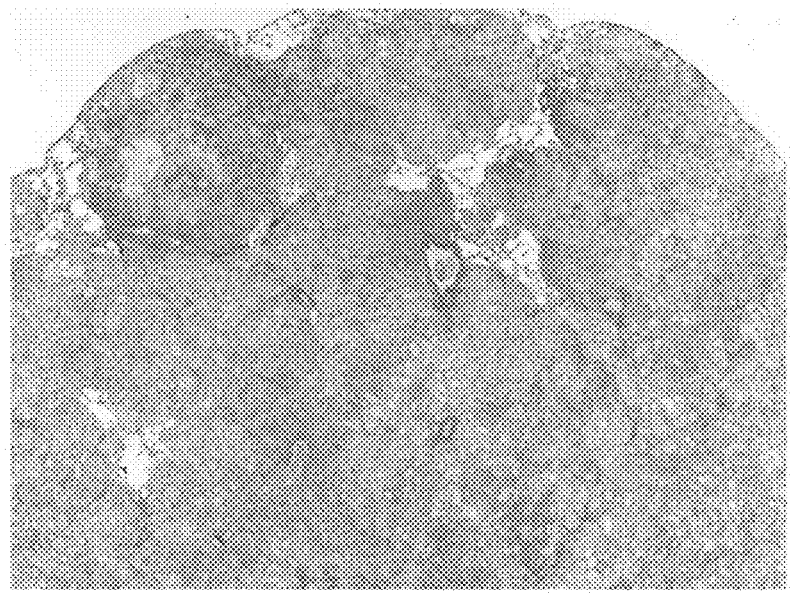
FIG. 22 is a photomicrograph of H&E Stained Orthotopic Lung Cancer tissue slide—2010 (IV Abraxane) Adenocarcinoma-3, Primitive-1, Regression-0. Primary characteristics of the lung tumor masses. (2×).

FIG. 22: Subject 2010 (IV Abraxane) Adenocarcinoma-3, Primitive-1, Regression-0. Low-power magnification (2×) showing the general distribution of large expansive tumor mass filling most alveolar spaces as well as neoplastic cells in the periphery. Most tumor cells are predominantly undifferentiated, pleomorphic, large, anaplastic with pale amphophilic-staining. The primitive cells are smaller, ovoid, and have more basophilic staining cytoplasm with variable, vesicular nuclei and moderate to marked anisokaryosis. Inflammatory cell infiltration are predominantly neutrophils and macrophages. This image demonstrates an absence of tumor regression.

Figure 23:
FIG. 23 is a photomicrograph of H&E Stained Orthotopic Lung Cancer tissue slide—4009 (IH NanoPac® 1× High) Adenocarcinoma-0, Primitive-0, Regression-4. Characteristics of the lung tumor masses that have undergone complete regression. (2×).

FIG. 23: Subject 4009 (IH NanoPac® 1×/wk High) Adenocarcinoma-0, Primitive-0, Regression-4. Low-power magnification (2×) showing the general distribution of previously populated tumor masses, the presence of multiple small areas of fibrous connective tissue, central collagenous stroma and fibrocytes are seen at the peripheral alveolar spaces as well as thickened alveolar septae supports evidence of tumor regression. In addition, the alveolar spaces are commonly filled with infiltrate of macrophages and lymphocytes together with additional evidence of tumor regression.

Figure 24:
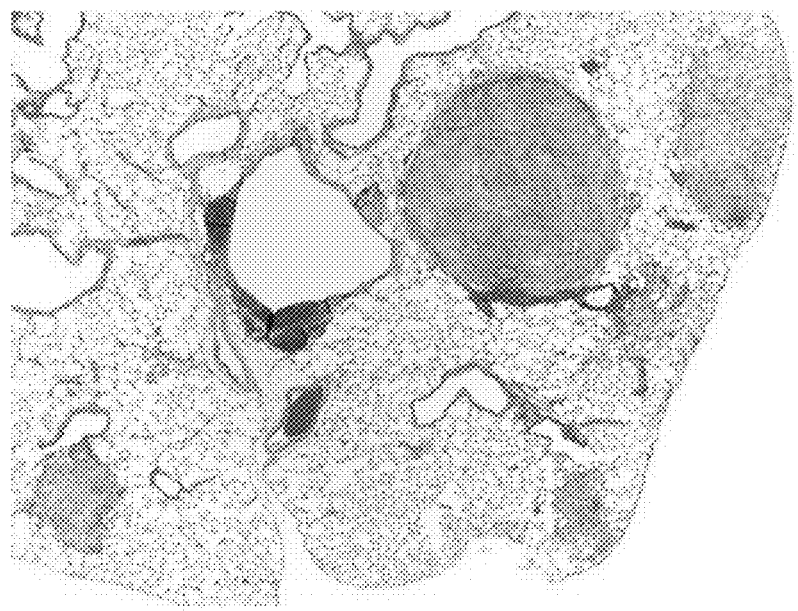
FIG. 24 is a photomicrograph of H&E Stained Orthotopic Lung Cancer tissue slide—5010 (IH NanoPac® 2× Low) Adenocarcinoma-1, Primitive-0, Regression-3. Characteristics of the lung tumor masses undergoing regression. (2×).

FIG. 24: Subject 5010 (IH NanoPac® 2×/wk Low) Adenocarcinoma-1, Primitive-0, Regression-3. Low-power magnification (2×) showing the general distribution of previously populated tumor masses. Regressing masses are variably small and randomly distributed. Fibrous connective tissue is seen filling/replacing alveolar spaces and suggests foci of regressing adenocarcinoma. Acute necrosis, fibrous connective scaffolding, mixed cell infiltration of macrophages, giant cells and lymphocytes in the epithelium as well as around the stroma are signs of tumor regression.

Figure 25:
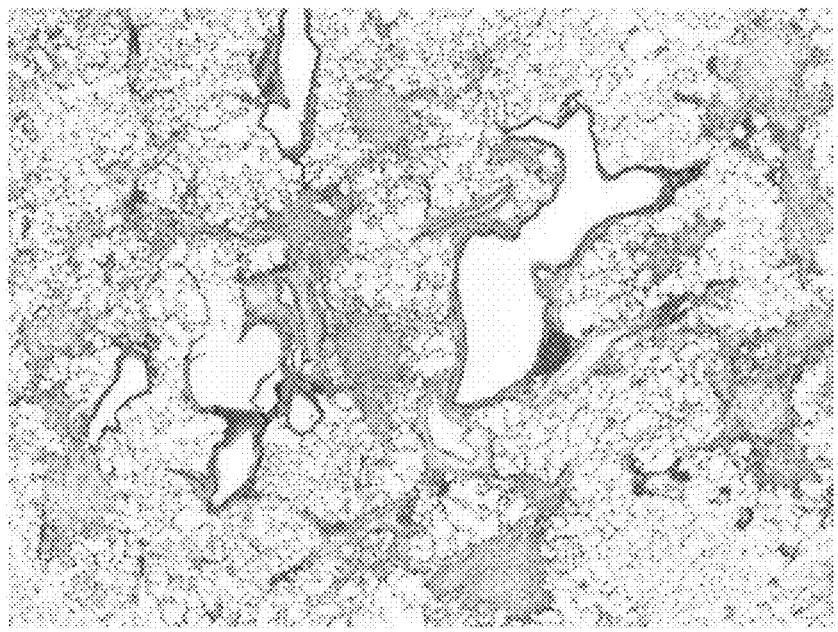
FIG. 25 is a photomicrograph of H&E Stained Orthotopic Lung Cancer tissue slide—6005 (IH NanoPac® 2× High) Adenocarcinoma-1, Primitive-0, Regression-4. Characteristics a lung tumor mass that is undergoing regression. (2×).
Figure 26:
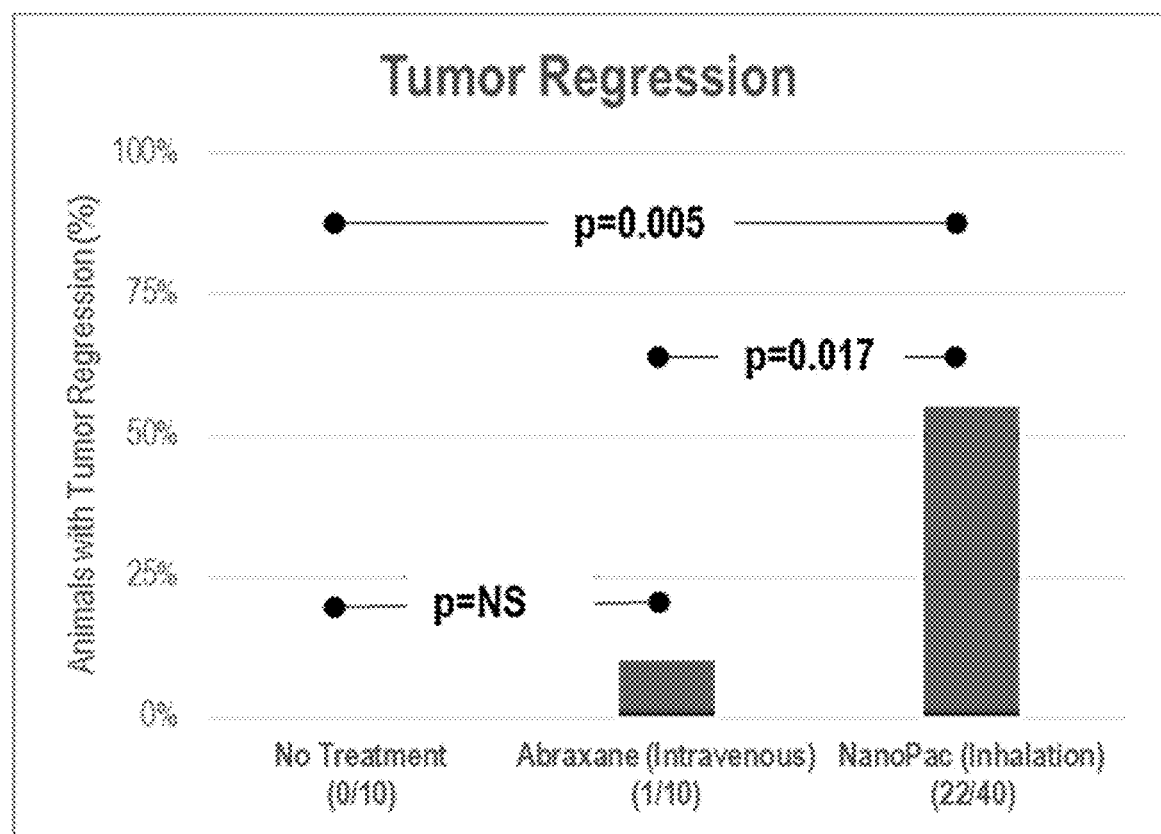
FIG. 26 is a plot of tumor regression from Orthotopic Lung Cancer study.

FIG. 25: Subject 6005 (IH NanoPac® 2×/wk High) Adenocarcinoma-1, Primitive-0, Regression-4. Low-power magnification (2×) showing the general distribution of previously populated tumor masses in multiple small areas of fibrous connective tissue filling/replacing the alveolar spaces suggesting foci of previous infiltrates of adenocarcinoma cells. Tumor regression is evidenced by fibrosis of previously populated tumor masses, central collagenous stromal core and fibrous connective tissue at the periphery filling/replacing the alveolar spaces, thickening of the septae as well as the presence of fibrocytes filling the alveolar space infiltrated by lymphocytes and macrophages.

Results of the Additional Morphologic and Immunohistochemical (IHC) Studies

After a review of H&E slides of all 120 animals in the study, it was noted that a possible immune response was seen in treatment groups. To further investigate this finding, a subset of animals was chosen from each group for further immunohistochemical evaluation.

Firstly, the trend of tumor regression as evaluated by a pathologist reviewing all 120 animals was compared to a different pathologist reviewing a subset of 17 animals to show a similar trend between the sample sizes.

Initial evaluation of the degree of tumor regression on all 120 animals was done via a pathologist grading semi-quantitively using a point scale indicating the percent of involvement of the overall lung tissue. The grading system is based on a grading scale of: 0=no evidence, 1=1-25% total area of lung sections, 2=25-50% total area of lung sections, 3=50-75% total area of lung sections, 4=75-100% total area of lung sections. This evaluation showed the incidence of animals presenting with tumor regression scored as follows, 0% of non-treated controls, 10% of IV Abraxane, 55% of IH NanoPac® low-dose once weekly, 55% of IH NanoPac® low-dose twice weekly, 55% of IH NanoPac® high-dose once weekly and 65% of IH NanoPac® high-dose twice weekly.

A review of the subset of 17 animals performed by a separate pathologist evaluating tumor regression using as similar semi-quantitative grading scale (0=no evidence, 1=1-19% total area of lung sections, 2=11-50% total area of lung section, 3=greater than 50% total area of lung sections, 4=complete regression). This evaluation showed the incidence of animals presenting with tumor regression scored as follows: 0% of non-treated controls, between 65-69% of IV Abraxane, 100% of IH NanoPac® low-dose once weekly, 100% of IH NanoPac® low-dose twice weekly, 100% of IH NanoPac® high-dose once weekly and 100% of IH NanoPac® high-dose twice weekly. This review (17 animals) presented a similar pattern to the previous review (120 animals) with the inhaled groups showing the greatest percent of animals with tumor regression.

Upon histological review of the subset of 17 animals from the study, interesting patterns with respect to tumor regression and immune response were seen. Two main features differed amongst the various groups, notably the presence and degree of tumor regression and the presence and intensity of an accompanying immune response. Below are the observations and remarks of the histological review.

No Treatment Group

Figure 27:
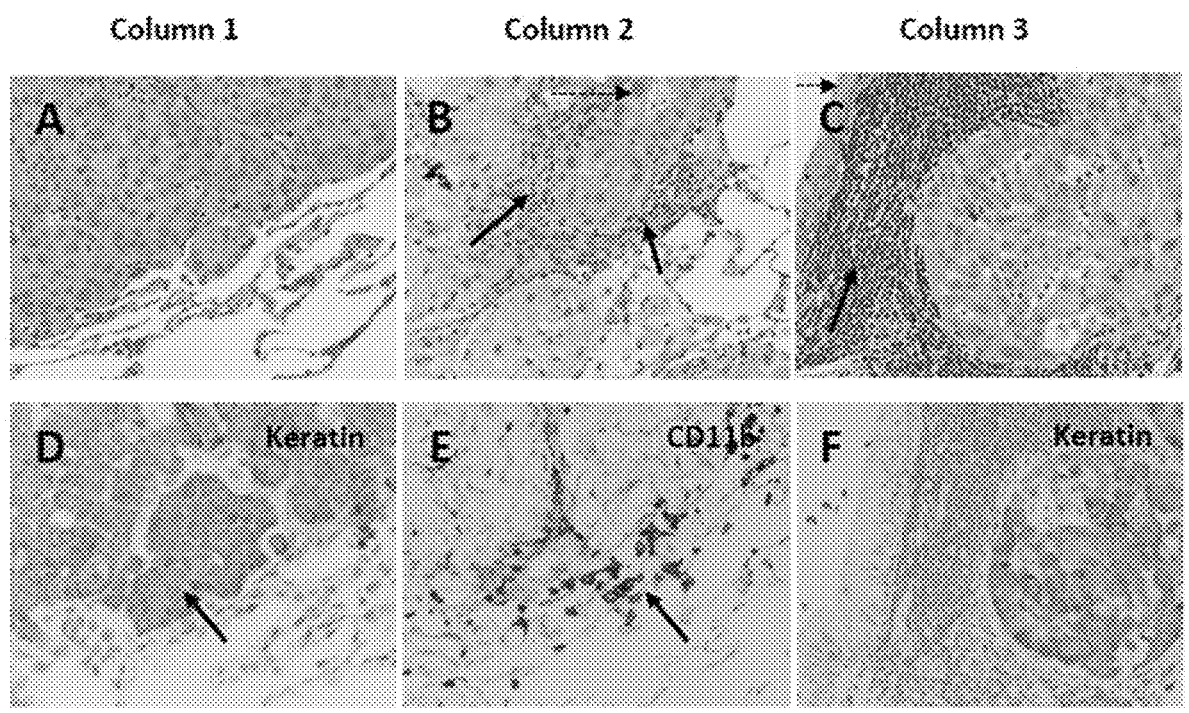
FIG. 27 are various photomicrographs of the Orthotopic Lung Cancer tissue slides—(Control). Top row: H/E stained sections. Bottom row: Immunohistochemical staining with Keratin or CD11b.

Observations: FIG. 27: Control cases. Top row: H/E stained sections. Bottom row: Immunohistochemical staining.

Column 1: (A) Poorly differentiated area of adenocarcinoma composed of sheets of large cells with pleomorphic nuclei, increased mitoses and lack of glandular differentiation. Note dense compact arrangement of tumor cells, sharp demarcation from surrounding normal lung in lower right corner and the lack of a fibrotic capsule surrounding the tumor. (D) Corresponding keratin immunostain from same area shown in A. This demonstrates sensitive and specific labeling of carcinoma cells with pancytokeratin (solid arrow).

Column 2: (B) Adenocarcinoma with focal rudimentary duct formation (dashed arrow at top right). Note the focal, limited immune cell component in the center, consisting of small lymphocytes and focal macrophages (solid arrows in center). (E) CD11b stain showing minimal numbers of NK cells and macrophages at the periphery of a tumor cell nodule (solid arrow).

Column 3: (C) Adenocarcinoma growing adjacent to a focus of bronchial associated lymphoid tissue (BALT) that consists of densely packed small mature lymphocytes (marked with solid arrow). Note the close association of the BALT with the adjacent normal bronchial lining (dashed arrow top left corner). (F) Corresponding focus to that seen in C, stained with keratin, showing positive staining in carcinoma cells and lack of staining in the lymphoid cells.

Remarks: Both animals presented uniform growth of solid, densely packed collections of adenocarcinoma. The tumors had relatively well demarcated margins bordering the surrounding normal lung parenchyma with no evidence of tumor regression and unabated tumor cell growth. The lymphoid infiltrate in these animals was mild and tertiary lymphoid structures were sparse.

Intravenous (IV) Abraxane Positive Treatment Control Group

Figure 28:
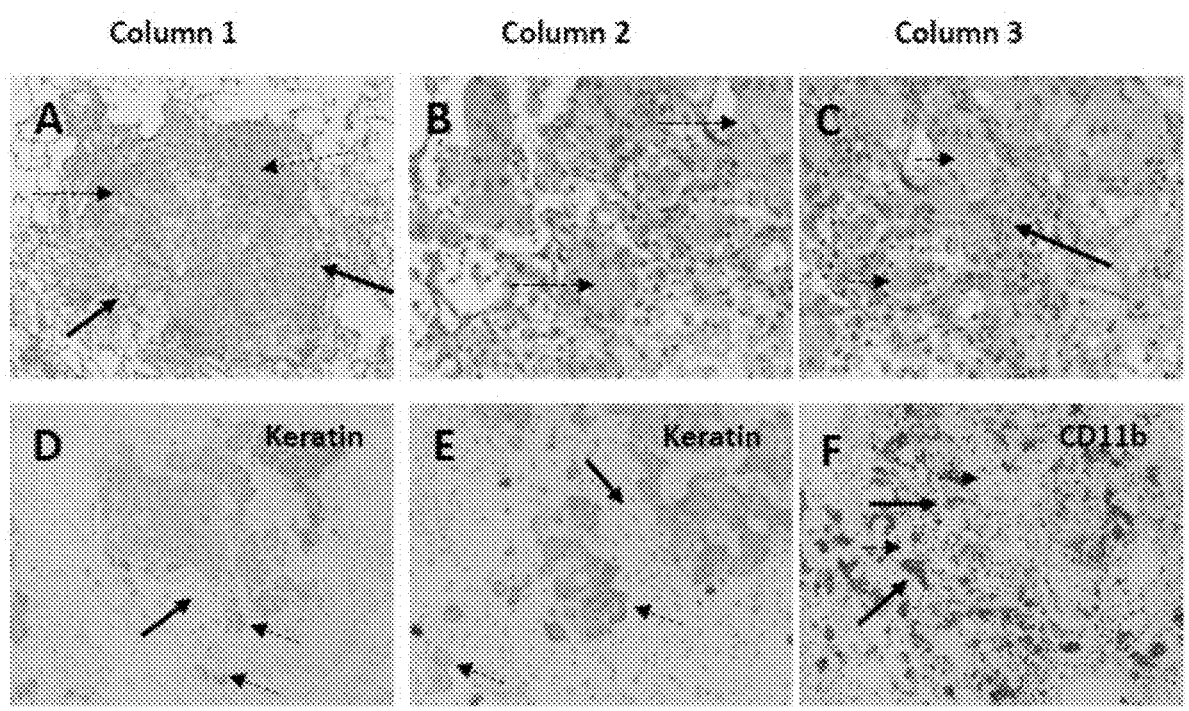
FIG. 28 are various photomicrograph of the Orthotopic Lung Cancer tissue slides—(IV Abraxane). Top row: H/E stained sections. Bottom row: Immunohistochemical staining with Keratin or CD11b.

Observations: FIG. 28: IV Abraxane case (2003) showing a nodule of adenocarcinoma with tumor regression consisting of separation of the tumor towards the periphery of the nodule into progressively smaller tumor cell clusters and single tumor cells, with an associated increased immune cell infiltrate.

Column 1: (A) Low power view of a nodule of invasive adenocarcinoma (highlighted by dashed arrows). Note the irregular peripheral border of the nodule due to progressive separation of tumor cells at the periphery and increased immune cell response (solid arrows). (D) Corresponding keratin immunostain from same area shown in A. This clearly demonstrates the progressively smaller size of tumor cell nodules toward the periphery (dashed arrows) and the increased intervening stroma between them (solid arrow).

Column 2: (B) High power view of the area in image A, showing the progressively smaller clusters of tumor cells (dashed arrows). (E) Higher power view of the keratin stained area shown in D, highlighting the separated smaller tumor cell nodules. Note the progressive decrease in tumor cell cluster size moving from the top right corner toward the bottom left corner where the tumor is present as individual single tumor cells (dashed arrows). The solid arrow highlights the increased intervening stroma with immune cells.

Column 3: (C) Immune cells (highlighted with solid arrow) seen within the center of a tumor nodule (dashed arrows highlight the tumor cells). (F) Low power view of a CD11b-stained section highlighting the same area seen in image A. This shows the increased density of immune cells (solid arrows) at the periphery of the nodule and within the tumor nodule. Dashed arrows highlight residual carcinoma cells that are not labeled with the CD11b antibody.

Remarks: All three animals presented tumor growth in densely packed collections of adenocarcinoma, however, two of the animals showed some features compatible with tumor regression. This regression was characterized by the presence of progressive separation and loss of tumor cell clusters at the periphery of the tumor nodules with ill-defined demarcated margins bordering the surrounding normal lung parenchyma. The lymphoid infiltrate in the areas showing tumor loss showed an increase in lymphoid infiltrate in the stroma.

Inhaled NanoPac® Treatment Groups

Figure 29:
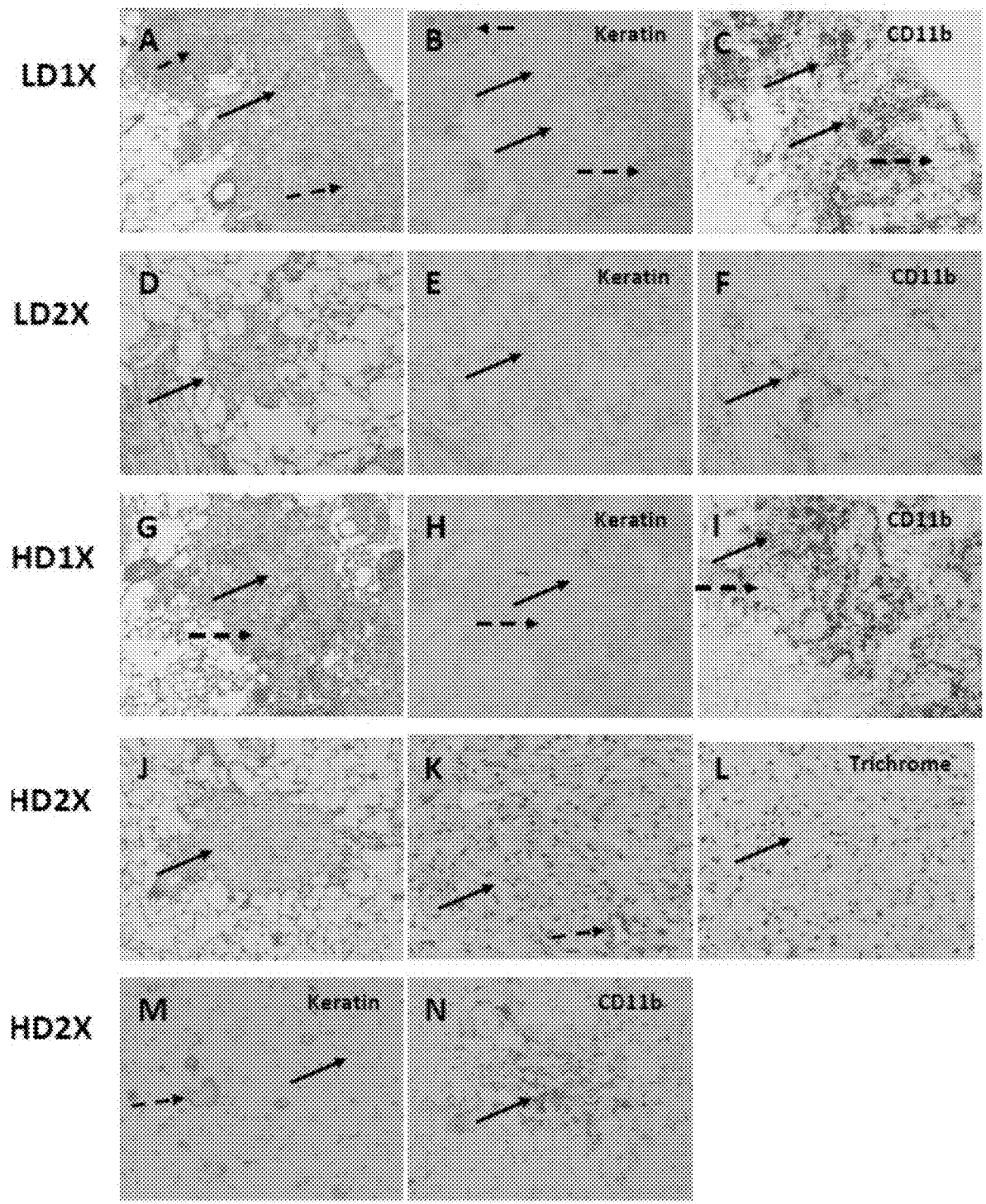
FIG. 29 are various photomicrographs of the Orthotopic Lung Cancer tissue slides 13 (Inhaled NanoPac®). Various staining with H/E stain, Trichrome, Keratin and CD11b.

Observations: FIG. 29: Inhaled NanoPac® cases.

Top row: Low dose, 1×/week (LD1×) (case 3006). (A) H/E staining showing tumor regression with in a nodule with prominent separation and loss of tumor cells at the periphery (dashed arrows show residual tumor and solid arrows show intervening stroma with inflammation). (B) Keratin stain highlights the residual carcinoma (dashed arrows) with a large intervening area of tumor loss (solid arrows) composed of background stroma with lymphocytes and macrophages. (C) CD11b immunostain highlights a marked lymphohistiocytic immune cell infiltrate in the areas where there is tumor cell dropout (solid arrows). Residual unstained carcinoma is highlighted with dashed arrow.

Second row: Low dose, 2×/week (LD2×) (case 4009). (D) H/E staining showed no residual viable adenocarcinoma. This case contained scattered foci such as this that were composed of collections of small lymphocytes and macrophages within background stroma. No diagnostic viable tumor cells were seen in these nodules, or elsewhere in the lung sections. (E) Keratin stain in the same area as D, showing lack of staining, thus adding immunohistochemical support for the interpretation of no residual viable carcinoma and complete regression. (F) CD11b stain shows that this focus has a mild-moderate immune cell infiltrate.

Third row: High dose, 1×/week (HD1×) (case 5008). (G) H/E staining showing tumor regression in a nodule with prominent separation and loss of tumor cells at the periphery (dashed arrows show residual tumor and solid arrows show intervening stroma with inflammation). (H) Keratin stain highlights the residual carcinoma (dashed arrows) and a large unstained area of tumor loss (solid arrows) composed of background stroma with lymphocytes and macrophages. (I) CD11b immunostain highlights a marked immune cell infiltrate in the areas where there is tumor cell dropout (solid arrow). Residual pockets of unstained carcinoma are highlighted with dashed arrow.

Fourth row: High dose, 2×/week (HD2×) (case 6005). (J) H/E staining showed numerous collections such as this one that contains cells with eosinophilic and foamy cytoplasm (low power). (K) Higher power of same area shows cells with spindled nuclei (solid arrow) and rare possible duct-like structures or regenerating small blood vessels (dashed arrow). (L) Masson trichrome stain shows blue staining of stroma consistent with early collagen fibrosis and organization.

Fifth row: High dose, 2×/week (HD2×) (case 6005 continued). (M) Keratin stain shows labeling of focal single cells and duct-like structures (dashed arrow). Intervening cells are negative for keratin (solid arrow). (N) CD11b immunostain highlights an immune cell infiltrate in the area where there is tumor cell dropout (solid arrow). The magnification in this image matches that in J.

Remarks: Of the 12 animals one animal presented no residual adenocarcinoma and was interpreted as a complete responder (versus non-engraftment). One animal presented as difficult to classify as it contained rare instances of tumor positive staining that were difficult to differentiate as tumor or as regenerative small blood vessels and/or regenerative/atrophic non-neoplastic lung parenchyma. As such, this second case also was interpreted as extensive and near-complete responder. In these two cases, there were scattered foci of immune cells in areas presumed to previously contain solid clusters of adenocarcinoma. One case presented evidence of organization with deposition of fibrous collagen noted by Masson's Trichrome staining. All remaining 10 animals presented tumor nodules with varying degrees of apparent tumor regression with 8 of the 10 animals presenting tumor regression in >50% of the tumor nodules. The inhaled NanoPac® group presented with lymphoid infiltrate that varied from well-defined organized collections of densely packed mature lymphoid cells with well-defined lymphoid follicles and germinal centers and interfollicular areas and paracortical zones. As well as smaller dense collections of lymphoid tissue at the periphery and focally within the center of the tumor nodules.

Observation of Tertiary Lymphoid Structures (TLSs)

Secondary lymphoid organs develop as part of a genetically preprogrammed process during embryogenesis and primarily serve to initiate adaptive immune response providing a location for interactions between rare antigen-specific naïve lymphocytes and antigen-presenting cells draining from local tissue. Organogenesis of secondary lymphoid tissues can also be recapitulated in adulthood during de novo lymphoid neogenesis of tertiary lymphoid structures (TLS) and form in the inflamed tissue afflicted by various pathological conditions, including cancer. Organogenesis of mucosal-associated lymphoid tissue such as bronchial-associated lymphoid tissue is one such example. The term TLS can refer to structures of varying organization, from simple clusters of lymphocytes, to sophisticated, segregated structures highly reminiscent of secondary lymphoid organs. A notable difference between lymph nodes and TLS's is the that where lymph nodes are encapsulated, TLS's represent a congregation of immune and stromal cells confined within an organ or tissue.

Figure 30:
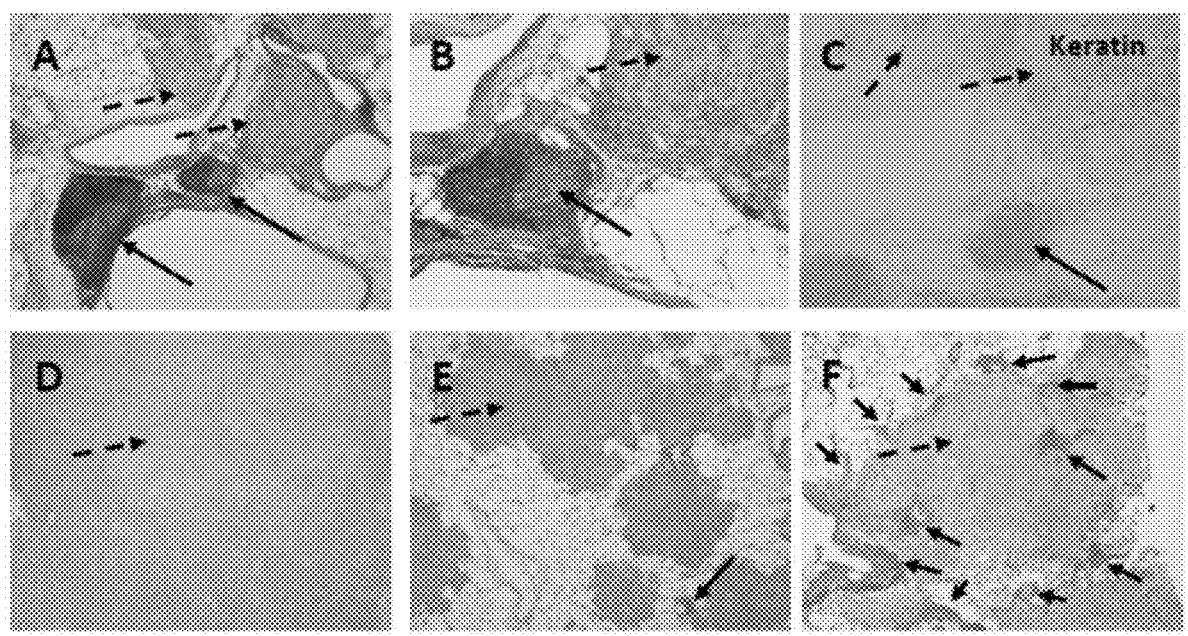
FIG. 30 are various photomicrograph of the Orthotopic Lung Cancer tissue slides showing presence of TLSs.

Observations: FIG. 30: Lymphoid structures in treated and untreated cases.

Top row: Inhaled NanoPac® case demonstrating tertiary lymphoid structures (TLSs) with follicular hyperplasia. High dose, 2×/week (HD2×) (case 6007). (A) H/E stain showing two adjacent TLSs (highlighted with solid arrows). In the lung these are referred to as bronchial associated lymphoid tissue (BALT). Note the organoid appearance of these TLSs in that they are composed of well-circumscribed collections of dense lymphoid tissue with distinct topology that includes lymphoid follicles with prominent germinal centers, interfollicular areas and paracortical zones. Dashed arrows highlight adjacent foci of tumor with irregular peripheral borders consistent with tumor regression. (B) Higher power image from area in A. The smaller TLS contains a lymphoid follicle with a prominent germinal center (paler area at tip of arrow). This process of germinal center formation in lymphoid follicles is referred to as follicular lymphoid hyperplasia and is indicative of lymphoid tissue that is activated and is in the process of mounting an immune response to various antigens including foreign material and tumor debris. Germinal centers characteristically show polarization with light and dark zones of lymphoid cells. In this image, the pale zone of the germinal center is pointing toward the adjacent tumor nodule. (C) Keratin stain showing the adjacent carcinoma nodules that have irregular peripheral borders. Solid arrow shows the TLS. This TLS appears smaller in this section as this tissue section was from a deeper portion of the paraffin embedded tissue compared to that in the H/E stained section shown in A and B.

Second row: Comparison between control (D), IV Abraxane (E) and NanoPac® (F) cases to illustrate the differences in the number and density of smaller lymphoid collections associated with tumor nodules in the different groups. These three images are all at the same lower power magnification (4× objective). (D) Control case (1003) shows densely packed adenocarcinoma (dashed arrow) without any discrete lymphoid collections. (E) IV Abraxane case (2009) showing nodules of adenocarcinoma (dashed arrow) and only a single rare small lymphoid collection at the lower right (solid arrow). (F) NanoPac® case, high dose 2×/week (HD2×) showing adenocarcinoma nodules (dashed arrow) with numerous associated small and medium sized collections of small lymphoid cells. These are arranged at the periphery of the tumor and also focally within the tumor (solid arrows).

Remarks: The inhaled NanoPac® groups showed increased numbers and density of TLSs (2 per low power field) compared to controls and the IV Abraxane group (1 per low power field), and more of these TLSs showed increased size and activation with follicular lymphoid hyperplasia containing prominent germinal centers.

In summary, the sub-review of 17 animals presented some interesting patterns with respect to tumor regression and immune response. In particular, all of the animals treated with NanoPac® showed at least some features compatible with tumor regression which includes two animals showing complete and/or near complete regression, while 8 of the remaining 10 animals in this group showed some features compatible with tumor regression in >50% of the tumor nodules. This was an increased response compared to the control groups where there was no animal showed a response, and the IV Abraxane group where 2 of 3 animals showed tumor regression in 1-10% of the tumor nodules.

Evaluating the NanoPac® groups with each other, a higher dose and increased frequency in dosage (2×/week versus 1×/week) were both associated with a greater effect on tumor response. The data supports an immune based association with tumor regression, the NanoPac® groups also showed increased numbers, and density of TLSs (2 per low power field) compared to controls and the IV Abraxane group (1 per low power field), and more of these TLSs showed increased size and activation with follicular lymphoid hyperplasia containing prominent germinal centers. There was also a greater density of immune cells at the periphery of tumor nodules and within tumor nodules in the NanoPac® groups.

Conclusions

One hundred twenty-seven (127) NIH-rnu Nude Rats were x-irradiated to induce immunosuppression on Day −1. On Day 0 animals were dosed with Calu3 tumor cells by intratracheal (IT) instillation. Animals underwent a growth period of three weeks. During the third week, animals were randomized by body weight stratification into the groups. Starting Week 4, animals in Group 2 received a once weekly dose of Abraxane® by intravenous (IV) dosing (5 mg/kg) on Days 22, 29 and 36. Animals in Groups 3 and 4 received once weekly (Monday) inhalation (INH) dose of NanoPac® at low (0.5 mg/kg) and high (1.0 mg/kg) target doses, respectively. Animals in Groups 5 and 6 received a twice weekly (Monday and Thursday) target inhalation dose of NanoPac® at low (0.50 mg/kg) and high (1.0 mg/kg) doses respectively. Animals in Group 1 were left untreated as a control of normal tumor cell growth. All animals were necropsied during Week 8.

All animals survived to their designated necropsy timepoint. Clinical observations related to the model included skin rash, labored breathing. All groups gained weight at about the same rate through the course of the study.

The inhalation exposure average Paclitaxel aerosol concentration for once weekly Low Dose and twice weekly Low Dose NanoPac® groups was 270.51 µg/L and 263.56 µg/L, respectively. The inhalation exposure average Paclitaxel aerosol concentration for once weekly High Dose and twice weekly High Dose NanoPac® groups was 244.82 µg/L and 245.76 µg/L, respectively.

Doses were based on average aerosol paclitaxel concentration, most recent average group bodyweight, assumed deposition fraction of 10% and exposure duration of 33 or 65 minutes. During four weeks of treatment, the average achieved rodent deposited dose for the once weekly Low Dose NanoPac® group and twice weekly Low Dose NanoPac® group were 0.655 mg/kg and 0.640 mg/kg (1.28 mg/kg/week), respectively. The average achieved rodent deposited dose for the once weekly High Dose NanoPac® group and twice weekly High Dose NanoPac® group were 1.166 mg/kg and 1.176 mg/kg (2.352 mg/kg/week), respectively. For the group receiving IV injections of Abraxane®, the average dose on Day 22, 29 and 36 was 4.94, 4.64 and 4.46 mg/kg respectively.

At scheduled necropsy, the majority of animals from each group had tan nodules on the lungs and/or red or tan patchy discolorations of the lung. Other sporadic observations included an abdominal hernia in one animal and nodule on the pericardium of another animal. No other abnormal gross observations were noted at necropsy.

In Abraxane treated animals, lung weights, lung to BW ratios and lung to brain weight ratios were significantly lower compared to Untreated Controls. The once weekly NanoPac® High Dose group had similar weights to the Abraxane group and significantly lower lung weights and lung to brain ratios compared to Untreated Controls.

Compared to the positive control Grp. 1 and the Abraxane treated comparative Grp. 2, there was a therapeutic effect as measured by lower lung/brain weight ratio and lower overall lung tumor burden without apparent adverse events. Histological analysis of lung tumor burden treated with inhaled NanoPac® showed a decrease in tumor mass, a decrease in primitive tumor cell population, and an increase in tumor regression. Extensive mononuclear cell infiltration was observed in the lungs of animals receiving NanoPac® through inhalation. As the model used is T cell deficient, it is likely that the cells are B cells or NK cells. It is hypothesized that the localized, likely higher concentration exposure of the tumor to NanoPac® affected the tumors leading to an alteration in the environment to draw the mononuclear cellular infiltrate into the lung.

Example 14—Human Bladder Cancer (UM-UC-3) Mouse Xenograft Study

A study was conducted to evaluate the effect of 1, 2, and 3 weekly intratumoral injection (IT) administrations (administration cycles) of NANODOCE® (nanoparticle docetaxel as disclosed herein, approximately 99% docetaxel with a mean particle size (number) of 1.078 microns, a SSA of 37.2 m$^2$/g, and a bulk density (not tapped) of 0.0723 g/cm$^3$ used in this example) suspension on growth of subcutaneous (SC) UM-UC-3 bladder cancer cell line (ATCC-CRL-1749) tumors in immunocompromised (Hsd:Athymic Nude-Foxn1nu nude) mice. Intratumoral injection administration of a vehicle and intravenous (IV) administration of docetaxel solution were also incorporated into the study as control groups.

Tumors were implanted with 1×10$^7$ cells (100 μL volume) into right flank (PBS 1:1 with matrigel: BD356234). Tumor volume was determined with calipers. Formula: V=(r length*r width*r height)*π*4/3. Animals were weighed 2×/week. Tumor volumes were determined every 3 to 4 days following tumor implant (total of ~20 measurements) and on day of euthanasia. Photo images of tumors were obtained at 2, 3 and 4 weeks post implantation and on day of euthanasia. Animals were euthanized once the tumor reached a size of 3,000 mm$^3$ or up to the point of significant tumor ulceration. At the time of euthanasia, tumors were isolated and halved. One half of the tumor was flash frozen in LN2 stored at −80° C. and will subsequently be analyzed. The second half of the tumor was fixed in formalin. Two H&E stained slides/tumor were prepared (up to 4 tumor/group were processed).

At day 18 after tumor implant, when average tumor size was between 50-325 mm$^3$, animals were sorted into five groups with equal average tumor sizes and were treated as shown in Table 25 below.

TABLE 25

Main Study Design

| Group | Name | Treatment | Weekly Admin Cycles | n |
|---|---|---|---|---|
| A | Vehicle IT 3 cycles | Vehicle (IT) 63 μl/tumor | 3 | 10 |
| B | Docetaxel IV 3 cycles | Docetaxel Solution 30 mg/kg (IV) Docetaxel = 3 mg/mL | 3 | 9 |
| C | NanoDoce® IT 1 cycle | NanoDoce® Suspension 100 mg/kg (IT) NanoDoce® = 40 mg/mL; 63 μl/tumor (2.5 mg NanoDoce®) | 1 | 10 |
| D | NanoDoce® IT 2 cycles | NanoDoce® Suspension 100 mg/kg (IT) NanoDoce® = 40 mg/mL; 63 μl/tumor (2.5 mg NanoDoce®) | 2 | 9 |
| E | NanoDoce® IT 3 cycles | NanoDoce® Suspension 100 mg/kg (IT) NanoDoce® = 40 mg/mL; 63 μl/tumor (2.5 mg NanoDoce®) | 3 | 9 |

For IT administration (Vehicle/NANODOCE®), injections (using 27G, ½" needle) were administered at three sites within the tumor (total calculated injection volume based on 40 mg/mL NANODOCE® stock and 25 g mouse=63 μL; split evenly across the three injection sites) to maximize distribution of the test formulation throughout the tumor. The second treatments (2$^{nd}$ cycle) occurred 7 days following first treatment (1st cycle) and third treatments (3rd cycle) occurred 14 days following the first treatment. The docetaxel solution IV was administered via the tail vein.

Figure 31:
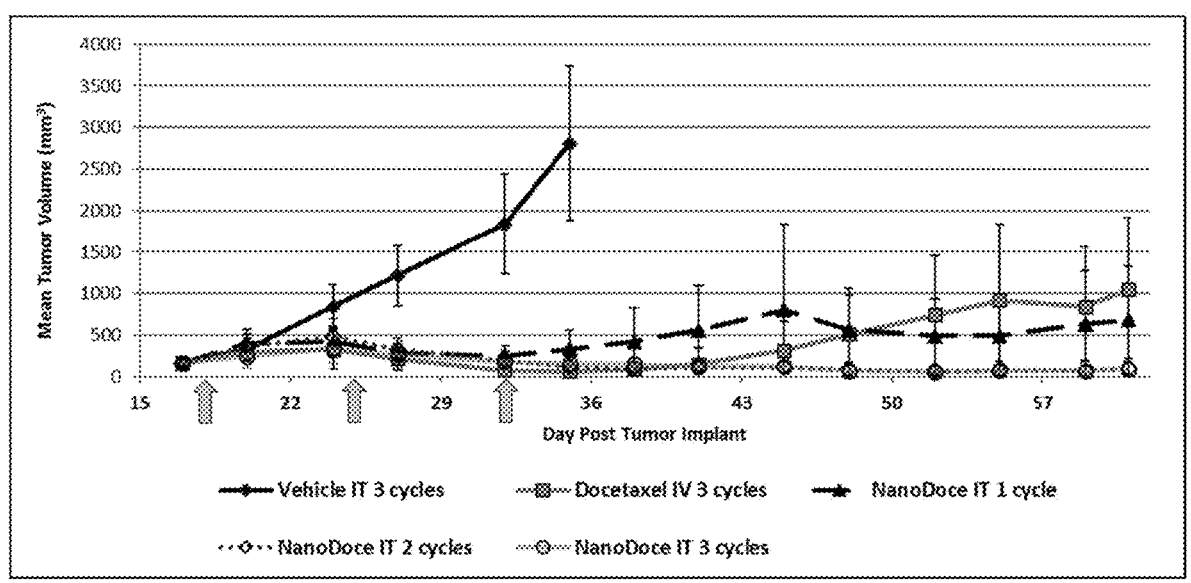
FIG. 31 is a graph of mean tumor volumes over time from the bladder cancer xenograft study. The arrows on the x-axis represent the administration points.
Figure 32:
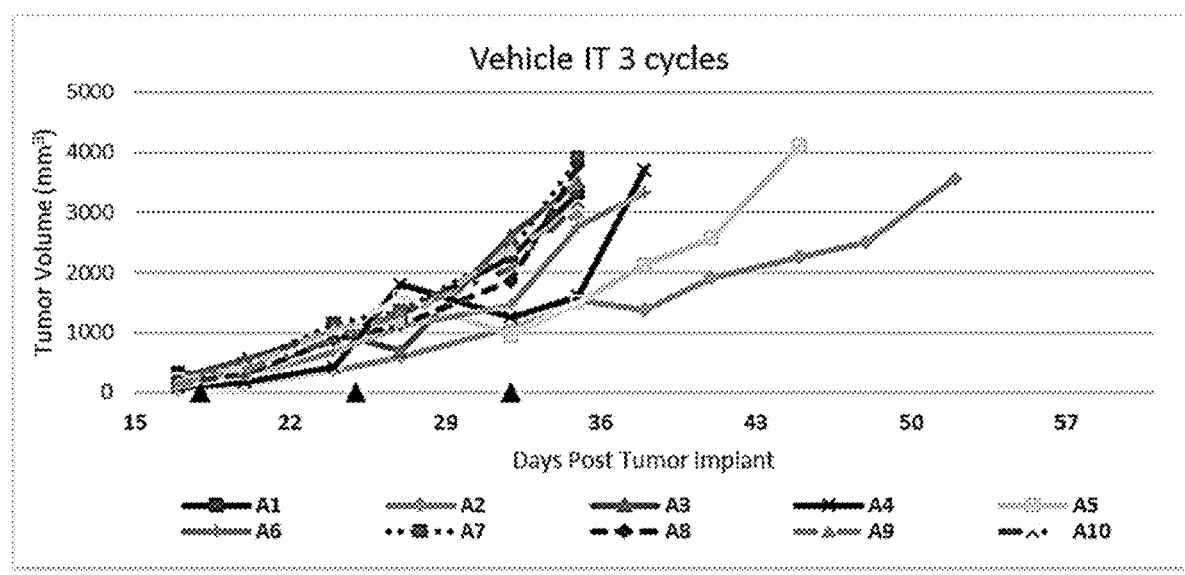
FIG. 32 is a graph of individual tumor volumes over time for Vehicle 3 cycles from the bladder cancer xenograft study. The triangles on the x-axis represent an administration point.
Figure 33:
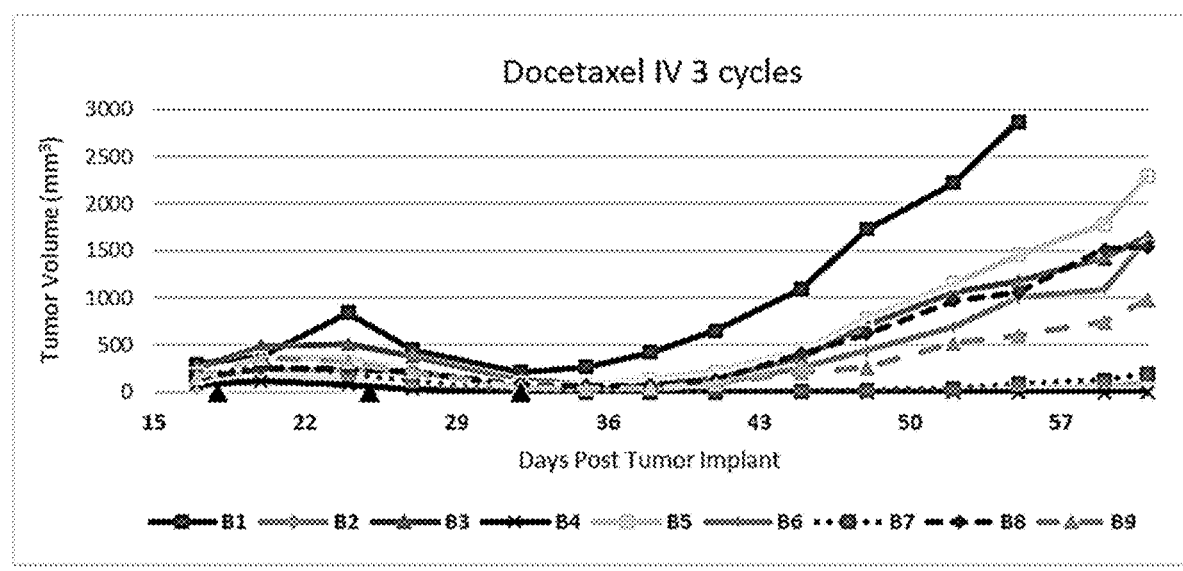
FIG. 33 is a graph of individual tumor volumes over time for the Docetaxel IV 3 cycles from the bladder cancer xenograft study. The triangles on the x-axis represent the administration points.
Figure 34:
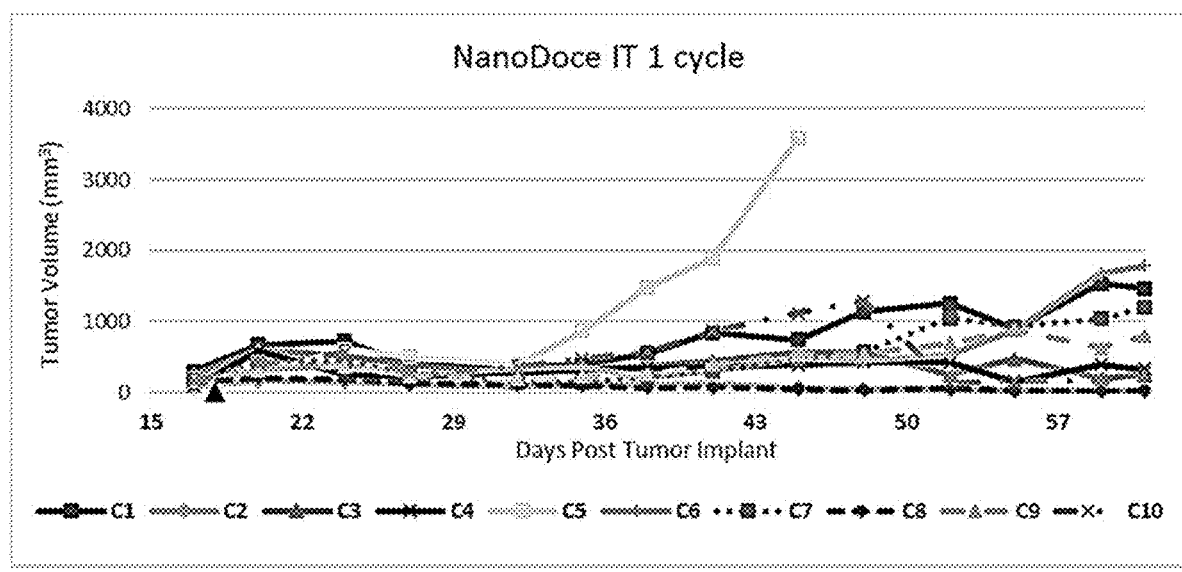
FIG. 34 is a graph of individual tumor volumes over time for the NanoDoce® IT 1 cycle from the bladder cancer xenograft study. The triangle on the x-axis represent the single administration point.
Figure 35:
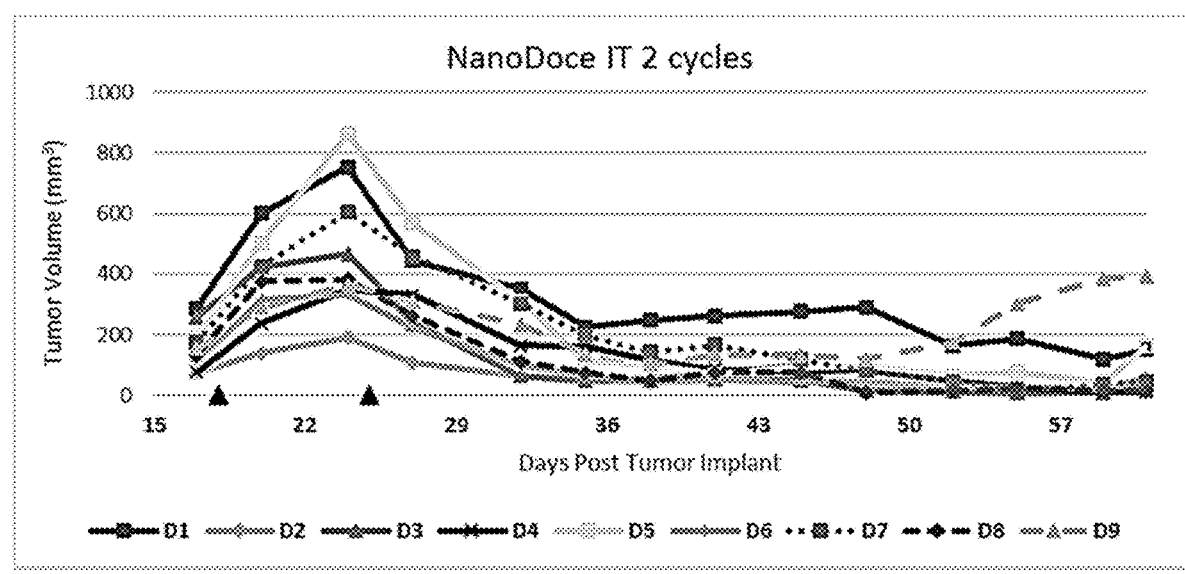
FIG. 35 is a graph of individual tumor volumes over time for the NanoDoce® IT 2 cycles from the bladder cancer xenograft study. The triangles on the x-axis represent the administration points.
Figure 36:
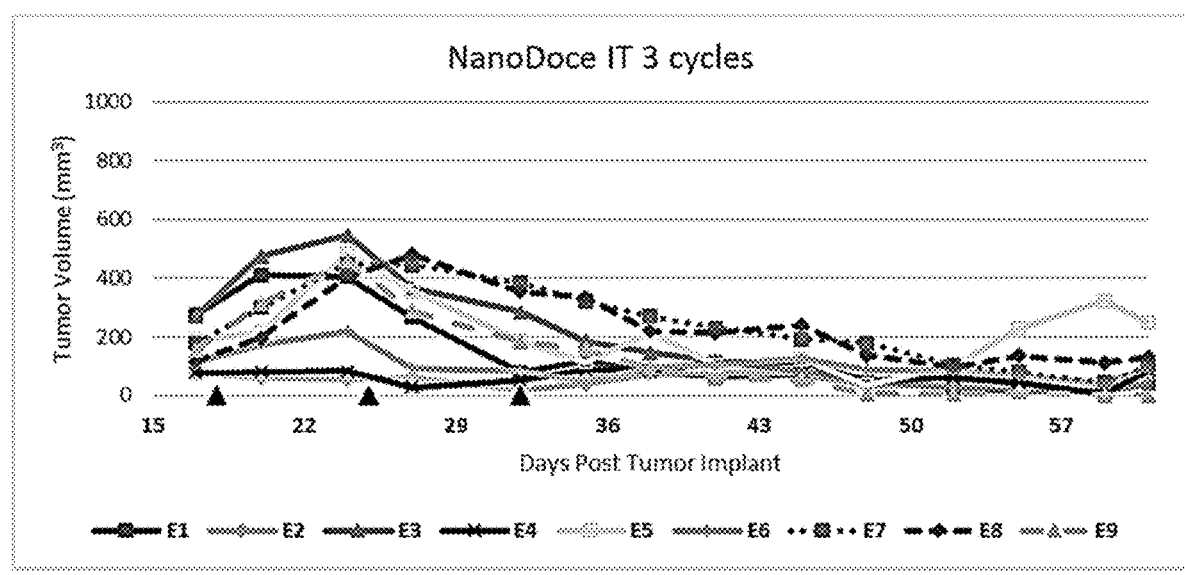
FIG. 36 is a graph of individual tumor volumes over time for the NanoDoce® 3 cycles from the bladder cancer xenograft study. The triangles on the x-axis represent the administration points.

The test formulations were prepared as follows:
Vehicle (Control): Diluted 1 ml of the 1% Polysorbate 80/8% Ethanol in normal saline (0.9% Sodium Chloride for Injection) reconstitution solution with 1.5 mL of normal saline (0.9% Sodium Chloride for Injection, USP). The final concentration of polysorbate 80 was 0.4% and the final concentration of ethanol was 3.2% in the Vehicle.
NANODOCE® Suspension: Added 1 ml of the 1% Polysorbate 80/8% Ethanol in normal saline (0.9% Sodium Chloride for Injection) reconstitution solution into the vial of NANODOCE® particles powder (100 mg/60 cc vial). The mean particle size (number) of the NANODOCE® particles powder was 1.0 micron. Vigorously hand shook the vial with inversions for 1 minute. Immediately after shaking, added 1.5 ml of normal saline solution (0.9% Sodium Chloride for Injection USP) to the vial and hand shook the vial for another 1 minute to make a 40 mg/mL suspension. Allowed the suspension to sit undisturbed for at least 5 minutes to reduce entrapped air and foam.
Docetaxel Solution: Prepared a 20 mg/mL docetaxel stock solution in 50% Ethanol/50% Polysorbate 80. Added normal saline solution (0.9% Sodium Chloride for Injection) to stock solution to make a final, 3 mg/mL docetaxel solution. Vortexed to mix.
Results:

Tumor volumes were determined 2×/week for the duration of the study (61 days). The results of the study are shown in FIG. 31, FIG. 32, FIG. 33, FIG. 34, FIG. 35, FIG. 36, FIG. 37, FIG. 38, FIG. 39 & FIG. 40. As seen in FIG. 31, tumor volumes decreased and tumors were effectively eliminated for dosages of NanoDoce® IT 2 cycles and NanoDoce® IT 3 cycles. Tumor volumes decreased initially for dosages of NanoDoce® IT 1 cycle and Docetaxel IV 3 cycles, but subsequently increased. These observations are also reflected in FIG. 32, FIG. 33, FIG. 34, FIG. 35, FIG. 36, FIG. 39 & FIG. 40.

Figure 37:
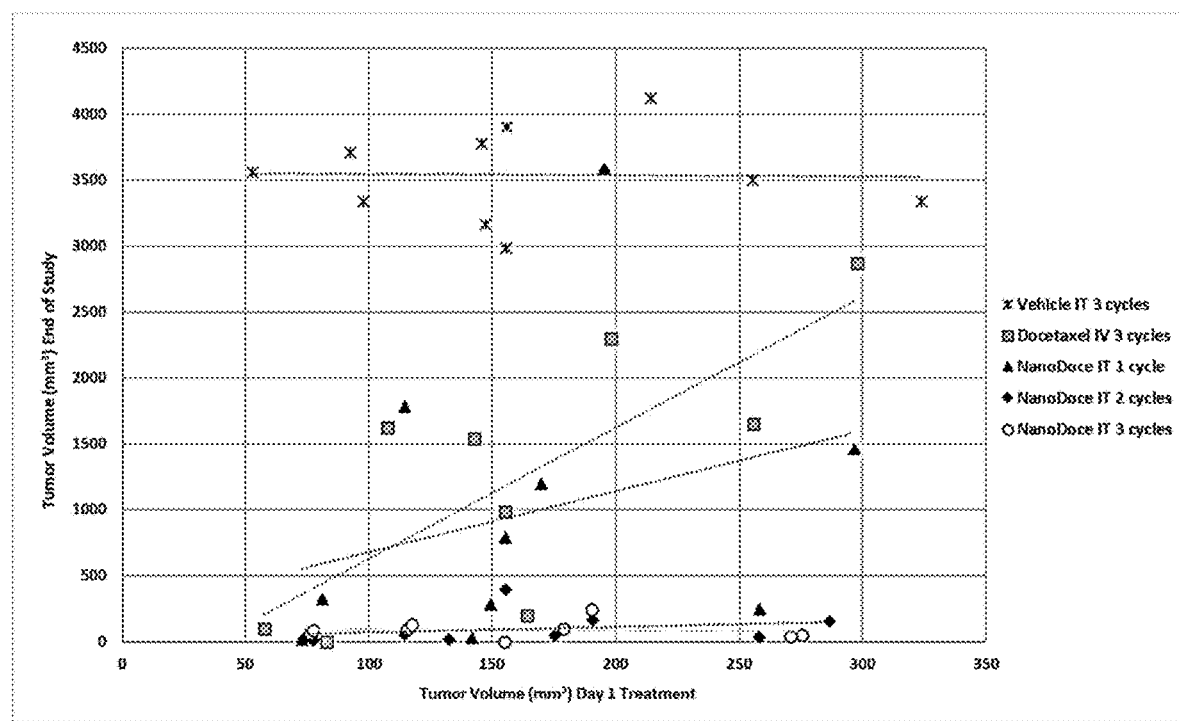
FIG. 37 is a scatter plot of tumor volumes at end of study over tumor volumes at Day 1 treatment from the bladder cancer xenograft study.

The scatter plot in FIG. 37 shows tumor volumes per animal on Day 1 of treatment vs. end of study (day of sacrifice). As can be seen in FIG. 37, the volume of the tumor in a given animal at the end of study was not dependent upon the initial size of the tumor of the same animal for the animals treated with NanoDoce® IT 2 cycles and NanoDoce® IT 3 cycles, as essentially all the tumors were effectively eliminated. However, for animals treated with Docetaxel IV 3 cycles, the volume of the tumor at the end of the study was generally dependent upon the initial tumor volume for a given animal, i.e., the larger the initial tumor volume, the larger the tumor volume at the end of the study. The treatment with Docetaxel IV 3 cycles was somewhat effective at treating small tumors, but not very effective in treating large tumors. Administering NanoDoce® IT (intratumorally) for 2 cycles or 3 cycles effectively treated the tumors regardless of the initial tumor size.

Figure 38:
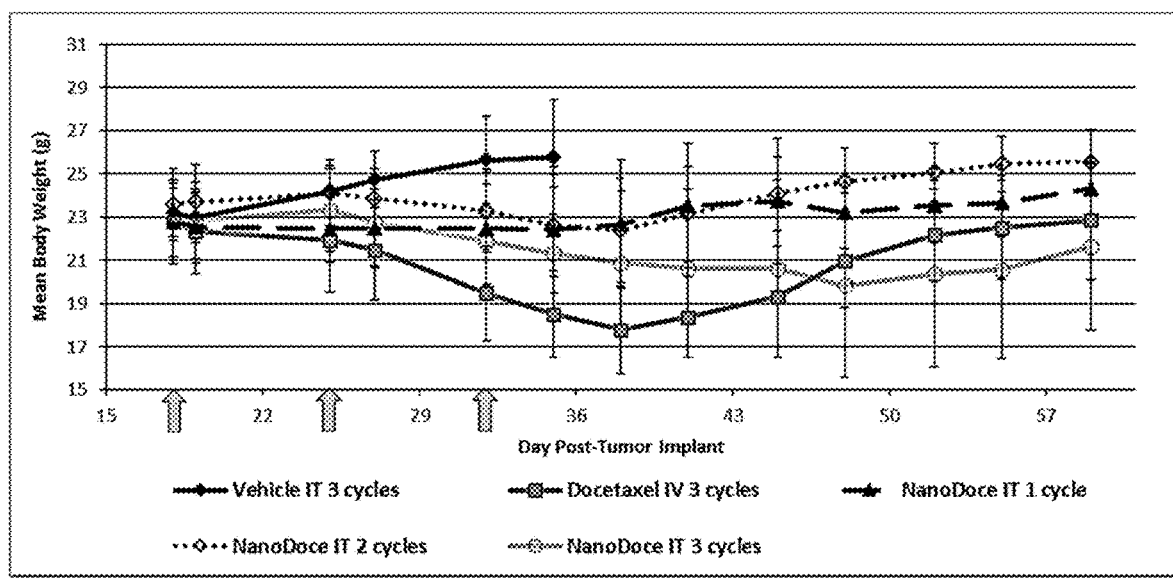
FIG. 38 is a graph of mean body weights over time from the bladder cancer xenograft study. The arrows on the x-axis represent the administration points.
Figure 39:
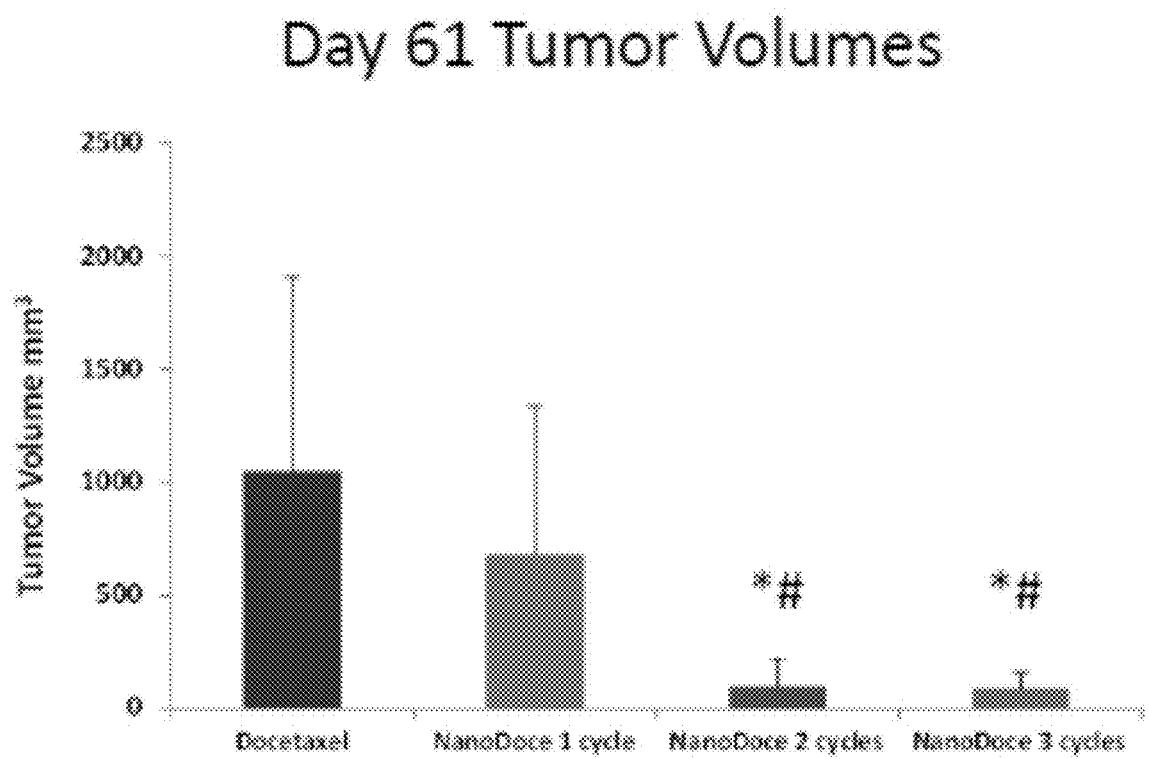
FIG. 39 is a graph of mean tumor volumes at Day 61 for each administration group from the bladder cancer xenograft study.
Figure 40:
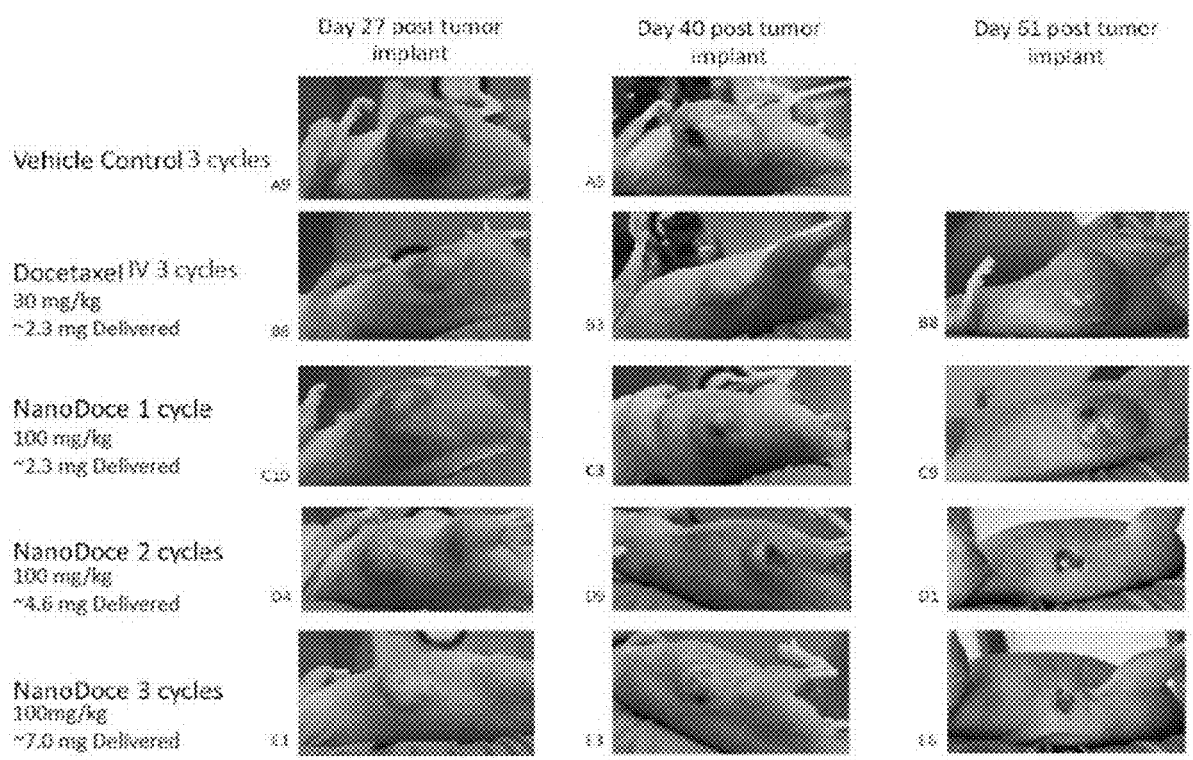
FIG. 40 are photos of animals from each administration group at Day 27, Day 40 and Day 61 post tumor implant from the bladder cancer xenograft study.

As can be seen in FIG. 38, the initial animal weight loss for animals treated with Docetaxel IV 3 cycles was generally greater than that of animals treated with NanoDoce® IT 1 cycle, NanoDoce® IT 2 cycles, and NanoDoce® IT 3 cycles. Weights eventually recovered to some degree in all treatments. This may suggest that the side effect of initial appetite loss is greater with Docetaxel IV administration than with NanoDoce® IT administrations. It was also observed that animals treated with Docetaxel IV 3 cycles had greater signs of peripheral neuropathy than did those treated with NanoDoce® IT 3 cycles, and no signs of peripheral neuropathy were observed in those treated with NanoDoce® IT 1 cycle or 2 cycles.

Figure 41:
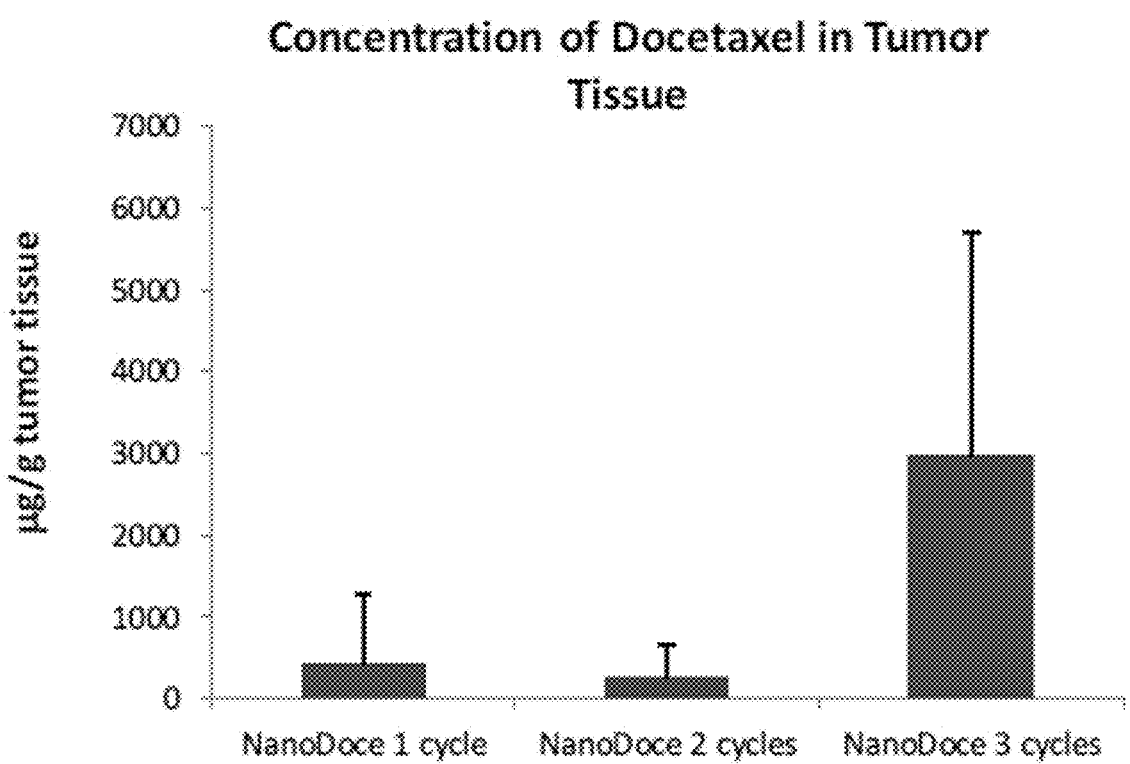
FIG. 41 a graph of concentrations of docetaxel in tumor tissue for NanoDoce® 1 cycle, 2 cycles, and 3 cycles from the bladder cancer xenograft study.
Figure 42:
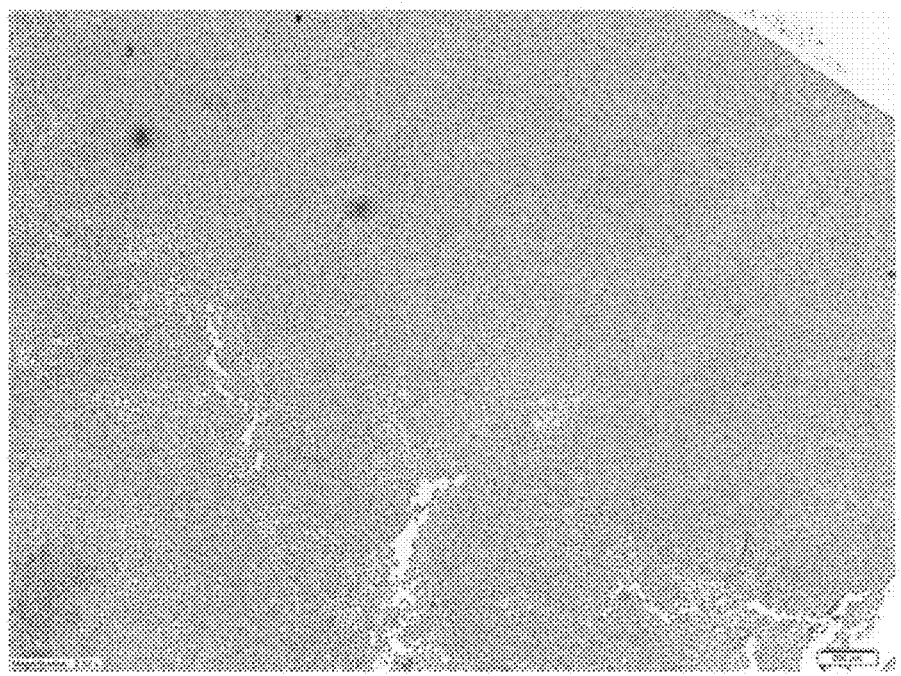
FIG. 42 is a photomicrograph of bladder cancer xenograft tissue slide—IT Vehicle Control. H&E. Magnification 2.52×.
Figure 43:
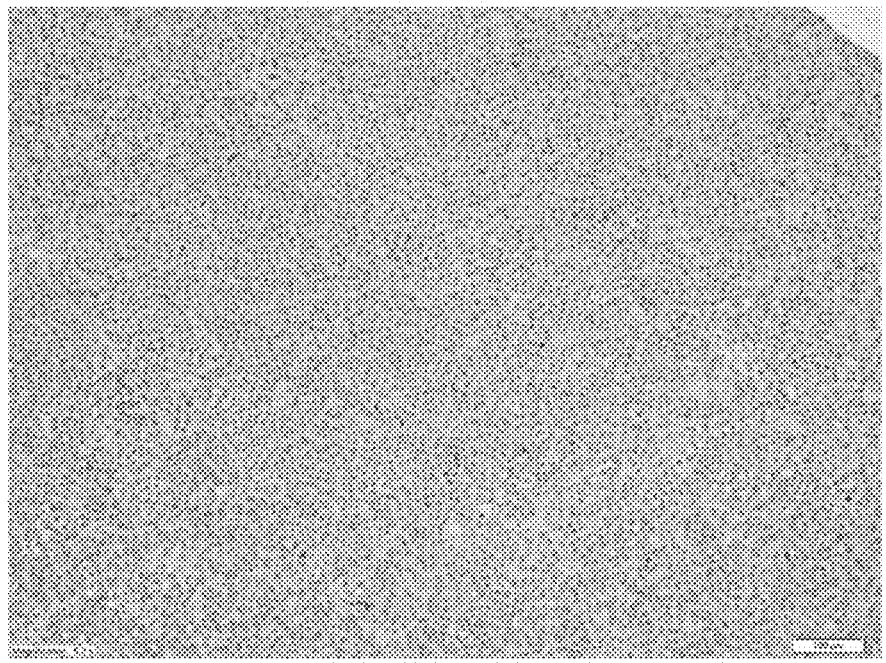
FIG. 43 is a photomicrograph of bladder cancer xenograft tissue slide—IT Vehicle Control. H&E. Magnification 6.3×.
Figure 44:
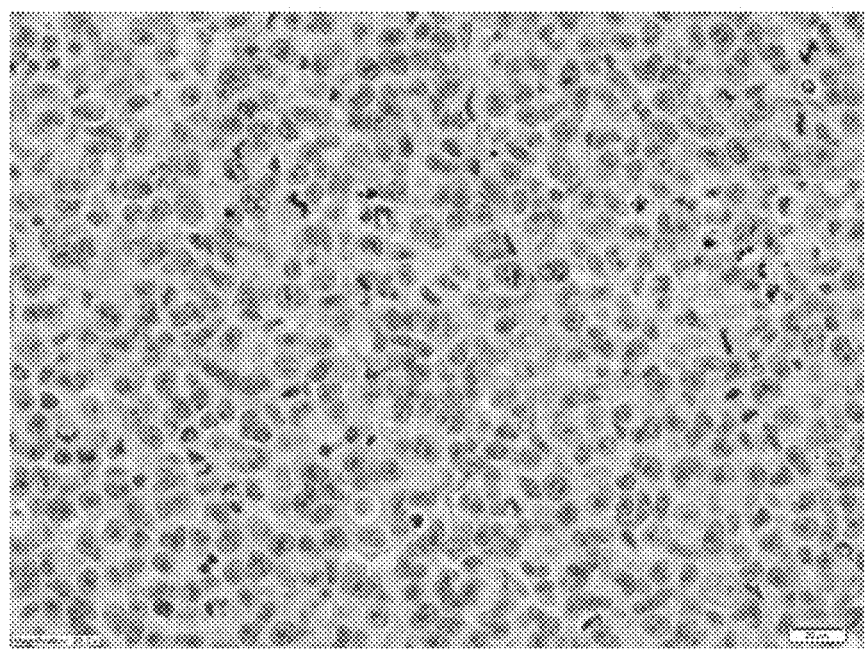
FIG. 44 is a photomicrograph of bladder cancer xenograft tissue slide—IT Vehicle Control. H&E. Magnification 25.2×.
Figure 45:
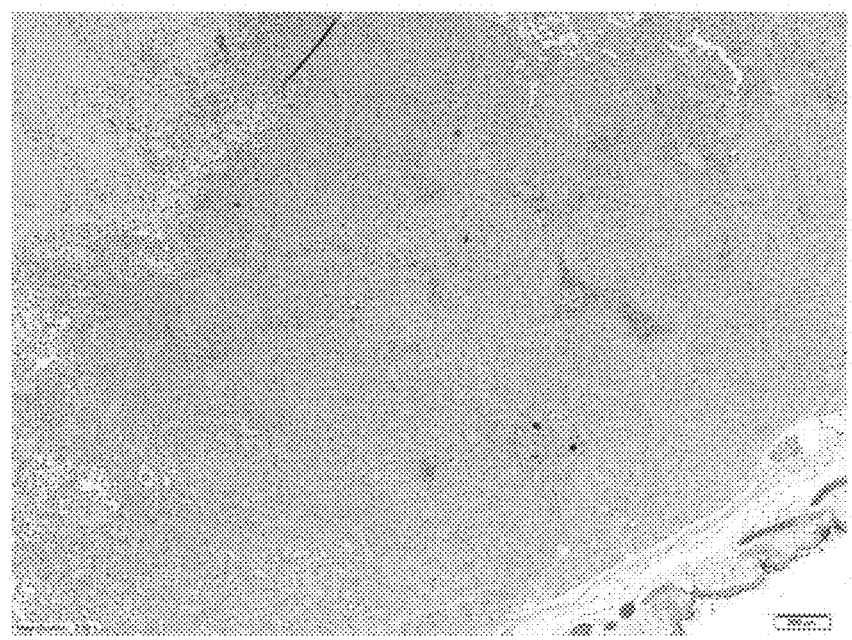
FIG. 45 is a photomicrograph of bladder cancer xenograft tissue slide—IV Docetaxel 3 cycles. H&E. Magnification 2.52×.
Figure 46:
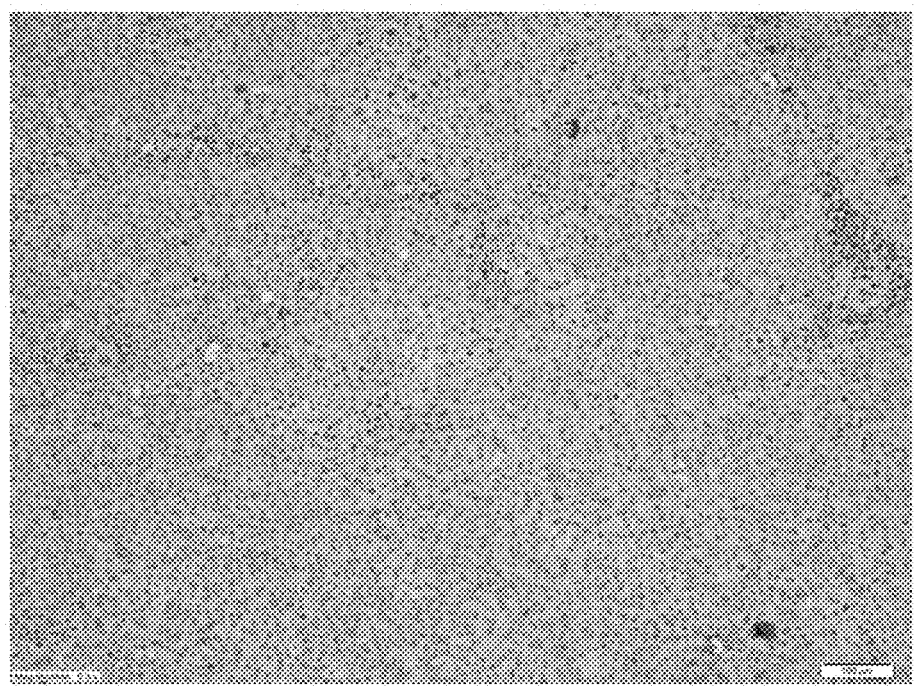
FIG. 46 is a photomicrograph of bladder cancer xenograft tissue slide—IV Docetaxel 3 cycles. H&E. Magnification 6.3×.
Figure 47:
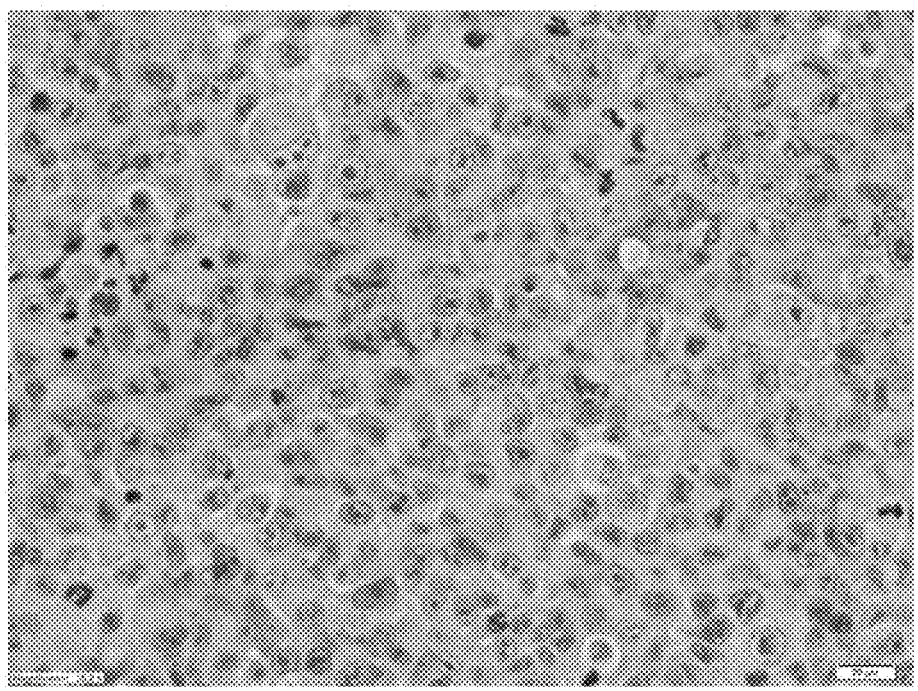
FIG. 47 is a photomicrograph of bladder cancer xenograft tissue slide—IV Docetaxel 3 cycles. H&E. Magnification 25.2×.
Figure 48:
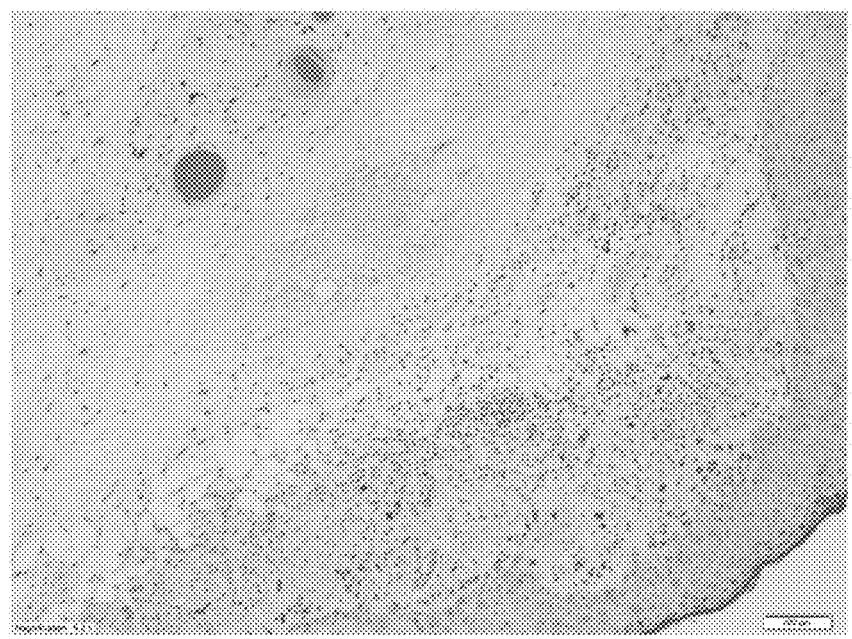
FIG. 48 is a photomicrograph of bladder cancer xenograft tissue slide—IT NanoDoce® 2 cycles. H&E. Magnification 2.52×.
Figure 49:
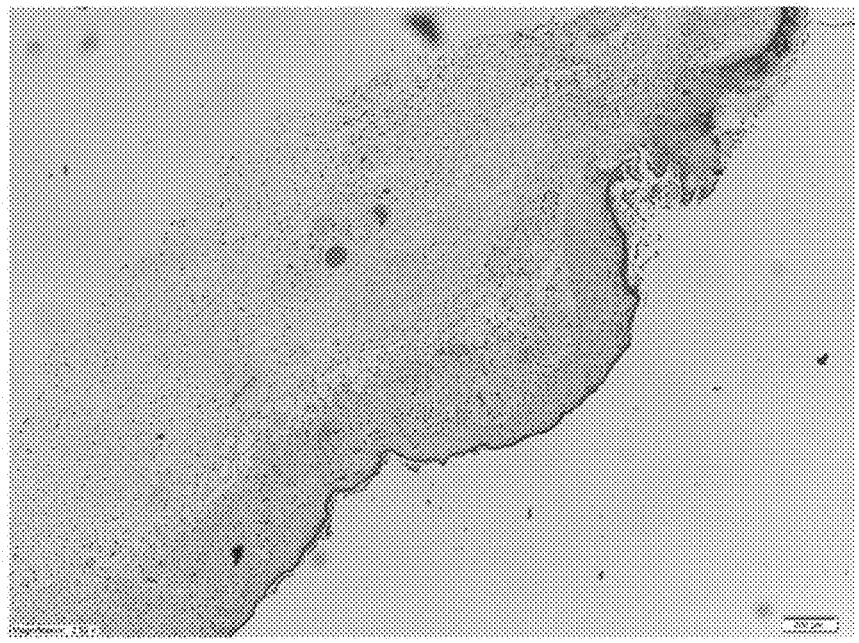
FIG. 49 is a photomicrograph of bladder cancer xenograft tissue slide—IT NanoDoce® 2 cycles. H&E. Magnification 6.3×.
Figure 50:
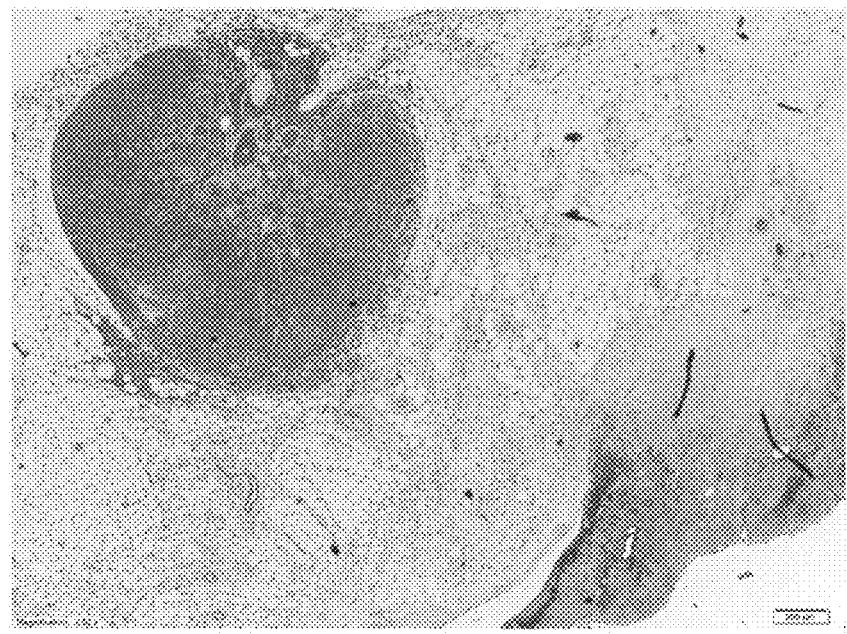
FIG. 50 is a photomicrograph of bladder cancer xenograft tissue slide—IT NanoDoce® 3 cycles. H&E. Magnification 2.52×.
Figure 51:
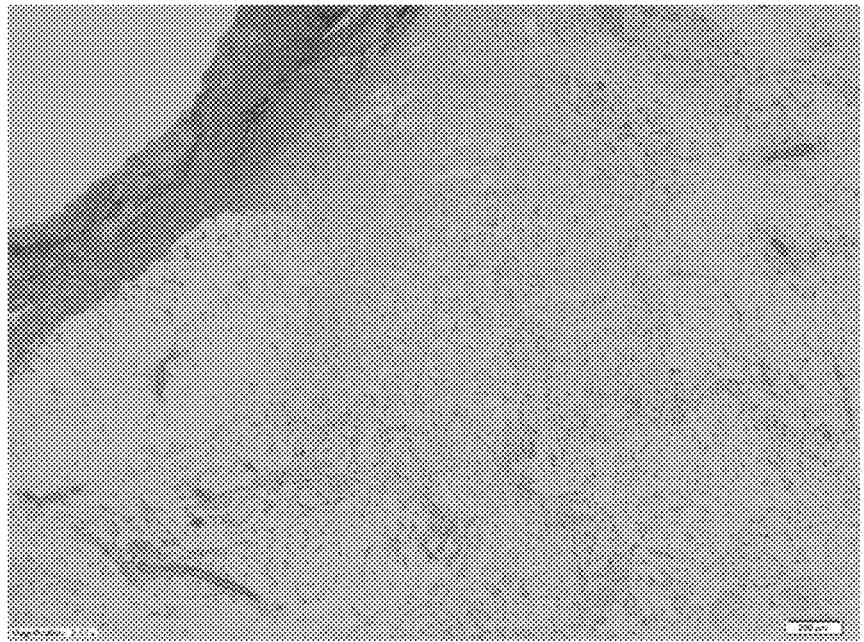
FIG. 51 is a photomicrograph of bladder cancer xenograft tissue slide—IT NanoDoce® 3 cycles. H&E. Magnification 2.52×.
Figure 52:
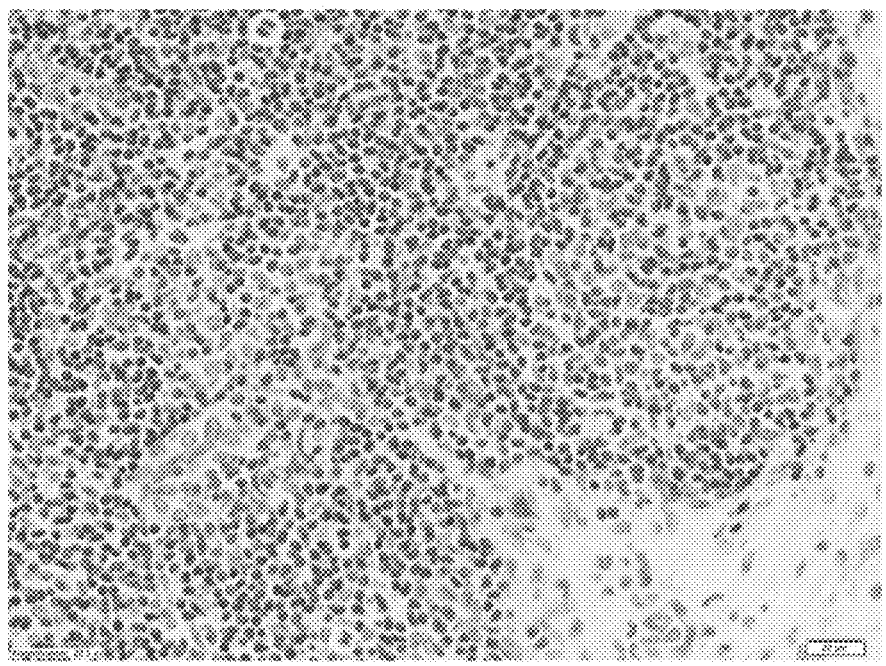
FIG. 52 is a photomicrograph of bladder cancer xenograft tissue slide—IT NanoDoce® 3 cycles. H&E. Magnification 25.2×.
Figure 53:
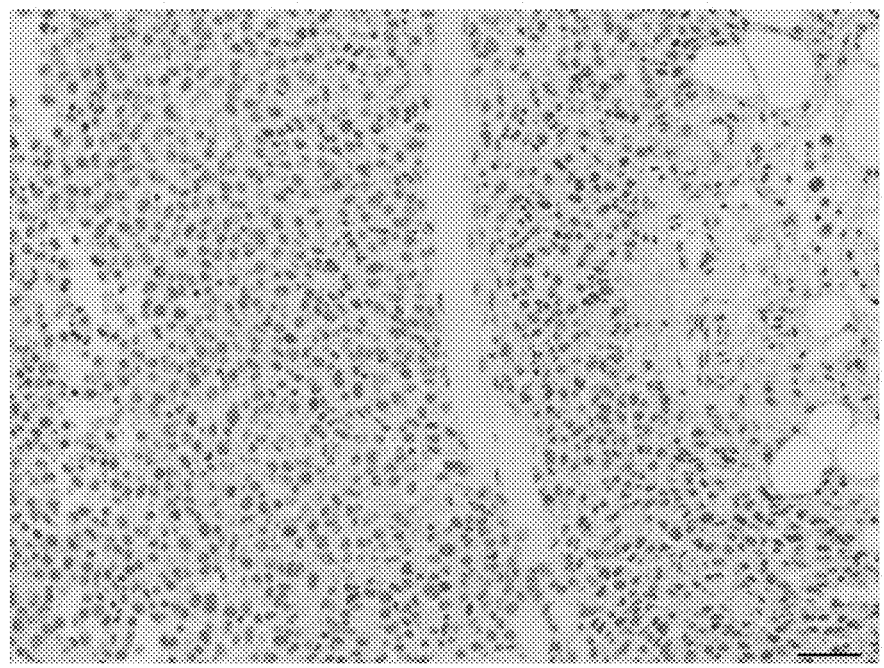
FIG. 53 is a photomicrograph of bladder cancer xenograft tissue slide—IT Vehicle Control 3 cycles F4/80 stain. Magnification 2.52×.
Figure 54:
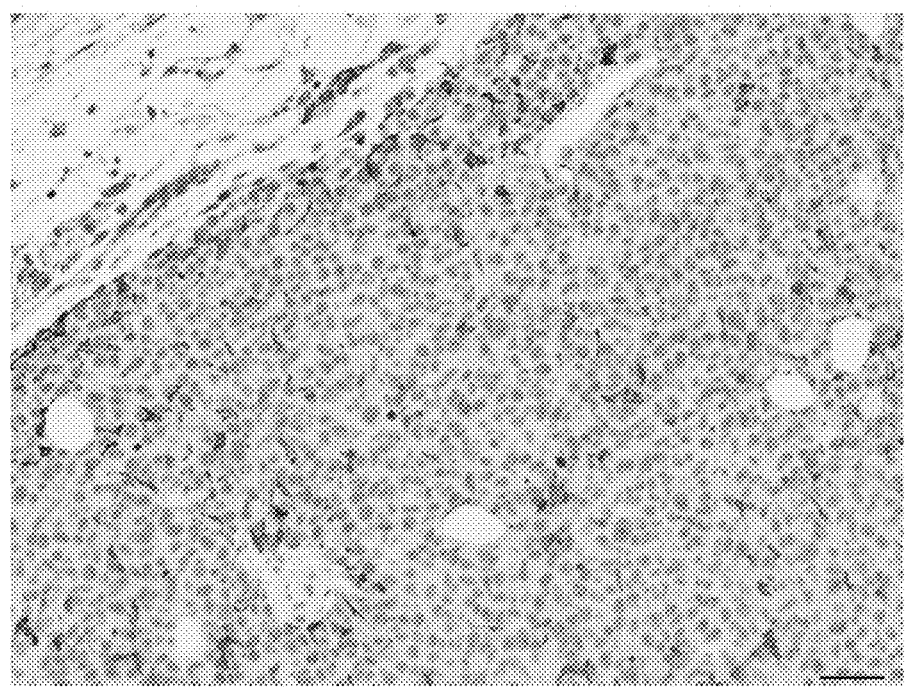
FIG. 54 is a photomicrograph of bladder cancer xenograft tissue slide—IV Docetaxel 3 cycles F4/80 stain. Magnification 2.52×.
Figure 55:
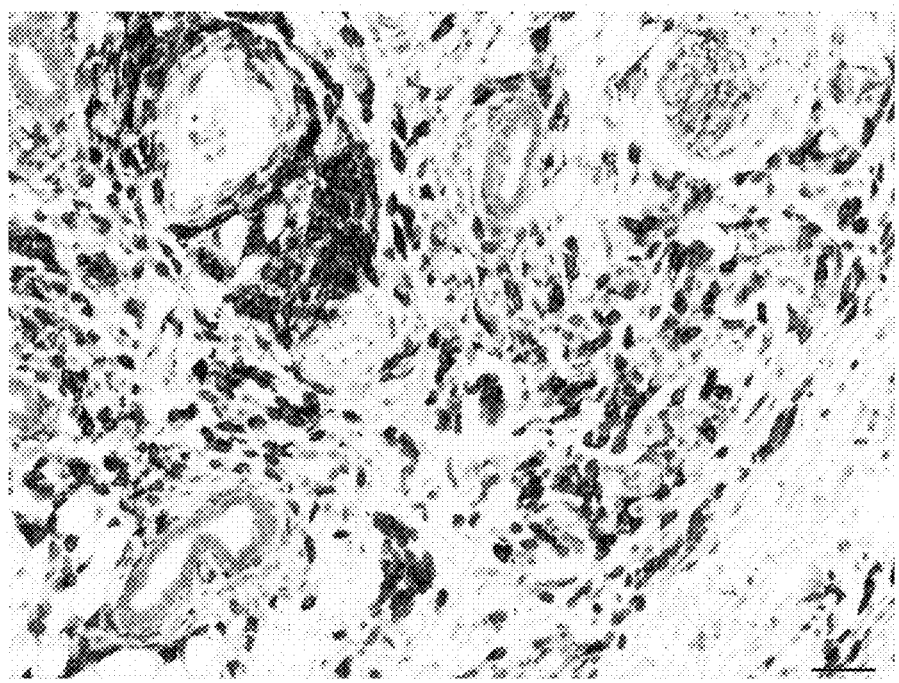
FIG. 55 is a photomicrograph of bladder cancer xenograft tissue slide—IT NanoDoce® 3 cycles F4/80 stain. Magnification 2.52×.
Figure 56:
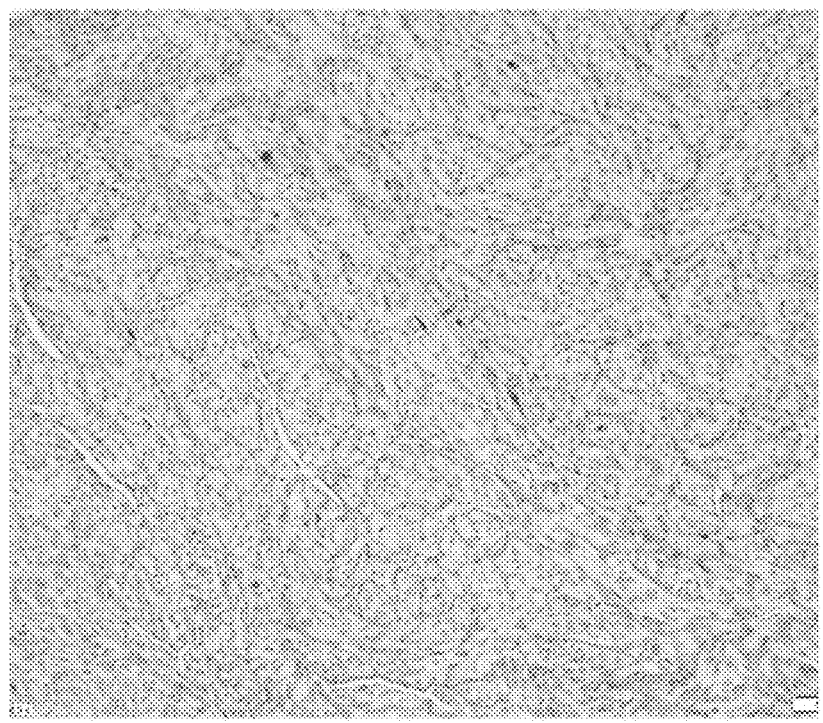
FIG. 56 is a photomicrograph of renal cell adenocarcinoma xenograft tissue slide from female rat—Non-treated. H&E. Magnification 6.3×.

On the day of death or euthanasia, tumor tissues samples were collected and frozen in LN2 for docetaxel analysis, histology, and immunohistochemistry (IHC) observations. In the IV docetaxel control group, only 1 tumor (of 7 measured) had docetaxel levels above the limit of quantitation of the assay (1 ng/g). Measurable levels of docetaxel were found in all tumors from the IT NanoDoce® groups with the NanoDoce® 3 cycle group tending to have the highest concentrations of docetaxel remaining in the tumors (see FIG. 41). Photomicrographs of histology slides, H&E stain, are shown in FIGS. 42 to 52. Photomicrographs of IHC slides stained with F4/80 antibody stain are shown in FIG. 53, FIG. 54, and FIG. 55.

Histological Overview of Photomicrographs in FIGS. 42 to 52

General Observations:

Control: Extensive levels of viable tumor with proliferating cells and little to no mononuclear immune cell infiltration, occasional macrophages noted.

Docetaxel Solution: many viable appearing tumor masses with some macrophage and occasional lymphocytic response along with some tumor necrosis.

NanoDoce® 2 cycles: Some remaining isolated tumor cells, small area of skin injury, scar/fibrosis seen, immune cell infiltrate including macrophages and mononuclear cells.

NanoDoce® 3 cycles: Some remaining isolated tumor cells, small area of skin injury, scar/fibrosis seen, immune cell infiltrate including macrophages and mononuclear cells Extensive mononuclear cell infiltration was observed at the site of tumor implantation in the subcutaneous space in animals receiving intratumoral injection of NanoDoce®. With increased numbers of cycles, there is increased tumor response, but there is some skin injury, perhaps due to the small space and shallow area for injection on the flank of a nude mouse (e.g., tumor right up against skin that is tightly drawn over the tumor). As the model used is T cell deficient, it is likely that the lymphocytic cells are B cells or NK cells. B cells are responsible for the production of cytotoxicity (the antibodies bind to cells expressing Fc Receptors and enhance the killing ability of these cells. NK cells are innate lymphoid cells that are crucial in the killing of tumor cells. In patients with tumors, NK cell activity is reduced allowing for the growth of the tumor. Along with T cells, NK cells are the target of some check point inhibitors to increase their activity. In all histological samples provided, macrophages were present in the tumor, but the number did not appear to significantly increase.

By the use of a wide array of surface receptors capable of delivering either triggering or inhibitory signals, NK cells can monitor cells within their environment to ascertain if the cell is abnormal (tumor or virally infected) and should be eliminated through cytotoxicity. The cytotoxicity and chemotaxis of NK cells can be modified by many pathological processes including tumor cells and their byproducts. In response to certain signals their functions are enhanced or potentiated. In response to several Pathogen Associated Molecular Patterns (PAMPs) by using different Toll Like Receptors (TLR); NK cells can increase cytokine production and/or cytolytic activity. Cytokines, including IL-2, IL-15, IL-12, IL-18, and IFNs $\alpha/\beta$ can also modify the activity of NK cells. NK cells are not simple cells that are only cytolytic effectors capable of killing different tumor cell targets; rather, they represent a heterogeneous population which can finely tune their activity in variable environmental contexts.

The tumor burden is significantly reduced in the site of xenograft injection in the animals treated with NanoDoce® and the intratumoral injection is more effective than intravenous docetaxel. Therefore, the localized administration of docetaxel in the form of NanoDoce® provides additional potency. This is likely due to both the longer exposure to the chemotherapy over time and the vigorous cellular infiltration to the site of the tumor. This latter response appeared to be dependent on the dose density (actual dose and dose frequency). Anatomically, macrophages are present at high numbers at the margins of tumors with decreasing frequency throughout the stroma moving deeper within the tumor.

Immunohistochemistry Overview of FIG. 53, FIG. 54, and FIG. 55

FIG. 53: Vast sheet of viable tumor cells and no mononuclear immune cells (no brown staining).

FIG. 54: Very little tumor cell destruction and few scattered mononuclear immune cells among vast number of viable tumor cells.

FIG. 55: Virtually no tumor cells left and vast numbers of mononuclear immune cells organized into distinct patterns (likely mostly macrophages).

Example 15—Drug Efficacy Study in Rat Xenograft Model of Human Renal Cell Adenocarcinoma A non-GLP study was conducted to determine the drug efficacy of NanoPac® (nanoparticle paclitaxel) suspension and NanoDoce® (nanoparticle docetaxel) suspension administered by intratumoral injections in a rat xenograft model of human renal cell adenocarcinoma.

Objectives

The objective of this study was to investigate the potential efficacy of NanoPac® (nanoparticle paclitaxel) and NanoDoce® (nanoparticle docetaxel), administered by intratumoral (IT) injections over a period of time in the Sprague-Dawley Rag2; Il2rg null (SRG®) rat xenograft model of human renal cell adenocarcinoma (786-O cell line) (ATCC®CRL-1932™). Five to seven weeks old SRG rats were inoculated with 5 million 786-O cells in Cultrex® subcutaneously to develop tumor xenograft. Once the tumor volume reached 150-300 mm³, the rats were enrolled on a rolling basis into treatment groups consisting of the test articles (administered IT); positive controls (paclitaxel and docetaxel; administered intravenous (IV)) and a vehicle control (administered IT), then monitored for the tumor growth or regression.

Cell Culture

Cell lines: 786-O cell line (ATCC®CRL-1932™). Cells were stored in liquid nitrogen. Upon thawing, cells were cultured at 37° C., 5% CO2. After cells were prepared for transplant, they were maintained on ice until injection.

Cell culture conditions: Cells were cultured in RPMI 1640 (Gibco #410491-01)+10% FBS on tissue-culture treated flasks at 37° C., 5% CO2. Cells were expanded for 2-3 weeks prior to inoculation. Cell thawing, culturing and passaging was carried by ATCC (www.atcc.org/Products/All/CRL-1932.aspx)

Cell Inoculation: $5 \times 10^6$ cells per rat; subcutaneous left hind flank, dorsal side.

Inoculation vehicle: 50% Cultrex BME type 3 (Trevigen #3632-001-02; a type of basement membrane matrix like Matrigel® formulated for in vivo tumor growth) 50% Media in a total volume of 0.5 ml. Cell suspension mixed 1:1 with 10 mg/mL Cultrex for a final concentration of 5 mg/mL Cultrex. Final inoculation volume is 500 ul.

Preparation of Test Articles (NanoPac® and NanoDoce® Suspension)

Drug: NanoPac® (nanoparticle paclitaxel powder, approximately 98% paclitaxel with a mean particle size (number) of 0.878 microns, a SSA of 26.7 $m^2/g$, and a bulk density (not tapped) of 0.0763 $g/cm^3$ used in this example) 306 mg in a 60 mL vial; and NanoDoce® (nanoparticle docetaxel powder, approximately 99% docetaxel with a mean particle size (number) of 1.078 microns, a SSA of 37.2 $m^2/g$, and a bulk density (not tapped) of 0.0723 $g/cm^3$ used in this example) 100 mg in a 60 mL vial.

For NanoPac® Suspension (Final concentration: 20 mg/mL NanoPac® and 0.32% Polysorbate 80 in normal saline solution—Final volume: 15.3 mL per vial):

Using a sterile syringe with a sterile 18-gauge needle or larger, added 5.0 mL of a sterile 1% polysorbate 80 reconstitution solution into the 60 ml NanoPac® powder vial (containing 306 mg NanoPac® powder).

Vigorously hand shook the vial with inversions to make sure all the particles adhering to the interior of the vial and stopper are wetted.

Continued shaking for 1 minute and examined the suspension for any large clumps of particles.

Immediately after shaking, used a sterile syringe with a sterile 18-gauge needle or larger to add 10.3 mL of a normal saline solution (0.9% sodium chloride solution for injection) to the vial and hand shook the vial for another 1 minute. Periodically examined the suspension for any large visible clumps. If present, continued hand mixing until the suspension was properly dispersed.

After mixing, allowed the suspension to sit undisturbed for at least 5 minutes to reduce entrapped air and foam.

For NanoDoce® Suspension (Final concentration: 20 mg/mL NanoDoce®, 0.20% Polysorbate 80, and 1.6% ethanol in normal saline solution—Final volume: 5 mL per vial):

Using a sterile syringe with a sterile 18-gauge needle or larger, added 1 mL of a sterile 1% polysorbate 80/8% ethanol reconstitution solution into the 60 ml NanoDoce® powder vial (containing 100 mg NanoDoce® powder).

Vigorously hand shook the vial with inversions to make sure all the particles adhering to the interior of the vial and stopper are wetted.

Continued shaking for 1 minute and examined the suspension for any large clumps of particles.

Immediately after shaking, used a sterile syringe with a sterile 18-gauge needle or larger to add 4 mL of normal saline solution (0.9% sodium chloride for injection) to the vial and hand shook the vial for another 1 minute. Periodically examined the suspension for any large visible clumps. If present, continued hand mixing until the suspension was properly dispersed.

After mixing, allowed the suspension to sit undisturbed for at least 5 minutes to reduce entrapped air and foam.

Intratumoral (IT) Vehicle (Final concentration: 0.2% Polysorbate 80 and 1.6% ethanol in normal saline solution): Each 1 mL of a 1% Polysorbate/8% ethanol reconstitution solution was diluted with 4 mL of normal saline solution (0.9% sodium chloride solution for injection).

Preparation of Positive Controls Formulation

Drug: Docetaxel: CAS 114977-28-5, and Paclitaxel: CAS 33069-62-4. Purity >97%

For Docetaxel Solution: Made a 20 mg/mL solution of docetaxel in 50% ethanol:50% Polysorbate 80. Vortexed to mix. Added normal saline solution to dilute to a 3 mg/mL solution of docetaxel.

For Paclitaxel Solution: Used bulk paclitaxel to make 6 mg/mL formulation in 50% ethanol: 50% Cremophor EL. Vortexed as needed to mix. Added normal saline solution to dilute to a 3 mg/mL solution of paclitaxel. Vortex to mix.

Test System

Species/Strain: Rat (*Rattus norvegicus*)/Rag2$^{-/-}$; 112rg$^{-/-}$ on Sprague Dawley background (SRG®).

Number of Animals/Approximate Age and Weight: Sixty healthy rats (30 males and 30 females) were assigned for this study and used for xenograft development. At least 54 tumor-bearing animals in total were enrolled for treatment (27 males and 27 females) as they reached the required tumor volume. These animals were inoculated with 786-0 cells in staggered batches on the same day, pending animal availability. Animals were approximately 5-7 weeks of age at the onset of the study. Approximate weight was 150-275 g. Animals were enrolled in the treatment groups on a rolling basis when the tumor size reached 150-300 $mm^3$.

Organization of Treatment Groups, Dosage Levels and Treatment Regimen

Table 26 below presents the study group arrangement.

TABLE 26

| Group | Treatment | Dose route, Dose Schedule | Dosage level (mg/kg/day) | Dose concentration (mg/ml) | Dose volume (ml/kg) ** | Number of rats* |
|---|---|---|---|---|---|---|
| 1 | Vehicle | IT, QWX3 | 0 | N/A | 1 | 6 |
| 2 | Paclitaxel | IV, QWX3 | 5 | 3 | 1.67 | 6 |
| 3 | NanoPac ® | IT, QWX1 | 20 | 20 | 1 | 6 |
| 4 | NanoPac ® | IT, QWX2 | 20 | 20 | 1 | 6 |
| 5 | NanoPac ® | IT, QWX3 | 20 | 20 | 1 | 6 |
| 6 | Docetaxel | IV, QWX3 | 2.5-5 | 3 | 0.835-1.67 | 6 |

TABLE 26-continued

| Group | Treatment | Dose route, Dose Schedule | Dosage level (mg/kg/day) | Dose concentration (mg/ml) | Dose volume (ml/kg) ** | Number of rats* |
|---|---|---|---|---|---|---|
| 7 | NanoDoce® | IT, QWX1 | 20 | 20 | 1 | 6 |
| 8 | NanoDoce® | IT, QWX2 | 20 | 20 | 1 | 6 |
| 9 | NanoDoce® | IT, QWX3 | 20 | 20 | 1 | 6 |

*3 males and 3 females were allocated per group.

Treatment Regimen:

All rats that developed tumors that reached 150-300 mm$^3$ in volume were enrolled in treatment. All treatment will commence after 7 days post inoculation when tumors are >150 mm$^3$.

Groups 3, 4 and 5 rats received NanoPac® and groups 7, 8 and 9 rats received NanoDoce®. Groups 3 and 7 received IT injections only on staging day (first day of treatment), groups 4 and 8 received IT injections on staging day and 7 days post initiation of treatment, and groups 5 and 9 received IT injections on staging day, 7 and 14 days post initiation of treatment. Positive control test articles (paclitaxel and docetaxel) were administered intravenously by tail vein injection on staging day, 7 and 14 days post-initiation of treatment to Groups 2 (paclitaxel) and 6 (docetaxel) rats. The vehicle control was administered by IT injection on staging day, 7 and 14 days post-initiation of treatment to group 1 animals.

Methods of Administration:

The test articles and the vehicle were administered by IT injections or IV injections depending on the dosing group, with sterile needles and syringes. All IV injections were administered using a 27G needle.

IT injections were distributed across the tumor in 6 injections when the tumor was intact and 3 injections in case of an ulcerating tumor. The number of IT injections per tumor during all dosing days were recorded in the raw data.

The dose volume was 1 mL/kg for the vehicle, NanoPac® and NanoDoce® and 1.67 mL/kg for paclitaxel and docetaxel. For group 6, the dosage of Docetaxel was changed to 2.5 ml/kg and the dose volume was decreased to 0.835 ml/kg. At the time of dose administration, NanoPac® and NanoDoce® vials were inverted gently 5-10 times immediately prior to dose removal to ensure uniformity of the suspension.

Using a sterile syringe with a sterile 18-gauge* needle or larger bore, inverted the vial and inserted the needle into the septum of the inverted vial. Withdrew just over the amount of suspension needed, removed the needle from the vial and adjusted to the desired volume. Recapped the needle. *Note: for IT injections, a 27G needle was used for administration.

IT injections were administered across the tumor in a Z pattern (across top, diagonal through, then across bottom) and reversed each following dosing occasion(s). The injections were administered with the needle bevel facing down to minimize leakage of the TA post injection. The skin was also pulled slightly back prior to needle entry and during the injection to also minimize TA leakage post injection. Efforts were made to ensure IT injection administration patterns are consistent across all animals and dosing days.

NanoPac® was used within 1 hour and NanoDoce® within 24 hours of reconstitution. The positive controls and docetaxel were maintained at room temperature and used within 8 hours of formulation while paclitaxel was kept in warm water after reconstitution and used within 20 minutes.

Observations:

Individual Body Weights: Three times weekly (M, W, F) starting at the time of inoculation.

Individual Tumor Volumes: Animals were palpated daily starting the day after tumor inoculation. Tumor length and width were measured with digital calipers and recorded starting when tumor volume reached 50 mm$^3$, at which point tumors were measured three times weekly (M, W, F) and at the time of necropsy. Tumor volume (mm$^3$) was calculated as $=(L \times W^2)/2$ where 'L' is the largest diameter.

Tumor Imaging: Photographs of all tumors were taken on staging day prior to commencement of treatment and 7, 14, 21, 28, 35, and 42 days post initiation of treatment. Additional tumor photographs were also taken at the time of necropsy of all rats including animals reaching end-point before study termination. All photographs will be taken with the animal in an anterior-posterior orientation with a photo-tag that states the animal I.D., study day and date.

Blood Sample Collection for Analysis: 200-250 µl of blood was collected from the tail or jugular vein of all treated animals at study termination, i.e. 50 days post initiation of treatment.

Scheduled Necropsy: All animals were scheduled for necropsy 50 days post the initiation of the treatment. Day 0 was day of tumor inoculation.

Anatomic Pathology:

Macroscopic Examination: A necropsy was conducted on all animals dying spontaneously, euthanized in extremis or at the scheduled necropsy after 50 days post initiation of treatment. Animals euthanized in extremis or at study termination were euthanized by CO2 inhalation. Necropsy included examination of the external surface, all orifices and the thoracic, abdominal and pelvic cavities, including viscera. At the time of necropsy, a final body weight and body condition score was collected.

Tissue Collection: Primary Tumor (Inoculation site)—A final tumor measurement was taken prior to excision. Tumors were weighed after excision. Approximately ½ of each tumor (based on visual assessment) was flash frozen in 2-methylbutane on dry ice, the tumor piece was weighed when possible before it is flash frozen. The remaining was fixed in 10% neutral buffered formalin. Tumors were also collected from animals not reaching enrollment volume. Secondary Tumors—Any organ with visible tumors were collected and fixed in 10% neutral buffered formalin. Formalin fixed tissues were stored at room temperature. Frozen tissues were stored at −80° ° C. All tissue was stored for up to 3 months. Pictures of all tumors; primary and secondary if present, were taken.

Microscopic Examination: Tissues fixed with 10% NBF were embedded in paraffin. Each tumor was cut into 2-3 pieces and embedded and sectioned together. For each tumor, 3 slides were prepared and stained with H&E. Photomicrographs of preliminary histology slides from female rats for Non-Treated, Vehicle Control (IT) 3 cycles, Docetaxel (IV) 3 cycles, and NanoDoce® (IT) 3 cycles are shown in FIG. 56, FIG. 57, FIG. 58, and FIG. 59, respectively.

Figure 59:
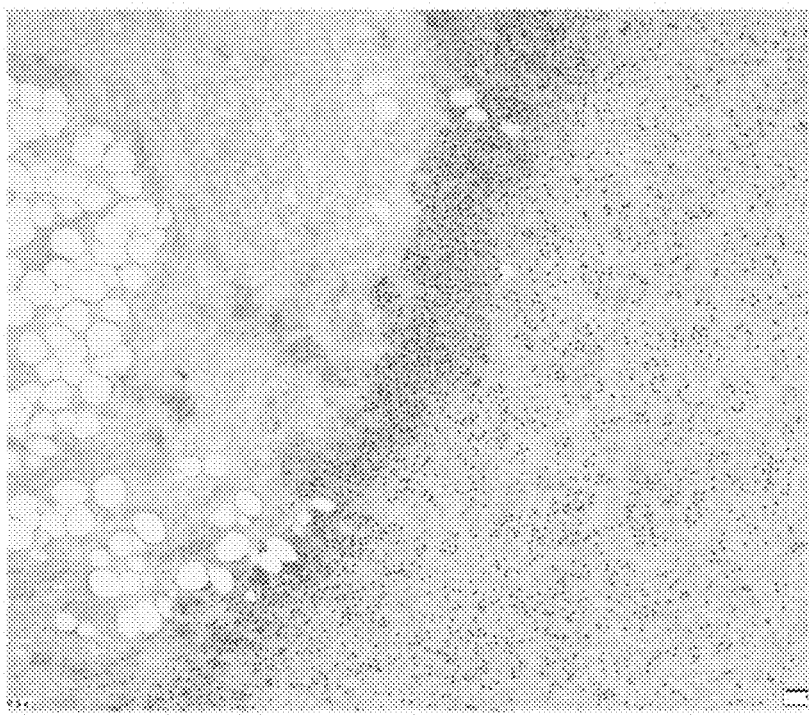
FIG. 59 is a photomicrograph of renal cell adenocarcinoma xenograft tissue slide from female rat—NanoDoce® (IT) 3 cycles. H&E. Magnification 6.3×.
Figure 60:
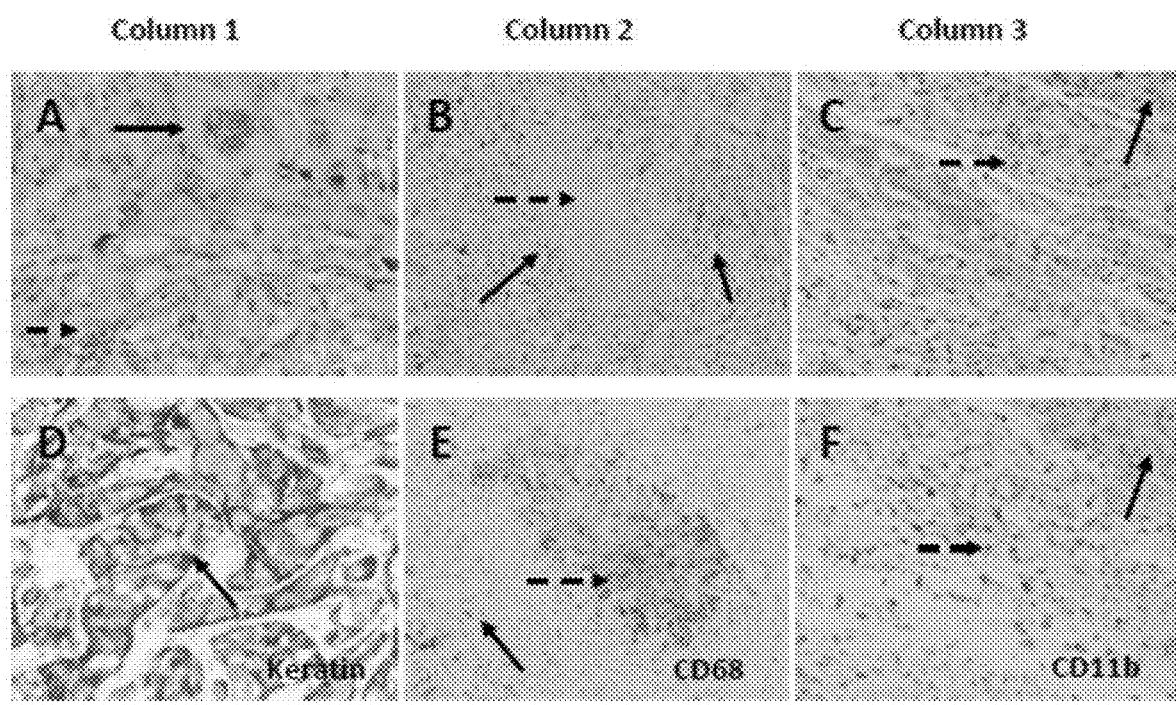
FIG. 60 are various photomicrographs of Control Cases of renal cell adenocarcinoma xenograft tissue slides. Top row: H&E stained sections. Bottom row: Immunohistochemical staining.
Figure 61:
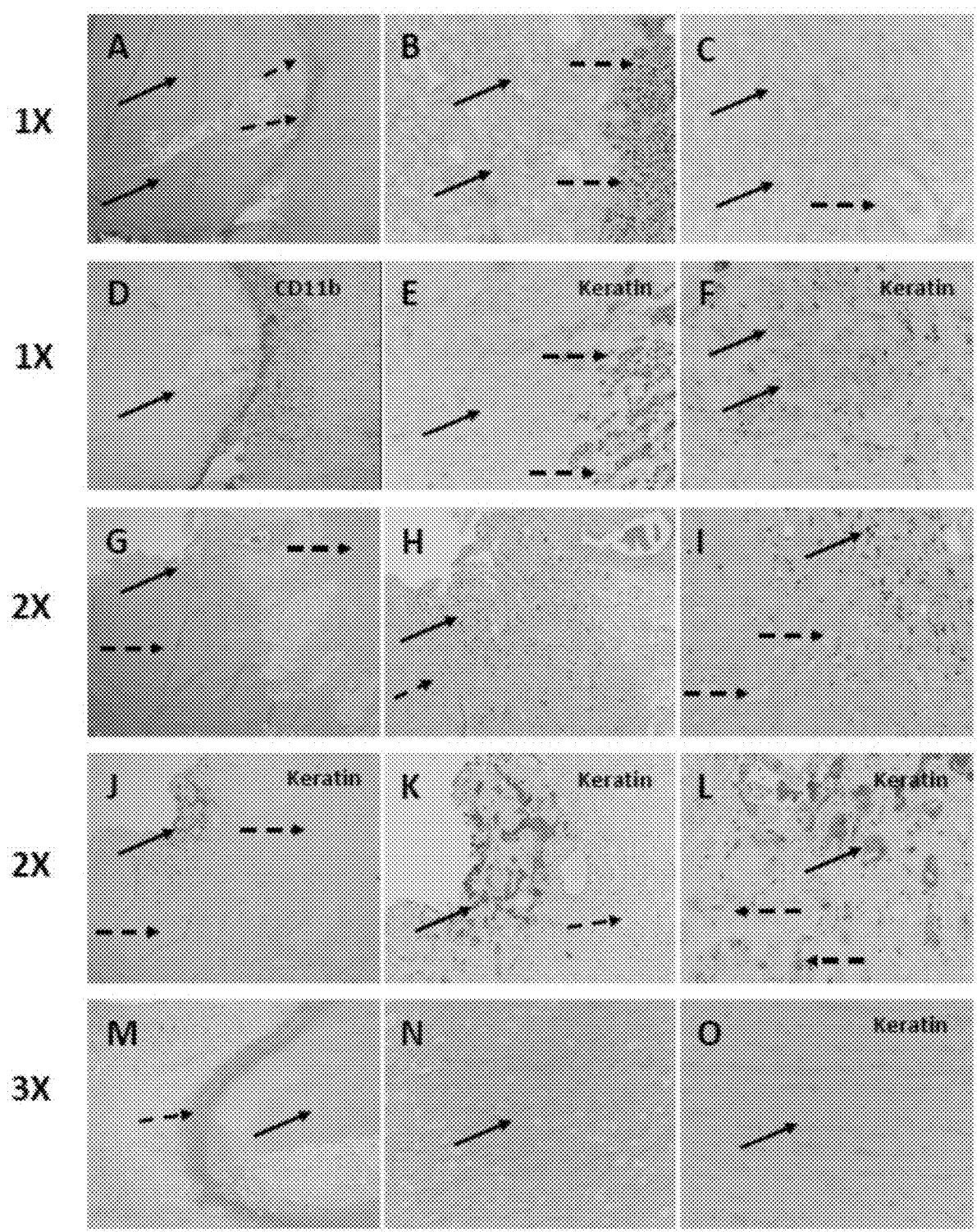
FIG. 61 are various photomicrographs of IT NanoDoce® cases of renal cell adenocarcinoma xenograft tissue slides. Top row: One cycle NanoDoce® (1×). Second row: One cycle NanoDoce® (1×). Third row: Two cycles NanoDoce® (2×). Fourth row: Two cycles NanoDoce® (2×). Fifth row: Three cycles NanoDoce® (3×).

Additional H&E and Immunohistochemical (IHC) evaluations were conducted on formalin-fixed tissue from animals from the Docetaxel group and are shown in FIGS. 60 and 61. Histology Overview of Photomicrographs in FIG. 57, FIG. 58, and FIG. 59.

Figure 57:
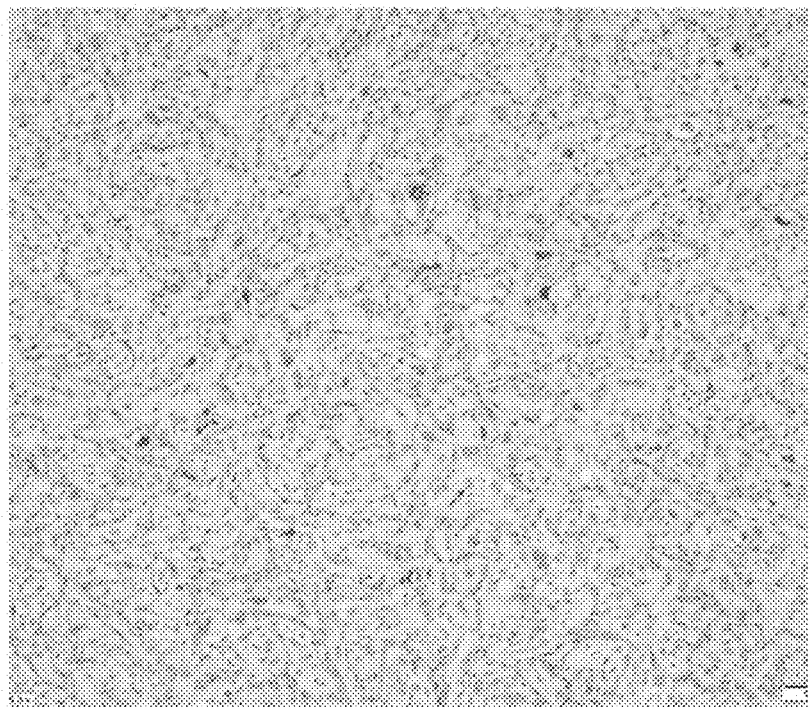
FIG. 57 is a photomicrograph of renal cell adenocarcinoma xenograft tissue slide from female rat—Vehicle Control (IT) 3 cycles. H&E. Magnification 6.3×.

Vehicle Control (IT) 3 cycles, FIG. 57: The photomicrograph shows "packets" of multi-/bi-nucleate tumor cells surrounded by extracellular matrix.

Figure 58:
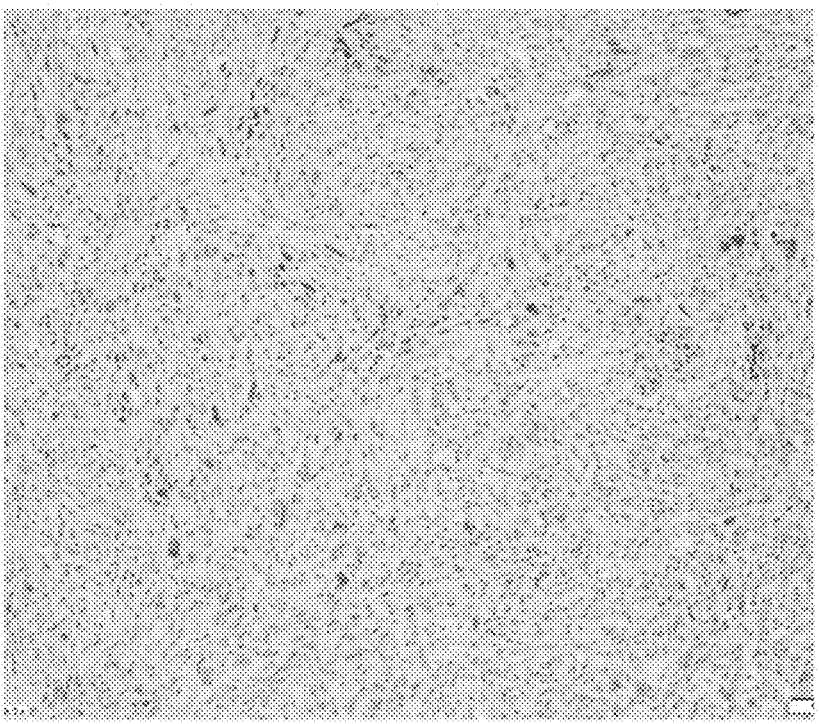
FIG. 58 is a photomicrograph of renal cell adenocarcinoma xenograft tissue slide from female rat—Docetaxel solution (IV) 3 cycles. H&E. Magnification 6.3×.

Docetaxel (IV) 3 cycles, FIG. 58: The photomicrograph shows morphologically similar "packets" of viable renal cell carcinoma seen in the vehicle control: no difference.

NanoDoce® (IT) 3 cycles, FIG. 59: The photomicrograph shows a band of mononuclear cells representing a robust immune response to the tumor cells. Some dead tumor or dying tumor is present characterized as cellular "ghosts" (shown left of the mononuclear immune cell band). To the right of the mononuclear cell band are "ghosts" covered by a "sprinkling" of mononuclear immune cells.

Additional H&E and Immunohistochemical (IHC) evaluation of the Docetaxel Groups

Observations: FIG. 60 Control Cases. Top row: H&E stained sections. Bottom row: Immunohistochemical staining.

Column 1: (A) Renal cell carcinoma composed of closely apposed cohesive clusters and cords of large tumor cells with pleomorphic nuclei and visible nucleoli. Note the minimal intervening stroma that contains scattered small blood vessels (dashed arrow bottom left). Note multinucleated carcinoma cell at top of image (solid arrow). (D) Keratin (AE1/AE3) immunostain performed on the same tumor shown in A. This demonstrates sensitive and specific labeling of carcinoma cells with pancytokeratin (solid arrow).

Column 2: (B) Focal area of tumor cell necrosis composed of uniformly homogenous amorphous eosinophilic material (dashed arrow). Note the discrete nature of this focus with sharp demarcation from the surrounding viable carcinoma cells (solid arrows). This was the typical appearance of necrosis in the control groups. This was present in central areas of the tumor and occupied less than 5% of the tumor area. (E) CD68 stain (macrophage marker) highlighting the same area shown in image B. This shows limited numbers of macrophages in the viable carcinoma (solid arrow) and markedly increased macrophages in the focus of necrosis (dashed arrow). The latter finding illustrates the characteristic macrophage function of necrotic debris phagocytosis.

Column 3: (C) Limited numbers of small lymphocytes in the peritumoral surrounding non-neoplastic stroma (dashed arrow). Note carcinoma in top right corner (solid arrow). In the control groups, there were typically very few lymphocytes within the tumor itself and the peritumoral soft tissue generally contained a mild lymphoid infiltrate. (F) Corresponding focus to that seen in C, stained with CD11b, showing positive staining in lymphoid cells (dashed arrow). Note carcinoma in top right corner (solid arrow).

Remarks: The two control cases demonstrated similar findings at the morphologic and immunohistochemical level. Both contained a dense nodule of invasive carcinoma that was sharply demarcated from the surrounding normal stromal tissue without a discrete well-formed fibrous capsule. Within the tumor nodule, the carcinoma cells were arranged into small organized clusters and cords of tumor cells and these were closely packed together with a minimal amount of intervening stoma that contained compressed small blood vessels (FIG. 60—Slide A). The tumor cells were large with pleomorphic nuclei that had vesicular chromatin and prominent eosinophilic nucleoli that were clearly visible at 100× magnification (10× eyepiece and 10× objective lens). The nuclei included rounded and spindled forms and scattered multinucleated giant tumor cells were present (FIG. 60—Slide A). The tumor cells had an abundant amount of lightly eosinophilic and clear cytoplasm and they showed increased mitotic activity (13 mitoses per 10 high power fields [400× hpf]). Scattered discrete foci of coagulative tumor cell necrosis were present and these were more frequent within central portions of the tumor nodule (FIG. 60—Slide B). The foci of necrosis consisted of homogenous eosinophilic necrotic debris that was relatively well demarcated from surrounding viable tumor cells. The foci of necrosis occupied less than 5% of the tumor cell area. Immunohistochemical staining for pancytokeratin (AE1/AE3) highlighted the tumor cells and displayed cytoplasmic and membranous localization (FIG. 60—Slide D). The keratin labeling was strong, sensitive and specific, with sharp demarcation between positively stained tumor cells and negatively stained surrounding non-carcinomatous tissue. There was no overt tumor regression noted in either of the two control group animals. There was no significant lymphoid infiltrate within the tumor and in particular, there were no discrete small lymphoid collections or tertiary lymphoid structures (TLS) in the tumor tissue or in the surrounding non-neoplastic stromal tissue. The surrounding stroma contained a patchy mild lymphoid infiltrate composed of scattered small lymphocytes that were mainly arranged as single cells (FIG. 60—Slide C). Immunohistochemical staining for CD11b (marker of NK cells and histiocytes) highlighted the mild immune cell infiltrate in the surrounding non-neoplastic stroma (FIG. 60.—Slide F); however, there was no significant lymphoid component within the tumor. Immunohistochemical staining for CD68 (marker of macrophages) highlighted a mild macrophage infiltrate within and around the tumor with increased density of staining within the foci of tumor necrosis, consistent with increased macrophages in areas containing increased cellular debris (FIG. 60.—Slide E).

Observations: FIG. 61. Intratumoral NanoDoce® cases (representative images from all groups included: 1 cycle, 2 cycles and 3 cycles).

Top row: One cycle NanoDoce® (1×) (case 750-258). (A) Low power H&E staining showing extensive geographic tumor cell necrosis consisting of homogeneous eosinophilic staining of non-viable necrotic material (solid arrows). Note the central vertical line of demarcation consisting of a dense band of necrotic debris and admixed immunecells (dashed arrows) (B) High power view of line of demarcation. Note the dense collection of immune cells and admixed debris (dashed arrows at right). On the left of the image there is extensive necrotic material with no viable tumor cells (solid arrows) (C) High power view of the central portion of necrosis corresponding to the left half of image A. Solid arrows point to ghost outlines of necrotic tumor cells. The dashed arrow highlights a degenerating small blood vessel.

Second row: One cycle NanoDoce® (1×) (case 750-258). Each image corresponds to the H&E image above it. (D) CD11b immunostain of area seen in image A. This highlights the dense collection of immune cells in the central band of necrotic debris and immune cell infiltrate This stain also highlights immune cell response in the surrounding tissue at right but there is a lesser degree of inflammation in the central area of tumor necrosis at left. (E) Keratin stain showing the same area as seen in B. This shows complete absence of staining, thus adding strong immunohistochemical support for the interpretation of no residual viable carcinoma in this area. (F) Keratin stain from central area of necrosis shown in image C. This shows keratin labeling of degenerating keratin filaments in the necrotic ghost cell outlines (solid arrows) which supports the hypothesis that viable carcinoma subsequently underwent complete regression and necrosis; however, there are no residual viable tumor cells present in this area (lack of viable nuclei best appreciated in H&E image above).

Third row: Two cycles NanoDoce® (2×) (case 748-827). (G) H&E staining showing a 0.9 mm residual focus of viable carcinoma (solid arrow) surrounded by extensive necrotic material (dashed arrows). (H) Same focus of carcinoma at higher power showing viable tumor cells with retained nuclei (solid arrow). Note the progressive loss of viable tumor cells toward the lower left corner (dashed arrow) (I) Higher power of same focus illustrating the leading edge of the viable tumor (solid arrow) and the adjacent zone of tumor cell death. Here, remnants of tumor cells in progressive stages of cell death are evidenced by progressive loss of nuclei and loss of discrete cytoplasmic membrane outlines (dashed arrows).

Fourth row: Two cycles NanoDoce® (2×) (case 748-827). Each image corresponds to the H&E image above it. (J) Low power view of keratin stain with the focus of residual viable carcinoma in top left of image (solid arrow). Surrounding this focus is a lack of keratin staining (dashed arrows), exhibiting the extent of the necrotic material. (K) Higher power view of the same keratin-stained tumor showing viable nucleated carcinoma cells that label strongly with keratin antibody (solid arrow) and surrounding necrotic tissue that is negative for keratin staining (dashed arrow). (L) Keratin stain of the same area, illustrating progressive transition from viable nucleated keratin-positive carcinoma cells in top right (solid arrows) to tumor cells in varying stages of necrosis towards bottom left corner (dashed arrows). The latter include anuclear ghost outlines of tumor cells that show keratin labeling of residual degenerating tumor cell keratin intermediate filaments; however, these cells are non-viable. This supports the impression that the necrotic material surrounding the viable carcinoma previously contained viable carcinoma that subsequently died following therapy.

Fifth row: Three cycles NanoDoce®(3×) (case 748-822). (M) Low power H&E stained section showing dense amorphous necrosis on the right (solid arrow) that is demarcated from surrounding zone of degenerating fibrofatty tissue on the left by a band of necrotic debris and admixed immune cells (dashed arrow). (N) High power view of necrotic area showing no viable nucleated carcinoma cells (solid arrow). (O) Keratin stained section of same area in image N, showing complete absence of staining (solid arrow), thus further supporting an absence of residual carcinoma in this area following therapy.

Remarks:

Intratumoral NanoDoce® 1 cycle:

Two of the three animals in this group contained residual viable invasive carcinoma. When measured on the H/E stained slide this was significantly smaller in size (up to 5 mm in maximum cross-sectional dimension on the slide) compared to the control, IT vehicle and IV docetaxel groups (range of 9-15 mm with most of these being closer to 15 mm in maximum cross-sectional dimension on the slide). Where present, the morphology of the tumor cells in these two IT NanoDoce® cases was essentially identical to that seen in the above-mentioned non-IT docetaxel groups. Both IT NanoDoce® cases did not have sufficient a non-viable tumor or non-neoplastic stroma for evaluation of surrounding necrosis although one of these did have a focal peripheral rim of necrosis that occupied <5% of the submitted tissue. Similar to the control groups, there was only a mild immune cell infiltrate associated with these tumors in the surrounding non-neoplastic stromal tissue (where evaluable) and this was highlighted by a CD11b immunostain. No tertiary lymphoid structures (TLS) were noted in the sections examined. The third animal in this group showed no viable residual invasive carcinoma and extensive geographic tumor cell coagulative necrosis. Extensive areas of necrosis blended with surrounding stromal fibrous, fatty and skeletal muscle tissue. In areas there was a line of demarcation between the amorphous necrosis and adjacent degenerating fibrofatty tissue which this consisted of a dense band of necrotic debris and admixed immune cells (FIG. 61—Slide A and B). No diagnostic viable tumor cells were noted on H/E stained section examination (FIG. 61—Slide B); however, in the central portion of the amorphous necrotic material there was a small area where ghost outlines of nuclear necrotic tumor cells were noted (FIG. 61—Slide C). This was also highlighted on the keratin-stained section where the keratin antibody labeled degenerating keratin filaments in the necrotic cell outlines (FIG. 61—Slide F). In addition, very focally within the degenerating and necrotic fibrofatty tissue, the keratin stained section of this animal showed focal cytoplasmic labeling that appeared consistent with histiocytic engulfment of degenerating keratin intermediate filaments. Of importance, the keratin stain did not show discrete cytoplasmic membrane labeling of viable carcinoma cells and it did not show any cohesive collections of keratin-labeled diagnostic viable tumor cells. In some areas there were abundant granular blue material that coalesced into small homogenous structures focally that were suggestive of dystrophic calcification. This granular material was difficult to definitively identify, and the differential diagnosis included granular necrotic debris and calcium, degenerating skeletal muscle fibers and nanoparticles. Immunohistochemical staining for CD11b in the animal with complete tumor regression highlighted by a moderate macrophageinfiltrate in the non-neoplastic tissue and the CD11b stain also highlighted the zone of debris and admixed inflammation (FIG. 61—Slide D). Immunohistochemical staining for CD68 (marker of histiocytes) highlighted a moderate macrophage infiltrate. No TLSs were noted in any of the three animals.

Intratumoral NanoDoce® 2 cycles:

Two of the three animals (750-254 and 748-827) in this group contained residual viable invasive carcinoma. When measured on the H&E stained slide this was significantly smaller in size (3 mm and 0.9 mm in maximum cross-sectional dimension on the slide respectively) compared to the control, IT vehicle and IV docetaxel groups (range of 9-15 mm with most of these being closer to 15 mm in maximum cross-sectional dimension on the slide). In both IT NanoDoce® cases with residual carcinoma, there was extensive geographic tumor cell necrosis surrounding the small foci of residual viable invasive carcinoma (FIG. 61—Slides G, H and I). Higher power examination of H&E stained and keratin stained sections from the smaller of these residual tumors showed a progressive transition from viable carcinoma cells to necrotic carcinoma cells with the latter being identified by labeling of their residual degenerating keratin intermediate filaments with the pancytokeratin immunostain (FIG. 61—Slides I and L). In both animals with residual carcinoma, immunohistochemical staining for CD11b highlighted a moderate immune cell infiltrate in the necrotic tissue.

Immunohistochemical staining for CD68 (marker of histiocytes) highlighted a moderate macrophage infiltrate within the necrotic areas in both cases. The third case (748-826) in this group showed extensive geographic tumor cell coagulative necrosis with no residual viable invasive carcinoma noted on H&E or keratin-stained sections. Immunohistochemical staining for CD11b highlighted a patchy moderate immune cell infiltrate. Immunohistochemical staining for CD68 (marker of macrophages) highlighted a patchy moderate macrophage infiltrate. No TLSs were noted in any of the three animals.

Intratumoral NanoDoce® 3 cycles:

Both cases in this group (748-797 and 748-822) showed extensive geographic tumor cell coagulative necrosis with no residual viable invasive carcinoma noted on H&E or keratin-stained sections (FIG. 61—Slides M-O). Immunohistochemical staining for CD11b highlighted a moderate and marked immune cell infiltrate in the necrotic tissue in the two animals respectively. Immunohistochemical staining for CD68 (marker of histiocytes) highlighted a mild and marked macrophage infiltrate within the necrotic areas in these two cases, respectively. No TLSs were noted in either of these two animals.

Note: Animals in NanoDoce® treatment groups had tumors with white "calcified" areas, likely resulting from nanoparticle deposits that remained within the tumor.

Additional Observations: (No Figures)

IT NanoDoce® Vehicle Group: The two intratumoral vehicle cases demonstrated similar findings at the morphologic and immunohistochemical level and both essentially had an identical morphologic and immunohistochemical appearance to that seen in the control group.

IV Docetaxel: The two intratumoral IV docetaxel cases demonstrated similar findings at the morphologic and immunohistochemical level and both essentially had an identical morphologic and immunohistochemical appearance to that seen in the control and IT vehicle groups.

Tumor volume results for Paclitaxel Group and Docetaxel Group:

Animals were weighed, and tumor length and width were measured with digital calipers three times weekly for 58 days and at the time of necropsy. Tumor volume (V) was calculated as follows: $V(mm^3)=((L*W^2))/2$ where L is the largest diameter and W is the width (in mm) of the tumor. Study Log® was employed for statistical analysis of tumor volume and body weight.

Figure 62:
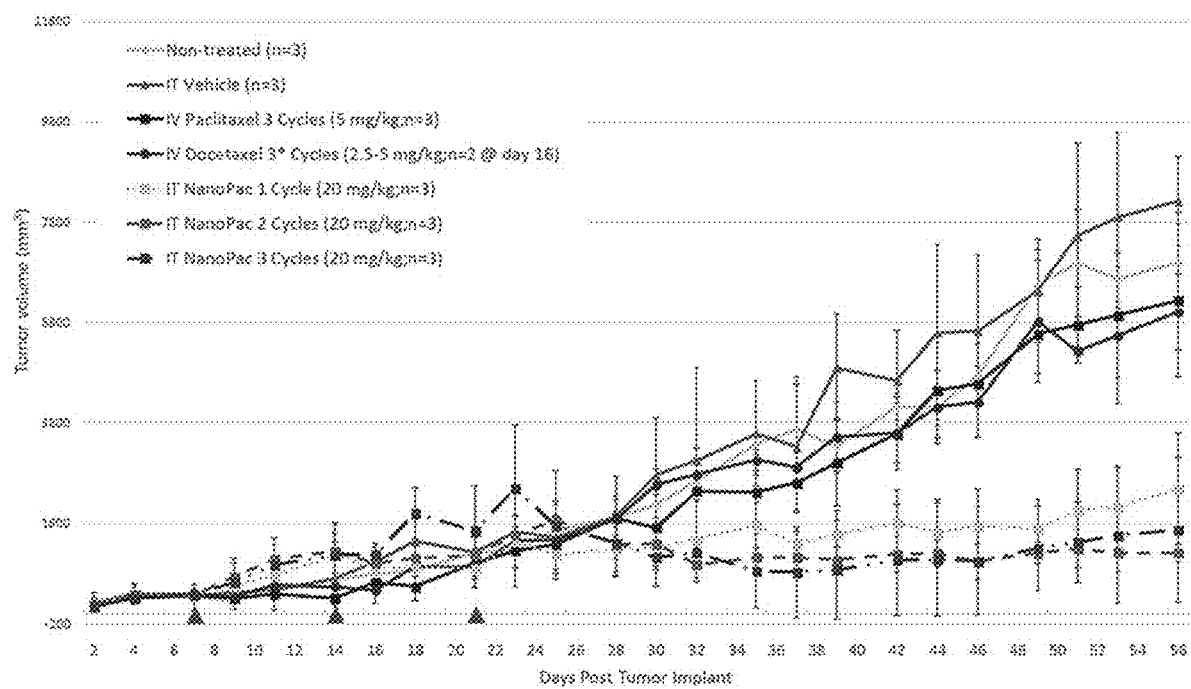
FIG. 62 is a graph of mean tumor volumes over time of rats in the NanoPac® groups from the renal cell adenocarcinoma xenograft study. The triangles on the x-axis represent the administration points.
Figure 63:
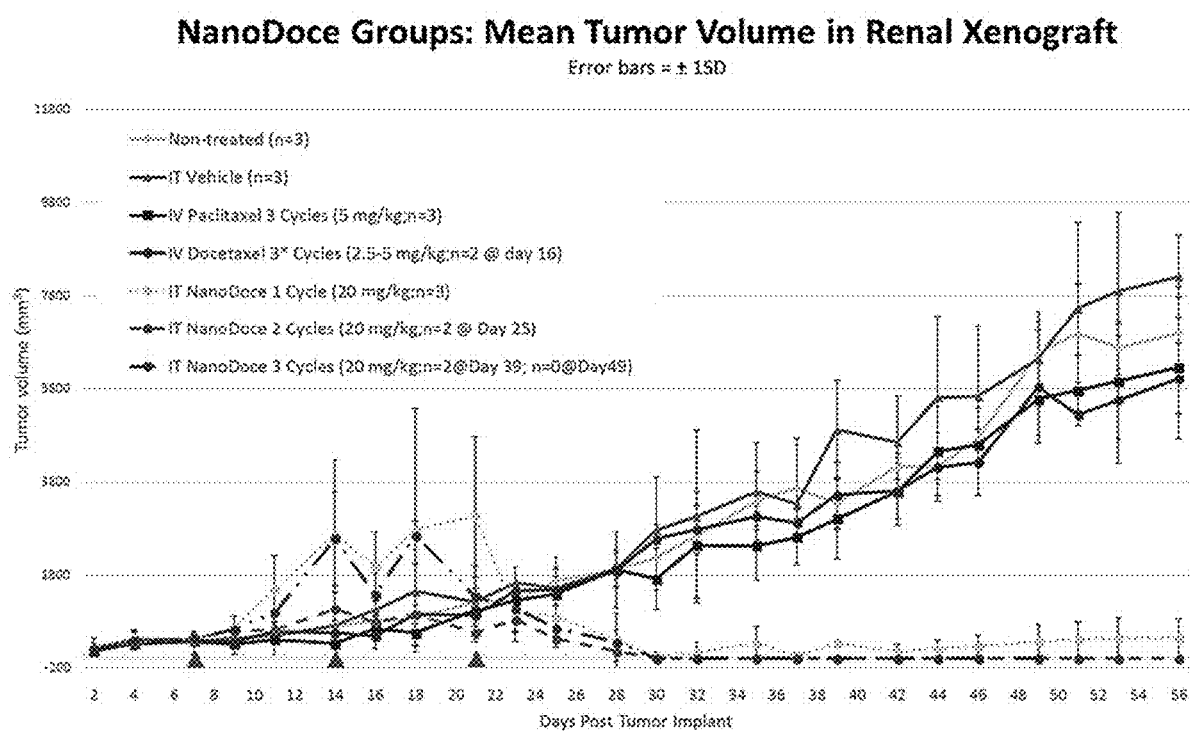
FIG. 63 is a graph of mean tumor volumes over time of rats in the NanoDoce® groups from the renal cell adenocarcinoma xenograft study. The triangles on the x-axis represent the administration points.

The mean tumor volume results for the Paclitaxel groups are shown in FIG. 62. Mean tumor volume results for the Docetaxel groups are shown in FIG. 63. As can be seen in the figures, IT NanoPac® and IT NanoDoce® both effectively treated the tumors.

Regarding the tumor volume results for the Docetaxel groups, the first measurable tumors for both males and females were observed at 2 days post-inoculation.

Non-treated and vehicle control-treated tumors continued to grow throughout treatment, with final volumes in female rats ranging from 5656 mm³ to less than 10,000 mm³. IV docetaxel treatment resulted in partial tumor growth inhibition compared to vehicle control.

NanoDoce® delivered IT was the most efficacious treatment compared to vehicle and all other treatments. In most animals, the tumors treated with one, two or three cycles of IT NanoDoce® appeared to have completely regressed with only necrotic tissue remaining at the original tumor site.

Upon necropsy, animals in NanoDoce® treatment groups had tumors with white "calcified" areas, likely resulting from nanoparticle deposits that remained within the tumor.

Docetaxel Group Results:

Docetaxel Concentration in Tissue: Tumor tissue concentrations of docetaxel were determined by LC-MS/MS analysis using its deuterated analogue docetaxel-$d_9$ as the internal standard. Using a method previously developed by Frontage, concentrations of docetaxel were obtained from calibration curves constructed by plotting the peak area ratios (analyte to internal standard) versus analyte concentration using linear regression with a weighting of $1/x^2$. The nominal concentration range was 1.00-2,000 ng/g for docetaxel in tumor tissue. A calibration curve, prepared in rat control tumor tissue homogenate, was analyzed at the beginning and the end of each analytical run. Two sets of quality control (QC) samples were prepared at four concentration levels (low, mid-1, mid-2 and high) and were used to ensure reliability of the assay.

Thirty-eight days following the last of three weekly cycles of IV docetaxel (5-2.5 mg/kg), one of four animals evaluated had a detectable (LOQ=1.00 ng/g) docetaxel level of 21.8 ng/g. All three animals in the NanoDoce® QWX1 group had detectable docetaxel levels ranging from 659 ng/g to 1.4× $10^5$ ng/g 51 days post-treatment. Two animals from the NanoDoce® QWX2 group were evaluated and had levels of 2.49 and 5.26 µg/g 44 days post-treatment. As there was no tumor available for analysis in the NanoDoce® QWX3 group, no analysis was performed.

Animals: Throughout the treatment period, animals across all groups displayed relatively normal weight gain compared to non-treated animals and vehicle control with a few exceptions. One animal that received NanoDoce® QWX1 had weight loss at treatment day 9. Despite supplementation she continued to lose weight and was subsequently euthanized on treatment day 16 due to reaching weight loss endpoints. One animal that received NanoDoce® QWX3 lost a significant amount of weight, reaching endpoints at treatment day 39 despite supplementation.

Other observations include ulceration and apparent peripheral neuropathy. All animals that received NanoDoce® exhibited ulcerations or lesions on the surface of the tumor. These lesions were described as "scabs", areas of dry, rigid tissue. In most cases the wounds remained intact. A single animal that received NanoDoce® QWX3 showed hindlimb weakness and limited mobility on day 35 post-treatment. With intervention, the weakness stabilized enough for the animal to remain in the study. However, the animal was euthanized on day 49 due to ulcerations that covered >50% of the tumor surface.

The ranges of sizes (the maximum cross-sectional dimension of the viable carcinoma as measured in millimeters on the slide) of the residual tumors in the six groups are shown in Table 27.

TABLE 27

| Group | # | No viable tumor | <1 mm | 1-5 mm | 6-10 mm | >10 mm |
|---|---|---|---|---|---|---|
| Control | 2 | | | | | 2 |
| IT vehicle | 2 | | | | 1 | 1 |
| IV docetaxel | 2 | | | | | 2 |
| IT NanoDoce ® 1 | 3 | 1 | | 2 | | |
| IT NanoDoce ® 2 | 3 | 1 | 1 | 1 | | |
| IT NanoDoce ® 3 | 2 | 2 | | | | |

A condensation of the data in Table 27 which directly compares the size of the residual carcinoma nodules in the three non-NanoDoce® groups (6 animals in total) with the three NanoDoce® groups (8 animals in total) is shown in Table 28.

TABLE 28

| Groups | # | No viable tumor | <1 mm | 1-5 mm | 6-10 mm | >10 mm |
|---|---|---|---|---|---|---|
| non-NanoDoce ® | 6 | | | | 1 | 5 |
| IT NanoDoce ® | 8 | 4 | 1 | 3 | | |

Five of the six non-NanoDoce® animals, including both IV docetaxel animals, had residual viable carcinoma nodules that measured greater than 10 mm, and most of these were closer to 15 mm. The remaining non-NanoDoce® animal had viable carcinoma measuring 9 mm in maximum dimension. By contrast, half (4/8) of the animals treated with IT NanoDoce® had no residual viable carcinoma on the slide to measure. All the remaining 4 animals in the IT NanoDoce® group that had residual viable carcinoma had a viable carcinoma nodule that measured 5 mm or less in maximum dimension on the slide. This included one case where the tumor measured 0.9 mm, and this was not evident when the tumor was measured grossly prior to microscopic examination.

A comparison of the three IT NanoDoce® groups with respect to percentage of cases with no residual invasive carcinoma and the size of residual viable carcinoma nodules is shown in Table 29.

TABLE 29

| Groups | # | No viable tumor | <1 mm | 1-5 mm | Size of viable nodules (mm) | % of cases with no residual carcinoma |
|---|---|---|---|---|---|---|
| IT Nano 1 | 3 | 1 | | 2 | 4, 5 | 33% |
| IT Nano 2 | 3 | 1 | 1 | 1 | 0.9, 3 | 33% |
| IT Nano 3 | 2 | 2 | | | N/A | 100% |

IT NanoDoce® 1 and 2 cycle groups both had 1/3 of cases with no residual viable carcinoma while the IT NanoDoce® 3 cycle group had 2/2 of cases with no residual viable invasive carcinoma. Amongst the cases with residual viable carcinoma, progressive increase in the number of cycles of IT NanoDoce® was associated with a decrease in the size of the residual viable carcinoma nodule. Specifically, the residual viable carcinoma nodule measured 4 mm and 5 mm in the IT NanoDoce® 1 cycle group and in the IT NanoDoce® 2 cycle group the nodules measured 0.9 mm and 3 mm. There was no residual viable carcinoma to measure in the two cases in the IT NanoDoce® 3 cycle group.

A percentage of tissue showing necrosis is shown in Table 30.

TABLE 30

| Groups | # | 100% | >90% | 50-90% | 5-50% | <5% |
|---|---|---|---|---|---|---|
| Control | 2 | | | | | 2 |
| IT vehicle | 2 | | | | | 2 |
| IV Doce | 2 | | | | | 2 |
| IT Nano 1 | 3 | 1 | | | | 2* |
| IT Nano 2 | 3 | 1 | 1 | 1 | | |
| IT Nano 3 | 2 | 2 | | | | |

All six animals in the non-NanoDoce® group showed <5% necrosis. This consisted of focal small discrete foci of necrosis in the tumor that were small, occupying <5% of the tumor area, and they were within central portions of the tumor nodule, suggesting that these may be secondary to hypoxemia due to tumor outgrowing its blood supply. Four of the eight NanoDoce® animals showed complete necrosis of tumor. Two of the four NanoDoce® animals with residual carcinoma showed extensive necrosis in the surrounding tissue (>50% of tissue). *The two remaining NanoDoce® animals with residual carcinoma did not have sufficient surrounding tissue for definitive assessment of necrosis although one of these did contain a focal rim of necrosis that represented <5% of the submitted tissue area.

The lymphohistiocytic infiltrate density based on assessment of H/E and immunohistochemical staining with CD11b, graded semi quantitatively is shown in Table 31.

TABLE 31

| Groups | # | Mild | Moderate | Marked |
|---|---|---|---|---|
| Control | 2 | 2 | | |
| IT vehicle | 2 | 2 | | |
| IV Doce | 2 | 2 | | |
| IT Nano 1 | 3 | 2 | 1 | |
| IT Nano 2 | 3 | | 3 | |
| IT Nano 3 | 2 | | 1 | 1 |

All six animals in the non-NanoDoce® groups contained a mild immune cell infiltrate and this was present in the peritumoral non-neoplastic stroma without any significant immune cell infiltrate within the tumor. By contrast, 7 of the 8 animals in the NanoDoce® groups contained a moderate immune cell infiltrate while the remaining animal had a marked immune cell infiltrate. This correlated with the increased amount of necrosis in the IT NanoDoce®-treated animals.

Discussion of Docetaxel Group Results:

A review was conducted on the morphologic and immunohistochemical features of a subset of 14 female rats from the renal cell carcinoma study aimed to assess the efficacy of intratumoral NanoDoce® (the total study contained 30 animals). The current subset of 14 animals included two control animals, two animals given intratumoral vehicle, two animals treated with intravenous docetaxel (3 cycles) and eight animals treated with intratumoral NanoDoce®. The NanoDoce® group was separated into three groups based on the number of administered cycles: group 1 (1 cycle; 3 animals), group 2 (2 cycles; 3 animals), and group 3 (3 cycles; 2 animals).

The main feature that differed amongst the various groups was the presence and degree of tumor regression. In all animals in the intratumoral NanoDoce® groups, tumor regression was prominent, while in all animals in the other groups, tumor regression was absent.

All six animals in the non-NanoDoce® group (i.e. control, IT vehicle and IV docetaxel groups) had residual viable tumor. This consisted of a dense nodule of invasive carcinoma that was sharply demarcated from the surrounding normal stromal tissue. The carcinoma cells were closely packed together and while there were scattered discrete foci of coagulative tumor cell necrosis present, these were small in size, overall occupied <5% of the tumor area in each of the six animals, and were within central portions of the tumor nodule. These observations suggest that these areas of necrosis may be secondary to hypoxemia due to tumor outgrowing its blood supply (Table 10). Keratin staining showed strong, sensitive and specific staining of tumor cells. The maximum dimension of the viable tumor nodule, as measured on the stained slides, ranged from 9-15 mm in these six animals and in many this was closer to 15 mm (Tables 27 and 28). This tumor size on the slide corresponded to the tumor measurement taken at the time of gross dissection.

By contrast, four of the eight animals treated with intratumoral NanoDoce® had no residual viable carcinoma as determined by assessment of H&E and keratin-stained sections (complete response). Of the remaining four animals, the residual viable tumor, as measured on the stained slide, was markedly smaller than that seen in the non-NanoDoce® group (Tables 27 and 28). Specifically, the size of the residual viable tumor nodules in these four animals treated with IT NanoDoce® ranged from 0.9 mm to 5 mm in maximum dimension (Table 29). In three of these animals, the tumor size measured on the slide correlated with the tumor size measurement taken at the time of gross dissection. In the remaining animal with a 0.9 mm focus of invasive carcinoma, this was present amongst extensive necrosis and was not evident at the time of gross dissection.

In six of the eight NanoDoce® animals, there was extensive tumor cell coagulative necrosis that extended into adjacent necrotic skeletal muscle and fibrous tissue in some animals. In addition, focally within the necrotic areas there was keratin-staining of necrotic, non-viable, ghost tumor cell outlines, consistent with labelling of degenerating keratin intermediate filaments from dead tumor cells. This further supported that these areas previously contained viable carcinoma that had completely responded to therapy. In the slides from the two remaining animals there was very limited surrounding tissue for assessment of necrosis although one of these did contain a focal peripheral rim of necrosis in one area.

Within the non-NanoDoce® group there was a uniformly mild immune cell infiltrate, and this was seen primarily in the non-neoplastic tissue surrounding the tumor. There was no significant intratumoral immune cell infiltrate. By contrast, the intratumoral NanoDoce® group included two cases with a mild immune cell infiltrate, five cases with a moderate immune cell infiltrate and a single case with a marked immune cell infiltrate within the necrotic areas (Table 31). Like the non-NanoDoce® group, there was no significant intratumoral lymphoid infiltration. There were no diagnostic tertiary lymphoid structures (TLSs) seen in any of the 14 animals in this study group.

In summary, this review was limited to 14 female animals out of a study that contained 30 female animals; however, a striking difference in the type and degree of tumor response to therapy was noted when the intratumoral NanoDoce® group was compared to the non-NanoDoce® groups. None of the six non-NanoDoce® group animals showed any overt evidence of tumor regression and all had residual viable carcinoma nodules that ranged in size from 9-15 mm as measured on the slide. However, all eight animals in the intratumoral NanoDoce® group showed evidence of tumor response and extensive necrosis was noted in all six of the animals that had sufficient surrounding tissue for assessment. The tumor response included compete regression in half of this group (4/8), as demonstrated by lack of definitive residual viable carcinoma on examination of H&E and keratin-stained sections, while the remaining four animals contained a focal small residual viable carcinoma nodule, the largest of which measured 5 mm and the smallest of which measured 0.9 mm. In two of these four animals with residual carcinoma, there was sufficient surrounding tissue present on the slides for assessment and this showed extensive necrosis. Similarly, the degree of immune cell infiltrate in the non-NanoDoce® group was mild while it ranged from mild to marked in the NanoDoce® group suggesting an association with the degree of tumor response and resultant necrotic debris.

When the three IT NanoDoce® groups were compared with each other, it was noted that as the animals received increasing cycles of intratumoral NanoDoce® therapy they showed a greater degree of tumor response. In particular, of the 3 animals in the group receiving 1 cycle of IT NanoDoce®, one of three animals showed complete response while the remaining two animals had residual nodules measuring 4 and 5 mm. Of the three animals in the group receiving 2 cycles of IT NanoDoce®, one showed complete response while the remaining two animals had residual nodules measuring 0.9 and 3 mm. Finally, both animals in the group receiving 3 cycles of IT NanoDoce® showed complete response to therapy (two of two evaluated) (Table 29).

In conclusion, all eight animals with renal cell carcinoma in this study that were treated with intratumoral NanoDoce® exhibited a notable histological response which included a 50% rate of complete tumor regression as well as a marked decrease in residual tumor size in the remaining four animals. Associated extensive necrosis and increased immune response was noted in the NanoDoce® groups and focal areas of keratin-labelling of anuclear, non-viable, ghost tumor cell outlines in the necrotic areas further supported that these areas previously contained viable carcinoma that had completely responded to therapy. By contrast, there was no such tumor regression in the non-NanoDoce®-treated groups. Furthermore, increasing cycles of intratumoral NanoDoce® from 1 to 3 cycles resulted in a progressively greater degree of tumor regression and a progressively higher rate of complete regression within the IT NanoDoce® cohort.

Example 16—Combination Therapy Study—Phase II Study of the Pre-Treatment of Subjects with Recurrent or Metastatic Non-Small Cell Lung Cancer with Inhaled NanoPac® Prior to Treatment with Pembrolizumab Summary In this Phase II study, subjects with recurrent or metastatic non-small cell lung cancer scheduled for treatment by immunotherapy drug pembrolizumab will receive NanoPac® inhalation therapy via nebulizer 2 days prior to receiving pembrolizumab treatment.

This study will consist of two cohorts, 1) pembrolizumab monotherapy, and 2) inhaled NanoPac® prior to treatment with pembrolizumab combination therapy.

Pembrolizumab monotherapy will be administered via IV at 74 mg/m2 over 30 minutes every 3 weeks, Inhaled NanoPac® at a concentration of 7.08 mg/m2 will be administered using a jet nebulizer two days prior to pembrolizumab therapy.

Description of Study Agent:
  Test Article: The test article used for inhalation exposure is shown below:
NanoPac®:
  Identity: NanoPac® (sterile nanoparticulate Paclitaxel)
  Description: Novel dry powder formulation of Paclitaxel delivered as 306 mg/vial Vehicle The vehicles used for preparation of NanoPac® formulations are shown below:

1% Polysorbate 80 Solution

Identity: Sterile 1% Polysorbate 80 in 0.9% sodium chloride for injection

Description: Clear liquid

Normal Saline Diluent

Identity: Sterile 0.9% sodium chloride for injection, USP

Description: Clear liquid

The test article, NanoPac® (paclitaxel particles, vehicle and diluent), will be prepared for inhalation into the lung at a concentration of 5 mg/kg.

Population

Men and women ≥18 years of age with an ECOG performance status of 0 or 1

Histologically confirmed recurrent or metastatic NSCLC that has either progressed during or after platinum based chemotherapy.

Received at least 1 platinum based chemotherapy regimen.

Primary Objective

Determine overall response rate (ORR) by independent review and integrated medical oncologist disease assessment based on Response Evaluation Criteria in non-small cell tumors (RECIST) v.1.1 of pembrolizumab monotherapy and the combination of NanoPac® and pembrolizumab in subjects with recurrent or metastatic non-small cell lung cancer.

Secondary Objectives

Estimation of duration of response, estimation of progression-free survival (PFS) and overall survival (OS).

Determination of best overall response and response rate per immune-mediated response criteria (irRC) by investigators and by an independent review committee.

Results of the study will demonstrate that the combination therapy will have greater efficacy than the systemic immunotherapeutic agent therapy alone (monotherapy) as evidenced by the overall response rate, progression-free survival and overall survival.

Example 16—Intratumoral Injection of Paclitaxel Particles in Glioblastomas in Mice Brains In this study, the efficacy of paclitaxel particles against glioblastomas (GB) was assessed. Nude mouse brains were injected with GB cells to establish primary tumors, which were injected after two weeks with paclitaxel particles (Nanotax). We monitored survival benefit against a control group that received only saline injections and a control group that has received Taxol™ (formulated in cremophor) injections. We delivered a dose of 100 mg/m2 to the growing tumor by direct injection. Table 32 below shows four different tumor sizes and the corresponding dose of paclitaxel particles of the invention, assuming a spherical shape for the tumor. As a control experiment Taxol™ formulated in cremophor and diluted in saline to the correct concentration was used.

TABLE 32

| Tumor Radius (mm) | Tumor Surface (mm$^2$) | ng of Nanotax per injection* | Dilution Factor ** |
|---|---|---|---|
| 0.5 | 3.1 | 314.2 | 50 |
| 1 | 12.6 | 1256.6 | 13 |
| 1.5 | 28.3 | 2827.4 | 6 |
| 2 | 50.3 | 5026.5 | 3 |

*at a dose of 100 mg/m$^2$
** 5 µl injection; Nanotax stock solution: 3,150 ng/µl At the highest dose of 5 µg of Paclitaxel per injection no toxicity was observed.

Injected mice were kept alive for 8 to 9 days, after which no neurological symptoms were observed. After 9 days, the mice were sacrificed and the brains harvested; the brains were dissected along the injection path and analyzed. Neither the paclitaxel particle group nor the Taxol™ group showed necrosis or lesions. Brain slices were used without further preparation to be analyzed with three different imaging technologies to create a composite image (data not shown):

(a) 2nd harmonic generation (SHG): Images appear in blue, mostly collagen and vessels and paclitaxel particles.

(b) Two-photon excitation fluorescence (TPEF): Images appear in green, mostly reactive cells, microglia, macrophages, some neuronal bodies.

(c) Coherent Anti-Stokes Raman Scattering (CARS): Images appear in red, tuned to —CH2 vibrations to look at lipids—mostly to myelin in the CNS, but also lipid droplet containing cells called foam cells will give a positive signal. Degenerating cells and macrophages with lipid vacuoles will also show up.

Due to the non-linear optical properties of the paclitaxel particle crystals, the crystals can be seen directly with the second harmonic generation imaging technology. Clusters of paclitaxel particles were clearly visible at the injection site (i.e.: accumulated within the tumor) 9 days after injection in a mouse that was injected with 5 µg of paclitaxel particles and showed no neurological symptoms (data not shown).

Example 17—Pharmacokinetics and Tissue Distribution of Paclitaxel Particles Following Intraperitoneal Injection in Mice Purpose: This study was conducted to determine the level of absorption of paclitaxel from the peritoneal cavity into the systemic circulation following intraperitoneal delivery of a paclitaxel particle suspension. Tissue distribution of paclitaxel from the paclitaxel particle suspension following intraperitoneal administration was also evaluated.

Experimental Details: Female C57BL6 mice were inoculated with ID8 ovarian cancer cells and tumors were allowed to grow for 45 days. These mice were treated with paclitaxel particle suspension (36 mg/kg) in 0.9% saline via intraperitoneal administration in a total volume of 4 mL. Plasma and peritoneal fluid samples were collected at Time zero (pre-dose), 1, 6, 24 and 48 hours (at least four mice per time point) and paclitaxel in the plasma and peritoneal fluid was measured by LC-MS/MS. In addition, tissue samples were collected at Time zero (pre-dose), 1, 6, 24 and 48 hours post intraperitoneal administration of paclitaxel particles. Inguinal lymph nodes, peritoneal wall, ovary, liver, heart, lung, brain and tumor tissue samples from mice administered paclitaxel particles were analyzed by LC-MS/MS.

Results and Significance: The results of the paclitaxel levels in the plasma, peritoneal fluid and organ tissue samples are shown in the following table. Plasma paclitaxel remained at a very low level over the 48-hour period. The paclitaxel levels in the peritoneal fluid were much higher and demonstrated a substantial amount of variation. The limit of quantitation of the analytical method for paclitaxel was 0.01 μg/gm. The levels of paclitaxel in tissues inside the peritoneal cavity were consistently high as demonstrated by the results for the ovarian tumors, ovary, inguinal lymph nodes and peritoneal membrane. In contrast, the paclitaxel levels in tissues outside the peritoneal cavity were consistently lower as shown in the liver, heart, lung and brain tissues. These same results are shown in Table 33.

This data is significant because of the unexpectedly high levels of paclitaxel in the tissues that are in contact with the peritoneal fluid (ovarian tumors, ovary, inguinal lymph nodes and peritoneal membrane), and little paclitaxel to tissues not in contact with the peritoneal fluid. Based on these and other studies, the release of paclitaxel from the paclitaxel particles continues for several weeks and would be expected to provide a continuously high amount of paclitaxel, which would mean that the paclitaxel would accumulate in very high levels if injected directly into the tumor.

TABLE 33

Summary Levels of Paclitaxel in chemotherapeutic particles-treated Mouse Tissue, Plasma and Peritoneal Fluid (values in μg/g) (4 animals)

| Time (hours) | Tumor (μg/g) | Ovary (μg/g) | Lymph (μg/g) | Membrane (μg/g) | Liver (μg/g) | Heart (μg/g) | Plasma (μg/ml) | IP Fluid (μg/ml) | Lung (μg/g) | Brain (μg/g) |
|---|---|---|---|---|---|---|---|---|---|---|
| 0 | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
| 1 | 458.6 | 500.00 | 190.80 | 107.23 | 7.0 | 0 | 0.5 | 49.0 | 1.97 | 0.04 |
|   | 180.1 | 263.64 | 199.28 | 31.42 | 6.7 | 0 | 0.0 | 1.0 | BQL | 0.13 |
|   | 135.3 | 498.00 | 122.90 | 9.38 | 3.1 | 0 | 0.0 | 0.7 | 2.78 | BQL |
|   | 158.1 | 1193.75 | 296.36 | 133.47 | 9 | 0 | 0.2 | 24.6 | 0.78 | 0.36 |
| 6 | 126.2 | 1068.97 | 486.87 | 64.8 | 48.8 | 0 | 0.0 | 1.2 | 1.18 | 0.11 |
|   | 240.0 | 816.33 | 648.15 | 91.38 | 46.6 | 0 | 0.4 | 40.4 | 1.65 | BQL |
|   | 701.2 | 751.05 | 48.86 | 132.35 | 27.0 | 0 | 0.0 | 1.8 | 0.75 | BQL |
|   | 89.7 | 211.20 | 143.33 | 97.41 | 14.3 | 0 | 0.0 | 4.2 | 1.56 | 0.08 |
| 24 | 81.3 | 502.70 | 90.14 | 27.09 | 41.3 | 0 | 0.0 | 1.5 | 5.22 | 0.29 |
|   | 204.5 | 1706.42 | 86.83 | 65.31 | 41.9 | 2.77 | 0.2 | 24.0 | 0.92 | 0.08 |
|   | 241.2 | 335.58 | 238.64 | 109.96 | 50.3 | 0 | 0.0 | 5.1 | 0.83 | 1.36 |
|   | 208.8 | 603.64 | 254.00 | 124.41 | 29.7 | 3 | BQ | BQ | 1.10 | 0.82 |
| 48 | 294.0 | 529.94 | 124.17 | 270.95 | 116.4 | 0 | 0.1 | 12.0 | BQL | 0.05 |
|   | 400 | 1389.83 | 1795.45 | 79.5 | 44.2 | 0 | 0.0 | 1.5 | BQL | 0.06 |
|   | 505.4 | 711.48 | 81.94 | 80.33 | 76.6 | 0 | 0.0 | 5.2 | BQL | 0.18 |
|   | 174.9 | 1272.11 | 224.88 | 218.24 | 34.0 | 0 | 0.2 | 28.6 | BQL | BQL |

Example 18—Pilot Toxicity and Efficacy Testing of NanoPac® in Combination with Pembrolizumab Staggered Dosing in Hu-CD34-NSG™-SGM3 Bearing TM00302

Project Summary: Female hu-CD34 NSG™ SGM3 mice (NOD.Cg-Prkdescid Il2rgtm1Wjl Tg(CMV-IL3,CSF2, KITLG)1Eav/MloySzJ) that have been engrafted with human CD34+ cells and have >25% human CD45+ cells in the peripheral blood 10 weeks post engraftment or later will be used for the study. Cohorts of hu-CD34 NSG™ SGM3 mice engrafted with CD34+ cells from two or three donors (depending on the phase below) will be used. The mice will be car notched for identification and housed in individually and ventilated polysulfone cages with HEPA filtered air at a density of up to 5 mice per cage. Cages will be changed every two weeks. The animal room is lighted entirely with artificial fluorescent lighting, with a controlled 12 h light/dark cycle (6 am to 6 pm light). The normal temperature and relative humidity ranges in the animal rooms are 20-26° C. and 30-70%, respectively. The animal rooms will be set to have up to 15 air exchanges per hour. Filtered tap water, acidified to a pH of 2.5 to 3.0, and standard lab chow will be provided ad libitum.

1. hu-CD34 NSG™ mice from one CD34 donor will be implanted subcutaneously in the right flank with tumor fragments from the TM00302 PDX model.
2. Body weights and clinical observations will be recorded 1× to 2× weekly.

3. Digital caliper measurements will be initiated to determine tumor volume 1× to 2× weekly when tumors become palpable.
4. Mice will be randomized based on tumor volumes according to Table 34 when the tumor volumes reach ~100-200 mm3 (Study Day −1 or Study Day 0).
5. Mice will be dosed according to Table 34 starting on Study Day 0.

Note: IT injections will be performed by fan technique. The fan injection technique will consist of 2-5 compound deposition sites from a single epidermal puncture. The amount of compound deposition sites will be dictated by the size of the tumor. Tumors 100-200 mm$^3$ will receive 2 depositions, 200-400 will receive 3, 400-600 will receive 4, and 600+ will receive 5.

6. Body weights, clinical observations and digital caliper measurements will be recorded 2× weekly post dose initiation.
7. Animals that reach a body condition score of ≤2, a body weight loss of ≥20% or a tumor volume >2000 mm$^3$ will be euthanized before study terminus. Animals with ulcerated tumors will also be euthanized before study terminus.

Note: Tissues will not be collected from animals that are found dead.

8. On Study Day 35, all animals will be euthanized by $CO_2$ asphyxiation and tissues collected. Tumors will be collected and sent for flow cytometry characterization.

TABLE 34

Tumor Growth Curves

| Group | N* | Compound | Dose (mg/kg) | Dosing Route# | Dosing Frequency |
|---|---|---|---|---|---|
| 1 | 5 | Vehicle | NA | IT | 1x/wk for 3 wks starting SD0 |
|   |   | Vehicle | NA | IV | BIWx4 starting SD0 |
| 2 | 5 | NanoPac ® | 30 | IT | 1x/wk for 3 wks starting SD0 |
|   |   | Pembrolizumab | 5 | IV | BIWx4 starting SD0 |
| 3 | 5 | NanoPac ® | 30 | IT | 1x/wk for 3 wks starting SD0 |
|   |   | Pembrolizumab | 5 | IV | BIWx4 starting SD3 |

Study Includes

| # Mice | Mouse Type/ID | PDX Models | Study Duration | Data Collection | Tissue Collection |
|---|---|---|---|---|---|
| 15 | Hu-CD34__SGM3 013062 | TM00302 | 5 Weeks | Caliper Measurements, Body weight and Clinical Obs. 2x/wk | 15 Tumors (Fresh in media) 15 Whole Blood terminal (Fresh in media) |

*1 donor will be used.
IT injections will not exceed 50 ul.

Results will demonstrate that treatment with the combination of NanoPac® and Pembrolizumab will have greater efficacy than the treatment with vehicle as evidenced by:

(a) greater reduction of tumor size with the animals treated with the combination of NanoPac® and Pembrolizumab than with the animals treated with vehicle, or
(b) greater reduction in tumor growth with the animals treated with the combination of NanoPac® and Pembrolizumab than with the animals treated with vehicle, or
(c) one or more incidences of tumor elimination with the animals treated with the combination of NanoPac® and Pembrolizumab versus no incidences of tumor elimination with the animals treated with vehicle.

Example 19—Growth Curve Analysis of PDX Model TM00176 Followed by Efficacy Testing of NanoPac® Alone and in Combination with Pembrolizumab in Hu-CD34-NSG™-SGM3

Project Summary:
The study will be broken into 2 phases.
Phase 1: Preliminary drug toxicity and efficacy of staggered dosing in hu-SGM3 mice bearing TM00302. (n=10)
Phase 2: Efficacy study in Hu-CD34-NSG™-SGM3 mice (n=100)

Female hu-CD34 NSG™ SGM3 mice (NOD.Cg-Prkdcscid Il2rgtm 1 Wjl Tg(CMV-IL3,CSF2,KITLG)1Eav/MloySzJ) that have been engrafted with human CD34+ cells and have >25% human CD45+ cells in the peripheral blood 10 weeks post engraftment or later will be used for the study. Cohorts of hu-CD34 NSG™ SGM3 mice engrafted with CD34+ cells from two or three donors (depending on the phase below) will be used.

The mice will be ear notched for identification and housed in individually and ventilated polysulfone cages with HEPA filtered air at a density of up to 5 mice per cage. Cages will be changed every two weeks. The animal room is lighted entirely with artificial fluorescent lighting, with a controlled 12 h light/dark cycle (6 am to 6 pm light). The normal temperature and relative humidity ranges in the animal rooms are 20-26° C. and 30-70%, respectively. The animal rooms will be set to have up to 15 air exchanges per hour. Filtered tap water, acidified to a pH of 2.5 to 3.0, and standard lab chow will be provided ad libitum.

Phase 1:
1. hu-CD34 NSG™ mice from one CD34 donor will be implanted subcutaneously in the right flank with tumor fragments from the TM00302 PDX model.
2. Body weights and clinical observations will be recorded 1× to 2× weekly.
3. Digital caliper measurements will be initiated to determine tumor volume 1× to 2× weekly when tumors become palpable.
4. Mice will be randomized based on tumor volumes according to Table 35 when the tumor volumes reach ~100-200 mm3 (Study Day −1 or Study Day 0).
5. Mice will be dosed according to Table 35 starting on Study Day 0.

Note: IT injections will be performed by fan technique. The fan injection technique will consist of 2-5 compound deposition sites from a single epidermal puncture. The amount of compound deposition sites will be dictated by the size of the tumor. Tumors 100-200 mm3 will receive 2 depositions, 200-400 will receive 3, 400-600 will receive 4, and 600+ will receive 5.

6. Body weights, clinical observations and digital caliper measurements will be recorded 2× weekly post dose initiation.
7. Animals that reach a body condition score of ≤2, a body weight loss of ≥20% or a tumor volume >2000 mm3 will be euthanized before study terminus. Animals with ulcerated tumors will also be euthanized before study terminus.

Note: Tissues will not be collected from animals that are found dead.

8. On Study Day 35, all animals will be euthanized by CO2 asphyxiation and tissues collected.

Tumors will be collected and separated into fragments. 1 fragment will be fixed in 10% neutral buffered formalin (NBF) and sent for paraffin embedding (FFPE). FFPE blocks will be shipped to the Sponsor or third party as requested. 1 fragment will be flash frozen and shipped to the Sponsor or third party as requested.

TABLE 35

Tumor Growth Curves

| Group | N* | Compound | Dose (mg/kg) | Dosing Route# | Dosing Frequency |
|---|---|---|---|---|---|
| 1 | 5 | NanoPac ® | 30 | IT | 1×/wk for 3 wks starting SD0 |
|  |  | Pembrolizumab | 5 | IV | BIWx4 starting SD0 |
| 2 | 5 | NanoPac ® | 30 | IT | 1×/wk for 3 wks starting SD0 |
|  |  | Pembrolizumab | 5 | IV | BIWx4 starting SD3 |

Study Includes

| # Mice | Mouse Type/ID | PDX Models | Study Duration | Data Collection | Tissue Collection |
|---|---|---|---|---|---|
| 10 | Hu-CD34_SGM3 013062 | TM00302 | 5 Weeks | Caliper Measurements, Body weight and Clinical Obs. 2x/wk | 10 Tumors (FACS) 10 Whole Blood terminal (FACS) |

*1 donor will be used.
IT injections will not exceed 50 ul.

Phase 2:
1. hu-CD34 NSG™ mice from three CD34 donors will be implanted subcutaneously in the right flank with tumor fragments from a PDX model to be determined.
2. Body weights and clinical observations will be recorded 1× to 2× weekly.
3. Digital caliper measurements will be initiated to determine tumor volume 1× to 2× weekly when tumors become palpable.
4. Mice will be randomized based on tumor volumes according to Table 36 when the tumor volumes reach ~100-200 mm3 (Study Day −1 or Study Day 0). In addition, efforts will be made to distribute hu-CD34 NSG™ SGM3 mice from different donors evenly across study groups. Each group may be enrolled multiple times to reach the desired group size.
5. Mice will be dosed according to Table 36 starting on Study Day 0.
6. Note: IT injections will be performed by fan technique. The fan injection technique will consist of 2-5 compound deposition sites from a single epidermal puncture. The amount of compound deposition sites will be dictated by the size of the tumor. Tumors 100-200 mm3 will receive 2 depositions, 200-400 will receive 3, 400-600 will receive 4, and 600+ will receive 5.
7. Body weights, clinical observations and digital caliper measurements will be recorded 3× weekly post dose initiation.
8. Animals that reach a body condition score of ≤2, a body weight loss of ≥20% or a tumor volume >2000 mm3 will be euthanized before study terminus. Animals with ulcerated tumors will also be euthanized before study terminus.

Note: Tissues will not be collected from animals that are found dead.

9. On Study Day 41 or 42, pictures will be taken of each tumor.
10. On Study Day 42, all animals will be euthanized by CO2 asphyxiation and tissues collected.

Tumors will be collected, weighted, and separated into fragments.
1 fragment will be placed in media and shipped to Flow Contract Site Laboratory (FCS) for flow cytometry analysis. The following markers will be examined: CD45, CD3, CD4, CD8, 7AAD.
1 fragment will be fixed in 10% neutral buffered formalin (NBF) and sent for paraffin embedding (FFPE). FFPE blocks will be shipped to the Sponsor or third party as requested.
1 fragment will be flash frozen and shipped to the Sponsor or third party as requested.
Note: If the tumor is too small to cut into two pieces (≤400 mm3), the single piece of tumor will be processed according to the Sponsor's direction.
Note: in the case that mice must come down on a Friday, Saturday or Sunday the samples cannot be processed for flow cytometry and will instead be split into 2 fragments, one for FFPE and the other flash frozen.
Whole blood will be collected at the end of study.
~100 μL whole blood will be shipped to Flow Contract Site Laboratory (FCS) for flow cytometry analysis. The following markers will be examined: CD45, CD3, CD4, CD8, 7AAD The remaining blood will be processed to serum, flash frozen, and shipped to the Sponsor or third party as requested.
Note: in the case that mice must come down on a Friday, Saturday or Sunday the samples cannot be processed for flow cytometry and entire samples will be processed to serum, flash frozen, and shipped to the Sponsor or third party as requested.

TABLE 36

Efficacy Experiment Design

| Group | N* | Compound# | Dose (mg/kg) | Dosing Route** | Dosing Frequency |
|---|---|---|---|---|---|
| 1 | 25 | N/A Vehicle Control | N/A | IT | 1×/wk for 3 wks |
|   |   | N/A Vehicle Control | N/A | IV | BIW×4 |
| 2 | 25 | Pembrolizumab | 5 | IV | 1×/wk for 3 wks |
| 3 | 25 | NanoPac ® | 30 | IT | 1×/wk for 3 wks |
| 4 | 25 | NanoPac ® | 30 | IT | 1×/wk for 3 wks |
|   |   | Pembrolizumab | 5 | IV | BIW×4 |

Study Includes

| # Mice | Mouse Type/ID | PDX Models | Study Duration | Data Collection | Tissue Collection |
|---|---|---|---|---|---|
| 100 | Hu-CD34_SGM3 013062 | TBD TM00176 or TM00302 | 5 Weeks | Caliper Measurements, Body weight and Clinical Obs. 3×/wk Photos of tumors at takedown | 100 Tumors (1 fragments FACS, 1 fragment FFPE, 1 fragment flash frozen 100 Whole Blood (FACS, and Frozen Serum) |

TABLE 36-continued

Efficacy Experiment Design

| | Tumor weight on takedown | 100 Bone Marrow from Femurs (FACS and Frozen) |
|---|---|---|

*5 donors will be used. The final number of animals from each donor enrolled per group will depend on the availability of animals with tumor volumes that meet the enrollment criteria at the time of experiment.
Group 4 Nanopac dosing will occur 72 hours +/− 4 hours after the Pembrolizumab dosing.
**IT injections will not exceed 50 ul.

The results of the study will demonstrate that treatment with the combination of NanoPac® and Pembrolizumab will have greater efficacy than the treatment with Pembrolizumab alone and/or the treatment with NanoPac® alone (monotherapy) as evidenced by at least one of the following:

(a) greater reduction of tumor size with the animals treated with the combination of NanoPac® and Pembrolizumab than with the animals treated with Pembrolizumab alone, or (b) greater reduction in tumor growth with the animals treated with the combination of NanoPac® and Pembrolizumab than with the animals treated with Pembrolizumab alone, or (c) one or more incidences of tumor elimination with the animals treated with the combination of NanoPac® and Pembrolizumab versus no incidences of tumor elimination with the animals treated with Pembrolizumab alone, or (d) greater reduction of tumor size with the animals treated with the combination of NanoPac® and Pembrolizumab than with the animals treated with NanoPac® alone, or (e) greater reduction in tumor growth with the animals treated with the combination of NanoPac® and Pembrolizumab than with the animals treated with NanoPac® alone, or (f) one or more incidences of tumor elimination with the animals treated with the combination of NanoPac® and Pembrolizumab versus no incidences of tumor elimination with the animals treated with NanoPac® alone, and/or the results of the study will demonstrate a synergistic effect on efficacy with the combination of NanoPac® and Pembrolizumab as evidenced by at least one of the following:

(g) the reduction of tumor size of the animals treated with the combination of NanoPac® and Pembrolizumab is greater than the sum of the reductions of the tumor size of the animals treated with Pembrolizumab alone plus those treated with NanoPac® alone, or (h) the reduction of tumor growth of the animals treated with the combination of NanoPac® and Pembrolizumab is greater than the sum of the reductions of the tumor growth of the animals treated with Pembrolizumab alone plus those treated with NanoPac® alone, or (i) the number of incidences of tumor elimination of the animals treated with the combination of NanoPac® and Pembrolizumab is greater than the sum of the number of incidences of tumor elimination of the animals treated with Pembrolizumab alone plus those treated with NanoPac® alone.

LITERATURE REFERENCES

Ashgate Handbook of Antineoplastic Agents, Gower Publishing Limited, 2000.

Bracci, L., Schiavoni, G., Sistigu, A., & Belardelli, F. (2014). Immune-based mechanisms of cytotoxic chemotherapy: implications for the design of novel rationale-based combined treatments against cancer. Cell Death and Differentiation, 21, 15-25.

Chang, C. L., Hsu, Y. T., Wu, C. C., Lai, Y. Z., Wang, C., Yang, Y. C., . . . Hung, C. F. (2013). Dose-Dense Chemotherapy Improves Mechanisms of Antitumor Immune Response. Microenvironment and Immunology, 73(1), 119-127.

Ghiringhelli, F., Menard, C., Puig, P. E., Ladoire S, Roux, S., & Martin F. (2007). Metronomic cyclophosphamide regimen selectively depletes CD4CD25 regulatory T-cells and restores T and NK effector functions in end stage cancer patients. Cancer Immunol Immunother, 56, 641-648.

Handbook of Pharmaceutical Excipients, Fifth edition, Pharmaceutical Press, 2006.

Javeed, A., Ashraf, M., Riaz, A., Ghafoor, A., Afzal, S., & Mukhtar, M. M. (2009). Paclitaxel and the Immune System. European Journal of Pharmaceutical Sciences, 38, 283-290.

McCutcheon's Emulsifiers & Detergents, 2001 North American Edition, The Manufacturing Confectioner Publishing Co.

Michels, T., Schurin, G. V., Naiditch, H., Sevko, A., Umansky, V., & Shurin, M. R. (2012). Paclitaxel promotes differentiation of myeloid-derived suppressor cells into dendritic cells in vitro in a TLR4-independent manner. J Immunotoxicol, 9, 292-300.

Osborne, David W., and Henke, Jill J., Skin Penetration Enhancers Cited in the Technical Literature, Pharmaceutical Technology, November 1997, 58-66.

Proietti, E., Moschella, F., Capone, I., & Belardelli, F. (2012). Exploitation of the propulsive force of chemotherapy for improving the response to cancer immunotherapy. Mol Oncol, 6, 1-14.

Remington, The Science and Practice of Pharmacy, 22nd ed., Pharmaceutical Press, 2013.

Rheology Modifiers Handbook—Practical Use and Application, Braun, William Andrew Publishing, 2000.

The International Cosmetic Ingredient Dictionary and Handbook (INCI), 12th Edition, The Cosmetic, Toiletry, and Fragrance Association, 2008.

Tsavaris, N., Kosmas, C., Vadiaka, M., Kanelopoulos, P., & Boulamatsis, D. (2002). Immune changes in patients with advanced breast cancer undergoing chemotherapy with taxanes. Br J Cancer, 87, 21-27.

Zhang, L., Dermawan, K., Jin, M., Liu, R., Zheng, H., Xu, L., Xiong, S. (2008). Differential impairment of regulatory T cells rather than effector T cells by paclitaxel-based chemotherapy. Clinical Immunology, 129, 219-229.

Zitvogel, L., Galluzzi, L., Smyth, M. J., & Kroemer, G. (2013). Mechanism of Action of Conventional and Targeted Anticancer Therapies: Reinstating Immunosurveillance. Immunity, 39, 74-88.

The invention claimed is:

1. A method of treating cancer in a subject, the method comprising:
   (a) administering a first composition comprising taxane particles to a subject, wherein the administration is selected from the group consisting of (i) topical administration to an affected area of a skin tumor of the subject, (ii) pulmonary administration, (iii) intratumoral, and (iv) intraperitoneal organ injection; and
   (b) systemically administering a second composition comprising an immunotherapeutic agent to the subject, thereby treating the cancer, wherein the taxane particles have a mean particle size (number) of from 0.1 microns to 5 microns, wherein the taxane particles comprise at least 95% of the taxane, and wherein the taxane particles have a specific surface area (SSA) of at least 18 $m^2/g$, and wherein steps (a) and (b) can be conducted in any order or at the same time.

2. The method of claim 1, wherein the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent.

3. The method of claim 1, wherein the first composition is administered at least one day prior to the administration of the second composition.

4. The method of claim 1, wherein the second composition is administered at least one day prior to the administration of the first composition.

5. The method of claim 1, wherein the first composition and the second composition are administered on the same day.

6. A kit comprising:
   (a) a first composition comprising taxane particles, wherein the taxane particles have a mean particle size (number) of from 0.1 microns to 5 microns, wherein the taxane particles comprise at least 95% of the taxane, and wherein the taxane particles have a specific surface area (SSA) of at least 18 $m^2/g$,
   (b) a second composition comprising an immunotherapeutic agent, and
   (c) instructions for
      (i) administering the first composition locally to a subject, and
      (ii) administering the second composition systemically to the subject.

7. The kit of claim 2, wherein the immunotherapeutic agent is a monoclonal antibody, a cancer vaccine, a non-specific immunotherapeutic agent, a cytokine, interferon, interleukin, a colony stimulating factor, a checkpoint inhibitor, an immune modulator, an adoptive cell transfer agent, a T-cell therapeutic agent, a cellular therapeutic agent, an oncolytic virus therapeutic agent, BCG, and/or an adjuvant immunotherapeutic agent.

8. The method of claim 1, wherein the taxane particles have a SSA of between 18 $m^2/g$ and 50 $m^2/g$.

9. The method of claim 1, wherein the taxane particles are selected from the group consisting of paclitaxel particles and docetaxel particles.

10. The method of claim 2, wherein the taxane particles have a SSA of between 18 $m^2/g$ and 50 $m^2/g$.

11. The method of claim 2, wherein the taxane particles are selected from the group consisting of paclitaxel particles and docetaxel particles.

12. The method of claim 8, wherein the taxane particles are selected from the group consisting of paclitaxel particles and docetaxel particles.

13. The method of claim 10, wherein the taxane particles are selected from the group consisting of paclitaxel particles and docetaxel particles.

14. The kit of claim 6, wherein the taxane particles have a SSA of between 18 $m^2/g$ and 50 $m^2/g$.

15. The kit of claim 6, wherein the taxane particles are selected from the group consisting of paclitaxel particles and docetaxel particles.

16. The kit of claim 7, wherein the taxane particles have a SSA of between 18 $m^2/g$ and 50 $m^2/g$.

17. The kit of claim 7, wherein the taxane particles are selected from the group consisting of paclitaxel particles and docetaxel particles.

18. The kit of claim 14, wherein the taxane particles are selected from the group consisting of paclitaxel particles and docetaxel particles.

19. The kit of claim 16, wherein the taxane particles are selected from the group consisting of paclitaxel particles and docetaxel particles.

\* \* \* \* \*